(12) United States Patent
Tariyal et al.

(10) Patent No.: US 11,864,740 B2
(45) Date of Patent: Jan. 9, 2024

(54) SAMPLE COLLECTION AND PRESERVATION DEVICES, SYSTEMS AND METHODS

(71) Applicant: NextGen Jane, Inc., Oakland, CA (US)

(72) Inventors: Ridhi Tariyal, Oakland, CA (US); Stephen K. Gire, Oakland, CA (US)

(73) Assignee: NEXTGEN JANE, INC., Oakland, CA (US)

( * ) Notice: Subject to any disclaimer, the term of this patent is extended or adjusted under 35 U.S.C. 154(b) by 0 days.

(21) Appl. No.: 17/888,136

(22) Filed: Aug. 15, 2022

(65) Prior Publication Data
US 2023/0064804 A1  Mar. 2, 2023

Related U.S. Application Data

(63) Continuation of application No. 16/153,389, filed on Oct. 5, 2018, now Pat. No. 11,446,011, which is a
(Continued)

(51) Int. Cl.
*A61B 10/00* (2006.01)
*B01L 3/00* (2006.01)
(Continued)

(52) U.S. Cl.
CPC ...... *A61B 10/0045* (2013.01); *A61B 10/0096* (2013.01); *B01L 3/00* (2013.01);
(Continued)

(58) Field of Classification Search
None
See application file for complete search history.

(56) References Cited

U.S. PATENT DOCUMENTS

| 2,905,169 A | 9/1959 | Nieburgs |
| 3,815,580 A | 6/1974 | Oster |

(Continued)

FOREIGN PATENT DOCUMENTS

| CN | 1639555 A | 7/2005 |
| CN | 1954203 A | 4/2007 |

(Continued)

OTHER PUBLICATIONS

Aagaard, et al., Primary human placental trophoblasts are permissive for Zika Virus (ZIKV) replication. Sci Rep 7:41389 (2017).
(Continued)

*Primary Examiner* — Benjamin S Melhus
(74) *Attorney, Agent, or Firm* — WILSON SONSINI GOODRICH & ROSATI

(57) ABSTRACT

The present disclosure provides systems, methods, devices, and kits for analysis of vaginal biological samples. A device for the analysis of vaginal biological samples can include a sample collector, an extractor, and an assay cartridge. A method for the analysis of vaginal biological samples can include detecting the presence or absence of a pathology, a disease, an immune disorder, a reproductive disorder of a subject. The method may further comprise preserving, storing, or transporting the vaginal biological samples. A kit for the analysis of vaginal biological samples can include probe, reagents and instructions for detecting a nucleic acid in the vaginal biological samples.

16 Claims, 18 Drawing Sheets

Related U.S. Application Data continuation of application No. PCT/US2017/027482, filed on Apr. 13, 2017.

(60) Provisional application No. 62/460,329, filed on Feb. 17, 2017, provisional application No. 62/321,987, filed on Apr. 13, 2016.

(51) Int. Cl.

| | | |
|---|---|---|
| *C12Q 1/6806* | (2018.01) | |
| *A61B 10/02* | (2006.01) | |
| *A01N 1/02* | (2006.01) | |
| *C12Q 1/6883* | (2018.01) | |
| *C12Q 1/04* | (2006.01) | |
| *C12M 1/30* | (2006.01) | |
| *G01N 1/02* | (2006.01) | |

(52) U.S. Cl.
CPC .............. *B01L 3/5029* (2013.01); *B01L 3/523* (2013.01); *C12Q 1/6806* (2013.01); *A01N 1/021* (2013.01); *A61B 2010/0006* (2013.01); *A61B 2010/0074* (2013.01); *A61B 2010/0216* (2013.01); *B01L 2200/0621* (2013.01); *B01L 2200/16* (2013.01); *B01L 2300/069* (2013.01); *B01L 2300/0832* (2013.01); *B01L 2300/0851* (2013.01); *B01L 2400/0683* (2013.01); *C12M 33/02* (2013.01); *C12Q 1/04* (2013.01); *C12Q 1/6883* (2013.01); *C12Q 2600/158* (2013.01); *G01N 2001/028* (2013.01)

(56) References Cited

U.S. PATENT DOCUMENTS

| | | |
|---|---|---|
| 3,876,503 A | 4/1975 | Mennen |
| 3,954,563 A | 5/1976 | Mennen |
| 4,257,427 A | 3/1981 | Bucalo |
| 4,675,286 A | 6/1987 | Calenoff |
| 4,770,853 A | 9/1988 | Bernstein |
| 4,927,605 A | 5/1990 | Dorn et al. |
| 5,128,104 A | 7/1992 | Murphy et al. |
| 5,393,496 A | 2/1995 | Seymour |
| 5,445,164 A | 8/1995 | Worthen et al. |
| 5,477,863 A | 12/1995 | Grant |
| 5,725,481 A | 3/1998 | Buck et al. |
| 5,750,341 A | 5/1998 | Macevicz |
| 5,830,199 A | 11/1998 | Chaffringeon |
| 5,843,575 A | 12/1998 | Wang et al. |
| 5,856,174 A | 1/1999 | Lipshutz et al. |
| 5,858,535 A | 1/1999 | Wang et al. |
| 5,891,126 A | 4/1999 | Osborn, III et al. |
| 6,007,498 A | 12/1999 | Buck et al. |
| 6,126,616 A | 10/2000 | Sanyal |
| 6,174,293 B1 | 1/2001 | Buck et al. |
| 6,206,839 B1 | 3/2001 | Zwelling-Aamot |
| 6,306,597 B1 | 10/2001 | Macevicz |
| 6,409,713 B1 | 6/2002 | Osborn, III et al. |
| 6,465,713 B1 | 10/2002 | Gell et al. |
| 6,479,727 B1 | 11/2002 | Roe |
| 6,524,530 B1 | 2/2003 | Igarashi et al. |
| 6,531,435 B1 | 3/2003 | Resheski-Wedepohl et al. |
| 6,649,359 B2 | 11/2003 | Mutter et al. |
| 6,656,913 B1 | 12/2003 | Resheski-Wedepohl et al. |
| 6,664,104 B2 | 12/2003 | Pourahmadi et al. |
| 6,702,759 B2 | 3/2004 | Pevoto |
| 6,811,549 B2 | 11/2004 | Fleming |
| 6,830,935 B1 | 12/2004 | El-Amin et al. |
| 6,888,043 B2 | 5/2005 | Geiser et al. |
| 6,890,325 B2 | 5/2005 | Edens et al. |
| 6,899,700 B2 | 5/2005 | Gehling et al. |
| 6,936,013 B2 | 8/2005 | Pevoto |
| 7,056,891 B2 | 6/2006 | Resheski-Wedepohl et al. |
| 7,083,924 B2 | 8/2006 | Hulten |
| 7,115,116 B2 | 10/2006 | Hlaban et al. |
| 7,115,400 B1 | 10/2006 | Adessi et al. |
| 7,128,877 B2 | 10/2006 | Quay et al. |
| 7,183,381 B2 | 2/2007 | Varadhachary et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,264,929 B2 | 9/2007 | Rothberg et al. |
| 7,291,477 B2 | 11/2007 | Alderete et al. |
| 7,314,453 B2 | 1/2008 | Kuo |
| 7,323,305 B2 | 1/2008 | Leamon et al. |
| 7,420,033 B2 | 9/2008 | Varadhachary et al. |
| 7,638,099 B2 | 12/2009 | Lloyd et al. |
| 7,648,829 B2 | 1/2010 | Alderete et al. |
| 7,776,525 B2 | 8/2010 | Kuroda et al. |
| 7,803,567 B2 | 9/2010 | Alderete et al. |
| 7,842,454 B2 | 11/2010 | Shomi et al. |
| 7,935,860 B2 | 5/2011 | Dodge et al. |
| 7,943,294 B2 | 5/2011 | Hussa et al. |
| 7,948,015 B2 | 5/2011 | Rothberg et al. |
| 7,994,387 B2 | 8/2011 | Minoguchi et al. |
| 8,008,018 B2 | 8/2011 | Quake et al. |
| 8,241,086 B2 | 8/2012 | Kim |
| 8,372,581 B2 | 2/2013 | Hussa et al. |
| 8,398,606 B2 | 3/2013 | Fleming |
| 8,641,642 B2 | 2/2014 | Giddings et al. |
| 8,685,748 B2 | 4/2014 | Lloyd et al. |
| 8,722,349 B2 | 5/2014 | Goldman |
| 8,852,872 B2 | 10/2014 | Hussa et al. |
| 8,911,988 B2 | 12/2014 | Miller |
| 9,056,291 B2 | 6/2015 | Battrell et al. |
| 9,060,753 B2 | 6/2015 | Lundkvist et al. |
| 9,078,642 B2 | 7/2015 | Vom et al. |
| 9,144,420 B2 | 9/2015 | Zavala |
| 9,168,028 B2 | 10/2015 | Shany et al. |
| 9,417,210 B2 | 8/2016 | Arlen et al. |
| 9,918,702 B2 | 3/2018 | Tariyal et al. |
| 10,087,440 B2 | 10/2018 | Lofquist et al. |
| 11,446,011 B2 | 9/2022 | Tariyal et al. |
| 2002/0072702 A1 | 6/2002 | Quay |
| 2002/0096469 A1 | 7/2002 | Faulkner et al. |
| 2002/0169433 A1 | 11/2002 | Osborn et al. |
| 2003/0045829 A1 | 3/2003 | Gehling et al. |
| 2003/0064526 A1 | 4/2003 | Niedbala et al. |
| 2003/0073147 A1 | 4/2003 | Alderete et al. |
| 2003/0113746 A1 | 6/2003 | Leyendecker |
| 2003/0120180 A1 | 6/2003 | Kaylor et al. |
| 2003/0120224 A1 | 6/2003 | Geiser et al. |
| 2003/0120225 A1 | 6/2003 | Everhart et al. |
| 2004/0053856 A1 | 3/2004 | Resheski-Wedepohl et al. |
| 2004/0078230 A1 | 4/2004 | Karas |
| 2004/0121379 A1 | 6/2004 | Ohan |
| 2004/0170536 A1 | 9/2004 | Daykin |
| 2004/0254557 A1 | 12/2004 | Kraemer |
| 2004/0266025 A1 | 12/2004 | Hickok et al. |
| 2005/0020937 A1 | 1/2005 | Reed et al. |
| 2005/0020993 A1 | 1/2005 | Fleming |
| 2005/0106753 A1 | 5/2005 | Wu et al. |
| 2005/0112547 A1 | 5/2005 | Youngkin et al. |
| 2005/0119589 A1 | 6/2005 | Tung et al. |
| 2005/0124003 A1 | 6/2005 | Atala et al. |
| 2005/0142031 A1 | 6/2005 | Wickstead et al. |
| 2005/0180882 A1 | 8/2005 | Tung et al. |
| 2005/0187507 A1 | 8/2005 | Reed et al. |
| 2005/0276836 A1 | 12/2005 | Wilson et al. |
| 2006/0024725 A1 | 2/2006 | Hussa et al. |
| 2006/0024757 A1 | 2/2006 | Hussa et al. |
| 2006/0036138 A1 | 2/2006 | Heller et al. |
| 2006/0252087 A1 | 11/2006 | Tang et al. |
| 2006/0287611 A1 | 12/2006 | Fleming |
| 2007/0231358 A1 | 10/2007 | Ebmeier et al. |
| 2008/0003144 A1 | 1/2008 | Cumberland et al. |
| 2008/0113358 A1 | 5/2008 | Kapur et al. |
| 2008/0113391 A1 | 5/2008 | Gibbons et al. |
| 2008/0160580 A1 | 7/2008 | Adessi et al. |
| 2008/0217246 A1 | 9/2008 | Benn et al. |
| 2008/0226554 A1 | 9/2008 | Colgan et al. |
| 2008/0286795 A1 | 11/2008 | Kawashima et al. |
| 2008/0299543 A1 | 12/2008 | Gailer |
| 2009/0011417 A1 | 1/2009 | Maltezos et al. |

(56) References Cited

U.S. PATENT DOCUMENTS

| | | |
|---|---|---|
| 2009/0043224 A1 | 2/2009 | Lundkvist et al. |
| 2009/0104650 A1 | 4/2009 | Walton et al. |
| 2009/0105678 A1 | 4/2009 | Minoguchi et al. |
| 2009/0148933 A1 | 6/2009 | Battrell et al. |
| 2009/0156965 A1 | 6/2009 | Fleming |
| 2009/0227930 A1 | 9/2009 | Crisp |
| 2009/0246750 A1 | 10/2009 | Lloyd et al. |
| 2010/0022916 A1 | 1/2010 | Esfandiari et al. |
| 2010/0030189 A1 | 2/2010 | Fleming |
| 2010/0035349 A1 | 2/2010 | Bau et al. |
| 2010/0086948 A1 | 4/2010 | Gold et al. |
| 2010/0184046 A1 | 7/2010 | Klass et al. |
| 2010/0216131 A1 | 8/2010 | Luthra et al. |
| 2010/0221752 A2 | 9/2010 | Gold et al. |
| 2010/0267003 A1 | 10/2010 | Goldman |
| 2010/0274155 A1 | 10/2010 | Battrell et al. |
| 2010/0296087 A1 | 11/2010 | Gailer |
| 2010/0304361 A1 | 12/2010 | Semikhodskii et al. |
| 2011/0027795 A1 | 2/2011 | Mantzaris et al. |
| 2011/0060137 A1* | 3/2011 | Tanigami ............ C12N 15/1006 536/23.1 |
| 2011/0086378 A1 | 4/2011 | Shany et al. |
| 2011/0111386 A1 | 5/2011 | Rogers et al. |
| 2011/0166432 A1 | 7/2011 | Fleming |
| 2011/0192239 A1 | 8/2011 | Selinfreund et al. |
| 2011/0195488 A1 | 8/2011 | Selinfreund et al. |
| 2011/0207621 A1 | 8/2011 | Montagu et al. |
| 2012/0122726 A1 | 5/2012 | Posada et al. |
| 2012/0149017 A1 | 6/2012 | Tabibzadeh et al. |
| 2012/0165217 A1 | 6/2012 | Gold et al. |
| 2012/0310113 A1 | 12/2012 | Giddings et al. |
| 2012/0316409 A1 | 12/2012 | Crisp |
| 2012/0329081 A1 | 12/2012 | Bennion et al. |
| 2013/0041236 A1 | 2/2013 | Pugia et al. |
| 2013/0085680 A1 | 4/2013 | Arlen et al. |
| 2013/0112016 A1 | 5/2013 | Hansen et al. |
| 2013/0252245 A1 | 9/2013 | Micallef et al. |
| 2013/0331298 A1 | 12/2013 | Rea |
| 2013/0337439 A1 | 12/2013 | Goncalves et al. |
| 2013/0344588 A1 | 12/2013 | Halushka et al. |
| 2014/0066807 A1 | 3/2014 | Lundkvist et al. |
| 2014/0074007 A1 | 3/2014 | McNeil |
| 2014/0099649 A1 | 4/2014 | Mitsuhashi |
| 2014/0128345 A1 | 5/2014 | Woodrow et al. |
| 2014/0134246 A1 | 5/2014 | Venkatesh et al. |
| 2014/0163419 A1 | 6/2014 | Bullington et al. |
| 2014/0302617 A1 | 10/2014 | Aronowitz |
| 2014/0309606 A1 | 10/2014 | Richlen et al. |
| 2015/0044708 A1 | 2/2015 | Hussa et al. |
| 2015/0065379 A1 | 3/2015 | Sanyal |
| 2015/0087935 A1 | 3/2015 | Davis et al. |
| 2015/0185184 A1 | 7/2015 | Guia et al. |
| 2015/0209017 A1 | 7/2015 | Fleming et al. |
| 2015/0217019 A1 | 8/2015 | Martello |
| 2015/0267240 A1 | 9/2015 | Armant et al. |
| 2015/0268135 A1 | 9/2015 | Hu et al. |
| 2015/0283284 A1 | 10/2015 | Azad et al. |
| 2015/0342577 A1 | 12/2015 | Fleming et al. |
| 2016/0011225 A1 | 1/2016 | Holmes |
| 2016/0045187 A1 | 2/2016 | Terbrueggen et al. |
| 2016/0143631 A1 | 5/2016 | Zavala |
| 2016/0273059 A1 | 9/2016 | Benshaul |
| 2017/0113221 A1 | 4/2017 | Hoffman et al. |
| 2017/0248599 A1 | 8/2017 | Armant et al. |
| 2017/0283789 A1 | 10/2017 | Yamamoto et al. |
| 2018/0128718 A1 | 5/2018 | Crum et al. |
| 2018/0242957 A1 | 8/2018 | Tariyal et al. |
| 2020/0206303 A1 | 7/2020 | Bowerman et al. |
| 2022/0091126 A1 | 3/2022 | Stockley et al. |

FOREIGN PATENT DOCUMENTS

| | | |
|---|---|---|
| CN | 1964789 A | 5/2007 |
| CN | 101389965 A | 3/2009 |
| CN | 103097883 A | 5/2013 |
| CN | 103776660 A | 5/2014 |
| EP | 0645447 A2 | 3/1995 |
| EP | 1148819 B1 | 10/2010 |
| GB | 2500658 A | 10/2013 |
| JP | 2000511078 A | 8/2000 |
| JP | 2004524060 A | 8/2004 |
| JP | 2006007328 A | 1/2006 |
| JP | 2007218503 A | 8/2007 |
| JP | 2010535346 A | 11/2010 |
| JP | 2012526990 A | 11/2012 |
| JP | 2013518259 A | 5/2013 |
| JP | 2017529199 A | 10/2017 |
| WO | WO-9107660 A1 | 5/1991 |
| WO | WO-9820352 A2 | 5/1998 |
| WO | WO-9855159 A2 | 12/1998 |
| WO | WO-0055173 A1 | 9/2000 |
| WO | WO-0170804 A1 | 9/2001 |
| WO | WO-0248820 A2 | 6/2002 |
| WO | WO-02095060 A2 | 11/2002 |
| WO | WO-03011144 A1 | 2/2003 |
| WO | WO-03020240 A2 | 3/2003 |
| WO | WO-03056954 A1 | 7/2003 |
| WO | WO-03057264 A1 | 7/2003 |
| WO | WO-03057305 A1 | 7/2003 |
| WO | WO-0248820 A3 | 8/2004 |
| WO | WO-2004071304 A1 | 8/2004 |
| WO | WO-2004071427 A2 | 8/2004 |
| WO | WO-2004076653 A1 | 9/2004 |
| WO | WO-2005102526 A1 | 11/2005 |
| WO | WO-2006017341 A2 | 2/2006 |
| WO | WO-2006017746 A2 | 2/2006 |
| WO | WO-2006083853 A2 | 8/2006 |
| WO | WO-2007080410 A1 | 7/2007 |
| WO | WO-2007131138 A2 | 11/2007 |
| WO | WO-2008089519 A1 | 7/2008 |
| WO | WO-2008112290 A2 | 9/2008 |
| WO | WO-2008115601 A1 | 9/2008 |
| WO | WO-2009014787 A2 | 1/2009 |
| WO | WO-2009035706 A1 | 3/2009 |
| WO | WO-2009077876 A2 | 6/2009 |
| WO | WO-2009139317 A1 | 11/2009 |
| WO | WO-2010042525 A1 | 4/2010 |
| WO | WO-2010085841 A1 | 8/2010 |
| WO | WO-2011043840 A1 | 4/2011 |
| WO | WO-2011064423 A1 | 6/2011 |
| WO | WO-2011127467 A1 | 10/2011 |
| WO | WO-2012078308 A1 | 6/2012 |
| WO | WO-2012151237 A1 | 11/2012 |
| WO | WO-2012177656 A2 | 12/2012 |
| WO | WO-2014015192 A1 | 1/2014 |
| WO | WO-2014063553 A1 | 5/2014 |
| WO | WO-2014081877 A1 | 5/2014 |
| WO | WO-2015042298 A1 | 3/2015 |
| WO | WO-2015050875 A1 | 4/2015 |
| WO | WO-2015059686 A1 | 4/2015 |
| WO | WO-2015066750 A1 | 5/2015 |
| WO | WO-2015191777 A2 | 12/2015 |
| WO | WO-2016025332 A1 | 2/2016 |
| WO | WO-2016025726 A1 | 2/2016 |
| WO | WO-2016028497 A1 | 2/2016 |
| WO | WO-2016033287 A1 | 3/2016 |
| WO | WO-2016033646 A1 | 3/2016 |
| WO | WO-2016094409 A1 | 6/2016 |
| WO | WO-2017176985 A1 | 10/2017 |
| WO | WO-2017180909 A1 | 10/2017 |

OTHER PUBLICATIONS

Bulletti, et al. Endometriosis and infertility. J Assist Reprod Genet. 27(8):441-7 (2010).

Burney et al., MicroRNA expression profiling of eutopic secretory endometrium in women with versus without endometriosis. Molecular Human Reproduction 15(10):625-631 (Aug. 2009).

Campbell, et al. Evaluation of the OSOM Trichomonas rapid test versus wet preparation examination for detection of Trichomonas vaginalis vaginitis in specimens from women with a low prevalence of infection. J Clin Microbiol. 46(10):3467-9 (2008).

(56) References Cited

OTHER PUBLICATIONS

Chang, et al. Effect of iron deficiency anemia in pregnancy on child mental development in rural China. Pediatrics. 131(3):e755-63 (2013).
Chudecka-Glaz, et al. Serum HE4, CA125, YKL-40, bcl-2, cathepsin-L and prediction optimal debulking surgery, response to chemotherapy in ovarian cancer. J Ovarian Res. 7:62 (2014).
Da Fonseca, et al. Prophylactic administration of progesterone by vaginal suppository to reduce the incidence of spontaneous preterm birth in women at increased risk: a randomized placebo-controlled double-blind study. Am J Obstet Gynecol. 188(2):419-24 (2003).
Deguchi, et al. Emergence and spread of drug resistant Neisseria gonorrhoeae. J Urol. 184(3):851-8 (2010).
Di Quinzio, et al. Proteomic analysis and characterisation of human cervico-vaginal fluid proteins. Aust N Z J Obstet Gynaecol. 47(1):9-15 (2007).
Dyson et al., Genome-Wide DNA Methylation Analysis Predicts an Epigenetic Switch for GATA Factor Expression in Endometriosis. PLOSE Genetics. 10(3):e1004158 (2014).
Eschenbach. History and review of bacterial vaginosis. Am J Obstet Gynecol. 169(2 Pt 2):441-5 (1993).
Filigheddu et al., Differential Expression of MicroRNAs between Eutopic and Ectopic Endometrium in Ovarian Endometriosis. J Biomed Biotechnol 2010:369549 (2009).
Gaydos, et al. Comparison of three nucleic acid amplification tests for detection of Chlamydia trachomatis in urine specimens. J Clin Microbiol. 42(7):3041-5 (2004).
Hale, et al. Hormonal changes and biomarkers in late reproductive age, menopausal transition and menopause. Best Pract Res Clin Obstet Gynaecol. 23(1):7-23 (2009).
Hatt, et al., A new marker set that identifies fetal cells in maternal circulation with high specificity. Prenat Diagn. 34(11):1066-72 (2014).
Hawkins et al., Functional MicroRNA involved in endometriosis. Mol Endocrinol. 25(5):821-832 (2011).
Imudia, et al. Transcervical retrieval of fetal cells in the practice of modern medicine: a review of the current literature and future direction. Fertil Steril. 93(6):1725-30 (2010).
Jashnani, et al. Alfa-fetoprotein secreting ovarian sex cord-stromal tumor. Indian J Pathol Microbiol. 56(1):54-6 (2013).
Javors, et al. Current status of carbohydrate deficient transferrin, total serum sialic acid, sialic acid index of apolipoprotein J and serum beta-hexosaminidase as markers for alcohol consumption. Addiction. 98 Suppl 2:45-50 (2003).
Kaastrup, et al. Polymerization-based signal amplification under ambient conditions with thirty-five second reaction times. Lab Chip. 12(20):4055-8 (2012).
Koukoura et al., DNA methylation in endometriosis (Review). Molecular Medicine Reports. 13:2939-2949 (2016).
Kumar, et al. Robbins Basic Pathology ((8th ed.) ed.). Saunders Elsevier. pp. 718-721. May 24, 2007.
Leitich, et al. Cervicovaginal fetal fibronectin as a marker for preterm delivery: a meta-analysis. Am J Obstet Gynecol. 180(5):1169-76 (1999).
Lin, et al. Relationships between folate and inflammatory features of asthma. J Allergy Clin Immunol. 131(3):918-20 (2013).
Lynge, et al. Cervical cancer screening at crossroads. APMIS. 122(8):667-73 (2014).

Meyers, et al. USPSTF recommendations for STI screening. Am Fam Physician. 77(6):819-24 (2008).
Moran. Gonorrhoea. BMJ Clin Evid. 2007:1604 (2007).
Mustafa, et al. Risk factors for cervical cancer: diagnosis and management. IOSR Journal of Dental and Medical Sciences. 15(6):104-110 (Jun. 2016).
Naqvi et al., Altered Genome-Wide Methylation in Endometriosis. Sage Journals Reproductive Sciences. 21(10):30 (Apr. 2014).
Negro, et al. Increased pregnancy loss rate in thyroid antibody negative women with TSH levels between 2.5 and 5.0 in the first trimester of pregnancy. J Clin Endocrinol Metab. 95(9):E44-8 (2010).
Paavonen, et al. Sexually transmitted diseases. Lower genital tract infections in women. Infect Dis Clin North Am. 1(1):179-98 (1987).
PCT/US2015/044312 International Search Report and Written Opinion dated Nov. 4, 2015.
PCT/US2017/027482 International Search Report and Written Opinion dated Aug. 11, 2017.
Peterson. Biomarkers for alcohol use and abuse—a summary. Alcohol Res Health. 28(1):30-7 (2004-2005).
Piek, et al. Ovarian carcinogenesis: an alternative hypothesis. Adv Exp Med Biol. 622:79-87 (2008).
Ratnam. The laboratory diagnosis of syphilis. Can J Infect Dis Med Microbiol. 16(1):45-51 (2005).
Rizzo, et al., The importance of HLA-G expression in embryos, trophoblast cells, and embryonic stem cells. Cell Mol Life Sci. 68(3):341-52 (2011).
Rochester. Bisphenol A and human health: a review of the literature. Reprod Toxicol. 42:132-55 (2013).
Sparks. Vaginitis. The Journal of Reproductive Medicine. 36(10):745-752 (1991).
Tabrizi, et al. A self-administered technique for the detection of sexually transmitted diseases in remote communities. J Infect Dis. 176(1):289-92 (1997).
Tal, et al. Characterization of women with elevated antimüllerian hormone levels (AMH): correlation of AMH with polycystic ovarian syndrome phenotypes and assisted reproductive technology outcomes. Am J Obstet Gynecol. 211(1):59.e1-8 (2014).
Tjiong, et al., Increased IL-6 and IL-8 levels in cervicovaginal secretions of patients with cervical cancer. Gynecol Oncol. 73(2):285-91 (1999).
U.S. Appl. No. 15/203,464 Office Action dated Feb. 7, 2017.
U.S. Appl. No. 15/203,464 Office Action dated May 19, 2017.
U.S. Appl. No. 15/203,464 Office Action dated Sep. 29, 2017.
U.S. Appl. No. 15/881,370 Office Action dated Apr. 14, 2021.
U.S. Appl. No. 15/881,370 Office Action dated Apr. 8, 2022.
U.S. Appl. No. 15/881,370 Office Action dated Jul. 23, 2021.
U.S. Appl. No. 15/881,370 Office Action dated Jun. 9, 2020.
U.S. Appl. No. 15/881,370 Office Action dated Sep. 22, 2020.
U.S. Appl. No. 16/153,389 Office Action dated Dec. 22, 2021.
U.S. Appl. No. 16/153,389 Office Action dated May 21, 2021.
U.S. Appl. No. 16/153,389 Office Action dated Oct. 14, 2020.
Verhaegen, et al. Accuracy of single progesterone test to predict early pregnancy outcome in women with pain or bleeding: meta-analysis of cohort studies. BMJ. 345:e6077 (2012).
Wang et al., Genome-Wide Microarray Analysis of Long Non-Coding RNAs in Eutopic Secretory Endometrium with Endometriosis. Cellular Physiology and Biochemistry. 37:2213-2245 (2015)
U.S. Appl. No. 15/881,370 Office Action dated Apr. 6, 2023.
U.S. Appl. No. 15/881,370 Final Office Action dated Aug. 17, 2023.

* cited by examiner

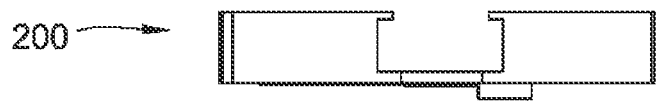
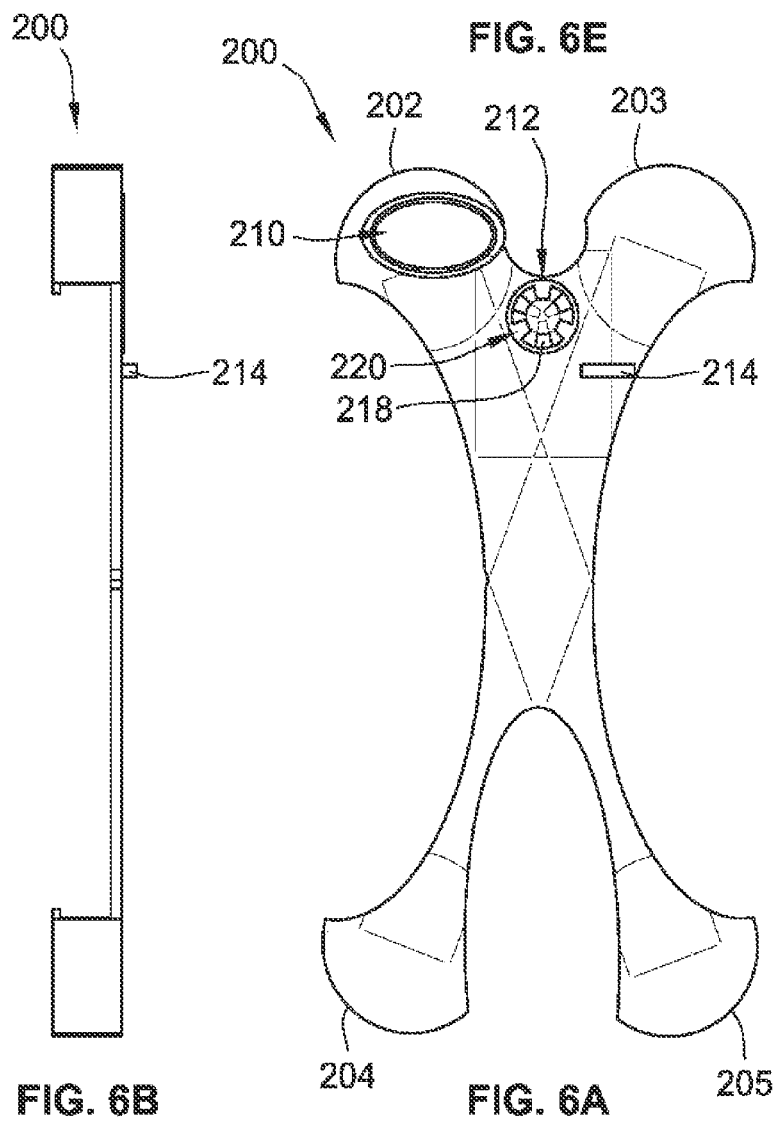
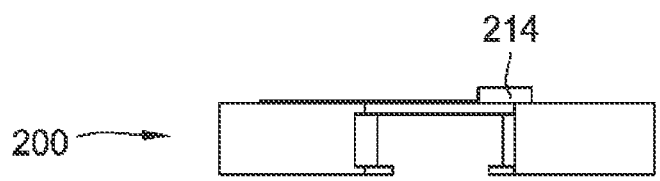

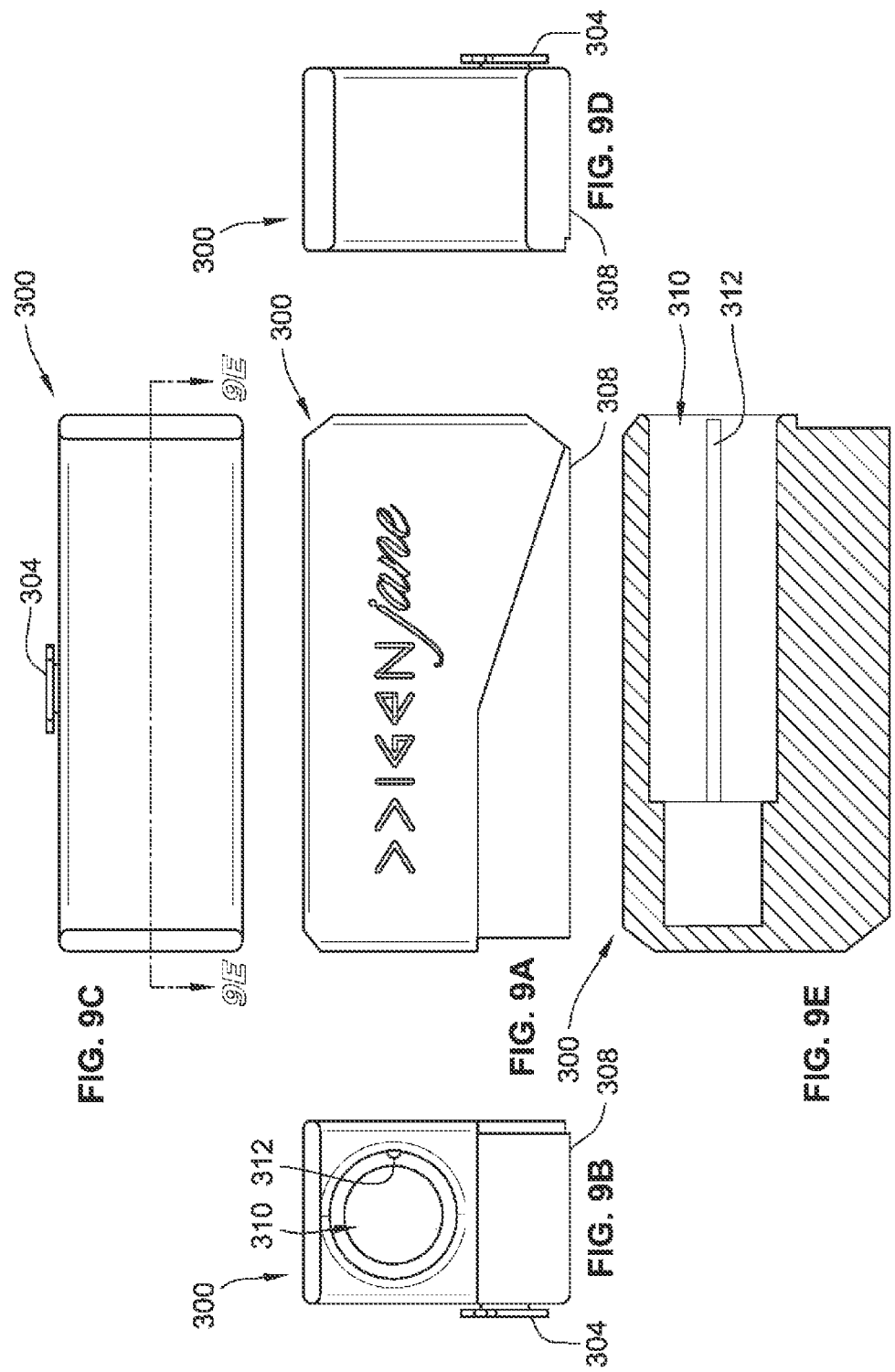

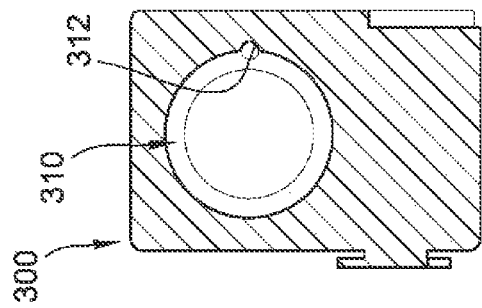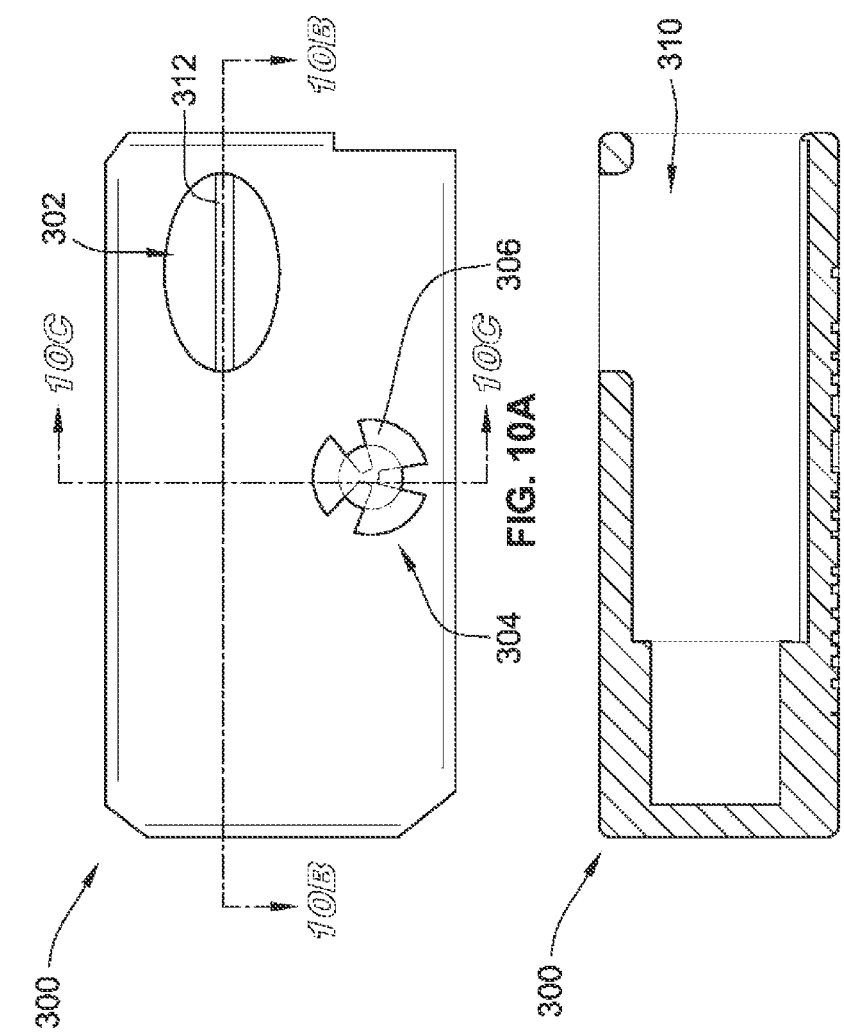

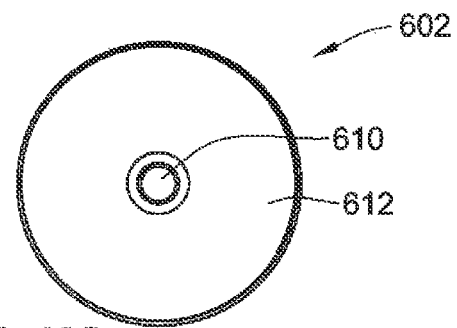
FIG. 12C
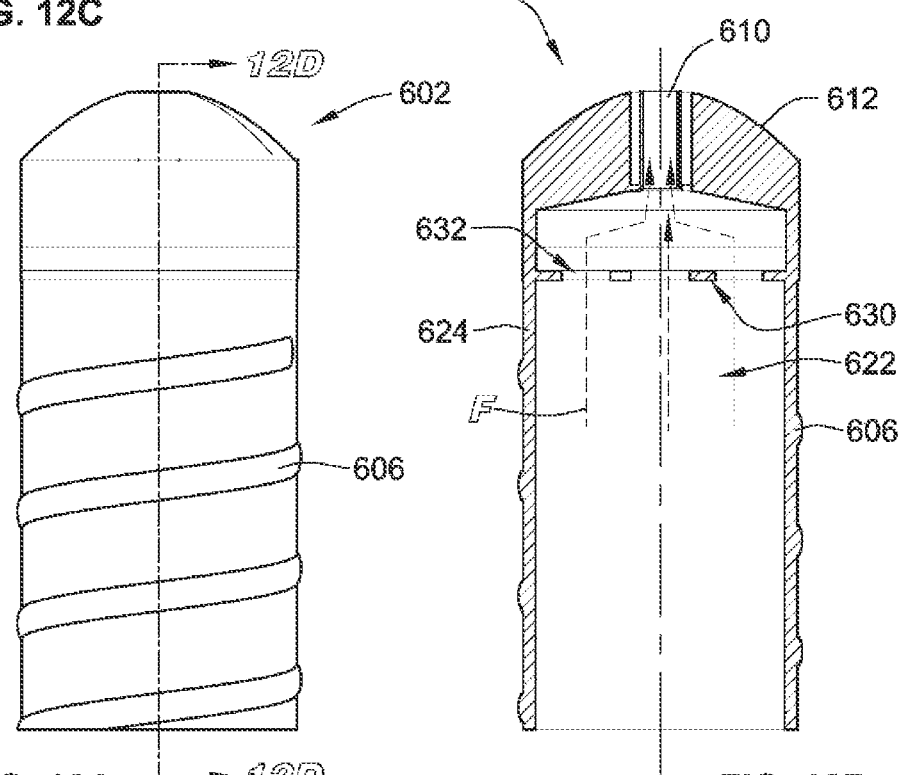
FIG. 12A
FIG. 12D
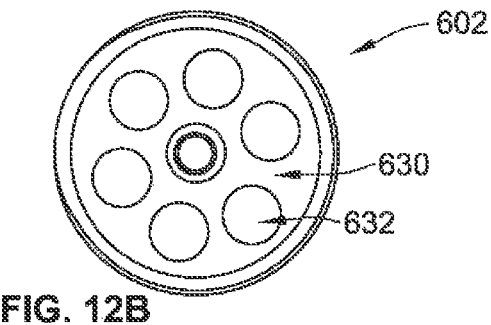
FIG. 12B

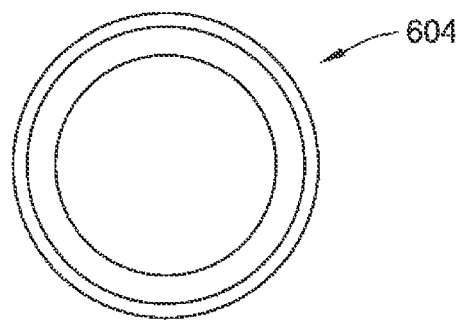
FIG. 13C
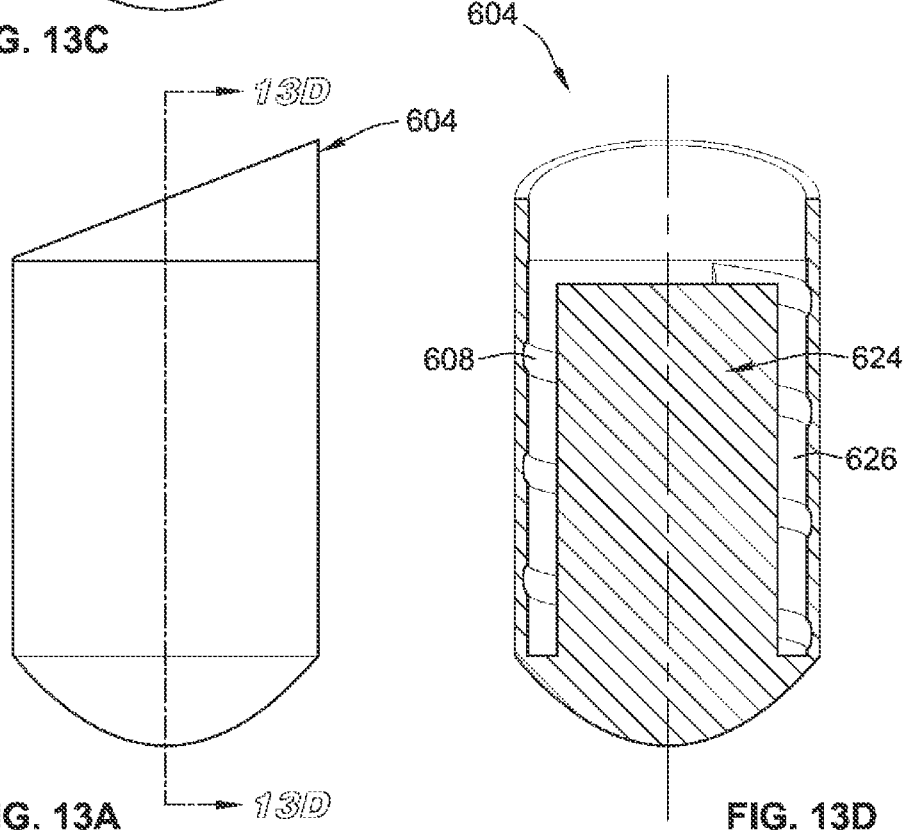
FIG. 13A
FIG. 13D
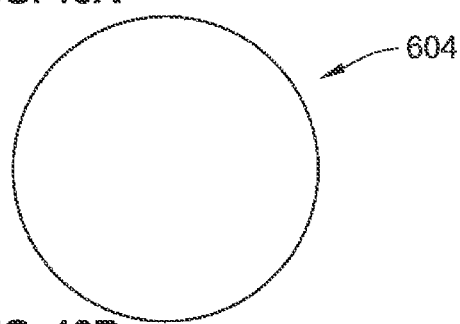
FIG. 13B

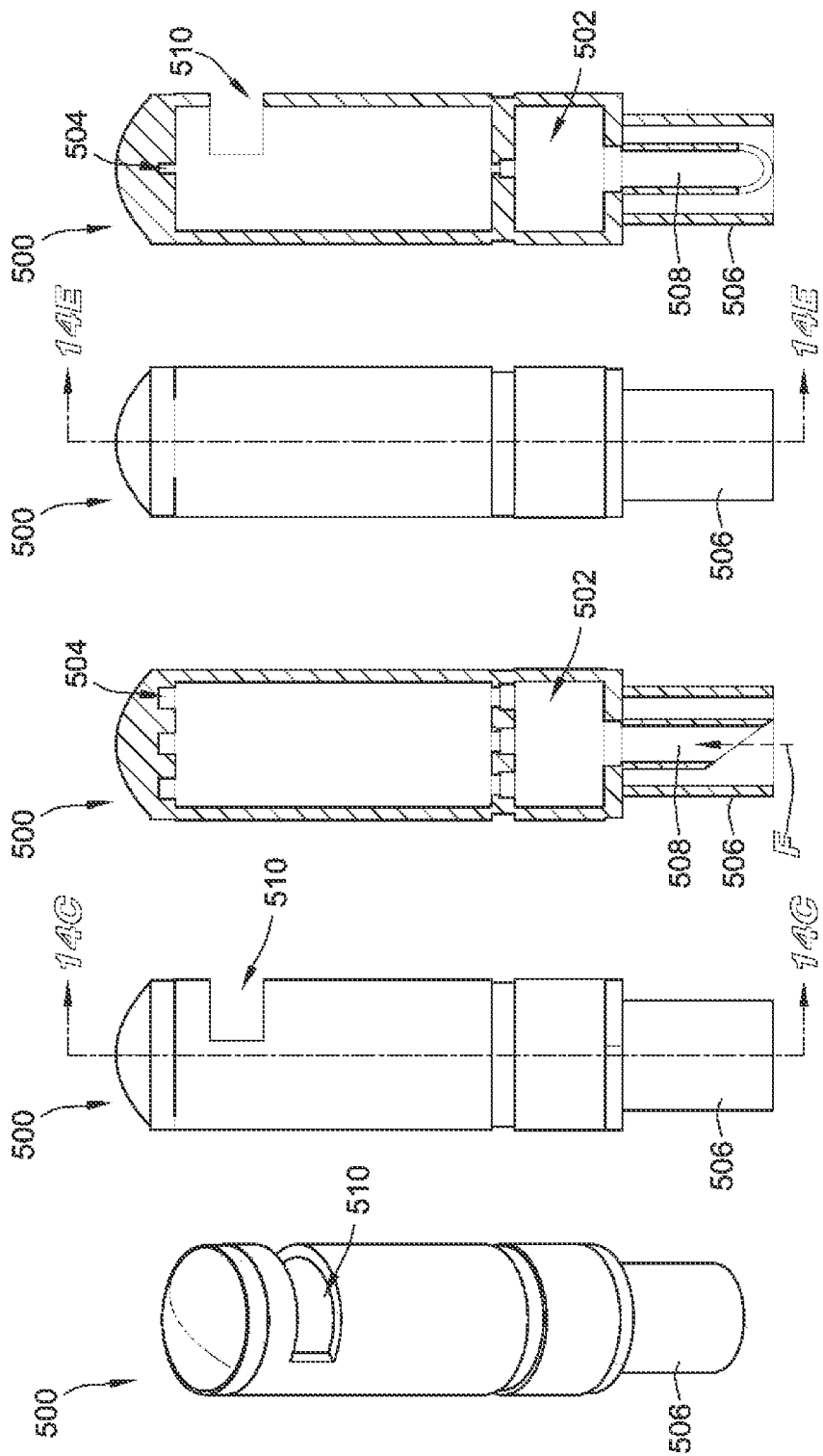

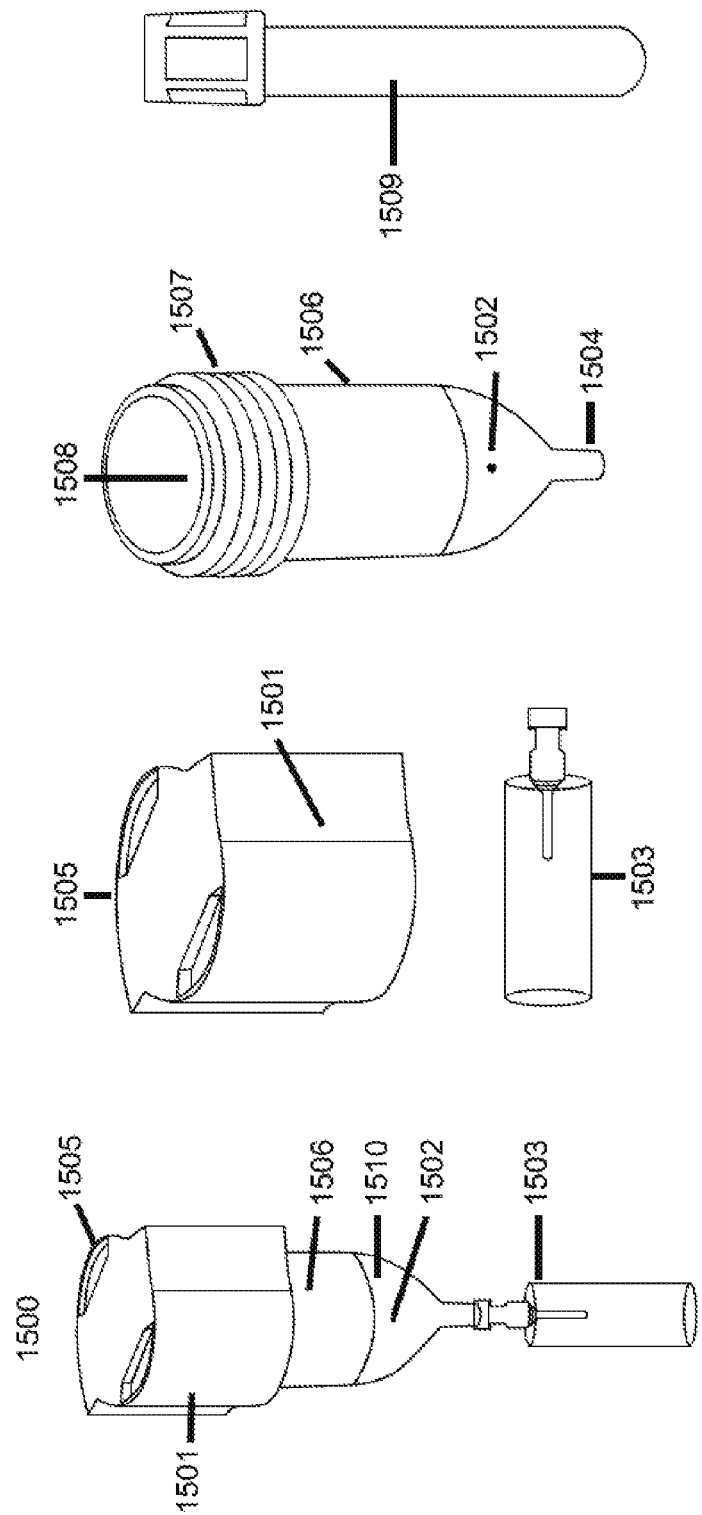

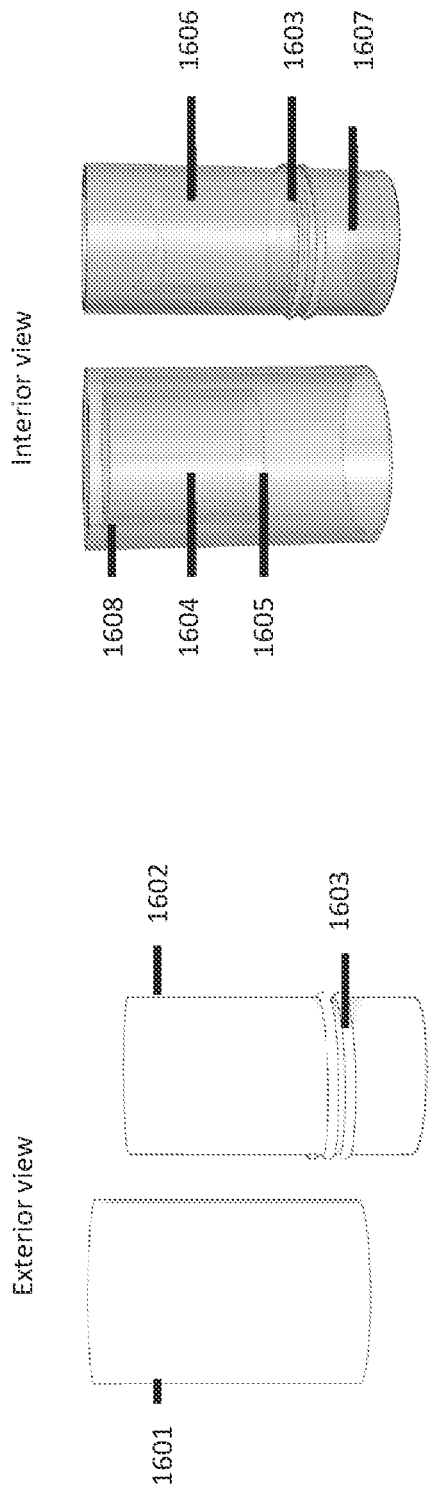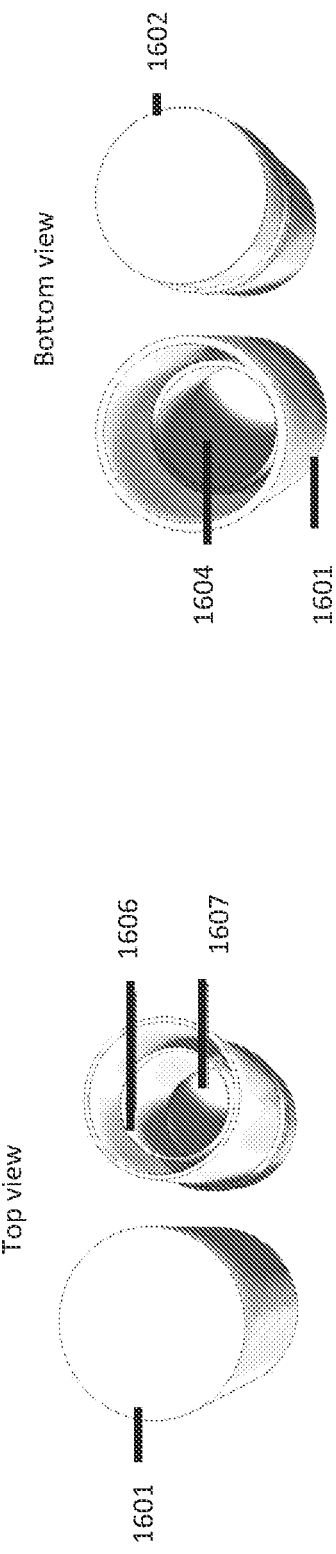

SAMPLE COLLECTION AND PRESERVATION DEVICES, SYSTEMS AND METHODS

CROSS-REFERENCE

This application is a continuation of U.S. patent application Ser. No. 16/153,389, filed Oct. 5, 2018, which is a Continuation Application of International Application No. PCT/US2017/027482, filed Apr. 13, 2017, which claims priority to U.S. Provisional Patent Application No. 62/321,987, filed Apr. 13, 2016, and U.S. Provisional Patent Application No. 62/460,329, filed Feb. 17, 2017, each of which is entirely incorporated herein by reference.

BACKGROUND

Although accurate statistics on sexual assault are hard to come by, it is estimated that one out of every six American adult women has been the victim of an attempted or completed sexual assault in her lifetime. Considering the social stigma, shame, and fear associated with rape, it is not surprising that rape is the most under reported crime. Accordingly, semen detection tests, confirmatory tests and forensic DNA testing are indispensable tools for solving a case of rape and assault in order to bring perpetrators to justice.

Along these lines, five of the top ten reportable diseases in the United States are sexually transmitted diseases ("STDs"). The Centers for Disease Control and Prevention ("CDC") estimates of February 2013 show that there are about 20 million new sexually transmitted infections ("STIs") in the United States each year, costing the American healthcare system nearly $16 billion in direct medical costs alone. The CDC's data suggests that there are more than 110 million total (both new and existing) STIs among women and men across the nation. Young people (ages 15-24) are particularly affected, accounting for half (50%) of all new STIs. Some of these STIs have the potential to cause serious health problems, especially if not diagnosed and treated early.

STIs remain a major public health challenge in the United States, more so among women, who often disproportionately bear the long-term consequences of STIs. Women are more at risk for STIs due to the large surface area and the thin lining of the vagina. Women are more likely to be asymptomatic for common STIs and also have a greater biological susceptibility to infections. Women are also more likely to confuse an STI with a tame yeast infection or to have internal symptoms that may go unnoticed. STIs such as gonorrhea and chlamydia can lead to pelvic inflammatory disease ("PID") when left untreated. Chlamydia in particular can also cause asymptomatic infection of the fallopian tubes, and consequently, infertility. Furthermore, pregnant women have an increased risk of passing STIs to their babies, either during pregnancy or during vaginal birth.

Besides STIs, there are myriad health conditions that are important, not only to women's health, but also to long-term fertility management. Reproductive cancers such as cervical, ovarian, uterine, and endometrial are of particular concern as they are often asymptomatic and present in late stages of disease.

Many nutritional deficiencies such as folate, iron, and other vitamins essential for the healthy development of the fetus, and anemia caused by deficiencies in these minerals, can cause birth defects, allergy sensitizations, and preterm birth.

Many hormones that work in concert to provide the optimal environment for pregnancy and fertility can often become dysregulated and may prevent a woman from getting or staying pregnant. Dysregulation can also cause diseases such as endometriosis and polycystic ovarian syndrome that may prevent a woman from becoming pregnant.

Even during pregnancy there are many health factors that a woman can monitor to help reduce the risk for preterm birth and infections such as yeast infections and Strep B. Fetal Fibronectin, which if found in vaginal secretions during 19-32 weeks of pregnancy can be indicative of a preterm birth.

A cascade of changes occur during perimenopause as women transition into their non-reproductive years that can be measured and provide information to women on what is going on in their bodies at a chemical level that may help inform them of health and lifestyle choices as they age.

Current blood-based diagnostic methods have reduced patient compliance because they require either a trip to an external facility, where a trained professional can perform venipuncture in a sterile environment, or a finger prick to collect a small aliquot of blood. Analysis of a blood sample is usually done in a laboratory by a different trained professional. Venipuncture in a doctor's office involves a non-trivial time commitment, travel and labor costs, and often psychological and physical pain that may prevent individuals from undergoing regular monitoring of blood-based health markers. Even finger pricks done at home can be psychologically daunting and difficult to enforce on a regular basis. In addition, finger pricks produce only a small amount of blood and subsequently limit the types of diagnostics that can be run at home. The friction that blood acquisition, alone, introduces into the health-care system down regulates the vigor with which consumers proactively monitor their health.

Although other diagnostic techniques, such as the Papanicolaou ("Pap") smear, do not involve a blood sample, they still involve a trip to the doctor's office. Current vaginal swab technologies involve a specific swab that is inserted into the vaginal cavity. The protocol of collecting specimens from the vaginal cavity using a traditional vaginal swab is very precise, and an inaccurate procedure can lead to loss of sample and unreliable identification of desired biomarkers. Because of this, a trained medical professional typically administers vaginal swab collections. Moreover, the United States Preventive Task Force ("USPTF") currently recommends Pap smears only every three years. Even an annual checkup by an obstetrics and gynecology professional ("OB-GYN") may not guarantee a gonorrhea or chlamydia screening, and it may not be ideal to detect a pathogen that can lead to inflammation of the genital tract within weeks. This screening frequency impairs the identification and diagnosis of asymptomatic infections in particular.

SUMMARY

The present disclosure relates generally to a medical system for detecting and monitoring health conditions. In some aspects, the present disclosure relates to medical devices, methods, systems, and kits for collecting and analyzing biological samples from cervicovaginal samples, such as cervicovaginal fluid. In some aspects, the present disclosure relates to medical devices, methods, systems, and kits for monitoring a subject's health status. In some aspects, the present disclosure relates to medical devices, methods, systems, and kits for collecting and identifying a nucleic acid modification associated with a disease, infection, immune disorder, nutritional deficiency, pregnancy and/or reproduction disorder.

Methods for screening for human papillomaviruses ("HPV"), and for screening human genital papillomaviruses that are associated with neoplasia such as cervical cancer, distinguish between different HPV types in a biological sample. However, such methods do not provide a device and method for self-analysis of one's blood samples.

Blood tests are often used in health care to determine physiological and biochemical states, such as disease, mineral content, pharmaceutical drug effectiveness, and organ function. However, current blood tests involve extracting blood from a subject with a needle, which often causes pain, and involves the performance of a trained professional. Menstrual flow contains more than just blood, cervicovaginal fluids, extracellular fluids, and plasma; it is also rich with cells shed by the ovaries and uterus. These samples can be paired with genomics tools to open up a window on a subject's health and give early warning of cancer and reproductive diseases as well as give health prophylactic advice.

Often, people are deterred from monitoring their health due to the inconvenience of visits to a doctor's office or other reasons such as privacy issues. Though tests for sexually transmitted infections are now available for free in clinics, privacy remains an issue. Women, for example, may benefit by monitoring themselves for common infections like chlamydia in private.

"Point of care" devices that are capable of detecting biological macromolecular activity or drug concentration levels are in high demand because they eliminate the need for patient lab visits, thus providing savings in both time and expense. Modern diagnostic technologies such as next generation sequencing and microarray provide the ability to detect STI, viral infection, bacterial infection, biological macromolecular dysfunction, and malformation or mutation resulting in disease.

A portable device for the collection, storage, transport, and separation of biological materials can be used to detect the presence of pathogens in a laboratory. However, such techniques involve the use of acquired skills as well as expensive and specialized equipment. Other methods include comparing the detection of STIs with results of tampon-collected specimens analyzed by polymerase chain reaction ("PCR"). However, such methods involve post-collection analysis work in a laboratory setting using specialized equipment.

Disclosed herein are devices, methods, systems, and kits for collecting biological materials from a subject. In various aspects, the devices, methods, systems, and kits provide extraction, analysis, storage and transportation of clinical samples such as blood, cervicovaginal fluids, vaginal mucosa, female genital tract microbes, yeast, fungi, bacteria, and semen. The biological sample may be collected without involvement of a surgery, biopsy, or other invasive procedures. The biological sample may be collected without involvement of a trained medical or health care personnel. The biological sample may be collected non-invasively without causing pain, bleeding, or other side effects. The devices and methods allow for collection and analysis of biological materials for STIs in a single device, without the need for further expensive laboratory equipment and professionals. In some aspects, the devices, methods, systems and kits provide acceptable, accurate, and available point-of-care ("POC") tests for diagnosing sexually transmitted diseases (STDs). Stigma, privacy, and confidentiality issues make STDs/STIs optimal areas for POC tests at healthcare facilities and for over-the-counter assays performed at home. In some aspects, the devices, methods, systems and kits provide storage and transportation of biological materials over a long period of time and/or distance for downstream clinical, molecular, genetics and pathological analysis. For example, biological samples collected using devices, methods, systems and kits disclosed herein can be used for clinical diagnostic or prophylactic analysis. Non-limiting applications include screening for Gonorrhea, Chlamydia, Trichomoniasis, Syphilis, Bacterial Vaginosis, pelvic inflammatory disease (PID), endometriosis, polycystic ovarian syndrome and ovarian reserve, human papillomavirus (HPV) infection, yeast infection, hepatitis virus infection, fetal trophoblasts, human immunodeficiency virus (HIV), CD4 monitoring, preterm birth and recurrent pregnancy loss, breast cancer, ovarian cancer, cancers, cervical cancer, uterine cancer, endometrial cancer, pre-pregnancy nutrition, metabolic hormones, fertility and menopause hormones, environmental toxins, alcohol abuse, drug abuse, nutrition deficiency, and semen exposure. As another example, biological samples collected using devices, methods, systems and kits disclosed herein can be used for identifying mutations, biomarkers, and chemical markers associated with a disease. The disease can be auto-immune conditions, endometriosis, uterine fibroids, polycystic ovarian syndrome, adenomyosis, and reproductive disorders. In some embodiments, the identification comprises sequencing the biomarker or nucleic acid of interest using established sequencing platform, e.g., an Illumina, Inc. ("Illumina") sequencing platform.

An aspect of the present disclosure provides a system for analysis of a vaginal biological sample, the system comprising: a sample collector insertable in a vaginal canal for collecting a vaginal biological sample; an extractor comprising: a sample receptacle configured to receive the sample collector via an opening, an extraction mechanism configured to provide pressure to the sample collector, and a reservoir, the reservoir being configured to receive the vaginal biological sample from the sample collector in response to the extraction mechanism being applied within the sample receptacle; and a cartridge comprising a chamber with a docking mechanism configured to fluidly communicate with the reservoir of the extractor, wherein the cartridge is under vacuum.

In some embodiments, the system comprises a filter configured to separate particles from components of fluid comprising the vaginal biological sample that is specific to the size of filter pores, and wherein the filter is engaged upon activation of the extraction mechanism. In some embodiments, the extraction mechanism comprises a mechanical, a pneumatic, or a hydraulic mechanism. In some embodiments, the extraction mechanism comprises a spring, threaded screw, lever, air-tight plunger, roller, or manual push syringe configured to force a compression element in the sample receptacle inwards into the sample receptacle in response to activation of the compression mechanism.

In some embodiments, the sample collector comprises an absorbent-diffuse material configured to collect, retain, or release the vaginal biological sample. In some embodiments, the absorbent-diffuse material comprises one or more of a plant fiber material, a disposable material, a flushable material, a biodegradable material, an organic material, a dissolvable material, a synthetic material, or polymatrix beads. In some embodiments, the sample collector comprises a cup, a rod, a cylinder, a pad, or a threaded matrix. In some embodiments, the docking mechanism is configured to bring the cartridge to the extractor via a docking unit. In some embodiments, the docking unit comprises a one-way pressure valve, a resealable slit, or cannula.

In some embodiments, the vaginal biological sample comprises one or more of cervicovaginal fluid, blood, vaginal mucosa, semen, interstitial fluid, cervical secretions, fetal tissues, reproductive cells, cervical cells, endometrial cells, fallopian cells, ovarian cells, natural flora in a female reproductive tract, invasive pathogens, and trophoblast cells. In some embodiments, the vaginal biological sample comprises blood. In some embodiments, the vaginal biological sample comprises an endometrial cell. In some embodiments, the vaginal biological sample comprises an ovarian cell. In some embodiments, the vaginal biological sample comprises cervicovaginal fluid.

In some embodiments, the extractor comprises a solution comprising a reagent for dissolving the sample collector. In some embodiments, the receptacle or cartridge contains a reagent for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample. In some embodiments, the system further comprises a container for storing or transporting the cartridge containing the vaginal biological sample.

In some embodiments, the system further comprises a cartridge reader for (1) detecting an analyte in the vaginal biological sample, and (2) capturing and interpreting a result from the detecting. In some embodiments, the analyte is for testing a presence or absence of a health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the system further comprises detecting a presence or absence of a biomarker in the vaginal biological sample. In some embodiments, a change of expression level of the biomarker indicates a pathological condition associated with endometriosis. In some embodiments, a change of expression level of the biomarker indicates a pathological condition associated with endometrial cancer. In some embodiments, a change of expression level of the biomarker indicates a pathological condition associated with an immune disorder in a female genital tract. In some embodiments, a change of expression level of the biomarker indicates a pathological condition associated with cervical cancer, ovarian cancer, or a sexually transmitted infection. In some embodiments, a change of nucleotide sequence of the biomarker indicates a pathological condition associated with endometriosis. In some embodiments, a change of nucleotide sequence of the biomarker indicates a pathological condition associated with endometrial cancer. In some embodiments, a change of nucleotide sequence of the biomarker indicates a pathological condition associated with an immune disorder in a female genital tract. In some embodiments, a change of nucleotide sequence of the biomarker indicates a pathological condition associated with cervical cancer, ovarian cancer, or a sexually transmitted infection. In some embodiments, the biomarker comprises a bacterial nucleotide sequence, a viral nucleotide sequence, a fungal nucleotide sequence, or a human nucleotide sequence. In some embodiments, the system further comprises sequencing nucleic acids in the vaginal biological sample.

In some embodiments, the cartridge comprises a clinical sample collection tube.

Another aspect of the disclosure provides a method for monitoring a health condition of a subject, the method comprising: using a sample collector to non-invasively collect a vaginal biological sample from a vaginal canal of the subject, wherein the sample collector is configured to collect and retain the vaginal biological sample from the vaginal canal; bringing the sample collector in proximity to an extractor comprising (i) a sample receptacle configured to receive the sample collector via an opening, and (ii) a reservoir, wherein the reservoir is configured to retain a solution comprising the vaginal biological sample from the sample collector when the sample collector is in the sample receptacle; depositing the sample collector through the opening into the extractor, thereby contacting the sample collector with the solution in the extractor; applying an extraction mechanism to the sample collector, thereby releasing the vaginal biological sample into the extractor, and docking a cartridge comprising a chamber with the extractor, wherein the chamber is under vacuum prior to docking, thereby bringing the chamber in fluid communication with the reservoir, and wherein upon the chamber coming in fluid communication with the reservoir, the solution comprising the vaginal biological sample is subjected to flow from the reservoir to the chamber.

In some embodiments, the sample collector comprises an absorbent-diffuse material configured to collect, retain, or release the vaginal biological sample. In some embodiments, the absorbent-diffuse material comprises one or more of a plant fiber material, a disposable material, a flushable material, a biodegradable material, an organic material, a dissolvable material, a synthetic material, and polymatrix beads. In some embodiments, the method further comprises inserting the sample collector in the vaginal canal of the subject. In some embodiments, the sample collector comprises a cup, a rod, a cylinder, a pad, or a threaded matrix.

In some embodiments, the vaginal biological sample comprises one or more of cervicovaginal fluid, blood, vaginal mucosa, semen, interstitial fluid, cervical secretions, fetal tissues, reproductive cells, cervical cells, endometrial cells, fallopian cells, ovarian cells, and trophoblast cells. In some embodiments, the vaginal biological sample comprises blood. In some embodiments, the vaginal biological sample comprises an endometrial cell. In some embodiments, the vaginal biological sample comprises an ovarian cell. In some embodiments, the vaginal biological sample comprises cervicovaginal fluid.

In some embodiments, the extractor contains a reagent for dissolving the sample collector. In some embodiments, the solution comprises a reagent for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample. In some embodiments, the method further comprises storing or transporting the cartridge containing the vaginal biological sample.

In some embodiments, the method further comprises using a cartridge reader for (1) detecting an analyte in the vaginal biological sample, and (2) capturing and interpreting a result from the detecting. In some embodiments, the method further comprises using the analyte for testing a presence or absence of the health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the method further comprises detecting a presence or absence of a biomarker in the vaginal biological sample. In some embodiments, a change of expression level of the biomarker indicates a pathological condition associated with endometriosis. In some embodiments, a change of expression level of the biomarker indicates a pathological condition associated with endometrial cancer. In some embodiments, a change of expression level of the biomarker indicates a pathological condition associate with an immune disorder in a female genital tract. In some embodiments, a change of expression level of the biomarker indicates a pathological condition associated with cervical cancer, ovarian cancer, or a sexually transmitted infection. In some embodiments, a change of nucleotide sequence of the biomarker indicates a pathological condition associated with endometriosis. In some embodiments, a change of nucleotide sequence of the biomarker indicates a pathological condition associated with endometrial cancer. In some embodiments, a change of nucleotide sequence of the biomarker indicates a pathological condition associate with an immune disorder in a female genital tract. In some embodiments, a change of nucleotide sequence of the biomarker indicates a pathological condition associated with cervical cancer, ovarian cancer, or a sexually transmitted infection. In some embodiments, the biomarker comprises a bacterial nucleotide sequence, a viral nucleotide sequence, a fungal nucleotide sequence, or a human nucleotide sequence.

In some embodiments, the method further comprises monitoring the health condition regularly. In some embodiments, the method further comprises monitoring the health condition about every 10 to 90 days. In some embodiments, the monitoring of the health condition is performed by the subject.

In some embodiments, the method further comprises transporting that the sample collector in the cartridge to a Clinical Laboratory Improvement Amendment (CLIA) certified laboratory for analysis. In some embodiments, the method further comprises sequencing nucleic acids in the vaginal biological sample.

In some embodiments, the cartridge comprises a clinical sample collection tube.

Another aspect of the disclosure provides a system for processing a vaginal biological sample of a subject, the system comprising: a sample collector that non-invasively collects the vaginal biological sample from a vaginal canal of a subject, wherein the sample collector collects and retains the vaginal biological sample from the vaginal canal; an extractor comprising (i) a sample receptacle configured to retain a reagent and receive the sample collector via an opening, wherein upon coming in contact with the reagent, the sample collector dissolves and releases the vaginal biological sample into the sample receptacle, and (ii) a reservoir, wherein the reservoir is configured to retain a solution comprising the vaginal biological sample from the sample collector when the sample collector is in the sample receptacle; and a cartridge comprising a chamber configured to come in fluid communication with the reservoir upon docking with the extractor, wherein upon the chamber coming in fluid communication with the reservoir, the solution comprising the vaginal biological sample is subjected to flow from the reservoir to the cartridge.

In some embodiments, the sample collector comprises an absorbent-diffuse material that collects, retains, or releases the vaginal biological sample. In some embodiments, the absorbent-diffuse material comprises one or more of a plant fiber material, a disposable material, a flushable material, a biodegradable material, an organic material, a dissolvable material, a synthetic material, or polymatrix beads. In some embodiments, the sample collector is insertable in the vaginal canal. In some embodiments, the sample collector comprises a cup, a rod, a cylinder, a pad, or a threaded matrix.

In some embodiments, the system further comprises a docking unit that brings the cartridge in fluid communication with the reservoir. In some embodiments, the docking unit comprises a one-way pressure valve, a resealable slit, or cannula. In some embodiments, the system further comprises a filter which separates particles and components of fluid comprising the vaginal biological sample that is specific to the size of filter pores.

In some embodiments, the vaginal biological sample comprises one or more of cervicovaginal fluid, blood, vaginal mucosa, semen, interstitial fluid, cervical secretions, fetal tissues, reproductive cells, cervical cells, endometrial cells, fallopian cells, ovarian cells, and trophoblast cells. In some embodiments, the vaginal biological sample comprises blood. In some embodiments, the vaginal biological sample comprises an endometrial cell. In some embodiments, the vaginal biological sample comprises an ovarian cell. In some embodiments, the vaginal biological sample comprises cervicovaginal fluid.

In some embodiments, the solution comprises a reagent for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample.

In some embodiments, the system further comprises a container for storing or transporting the cartridge containing the vaginal biological sample. In some embodiments, the system further comprises a cartridge reader for (1) detecting an analyte in the vaginal biological sample, and (2) capturing and interpreting a result from the detecting. In some embodiments, the analyte is for testing a presence or absence of a health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the system further comprises detecting a presence or absence of a biomarker in the vaginal biological sample. In some embodiments, a change of expression level of the biomarker indicates a pathological condition associated with endometriosis. In some embodiments, a change of expression level of the biomarker indicates a pathological condition associated with endometrial cancer. In some embodiments, a change of expression level of the biomarker indicates a pathological condition associated with an immune disorder in a female genital tract. In some embodiments, a change of expression level of the biomarker indicates a pathological condition associated with cervical cancer, ovarian cancer, or a sexually transmitted infection. In some embodiments, a change of nucleotide sequence of the biomarker indicates a pathological condition associated with endometriosis. In some embodiments, a change of nucleotide sequence of the biomarker indicates a pathological condition associated with endometrial cancer. In some embodiments, a change of nucleotide sequence of the biomarker indicates a pathological condition associated with an immune disorder in a female genital tract. In some embodiments, a change of nucleotide sequence of the biomarker indicates a pathological condition associated with cervical cancer, ovarian cancer, or a sexually transmitted infection. In some embodiments, the biomarker comprises a bacterial nucleotide sequence, a viral nucleotide sequence, a fungal nucleotide sequence, or a human nucleotide sequence. In some embodiments, the system further comprises sequencing nucleic acids in the vaginal biological sample. In some embodiments, the cartridge comprises a clinical sample collection tube.

Another aspect of the disclosure provides a method for monitoring a health condition of a subject, the method comprising: using a sample collector to non-invasively collect a vaginal biological sample from a vaginal canal of the subject, wherein the sample collector collects and retains the vaginal biological sample from the vaginal canal; bringing the sample collector in proximity to an extractor comprising (i) a sample receptacle configured to receive the sample collector via an opening, wherein the sample receptacle retains a reagent, and wherein upon coming in contact with the reagent, the sample collector dissolves and releases the vaginal biological sample into the sample receptacle, and (ii) a reservoir, wherein the reservoir retains a solution comprising the vaginal biological sample from the sample collector when the sample collector is in the sample receptacle; depositing the sample collector through the opening into the reservoir, thereby contacting the sample collector with the reagent in the reservoir; and docking a cartridge comprising a chamber with the extractor, thereby bringing the chamber in fluid communication with the reservoir, wherein upon the chamber coming in fluid communication with the reservoir, the solution comprising the vaginal biological sample is subjected to flow from the reservoir to the cartridge.

In some embodiments, the sample collector comprises an absorbent-diffuse material that collects, retains, or releases the vaginal biological sample. In some embodiments, the absorbent-diffuse material comprises one or more of a plant fiber material, a disposable material, a flushable material, a biodegradable material, an organic material, a dissolvable material, a synthetic material, and polymatrix beads. In some embodiments, the method further comprises inserting the sample collector in the vaginal canal of the subject. In some embodiments, the sample collector comprises a cup, a rod, a cylinder, a pad, or a threaded matrix.

In some embodiments, the vaginal biological sample comprises one or more of cervicovaginal fluid, blood, vaginal mucosa, semen, interstitial fluid, cervical secretions, fetal tissues, reproductive cells, cervical cells, endometrial cells, fallopian cells, ovarian cells, and trophoblast cells. In some embodiments, the vaginal biological sample comprises blood. In some embodiments, the vaginal biological sample comprises an endometrial cell. In some embodiments, the vaginal biological sample comprises an ovarian cell. In some embodiments, the vaginal biological sample comprises cervicovaginal fluid. In some embodiments, the solution comprises a reagent for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample. In some embodiments, the method further comprises storing or transporting the cartridge containing the vaginal biological sample.

In some embodiments, the method further comprises using a cartridge reader for (1) detecting an analyte in the vaginal biological sample, and (2) capturing and interpreting a result from the detecting. In some embodiments, the method further comprises using the analyte for testing a presence or absence of the health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the method further comprises detecting a presence or absence of a biomarker in the vaginal biological sample. In some embodiments, a change of expression level of the biomarker indicates a pathological condition associated with endometriosis. In some embodiments, a change of expression level of the biomarker indicates a pathological condition associated with endometrial cancer. In some embodiments, a change of expression level of the biomarker indicates a pathological condition associated with an immune disorder in a female genital tract. In some embodiments, a change of expression level of the biomarker indicates a pathological condition associated with cervical cancer, ovarian cancer, or a sexually transmitted infection. In some embodiments, a change of nucleotide sequence of the biomarker indicates a pathological condition associated with endometriosis. In some embodiments, a change of nucleotide sequence of the biomarker indicates a pathological condition associated with endometrial cancer. In some embodiments, a change of nucleotide sequence of the biomarker indicates a pathological condition associated with an immune disorder in a female genital tract. In some embodiments, a change of nucleotide sequence of the biomarker indicates a pathological condition associated with cervical cancer, ovarian cancer, or a sexually transmitted infection. In some embodiments, the biomarker comprises a bacterial nucleotide sequence, a viral nucleotide sequence, a fungal nucleotide sequence, or a human nucleotide sequence.

In some embodiments, the method further comprises monitoring the health condition regularly. In some embodiments, the method further comprises monitoring the health condition about every 10 to about 90 days. In some embodiments, monitoring of the health condition is performed by the subject.

In some embodiments, the method further comprises transporting that the sample collector in the cartridge containing the vaginal biological sample to a Clinical Laboratory Improvement Amendment (CLIA) certified laboratory for analysis. In some embodiments, the method further comprises sequencing nucleic acids in the vaginal biological sample.

In some embodiments, the cartridge comprises a clinical sample collection tube.

Another aspect of the disclosure provides a system for analysis of a vaginal biological sample, the system comprising: a sample collector for collecting a vaginal biological sample, an extractor comprising: a sample receptacle configured to receive the sample collector via an opening, wherein the receptacle comprises an outer shell enclosing the sample receptacle, and at least one chamber that contains a reagent compartment with a breakable (or pierceable) seal; and an extraction mechanism with a compression element, the compression element being movable towards the at least one chamber to apply a compression force in response to closure of the sample receptacle, wherein the compression force releases the vaginal biological sample into the at least one chamber, and wherein the closure of the sample receptacle removes air in the at least one chamber and breaks the breakable seal to release the reagent into the at least one chamber, thereby bringing the reagent into contact with the vaginal biological sample and forming a mixture of the reagent with the released vaginal biological sample.

In some embodiments, the system further comprises a hinge for opening and closing of the outer shell. In some embodiments, the system further comprises a fastening unit for closing and sealing the outer shell. In some embodiments, the at least one chamber is elastic. In some embodiments, the at least one chamber comprises a membrane or a monolithic bag. In some embodiments, the reagent compartment comprises a reagent for preserving, storing, or analyzing the vaginal biological sample.

In some embodiments, the system further comprises a cartridge for collecting the mixture of the reagent and the released vaginal biological sample, wherein the cartridge comprises a chamber with a docking mechanism configured to fluidly communicate with the sample receptacle. In some embodiments, the cartridge is under vacuum. In some embodiments, the system further comprises a sample reservoir for collecting the mixture of the reagent and the released vaginal biological sample. In some embodiments, the sample reservoir is connected with the at least one chamber via a one-way pressure valve, a resealable slit, or cannula. In some embodiments, the sample reservoir comprises a docking mechanism configured to fluidly communicate with a cartridge. In some embodiments, the cartridge is a vacutainer. In some embodiments, the extraction mechanism comprises a clamshell pressure mechanism.

In some embodiments, the sample collector comprises an absorbent-diffuse material that collects, retains, or releases the vaginal biological sample. In some embodiments, the absorbent-diffuse material comprises one or more of a plant fiber material, a disposable material, a flushable material, a biodegradable material, an organic material, a dissolvable material, a synthetic material, and polymatrix beads. In some embodiments, the sample collector comprises a cup, a rod, a cylinder, a pad, or a threaded matrix. In some embodiments, the vaginal biological sample comprises one or more of cervicovaginal fluid, blood, vaginal mucosa, semen, interstitial fluid, cervical secretions, fetal tissues, reproductive cells, cervical cells, endometrial cells, fallopian cells, ovarian cells, natural flora in a female reproductive tract, invasive pathogens, and trophoblast cells. In some embodiments, the vaginal biological sample comprises blood. In some embodiments, the vaginal biological sample comprises an endometrial cell. In some embodiments, the vaginal biological sample comprises an ovarian cell. In some embodiments, the vaginal biological sample comprises cervicovaginal fluid.

In some embodiments, the at least one chamber or cartridge contains a reagent for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample. In some embodiments, the system further comprises a container for storing or transporting the cartridge containing the vaginal biological sample.

In some embodiments, the system further comprises a cartridge reader for (1) detecting an analyte in the vaginal biological sample, and (2) capturing and interpreting a result from the detecting. In some embodiments, the analyte is for testing a presence or absence of a health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the system further comprises detecting a presence or absence of a biomarker in the vaginal biological sample. In some embodiments, a change of expression level of the biomarker indicates a pathological condition associated with endometriosis. In some embodiments, a change of expression level of the biomarker indicates a pathological condition associated with endometrial cancer. In some embodiments, a change of expression level of the biomarker indicates a pathological condition associated with an immune disorder in a female genital tract. In some embodiments, a change of expression level of the biomarker indicates a pathological condition associated with cervical cancer, ovarian cancer, or a sexually transmitted infection. In some embodiments, a change of nucleotide sequence of the biomarker indicates a pathological condition associated with endometriosis. In some embodiments, a change of nucleotide sequence of the biomarker indicates a pathological condition associated with endometrial cancer. In some embodiments, a change of nucleotide sequence of the biomarker indicates a pathological condition associated with an immune disorder in a female genital tract. In some embodiments, a change of nucleotide sequence of the biomarker indicates a pathological condition associated with cervical cancer, ovarian cancer, or a sexually transmitted infection. In some embodiments, the biomarker comprises a bacterial nucleotide sequence, a viral nucleotide sequence, a fungal nucleotide sequence, or a human nucleotide sequence. In some embodiments, the system further comprises sequencing nucleic acids in the biological sample.

In some embodiments, the cartridge comprises a clinical sample collection tube.

Another aspect of the disclosure provides a method for monitoring a health condition of a subject, the method comprising: using a sample collector to non-invasively collect a vaginal biological sample from a vaginal canal of the subject, wherein the sample collector collects and retains the vaginal biological sample from the vaginal canal; bringing the sample collector in proximity to an extractor comprising (i) a sample receptacle configured to receive the sample collector via an opening, wherein the receptacle comprises an outer shell enclosing the sample receptacle, and at least one chamber that contains a reagent compartment with a breakable seal (e.g., hermetic seal), and (ii) an extraction mechanism with a compression element, the compression element being movable towards the at least one chamber to apply a compression force in response to closure of the sample receptacle; depositing the sample collector through the opening into the sample receptacle; closing the sample receptacle to apply a compression force to move the compression element towards the at least one chamber, thereby applying a compression force to remove air in the at least one chamber, and to seal the sample receptacle, and to release the vaginal biological sample from the sample collector, wherein the closing breaks the breakable seal and releases the reagent from the reagent compartment, thereby contacting the released vaginal biological sample with the reagent in the at least one chamber and forming a mixture of the reagent and the released vaginal biological sample; and collecting the mixture of the reagent and the released vaginal biological sample in a cartridge. In some embodiments, the cartridge comprises a chamber with a docking mechanism configured to fluidly communicate with the sample receptacle. In some embodiments, the cartridge is under vacuum. In some embodiments, the method further comprises docking a cartridge comprising a chamber with the extractor, thereby bringing the chamber in fluid communication with the extractor, wherein upon the chamber coming in fluid communication with the extractor, the mixture comprising the reagent and the biological sample is subjected to flow from the reservoir to the cartridge In some embodiments, the sample receptacle comprises a hinge for opening and closing of the outer shell. In some embodiments, the sample receptacle comprises a fastening unit, such as a locking clasp, for closing and sealing the outer shell. In some embodiments, the at least one chamber is elastic. In some embodiments, the at least one chamber comprises a membrane or a monolithic bag. In some embodiments, the system further comprises preserving, storing, or analyzing the vaginal biological sample using the reagent released from the reagent compartment. In some embodiments, the sample receptacle further comprising a sample reservoir for collecting the mixture of the reagent and the released vaginal biological sample. In some embodiments, the sample reservoir is connected with the at least one chamber via a one-way pressure valve, a resealable slit, or cannula. In some embodiments, the sample reservoir comprises a docking mechanism configured to fluidly communicate with a cartridge. In some embodiments, the cartridge is a vacutainer. In some embodiments, the extraction mechanism comprises a clamshell pressure mechanism.

In some embodiments, the sample collector comprises an absorbent-diffuse material that collects, retains, or releases the vaginal biological sample. In some embodiments, the absorbent-diffuse material comprises one or more of a plant fiber material, a disposable material, a flushable material, a biodegradable material, an organic material, a dissolvable material, a synthetic material, and polymatrix beads. In some embodiments, the sample collector comprises a cup, a rod, a cylinder, a pad, or a threaded matrix.

In some embodiments, the method further comprises inserting the sample collector in the vaginal canal of the subject. In some embodiments, the vaginal biological sample comprise one or more of cervicovaginal fluid, blood, vaginal mucosa, semen, interstitial fluid, cervical secretions, fetal tissues, reproductive cells, cervical cells, endometrial cells, fallopian cells, ovarian cells, natural flora in a female reproductive tract, invasive pathogens, and trophoblast cells. In some embodiments, the vaginal biological sample comprises blood. In some embodiments, the vaginal biological sample comprises an endometrial cell. In some embodiments, the vaginal biological sample comprises an ovarian cell. In some embodiments, the vaginal biological sample comprises cervicovaginal fluid.

In some embodiments, the at least one chamber or cartridge contains a reagent necessary for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample. In some embodiments, the method further comprises storing or transporting the cartridge containing the mixture of the reagent and the vaginal biological sample.

In some embodiments, the method further comprises using a cartridge reader for (1) detecting an analyte in the vaginal biological sample, and (2) capturing and interpreting a result from the detecting. In some embodiments, the method further comprises using the analyte is for testing a presence or absence of a health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the method further comprises detecting a presence or absence of a biomarker in the vaginal biological sample. In some embodiments, a change of expression level of the biomarker indicates a pathological condition associated with endometriosis. In some embodiments, a change of expression level of the biomarker indicates a pathological condition associated with endometrial cancer. In some embodiments, a change of expression level of the biomarker indicates a pathological condition associated with an immune disorder in a female genital tract. In some embodiments, a change of expression level of the biomarker indicates a pathological condition associated with cervical cancer, ovarian cancer, or a sexually transmitted infection. In some embodiments, a change of nucleotide sequence of the biomarker indicates a pathological condition associated with endometriosis. In some embodiments, a change of nucleotide sequence of the biomarker indicates a pathological condition associated with endometrial cancer. In some embodiments, a change of nucleotide sequence of the biomarker indicates a pathological condition associated with an immune disorder in a female genital tract. In some embodiments, a change of nucleotide sequence of the biomarker indicates a pathological condition associated with cervical cancer, ovarian cancer, or a sexually transmitted infection. In some embodiments, the biomarker comprises a bacterial nucleotide sequence, a viral nucleotide sequence, a fungal nucleotide sequence, or a human nucleotide sequence. In some embodiments, the method further comprises sequencing nucleic acids in the biological sample.

In some embodiments, the cartridge comprises a clinical sample collection tube.

In some embodiments, method further comprises monitoring the health condition regularly. In some embodiments, method further comprises monitoring the health condition about every 10 to about 90 days.

According to one aspect of the present disclosure, a medical kit for analysis of vaginal biological samples includes a sample collector, an extractor, and an assay cartridge. The sample collector is insertable in a vaginal canal for collecting biological samples and is compressible.

The sample collector also includes a cup-shaped head configured to cradle a uterine cervix. The extractor includes a sample receptacle configured to receive the sample collector via an open end, and a compression mechanism with a compression element and a release element. The compression element is movable inwards into the open end of the sample receptacle to apply a compression force in response to activation of the release element. The extractor further includes a reservoir in fluid communication with the sample receptacle, the reservoir receiving the biological samples from the sample collector in response to the compression force being applied within the sample receptacle, through a filter that allows for purification of serum and other biological components from cellular debris. The assay cartridge has a docking mechanism configured to fluidly communicate with the reservoir of the extractor.

According to another aspect of the disclosure, a method for home-care monitoring of a health condition includes inserting a sample collector in a vaginal canal and collecting biological samples. The sample collector is removed from the vaginal canal and is placed inside a sample receptacle of an extractor. The sample collector is compressed within the sample receptacle by applying a force via a compression mechanism. In one embodiment, a diluent housed behind a punctureable membrane is released during the compression to wash the sample from the sample collector and release analytes of interest into the first chamber of the extractor. The biological samples are received from the sample collector into a reservoir of the extractor. An assay cartridge is docked in fluid communication with the reservoir, thereby allowing at least some of the biological samples to make contact with diluents or reagents of the assay cartridge. A health condition is determined based on a reaction between the biological samples and the diluents or reagents.

According to yet another aspect of the disclosure, a medical kit for analysis of biological samples includes a sample collector, an extractor, an assay cartridge, and a cartridge reader. The sample collector is insertable in a body cavity for collecting biological samples, is compressible, and includes an absorbent-diffuse material for absorbing and releasing fluids. The extractor acquires the biological samples from the sample collector, and includes a receptacle in which the sample collector is received. The extractor includes a compression mechanism for applying a force within the receptacle to release the biological samples from an inserted sample collector. The assay cartridge has an extractor interface and a reader interface, the extractor interface being configured to be coupled in fluid communication with the extractor. The biological samples are transferred from the extractor to the assay cartridge via the extractor interface. The cartridge reader has a cartridge interface configured for interfacing with the reader interface, the cartridge reader receiving assay data from the assay cartridge and communicating at least some of the assay data to a mobile device via a mobile interface.

According to yet another aspect of the disclosure, a sample-collection method and device utilizes proprietary and/or widely available commercial tampons without the need for a special swab that is not widely available to the general population. The sample-collection device also promotes correct insertion into the vaginal cavity and promotes more accurate and efficient collection of specimen due to its large surface area and precise contour. The sample-collection device further collects a larger volume of specimen than traditional vaginal swabs allowing for a more accurate analysis of the specimen and higher probability of capturing biomarkers or analytes of interest.

According to yet another aspect of the disclosure, a sample collection device for analysis of the cellular components of the vaginal canal, in which a removable filter cassette housed within the extractor filters out cellular components of cervicovaginal fluid including blood, cervical, endometrial, fallopian, ovarian, and trophoblast cells for analysis through microscopy or other cellular imagine technologies for assessment of the health of reproductive cells within the biological matrix collected through the collection device.

According to yet another aspect of the disclosure, a sample-collection device is suitable for regular and painless collection of cervicovaginal fluid and rich biological matrix without the need for skin puncture or a skilled technician. The sample-collection device can be included in a medical kit that provides a simple diagnostic assay that can be run in the privacy of one's home.

According to yet a further aspect of the disclosure, a device and method is directed to self-analysis of one's cervicovaginal fluid samples for pathogens, hormones, protein analytes (indicative of health status), mineral levels, genetic material (indicative of disease, disorders, or predispositions thereof), or the presence of semen.

According to yet a further aspect of the disclosure, a sample-collection device for regular, easy collection of specimen from the vaginal cavity. The sample collection kit may include preservation buffers to maintain sample quality for a mail-in service. The sample can be processed and analyzed in a centralized lab and results delivered to the customer at a later date.

In another aspect, disclosed herein is a system for analysis of a vaginal biological sample, the system comprising a sample collector for collecting a vaginal biological sample and an extractor. The extractor can comprise a first chamber comprising a sample receptacle configured to receive the sample collector via an opening; a second chamber comprising a reagent compartment capable of retaining a solution; at least a hard seal configured to separate the first chamber and the second chamber; and at least a frangible seal configured to separate the first chamber and the second chamber, wherein the frangible seal is breakable in response to a compression force, wherein the compression force releases the reagent contained in the second chamber into the first chamber containing the vaginal biological sample, thereby bringing the solution into contact with the vaginal biological sample and forming a mixture of the solution with the released vaginal biological sample.

In some embodiments, at least one chamber is elastic. In some embodiments, the reagent compartment further comprises a pouch configured to retain the solution.

In some embodiments, the solution is suitable for preserving, storing, or analyzing the vaginal biological sample.

The system can further comprise a cartridge for collecting the mixture of the solution and the released vaginal biological sample. The cartridge can be under vacuum. The cartridge can be connected with the second chamber via a one-way pressure valve, a resealable slit, or cannula. The cartridge can be a vacutainer. The cartridge can comprise a clinical sample collection tube. The cartridge can comprise a syringe used to collect the sample. The second chamber can further comprise a sample recovery port with a docking mechanism configured to fluidly communicate with a cartridge. The system can further comprise a container for storing or transporting the cartridge containing the vaginal biological sample.

The sample collector can comprise an absorbent-diffuse material that collects, retains, or releases the vaginal biological sample. The absorbent-diffuse material can comprise one or more of a plant fiber material, a disposable material, a flushable material, a biodegradable material, an organic material, a dissolvable material, a synthetic material, and polymatrix beads. The sample collector can comprise a cup, a rod, a cylinder, a pad, or a threaded matrix.

The vaginal biological sample can comprise one or more of cervicovaginal fluid, blood, vaginal mucosa, semen, interstitial fluid, cervical secretions, fetal tissues, reproductive cells, cervical cells, endometrial cells, fallopian cells, ovarian cells, natural flora in a female reproductive tract, invasive pathogens, and trophoblast cells.

In some embodiments, the vaginal biological sample comprises blood.

In some embodiments, the vaginal biological sample comprises an endometrial cell.

In some embodiments, the vaginal biological sample comprises an ovarian cell.

In some embodiments, the vaginal biological sample comprises cervicovaginal fluid.

In some embodiments, the second chamber can retain a solution comprising a reagent for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample.

The system can further comprise a cartridge reader for (1) detecting an analyte in the vaginal biological sample, and (2) capturing and interpreting a result from the detecting. The analyte can be for testing a presence or absence of a health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the analysis can comprise detecting a presence or absence of a biomarker in the vaginal biological sample. A change of expression level of the biomarker can indicate a pathological condition associated with endometriosis, a pathological condition associated with endometrial cancer, a pathological condition associated with an immune disorder in a female genital tract, or a pathological condition associated with cervical cancer, ovarian cancer, or a sexually transmitted infection. A change of nucleotide sequence of the biomarker can indicate a pathological condition associated with endometriosis, a pathological condition associated with endometrial cancer, a pathological condition associated with an immune disorder in a female genital tract, or a pathological condition associated with cervical cancer, ovarian cancer, or a sexually transmitted infection. The biomarker can comprise a bacterial nucleotide sequence, a viral nucleotide sequence, a fungal nucleotide sequence, or a human nucleotide sequence.

In some embodiments, the analysis can comprise sequencing nucleic acids in the biological sample.

In another aspect, disclosed herein is a method for monitoring a health condition of a subject, the method comprising: using a sample collector to non-invasively collect a vaginal biological sample from a vaginal canal of the subject, wherein the sample collector collects and retains the vaginal biological sample from the vaginal canal; bringing the sample collector in proximity to an extractor comprising (i) a first chamber comprising a sample receptacle configured to receive the sample collector via an opening; (ii) a second chamber comprising a reagent compartment capable of retaining a solution and being in fluid communication with the sample receptacle; (iii) a least a hard seal configured to separate the first chamber and the second chamber; and (iv) at least a frangible seal configured to separate the first chamber and the second chamber, wherein the frangible seal is breakable in response to a compression force, depositing the sample collector through the opening into the sample receptacle; closing the sample receptacle; applying a compression force, wherein the vaginal biological sample is released from the sample collector, and wherein the compression force breaks the frangible seal and releases the solution from the second chamber, thereby bringing the sample receptacle in fluid communication with the second chamber and contacting the released vaginal biological sample with the solution to form a mixture of the solution and the released vaginal biological sample; and collecting the mixture of the solution and the released vaginal biological sample in a cartridge.

In some embodiments, the second chamber can further comprise a sample recovery port with a docking mechanism configured to fluidly communicate with the cartridge. The second chamber can further comprise a pouch for retaining the solution. The second chamber can be connected with the cartridge via a one-way pressure valve, a resealable slit, or cannula.

In some embodiments, the cartridge can be under vacuum. The cartridge can be a vacutainer. The cartridge can be a clinical sample collection tube. The cartridge can comprise a syringe used to collect the sample.

In some embodiments, the method can further comprise docking a cartridge comprising a chamber with the extractor, thereby bringing the chamber in fluid communication with the extractor, wherein upon the chamber coming in fluid communication with the extractor, the mixture comprising the solution and the biological sample is subjected to flow from the second chamber to the cartridge.

In some embodiments, at least one of the two chambers can be elastic.

In some embodiments, the method can further comprise preserving, storing, or analyzing the vaginal biological sample using the solution released from the reagent compartment.

In some embodiments, the sample collector can comprise an absorbent-diffuse material that collects, retains, or releases the vaginal biological sample. The absorbent-diffuse material can comprise one or more of a plant fiber material, a disposable material, a flushable material, a biodegradable material, an organic material, a dissolvable material, a synthetic material, and polymatrix beads. The sample collector can comprise a cup, a rod, a cylinder, a pad, or a threaded matrix.

The method can further comprise inserting the sample collector in the vaginal canal of the subject.

In some embodiments, the vaginal biological sample can comprise one or more of cervicovaginal fluid, blood, vaginal mucosa, semen, interstitial fluid, cervical secretions, fetal tissues, reproductive cells, cervical cells, endometrial cells, fallopian cells, ovarian cells, natural flora in a female reproductive tract, invasive pathogens, and trophoblast cells.

In some embodiments, the vaginal biological sample comprises blood.

In some embodiments, the vaginal biological sample comprises an endometrial cell.

In some embodiments, the vaginal biological sample comprises an ovarian cell.

In some embodiments, the vaginal biological sample comprises cervicovaginal fluid.

In some embodiments, the second chamber can retain a solution comprising a reagent for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample.

In some embodiments, the method can further comprise storing or transporting the cartridge containing the mixture of the reagent and the vaginal biological sample.

In some embodiments, the method can further comprise using a cartridge reader for (1) detecting an analyte in the vaginal biological sample, and (2) capturing and interpreting a result from the detecting.

In some embodiments, the method can further comprise using the analyte for testing a presence or absence of a health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the method can further comprise detecting a presence or absence of a biomarker in the vaginal biological sample. A change of expression level of the biomarker can indicate a pathological condition associated with endometriosis, a pathological condition associated with endometrial cancer, a pathological condition associated with an immune disorder in a female genital tract, or a pathological condition associated with cervical cancer, ovarian cancer, or a sexually transmitted infection. A change of nucleotide sequence of the biomarker can indicate a pathological condition associated with endometriosis, a pathological condition associated with endometrial cancer, a pathological condition associated with an immune disorder in a female genital tract, or a pathological condition associated with cervical cancer, ovarian cancer, or a sexually transmitted infection. The biomarker can comprise a bacterial nucleotide sequence, a viral nucleotide sequence, a fungal nucleotide sequence, or a human nucleotide sequence.

In some embodiments, the analysis can comprise sequencing nucleic acids in the biological sample In some embodiments, the health condition can be monitored regularly. The health condition can be monitored about every 10 to about 90 days.

In another aspect, disclosed herein is a system for analysis of a vaginal biological sample. The system can comprise a sample collector for collecting a vaginal biological sample and an extractor. The extractor can comprise: a first chamber configured to receive the sample collector via an opening; and a second chamber adjacent to the first chamber, wherein the second chamber comprises a reagent compartment capable of retaining a solution, wherein at least one of the first chamber and the second chamber is breakable in response to a compression force, and wherein the compression force brings the first chamber in fluid communication with the second chamber, thereby bringing the solution into contact with the vaginal biological sample and to form a mixture of the solution with the vaginal biological sample.

In some embodiments, the extractor can further comprise a hard seal configured to separate the first chamber and the second chamber, wherein the hard seal does not break in response to the compression force.

In some embodiments, the extractor can further comprise a frangible seal configured to separate the first chamber and the second chamber, wherein the frangible seal is breakable in response to the compression force.

In some embodiments, the system comprises an outer shell configured to enclose the extractor, wherein, upon enclosure, the outer shell is configured to apply the compression force towards at least one of the first chamber and the second chamber. The outer shell can comprise a hinge configured to open or close the outer shell. The outer shell can comprise a fastening unit configured to close and seal the outer shell.

In some embodiments, the solution is suitable for preserving, storing, or analyzing the vaginal biological sample.

In some embodiments, the extractor comprises a docking unit. In some embodiments, the docking unit is at least one of a one-way pressure valve, a resealable slit, and a cannula.

In some embodiments, the system further comprises a cartridge for collecting the mixture of the solution and the vaginal biological sample. In some embodiments, the extractor comprises a docking unit, wherein the docking unit is configured to fluidly communicate with the cartridge. In some embodiments, the cartridge is under vacuum. In some embodiments, the cartridge is a vacutainer. In some embodiments, the cartridge comprises a clinical sample collection tube.

In some embodiments, the system can further comprise a cartridge reader for (1) detecting an analyte in the vaginal biological sample, and (2) capturing and interpreting a result from the detecting. In some embodiments, the analyte can be for testing a presence or absence of a health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the sample collector comprises an absorbent-diffuse material that collects, retains, or releases the vaginal biological sample. In some embodiments, the absorbent-diffuse material comprises one or more of a plant fiber material, a disposable material, a flushable material, a biodegradable material, an organic material, a dissolvable material, a synthetic material, and polymatrix beads.

In some embodiments, the sample collector comprises at least one of a cup, a rod, a cylinder, a pad, and a threaded matrix.

In some embodiments, the vaginal biological sample comprises one or more of cervicovaginal fluid, blood, vaginal mucosa, semen, interstitial fluid, cervical secretions, fetal tissues, reproductive cells, cervical cells, endometrial cells, fallopian cells, ovarian cells, natural flora in a female reproductive tract, invasive pathogens, and trophoblast cells.

In some embodiments, the vaginal biological sample comprises blood.

In some embodiments, the vaginal biological sample comprises an endometrial cell.

In some embodiments, the vaginal biological sample comprises an ovarian cell.

In some embodiments, the vaginal biological sample comprises cervicovaginal fluid.

In some embodiments, the solution comprises a reagent for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample.

In some embodiments, the analysis of the vaginal biological sample comprises detecting a presence or absence of a biomarker in the vaginal biological sample.

In some embodiments, a change of expression level of the biomarker is indicative of a pathological condition associated with endometriosis.

In some embodiments, a change of expression level of the biomarker is indicative of a pathological condition associated with endometrial cancer.

In some embodiments, a change of expression level of the biomarker is indicative of a pathological condition associated with an immune disorder in a female genital tract.

In some embodiments, a change of expression level of the biomarker is indicative of a pathological condition associated with at least one of cervical cancer, ovarian cancer, and a sexually transmitted infection.

In some embodiments, a change of nucleotide sequence of the biomarker is indicative of a pathological condition associated with at least one of endometriosis and endometrial cancer.

In some embodiments, a change of nucleotide sequence of the biomarker is indicative of a pathological condition associated with an immune disorder in a female genital tract.

In some embodiments, a change of nucleotide sequence of the biomarker is indicative of a pathological condition associated with at least one of cervical cancer, ovarian cancer, and a sexually transmitted infection.

In some embodiments, the biomarker comprises a bacterial nucleotide sequence, a viral nucleotide sequence, a fungal nucleotide sequence, or a human nucleotide sequence.

In some embodiments, the analysis comprises sequencing nucleic acids in the biological sample.

In another aspect, disclosed herein is a method for monitoring a health condition of a subject. The method can comprise: using a sample collector to non-invasively collect a vaginal biological sample from a vaginal canal of the subject, wherein the sample collector collects and retains the vaginal biological sample from the vaginal canal; bringing the sample collector in proximity to an extractor comprising (i) a first chamber configured to receive the sample collector via an opening and (ii) a second chamber adjacent to the first chamber, wherein the second chamber comprises a reagent compartment capable of retaining a solution, wherein at least one of the first chamber and the second chamber is breakable in response to a compression force; depositing the sample collector through the opening into the first chamber; and applying the compression force to bring the first chamber in fluid communication with the second chamber, thereby bringing the solution into contact with the vaginal biological sample to form a mixture of the solution with the vaginal biological sample.

In some embodiments, the extractor further comprises a hard seal configured to separate the first chamber and the second chamber, wherein the hard seal does not break in response to the compression force.

In some embodiments, the extractor further comprises a frangible seal configured to separate the first chamber and the second chamber, wherein the frangible seal is breakable in response to the compression force.

In some embodiments, the method can further comprise enclosing the extractor in an outer shell, wherein upon enclosure, the outer shell is configured to apply the compression force towards at least one of the first chamber and the second chamber. In some embodiments, the outer shell comprises a hinge configured to open or close the outer shell. In some embodiments, the outer shell comprises a fastening unit for closing and sealing the outer shell.

In some embodiments, the method can further comprise preserving, storing, or analyzing the vaginal biological sample by the solution.

In some embodiments, the extractor comprises a docking unit. In some embodiments, the docking unit is at least one of a one-way pressure valve, a resealable slit, and a cannula.

In some embodiments, the method can further comprise collecting the mixture of the solution and the vaginal biological sample in a cartridge. In some embodiments, the extractor comprises a docking unit, wherein the docking unit is configured to fluidly communicate with the cartridge. In some embodiments, the cartridge is under vacuum. In some embodiments, the cartridge is a vacutainer. In some embodiments, the cartridge comprises a clinical sample collection tube.

In some embodiments, the method can further comprise (1) reading the cartridge by a cartridge reader to detect an analyte in the vaginal biological sample, and (2) capturing and interpreting a result from the reading.

In some embodiments, the method can further comprise using the analyte to test a presence or absence of a health condition of the subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

In some embodiments, the sample collector comprises an absorbent-diffuse material that collects, retains, or releases the vaginal biological sample. In some embodiments, the absorbent-diffuse material comprises one or more of a plant fiber material, a disposable material, a flushable material, a biodegradable material, an organic material, a dissolvable material, a synthetic material, and polymatrix beads.

In some embodiments, the sample collector comprises at least one of a cup, a rod, a cylinder, a pad, and a threaded matrix.

In some embodiments, the vaginal biological sample comprises one or more of cervicovaginal fluid, blood, vaginal mucosa, semen, interstitial fluid, cervical secretions, fetal tissues, reproductive cells, cervical cells, endometrial cells, fallopian cells, ovarian cells, natural flora in a female reproductive tract, invasive pathogens, and trophoblast cells.

In some embodiments, the vaginal biological sample comprises blood.

In some embodiments, the vaginal biological sample comprises an endometrial cell.

In some embodiments, the vaginal biological sample comprises an ovarian cell. In some embodiments, the vaginal biological sample comprises cervicovaginal fluid.

In some embodiments, the method can further comprise using a reagent in the solution for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample.

In some embodiments, the method can further comprise detecting a presence or absence of a biomarker in the vaginal biological sample.

In some embodiments, a change of expression level of the biomarker is indicative of a pathological condition associated with at least one of endometriosis and endometrial cancer.

In some embodiments, a change of expression level of the biomarker is indicative of a pathological condition associated with an immune disorder in a female genital tract.

In some embodiments, a change of expression level of the biomarker is indicative of a pathological condition associated with at least one of cervical cancer, ovarian cancer, and a sexually transmitted infection.

In some embodiments, a change of nucleotide sequence of the biomarker is indicative of a pathological condition associated with at least one of endometriosis and endometrial cancer.

In some embodiments, a change of nucleotide sequence of the biomarker is indicative of a pathological condition associated with an immune disorder in a female genital tract.

In some embodiments, a change of nucleotide sequence of the biomarker is indicative of a pathological condition associated with at least one of cervical cancer, ovarian cancer, and a sexually transmitted infection.

In some embodiments, the biomarker comprises a bacterial nucleotide sequence, a viral nucleotide sequence, a fungal nucleotide sequence, or a human nucleotide sequence.

In some embodiments, the method can further comprise sequencing nucleic acids in the biological sample.

In some embodiments, the method can further comprise monitoring the health condition about every 10 days to about every 90 days.

In some embodiments, the method can further comprise closing the first chamber subsequent to depositing the sample collector in the first chamber.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

FIG. 6A is a front view of the Snap-on adapter shown in FIG. 5A.

FIG. 6B is a left view of the Snap-on adapter shown in FIG. 5A.

FIG. 6C is a bottom view of the Snap-on adapter shown in FIG. 5A.

FIG. 6D is a right view of the Snap-on adapter shown in FIG. 5A.

FIG. 6E is a top view of the Snap-on adapter shown in FIG. 5A.

FIG. 9A is a front view of the assay reader shown in FIG. 8A.

FIG. 9B is a left view of the assay reader shown in FIG. 8A.

FIG. 9C is a top view of the assay reader shown in FIG. 8A.

FIG. 9D is a right view of the assay reader shown in FIG. 8A.

FIG. 9E is a cross-sectional view along lines "9E-9E" of FIG. 9C.

FIG. 10A is a back view of the assay reader shown in FIG. 8A.

FIG. 10B is a cross-sectional view along lines "10B-10B" of FIG. 10A.

FIG. 10C is a cross-sectional view along lines "10C-10C" of FIG. 10A.

FIG. 12A is a side view of the extractor top shown in FIG. 11.

FIG. 12B is a bottom view of the extractor top shown in FIG. 11.

FIG. 12C is a top view of the extractor top shown in FIG. 11.

FIG. 12D is a cross-sectional view along lines "12D-12D" of FIG. 12A.

FIG. 13A is a side view of the extractor bottom shown in FIG. 11.

FIG. 13B is a bottom view of the extractor bottom shown in FIG. 11.

FIG. 13C is a top view of the extractor bottom shown in FIG. 11.

FIG. 13D is a cross-sectional view along lines "13D-13D" of FIG. 13A.

FIG. 14A is a perspective view of an assay cartridge, in accordance with one exemplary embodiment.

FIG. 14B is a side view of the assay cartridge shown in FIG. 14A.

FIG. 14C is a cross-sectional view along lines "14C-14C" of FIG. 14B.

FIG. 14D is a back view of the assay cartridge shown in FIG. 14A.

FIG. 14E is a cross-sectional view along lines "14E-14D" of FIG. 14D.

FIG. 15A depicts an assembled sample extraction device.

FIG. 15B depicts the top of the extractor and the luer lock adaptor device of the device shown in FIG. 15A.

FIG. 15C depicts the reservoir of the device shown in FIG. 15A.

FIG. 15D is a fluid port that connects to the luer lock adapter device shown in FIG. 15A.

FIG. 16A shows an exterior view of a sample storage device.

FIG. 16B shows an interior view of a sample storage device.

FIG. 16C shows a top view of a sample storage device.

FIG. 16D shows a bottom view of a sample storage device.

DETAILED DESCRIPTION

Figure 1:
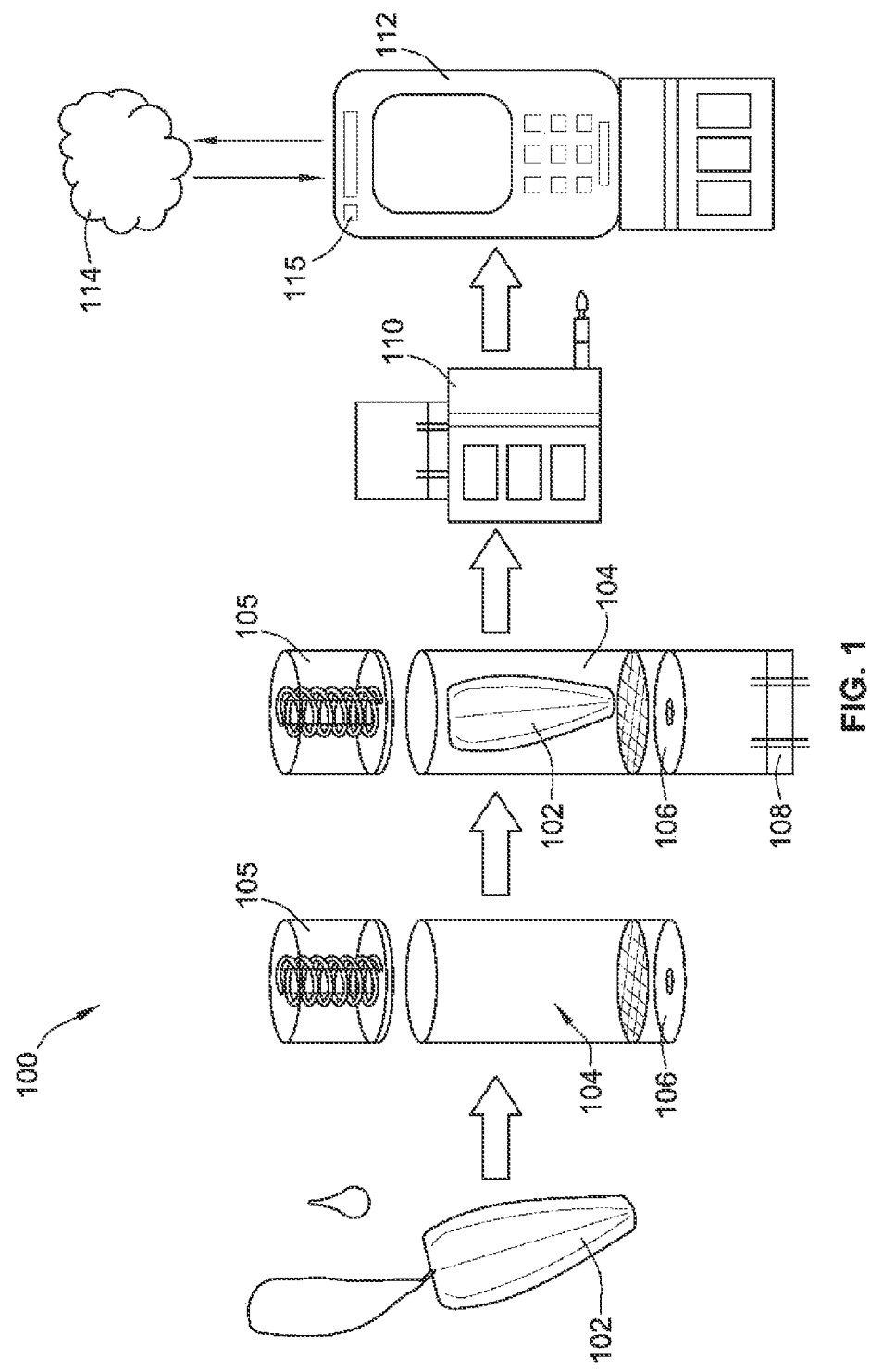
FIG. 1 is a schematic view illustrating a method and system for collecting and analyzing a biological sample.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless defined otherwise, all technical and scientific terms used in this disclosure have the same meanings as commonly understood by one of ordinary skill in the art to which this disclosure belongs.

As used herein the term "comprising" or "comprises" is used in reference to systems, methods, devices, kits, and respective component(s) thereof, that are essential to the disclosure, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" is equivalent to "includes." The abbreviation, "e.g." is derived from the Latin exempli gratia, and is used herein to indicate a non-limiting example. Thus, the abbreviation "e.g." is synonymous with the term "for example."

As used herein the term "consisting essentially of" refers to those elements required for a given embodiment. The term permits the presence of elements that do not materially affect the basic and novel or functional characteristic(s) of that embodiment of the disclosure.

The term "assay" as used herein refers to the analysis of a sample to determine the presence, absence, quantity or edited nature of one or more components.

The term "assay cartridge" or "cartridge" are used interchangeably herein. They refer to the part of the device that contains the diluents, materials, and reagents necessary for testing for certain markers. This cartridge can insert into a pressure valve of a reservoir end of an extractor, thus enabling the transfer of cervicovaginal fluid from the reservoir to the assay cartridge, where the cervicovaginal fluid comes into contact with the diluents and reagents.

The term "assay chamber," "chamber," and "sample collection chamber" are used interchangeably herein. They refer to the part of the device that comes in fluid communication with the reservoir. In some cases, they refer to the part of the device that comprises a reagent or buffer for releasing biological material from a sample collector, and/or for preserving or analyzing the released biological materials.

The terms "sample collection reservoir," "assay delivery reservoir" and "reservoir" are used interchangeable herein. They refer to the part of the device that receives the collected fluid from the extractor. In some cases, they refer to the part of the device that comprises a reagent or buffer for releasing the biological material from the sample collector, and/or for preserving or analyzing the released biological materials.

The terms "biological fluid," "biological sample," "biological material," and "collected fluid" are used interchangeably. They refer to the fluid, cells, tissues or debris released from the sample collector.

The term "subject," as used herein, generally refers to a biological entity containing expressed genetic materials. The biological entity can be a plant, animal, or microorganism, including, e.g., bacteria, viruses, fungal, and protozoa. The biological entity can be a mammal. The biological entity can be a human. The human may be diagnosed or suspected of being at high risk for a disease. The human may not be diagnosed or suspected or being at high risk for a disease. The biological entity can be a primate, an ape, or a monkey. The biological entity can be a shrew or a bat. The subject can be tissues, cells and their progeny of a biological entity obtained in vivo or cultured in vitro.

As used herein, a "nucleic acid sample" can refer to any substance containing or presumed to contain nucleic acid. The sample can be a biological sample obtained from a subject. The nucleic acids can be RNA, DNA, e.g., genomic DNA, mitochondrial DNA, viral DNA, synthetic DNA, or cDNA reverse transcribed from RNA. The nucleic acid may be extracted from a biological sample, e.g., from tissue, cell, or biopsy.

As used herein, a "biological sample" can refer to a sample collected from a subject. The biological sample can be a liquid sample, e.g., whole blood, plasma, serum, vaginal fluid, cervicovaginal fluid, menstrual flow, menstrual fluid, cervical secretion, mucosal secretion, ascites, cerebrospinal fluid, sweat, urine, tears, saliva, buccal sample, cavity rinse, or organ rinse. The liquid sample can be an essentially cell-free liquid sample (e.g., plasma, serum, sweat, blood, cerebrospinal fluid, vaginal fluid, cervicovaginal fluid, cervical secretion, mucosal secretion, urine, sweat, tears, saliva, sputum, amniotic fluid, and bodily fluid). The cell-free liquid sample can comprise cell-free DNA samples from the subject or microbes living in the subject's genital tract. The biological sample can be a solid biological sample, e.g., feces or tissue biopsy, e.g., a tumor biopsy. A biological sample can also comprise in vitro cell culture constituents (including but not limited to conditioned medium resulting from the growth of cells in cell culture medium, recombinant cells and cell components). The biological sample can comprise a single cell, e.g., a cancer cell, a circulating tumor cell, a cancer stem cell, and the like. A biological sample can be media, e.g., culture media obtained from cultured cells, e.g., human cell lines, e.g., human cell lines derived from tumor tissue. The media can comprise DNA, e.g., tumor DNA, e.g., circulating tumor DNA, e.g., circulating tumor nucleic acid molecules, e.g., circulating tumor RNA.

The terms "polynucleotides," "nucleic acid," "nucleotides" and "oligonucleotides" can be used interchangeably. They can refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "genomic sequence", as used herein, generally refers to a sequence that occurs in a genome. Because RNAs are transcribed from a genome, this term encompasses sequences that exist in the nuclear genome of an organism, as well as sequences that are present in a cDNA copy of an RNA (e.g., an mRNA) transcribed from such a genome.

As used herein, "amplification" of a nucleic acid sequence generally refers to in vitro techniques for enzymatically increasing the number of copies of a target sequence. Amplification methods include both asymmetric methods (in which the predominant product is single-stranded) and conventional methods (in which the predominant product is double-stranded). A "round" or "cycle" of amplification can refer to a PCR cycle in which a double stranded template DNA molecule is denatured into single-stranded templates, forward and reverse primers are hybridized to the single stranded templates to form primer/template duplexes, and primers are extended by a DNA polymerase from the primer/template duplexes to form extension products. In subsequent rounds of amplification the extension products are denatured into single stranded templates and the cycle is repeated.

The terms "template," "template strand," "template DNA" and "template nucleic acid" can be used interchangeably herein to refer to a strand of DNA that is copied by an amplification cycle.

The terms "determining," "measuring," "evaluating," "assessing," "assaying," and "analyzing" can be used interchangeably herein to refer to any form of measurement, and include determining if an element is present or not. These terms can include both quantitative and/or qualitative determinations. Assessing may be relative or absolute. "Assessing the presence of" can include determining the amount of something present, as well as determining whether it is present or absent.

The term "sequencing," as used herein, can refer to a method by which the identity of at least 10 consecutive nucleotides (e.g., the identity of at least 20, at least 50, at least 100, at least 200, or at least 500 or more consecutive nucleotides) of a polynucleotide are obtained.

The term "mutation," as used herein, generally refers to a change of the nucleotide sequence of a genome as compared to a reference. Mutations can involve large sections of DNA (e.g., copy number variation). Mutations can involve whole chromosomes (e.g., aneuploidy). Mutations can involve small sections of DNA. Examples of mutations involving small sections of DNA include, e.g., point mutations or single nucleotide polymorphisms, multiple nucleotide polymorphisms, insertions (e.g., insertion of one or more nucleotides at a locus), multiple nucleotide changes, deletions (e.g., deletion of one or more nucleotides at a locus), and inversions (e.g., reversal of a sequence of one or more nucleotides).

The term "locus," as used herein, can refer to a location of a gene, nucleotide, or sequence on a chromosome. An "allele" of a locus, as used herein, can refer to an alternative form of a nucleotide or sequence at the locus. A "wild-type allele" generally refers to an allele that has the highest frequency in a population of subjects. A "wild-type" allele generally is not associated with a disease. A "mutant allele" generally refers to an allele that has a lower frequency that a "wild-type allele" and may be associated with a disease. A "mutant allele" may not have to be associated with a disease. The term "interrogated allele" generally refers to the allele that an assay is designed to detect.

The term "single nucleotide polymorphism" or "SNP," as used herein, generally refers to a type of genomic sequence variation resulting from a single nucleotide substitution within a sequence. "SNP alleles" or "alleles of a SNP" generally refer to alternative forms of the SNP at particular locus. The term "interrogated SNP allele" generally refers to the SNP allele that an assay is designed to detect.

The term "copy number variation" or "CNV" refers to differences in the copy number of genetic information. In many aspects it refers to differences in the per genome copy number of a genomic region. For example, in a diploid organism the expected copy number for autosomal genomic regions is 2 copies per genome. Such genomic regions should be present at 2 copies per cell. For a recent review, see Zhang et al. Annu. Rev. Genomics Hum. Genet. 2009. 10:451-81. CNV is a source of genetic diversity in humans and can be associated with complex disorders and disease, for example, by altering gene dosage, gene disruption, or gene fusion. They can also represent benign polymorphic variants. CNVs can be large, for example, larger than 1 Mb, but many are smaller, for example between 100 bases and 1 megabases (Mb). More than 38,000 CNVs greater than 100 bases (and less than 3 Mb) have been reported in humans. Along with SNPs, these CNVs account for a significant amount of phenotypic variation between individuals. In addition to having deleterious impacts, e.g., causing disease, they may also result in advantageous variation.

The term "genotyping," as used herein, generally refers to a process of determining differences in the genetic make-up (genotype) of an individual by examining the individual's DNA sequence using biological assays and comparing it to another individual's sequence or a reference sequence.

As used herein in reference to fibers, the term "degradable" refers to a material that degrades when in contact with a reagent. The reagent may be acidic, alkaline, or have neutral pH. The reagent can be mucosal tissue. The reagent may resemble the pH of mucosal tissue. The reagent is non-toxic to cells or tissues in the form used, and do not provoke an inflammatory or immune response in the individual to whom they are administered. Degradation can occur over a range of minutes, hours, days, weeks or even months, but to the extent that a fibrous material is degraded or bioabsorbed over time, it is "degradable."

The term "biodurable" generally refers to fibers that do not substantially degrade when placed in contact with a reagent, e.g., mucosal tissue. Examples of biodurable fibers include polyethylene and polypropylene fibers.

As used herein, the term "biocompatible" refers to materials that are tolerated by the body and its tissues upon administration by, e.g., implantation, ingestion, or contacting with a mucosal tissue. Biocompatible materials are substantially not toxic to cells or tissues in the form used, and do not provoke an inflammatory or immune response in the individual to whom they are administered.

The term "binary readout" as used herein refers to the results given by the cartridge reader that are expressed as either "positive" or "negative."

The term "quantitative readout" as used herein refers to a reported measurement of a specific quantity of a substance and reflects an absolute amount or concentration.

The term "cartridge reader" as used herein refers to the part of the device that connects with the assay cartridge and gives a binary or quantitative readout of the test result.

The term "cradle" as used herein refers to how the sample collector fits against the os of the cervix. The fit can be partial or full, as long as the device absorbs fluid readily.

The term "dense" as used herein refers to the state of being closely compacted.

The terms "extractor" or "extraction device" as used herein refers to the part of the device that comprises the sample collector receptacle and the reservoir. The extractor can further comprise a puncturable membrane. The extractor can comprise a diluent or buffer. A filter separates the receptacle and the reservoir, and a pressure valve at the bottom of the reservoir can enable attachment of the assay cartridge and subsequent transfer of the cervicovaginal fluid into the cartridge. The extractor can have a cap that houses a spring-loaded compressor and a button, which, if pushed, compresses the sample collector, thereby allowing the cervicovaginal fluid from the sample collector to pass through the filter into the reservoir.

The term "filter" as used herein refers to the porous material between the sample collector receptacle and the reservoir, which serves to remove endometrial tissue, red blood cells, peripheral blood mononuclear cells and other cellular debris from the extracted sample to ultimately yield the filtered cervicovaginal fluid, as well as purified cellular material on the filter, which can be removed for downstream analysis. The filter can be located between any two compartments. The filter can be applied to any fluid path.

The term "mobile interface" as used herein refers to an interactive mobile application which ties data acquisition facilitated by the device to comprehensive behavioral management.

The term "sample collector" as used herein refers to a device that is inserted into the vagina to absorb cervicovaginal fluids and can both absorb quickly as well as release fluid with ease. Alternatively, a sample collector may be configured to collect cervicovaginal fluids outside the body.

The term "optimal" as used herein refers to the most favorable outcome.

The term "external orifice of the uterus," "ostium of uterus," "external os," "uterus cervix," "os of the cervix," or "cervical os" as used herein refers to the opening of the uterine cervix to a vagina which is covered by squamous epithelium.

The term "permeated thread matrix" as used herein refers to a thread matrix that is spread throughout the inner shell of the sample collector.

The term "plant fiber" as used herein refers to any fibers, threads, ribbons, or beads that are absorbent in nature.

The term "pressure valve" as used herein refers to the cylindrical pipe connected to the bottom of the reservoir. In one embodiment, this is a normally closed, low pressure, one-way check valve with a luer slip that facilitates the unidirectional movement of the filtered cervicovaginal fluid from the reservoir to the assay cartridge, and prevents back flow when the luer slip is engaged. Insertion of the assay cartridge and application of low pressure opens the valve.

The term "reinforced" as used herein refers to the state of being strengthened and supported so as to reduce leakage.

The term "reservoir" as used herein refers to the part of the extractor which receives the filtered blood or cervicovaginal fluid after it passes through the filter from the sample collector receptacle.

The term "spring-loaded compressor" as used herein refers to the elastic device inside the extractor cap, which compresses the sample collector (e.g., tampon), thereby allowing the cervicovaginal fluid from the sample collector to pass through the filter into the reservoir.

The term "sample receptacle" as used herein refers to the part of the extractor which houses the sample collector (e.g., used tampon).

The term "time-independent signal amplification immunoassay" as used herein refers to an immunoassay for the detection of analytes which can be flexibly conducted without rigid adherence to time limits or storage conditions.

The term "tooth-like shape" as used herein refers to two projections at the tip of a feminine hygiene device that is configured to fit the cervical os or uterine cervix.

The terms "cervicovaginal fluid," "menstruation," "menstrual fluid," and "menstrual flow" are used interchangeably herein. They refers to any biological fluids and/or matrix contained within or expelled from the vagina, such as blood, extracellular fluid, plasma, semen, vaginal mucosa, interstitial fluid, cervical secretions, or shed reproductive, endometrial and fetal tissues, or any combination thereof.

The term "web-based interface" as used herein refers to a website that facilitates bi-directional communication with a target audience.

Overview

Aspects of the application relate to systems, methods, devices and kits for collecting a biological sample from a subject for screening for a particular pathology, diagnosing a disease, monitoring for a status of a disease, or monitoring for effectiveness of a medical or therapeutic regimen. The biological sample can be collected from a subject's cervicovaginal canal. The biological sample can be menstrual flow from a subject. The biological sample can comprise blood, shed cells from the ovaries and/or uterus, cervicovaginal fluids, mucus or secretion from a subject's reproductive system. The subject can be a female. The subject can be a pre-menstrual female. The disease can be cancer, a disease related to the reproductive system, a disease related to the immune system, or other disease. The pathology can be related to a microbial infection, nutrition imbalance, or a disease.

Disclosed herein are systems, methods, devices and kits for monitoring a health condition, a status of a disease, monitoring effectiveness of a medical or therapeutic regimen, prognosis of a disease, or prophylactic treatment of a disease. The systems, methods, devices and kits may comprise collecting a biological sample from a subject. The systems, methods, devices and kits may comprise analyzing, preserving, storing, and/or transporting the collected biological sample. The systems, methods, devices and kits may further comprise capturing and interpreting a test result of the biological sample, and communicating the test result to the subject, a physician, a health care professional, or any personnel authorized by the subject. The systems, methods, devices and kits may further comprise prescribing or recommending a diet, supplement, medical or therapeutic regimen to the subject. The systems, methods, devices and kits described herein provides for self-monitoring of a health condition, a status of a disease, or effectiveness of a medical or therapeutic regimen in a regular basis. The self-monitoring can be performed about every day. The self-monitoring can be performed about every week. The self-monitoring can be performed about every month. The self-monitoring can be performed about every 28-40 days. The self-monitoring period can be synchronized with a woman's menstrual cycle. The subject can be a female. The subject can be pregnant. In some cases, the subject can be diagnosed with a disease, for example, HIV, HPV, STD, microbial infection (e.g., yeast infection, fungal infection, bacterial infection), female genital tract disease, immune disorder, reproductive disorder, nutrition deficiency, or a mental health issue. In some cases, the subject can be on a prescribed medical or therapeutic regimen for a diagnosed disease. In some cases, the subject can have never been diagnosed of a disease related to the female genital tract, reproductive system, immune system, HIV, HPV, or microbial infections. The systems, methods, devices and kits described herein provide for prophylactic treatment or prognosis of a disease in a subject, wherein monitoring a health condition in a subject's cervicovaginal canal protects the subject's reproductive system, immune system and prevents health problems.

Some aspects of the disclosure relates to a system for collecting a biological sample from a subject, comprising a sample collector that non-invasively collects the biological sample from the subject. The sample collector can be inserted into the subject's vaginal canal to collect the biological sample. The system described herein can collect a large volume of biological sample comprising menstrual blood, cervicovaginal fluid, secreted mucus, shed uterus cells, and shed ovary cells. The sample collector can be made of materials that are capable of collecting and retaining the biological sample. The sample collector can be made of highly absorbent materials that absorb a liquid sample rapidly. The sample collector can be made of materials that release absorbed liquid samples rapidly, such as when a compression mechanism (e.g., pressure, force) is applied to the sample collector. The system may comprise an extractor for extracting the biological sample from the sample collector. The extractor may comprise a component for applying a compression mechanism to the sample collector. Components for applying compression mechanisms can include but are not limited to a spring, threaded screw, lever, air-tight plunger, or roller-based compression. For example, the liquid sample absorbed on a sample collector can be extracted by applying a compression mechanism to the sample collector. The extractor may comprise a sample receptacle that receives the sample collector via an opening, and a reservoir that is in fluid communication with the sample receptacle for receiving the biological sample released from the sample collector. The reservoir and/or receptacle may contain a solution comprising one or more reagents for analyzing, preserving, storing, or transporting the collected biological sample. In some cases, the one or more reagents are necessary for hydrolyzing, diffusing, or releasing the biological sample. In some cases, the one or more reagents are necessary for analyzing, preserving, or extracting deoxyribonucleic acid, ribonucleic acid, or protein in the biological sample. In some cases, the one or more reagents are necessary for reducing analysis background noise. In some cases, the one or more reagents are necessary for precipitating or removing a contaminant in the biological sample. In some cases, the one or more reagents are necessary for testing the biological sample for a presence or absence of an analyte in the biological sample. In some cases, the receptacle contains a reagent that is necessary for dissolving the sample collector upon coming in contact with the sample collector. Accordingly, the sample collector can be made of materials that dissolve upon contact with the reagent stored in the receptacle, thereby releasing the biological sample into the reservoir. The system may further comprise a cartridge comprising a chamber, wherein the cartridge and/or the chamber is connected to the reservoir via a docking unit, such that upon the cartridge and/or the chamber coming in contact with the reservoir, the released biological sample flows into the cartridge and/or the chamber. The docking unit may comprise a one-way pressure valve. The docking unit may comprise a resealable slit. The cartridge containing the collected biological sample may be covered or sealed. The cartridge containing the collected biological sample may be transported without causing damage or degradation to the collected biological sample. In some cases, the system further comprises software or bioinformatics for analyzing the presence of a pathology or disease, and recommending a treatment. The software can be a FDA-approved software. For example, the system can comprise recommending a diet to a subject indicated of nutrition deficiency in the test results, without involving a dietitian or any health care professional.

Some aspects of the disclosure relate to a method for monitoring a health condition of a subject, comprising using a sample collector disclosed herein to non-invasively collect a biological sample from a vaginal canal of the subject. The disclosure provides a method for collecting a large volume of biological sample comprising menstrual blood, cervicovaginal fluid, secreted mucus, shed uterus cells, and shed ovary cells. In some cases, the sample collector is inserted into the subject's vaginal canal to collect the biological sample. The sample collector can be made of materials that are capable of collecting and retaining the biological sample, and rapidly releasing the biological sample from the sample collector, such as to a sample receptacle or reservoir. The method may further comprise bringing the sample collector in proximity to an extractor comprising a sample receptacle that is configured to receive the sample collector via an opening. The extractor can further comprise a reservoir that is in fluid communication with the sample receptacle such that any extracted biological sample can flow from the receptacle into the receptacle and/or reservoir. The method further comprises depositing the sample collector through the opening of the extractor into the reservoir. The reservoir and/or receptacle may contain a solution comprising one or more reagents for analyzing, preserving, storing, or transporting the collected biological sample. In some cases, the one or more reagents are necessary for hydrolyzing, diffusing, or releasing the biological sample. In some cases, the one or more reagents are necessary for analyzing, preserving, or extracting deoxyribonucleic acid, ribonucleic acid, or protein in the biological sample. In some cases, the one or more reagents are necessary for reducing analysis background noise. In some cases, the one or more reagents are necessary for precipitating or removing a contaminant in the biological sample. In some cases, the one or more reagents are necessary for testing the biological sample for a presence or absence of an analyte in the biological sample. The method may further comprise applying a compression mechanism to the sample collector to release the biological sample into the receptacle. A variety of compression mechanisms may be applied, including but not limited to pressing, twisting, pulling, pushing, and smashing. In some cases, releasing the biological sample from the sample collector involves dissolving the sample collector. The method may comprise adding a reagent necessary for dissolving the sample collector to the receptacle that contains the sample collector, and bringing the sample collector into contact with the reagent. The method may further comprise swirling or mixing the sample collector with the reagent to facilitate the dissolving. The dissolving may further comprise adding a catalyst into the reagent, and/or modifying pH value or temperature in the reagent. The method may comprise connecting the extractor with a cartridge, wherein the cartridge comprises a chamber. Connecting the extractor with the cartridge may comprise docking the cartridge with the extractor to bring the chamber in fluid communication with the reservoir, such that upon the chamber coming in contact with the reservoir, the released biological sample flows from the reservoir into the cartridge or the chamber. The method may further comprise covering or sealing the cartridge. The method may further comprise transporting the cartridge to a Clinical Laboratory Improvement Amendment (CLIA) certified laboratory for analysis. For example, the biological sample can be analyzed for a presence or absence of a health condition in the subject. The health condition being detected can be selected from the group consisting of sexually transmitted infections, yeast infections, fungal infections, bacterial infections, viral infections, viroid infections, parasite infections, protozoa infections, cancer, pregnancy, fertility, semen, hormone levels, endometriosis, polycystic ovarian syndrome, reproductive disorders, immune disorders, and nutrient levels. In some cases, the testing involves detecting the presence or absence of endometriosis in the subject. In some cases, the testing involves detecting the presence or absence of endometriosis in a biological sample collected from a particular menstrual phase (e.g., proliferation phase, early secretory phase, mid-secretory phase) of the subject. In some cases, the testing involves detecting the presence or absence of endometrial cancer. In some cases, the testing involves detecting the presence or absence of ovarian cancer. In some cases, the testing involves detecting the presence or absence of a sexually transmitted disease. In some cases, the testing involves detecting the presence or absence of a microbial infection. In some cases, the testing involves detecting the presence or absence of an immune disorder. In some cases, the testing involves detecting the presence or absence of nutrition deficiency. Detection of the presence of the pathology or disease can be achieved by detecting the presence or absence, or change of expression level of at least one biomarker disclosed herein. Detection of the presence of the pathology or disease can be achieved by detecting the presence or absence, or change of expression level of at least one set of biomarkers disclosed herein. The method provides for self-monitoring of a health condition. The method can be performed by the subject at home, or outside of a hospital or a clinic. The method can provide for self-diagnosis of a health condition. The method can provide for analyzing the presence of a pathology or disease and recommending a treatment. For example, the method can recommend a diet to a subject indicated of nutrition deficiency from the test, without involving a dietitian or any health care professional. The method can comprise regular monitoring of the subject's health condition. For example, the subject can be monitored for a health condition every day, week, or month. The subject can be monitored for a health condition every 28-40 days. The subject can be monitored for a health condition during the subject's menstruation period. The subject can be monitored for a health condition at any time of the day.

Some aspects of the disclosure relates to a kit for monitoring a health condition of a subject, comprising a system disclosed herein for collecting a biological sample from the subject. The system can comprise an extractor, wherein the extractor comprises a sample receptacle and a reservoir. The system can further comprise a cartridge comprising a chamber. The kit can further comprise a set of reagents for analyzing the collected biological sample. The kit can further comprise a set of reagents for preserving, storing, or transporting the collected biological sample. The kit can further comprise at least one probe for a biomarker for detecting a presence or absence of a pathology or disease in the collected biological sample. The kit can further comprise at least one set of probes for biomarkers for detecting a presence or absence of a pathology or disease in the collected biological sample. The kit can further comprise a set of instructions for detecting the presence or absence of a pathology or disease in the collected biological sample.

Components

As described herein, the system for collecting a biological sample from a subject comprises one or more components. The system can comprise a collection device, an extractor for extracting the biological sample, a receiving device or reservoir for receiving the extracted biological sample, and/or a detachable device or a cartridge or chamber for storing or transporting the collected biological sample. Different components can perform different combinations of one or more functions described herein. For example, an extractor can perform all of the functions of extracting, receiving, storing, and transporting of a biological sample.

One purpose of the collection device is to use cervicovaginal samples to regularly provide women with informative data about their health so that they can better and more accurately assess the complex nature of their personal fertility and overall well-being.

Referring to FIG. 1, a representative and exemplary system 100 includes at least a few of the following five components: a specialized sample collector 102 (illustrated by way of example in the form of a tampon) to optimize collection of biological materials or sample such as cervicovaginal fluid, blood, extracellular fluid, plasma, vaginal mucosa, female genital tract microbes, yeast, fungi, bacteria, or semen for testing; a biological matrix extractor 104 with a compression top 105 to pull the biological materials into an assay delivery reservoir 106, through a filter 150; an assay cartridge 108 to evaluate the biological content of the biological matrix; a cartridge reader 110 which automates assay development, result capture, and result interpretation; and a mobile application interface 112 (illustrated by way of example on a mobile phone with a camera 115) that interprets and tracks a user's results and curates validated recommendations for health and behavior. The cartridge reader may electronically interface with the mobile phone by coupling to the mobile phone, such as to one or more ports of the phone (e.g., headphone port, charging port, USB port, etc.). A web-based interface 114 can provide access to easy intervention services, such as food shopping, vitamin stores, and health facilities for therapeutics, and can provide a positive behavioral feedback loop to increase prevention adherence.

The biological materials may be collected in the assay delivery reservoir 106 and transported to a facility for downstream analysis. Exemplary facilities include but are not limited to Clinical Laboratory Improvement Amendments (CLIA) laboratories, College of American Pathologists (CAP) laboratories, American Society of Crime Lab Director (ASCLD) laboratories, government (e.g., Food and Drug Administration) approved diagnostic laboratories, private diagnostic test laboratories, pregnancy test centers, hospitals, and private clinics.

Sample Collector

Figure 2:
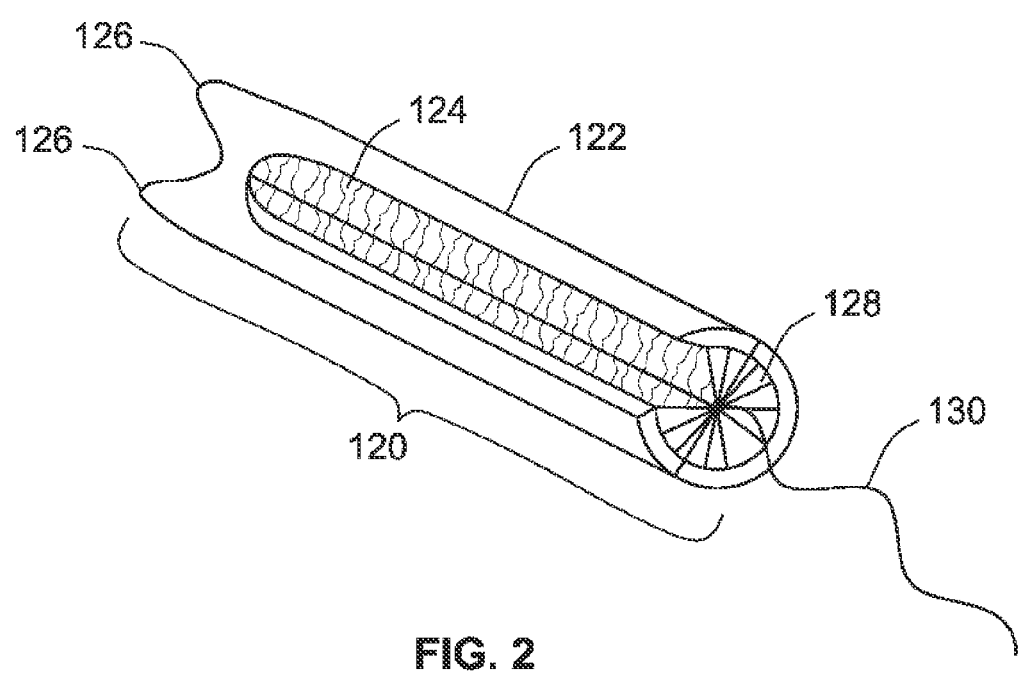
FIG. 2 is a partial cross-sectional perspective view of a feminine hygiene device, in accordance with one exemplary embodiment.
Figure 3:
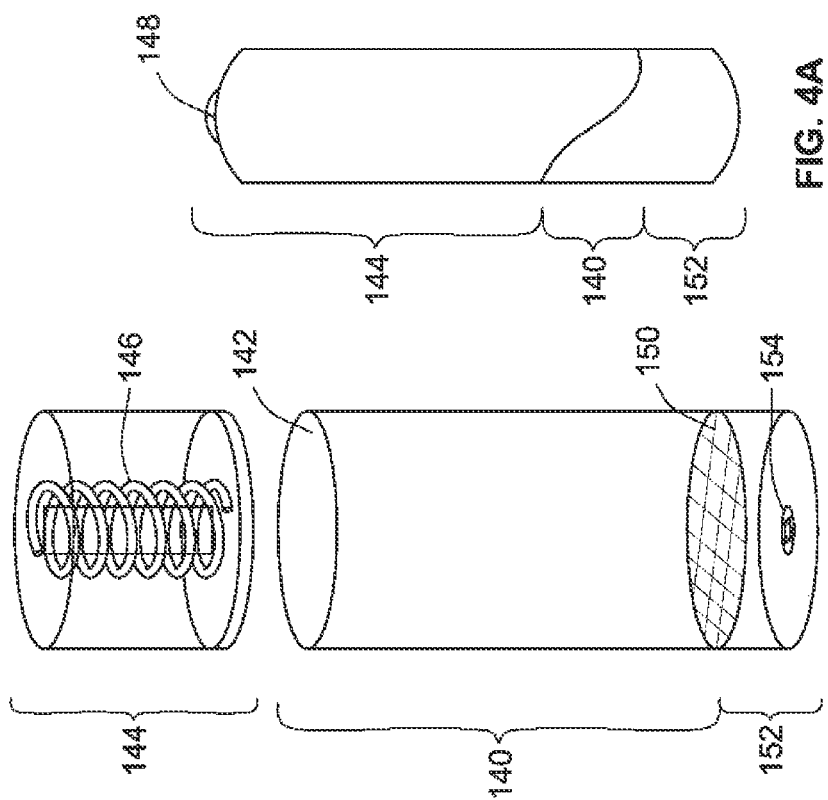
FIG. 3 is an exploded perspective view of an extraction device, in accordance with one exemplary embodiment.
Figures 4A, 4B:
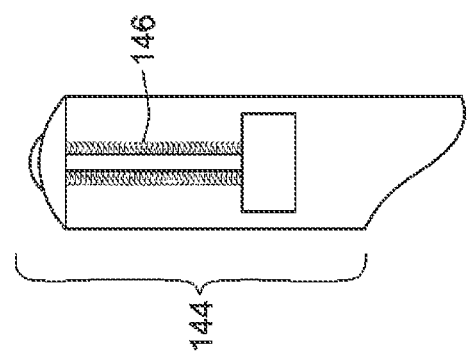
FIG. 4A is a side view of an extraction device, in accordance with another exemplary embodiment.
FIG. 4B illustrates a spring-loaded compressor of the extraction device shown in FIG. 3A.
Figure 4C:
FIG. 4C illustrates a reservoir of the extraction device shown in FIG. 3A.
Figure 5B:
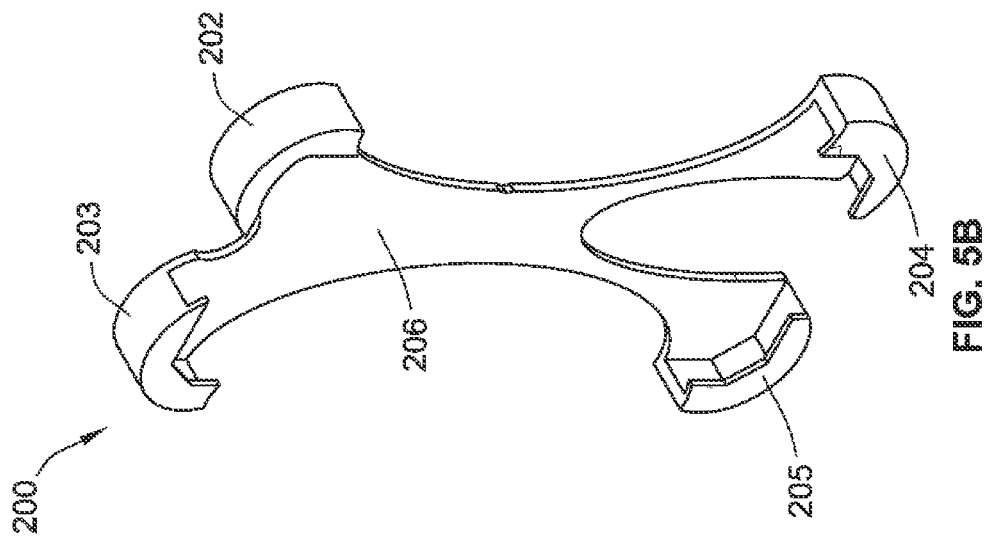
FIG. 5B is a back perspective view of the Snap-on adapter shown in FIG. 5A.
Figure 5A:
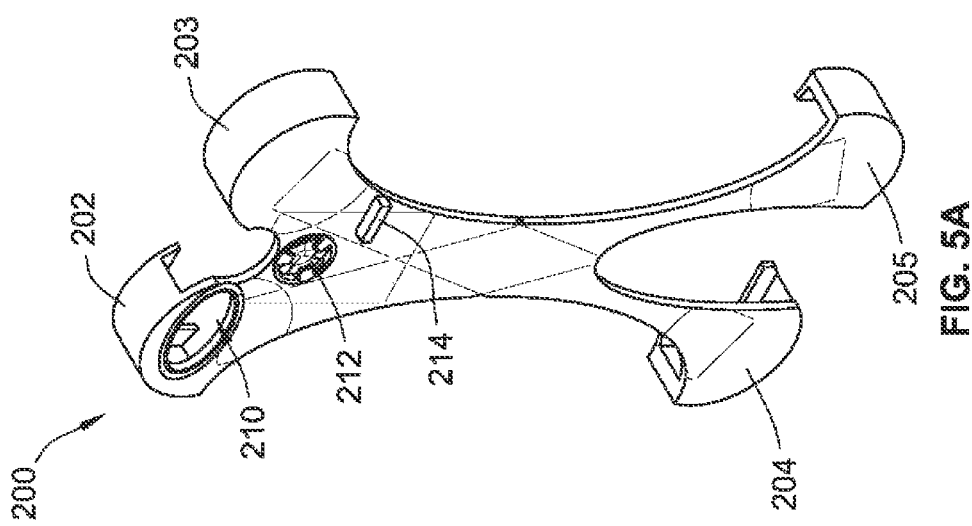
FIG. 5A is a front perspective view of a Snap-on adapter for attachment of an assay cartridge to a mobile telephone, in accordance with one exemplary embodiment.

Referring to FIG. 2, a sample collector 120 is configured to be inserted into a human body cavity (e.g., the vagina or vaginal canal), in accordance with one exemplary embodiment. Such use of the sample collector 120 has facilitated rapid device design and implementation. The sample collector 120 absorbs quickly and releases fluid with ease, as the volume of cervicovaginal fluid can vary for every woman. The sample collector can have a dense outer shell 122 of absorbent plant fiber. The plant fiber is of similar construction and make as that in a commercially available tampon. In other embodiments, the plant fiber is flax, hemp or bamboo.

An inner shell 124 of the sample collector can be looser than the dense outer shell 122. The inner shell can be diffusely permeated with a thread matrix. The threads can provide sufficient structure to help the sample collector maintain its shape and function. However, the threads can also be configured to be distributed in the inner chamber in such a manner as to facilitate collapse upon pressure applied via the extractor. This sample collector can soak up fluid readily, but can also compress easily to release fluid. In some embodiments, a tip 126 of the sample collector has a tooth-like shape that is bifurcated to specifically cradle the os of the cervix. This design maximizes correct placement of the sample collector around the os for optimal specimen collection. A base 128 of the sample collector may be composed of multiple layers of absorbent plant fiber material that form a reinforced seal to prevent leakage.

In some embodiments, the sample collector has a removal element 130 attached to the base 128. The removal element 130 can be configured for pulling. In some embodiments, the removal element 130 is a loop or a knot that can be pulled via hooking into the loop or the knot. In some embodiments, the removal element 130 is a string. In some embodiments, the sample collector is included in a monthly kit. In some cases, a commercially available product (e.g., branded tampons) may be provided. In other cases, custom tampons configured to have the abovementioned characteristics (e.g., absorbent and collapsible) may be provided.

Figures 7A, 7B, 7C:
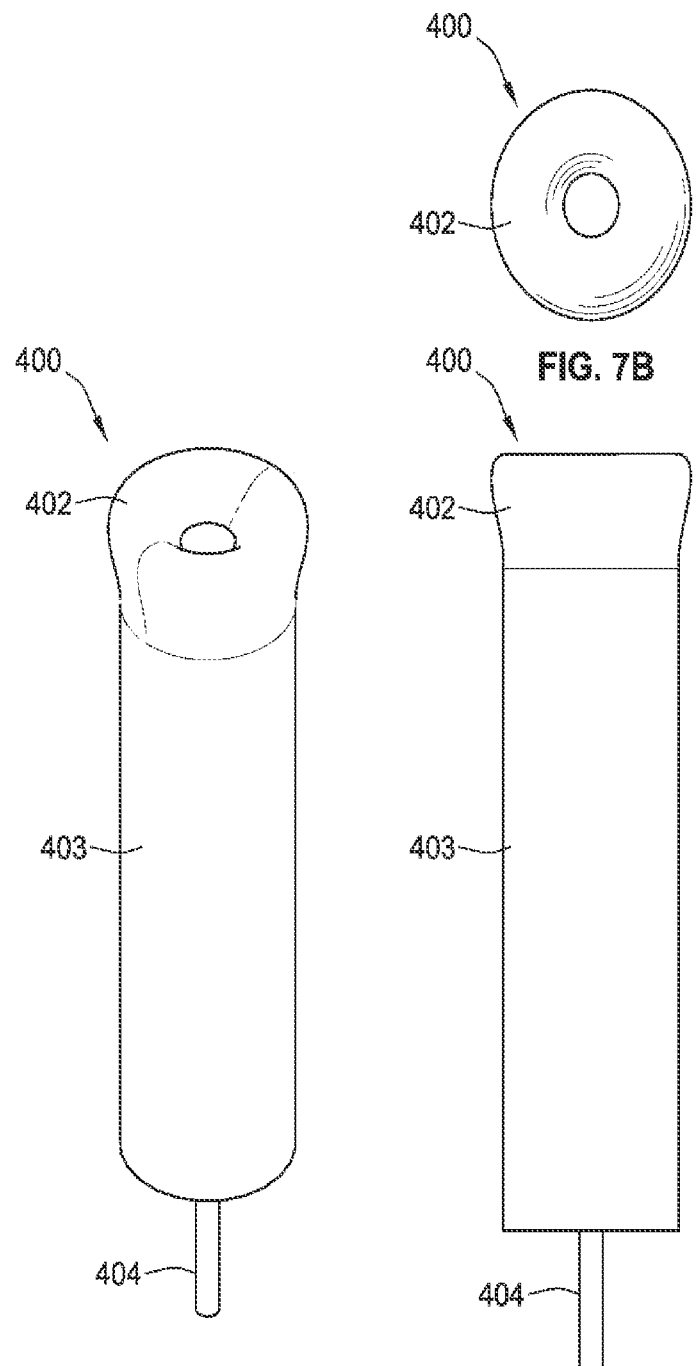
FIG. 7A is a perspective view of a sample collector, in accordance with one exemplary embodiment.
FIG. 7B is a top view of the sample collector shown in FIG. 7A.
FIG. 7C is a side view of the sample collector shown in FIG. 7A.

Referring to FIGS. 7A-7C, a sample collector 400 is configured to be inserted into a human body cavity (e.g., the vagina or vaginal canal), in accordance with one exemplary embodiment. For example, the sample collector 400 is a cylinder having a head 402 configured to cradle the os of the cervix. Opposite to the head 402, and separated by a main body 403, the sample collector 400 has a removal element 404 which can be used to remove the sample collector 400 from the body cavity, e.g., by pulling on the removal element 404. By way of example, the removal element 404 is a string.

The sample collector 400 can include a material configured to release collected biological samples, such as cervicovaginal fluids, and may include a hydrogel material and/or a dissolvable material. According to one embodiment, the sample collector 400 may include cotton or other organic fiber-based apparatus that is inserted into the vaginal canal for the purpose of collecting biological samples. The sample collector 400 can collect menstrual fluid, reproductive tissue, mucosa, shed uterus cells, shed ovary cells, female genital tract microbes, yeast, fungi, bacteria, and foreign bodies. The sample collector may collect a large volume of biological sample comprising menstrual blood, cervicovaginal fluid, secreted mucus, shed uterus cells, and shed ovary cells. The sample collector may collect a biological sample of between about 0.1 to 1000, 100 to 900, 200 to 800, 300 to 700, 400 to 600, 500 to 700, 600 to 800, 700 to 900, 1 to 90, 2 to 80, 3 to 70, 4 to 60, 5 to 50, 4 to 40, 3 to 30, 2 to 20, 10 to 30, 5 to 15, 4 to 12, 3 to 8, or 2 to 6 milliliters (mL). The sample collector may collect a biological sample of at least about 0.1 mL, 1 mL, 2 mL, 3 mL, 4 mL, 5 mL, 6 mL, 7 mL, 8 mL, 9 mL, 10 mL, 12 mL, 15 mL, 18 mL, 20 mL, 25 mL, 30 mL, 35 mL, 40 mL, 45 mL, 50 mL, 60 mL, 70 mL, 80 mL, 90 mL, 100 mL, 200 mL, 300 mL, 400 mL, 500 mL, 600 mL, 700 mL, 800 mL, 900 mL, 1000 mL, or more. The sample collector may collect a biological sample of at most about 0.1 mL, 1 mL, 2 mL, 3 mL, 4 mL, 5 mL, 6 mL, 7 mL, 8 mL, 9 mL, 10 mL, 12 mL, 15 mL, 18 mL, 20 mL, 25 mL, 30 mL, 35 mL, 40 mL, 45 mL, 50 mL, 60 mL, 70 mL, 80 mL, 90 mL, 100 mL, 200 mL, 300 mL, 400 mL, 500 mL, 600 mL, 700 mL, 800 mL, 900 mL, or 1000 mL. The sample collector 400 can be configured to be removed via a string, a loop, or other handle. The sample collector can be configured for insertion via an outer shell applicator. The sample collector 400 may be absorbent but diffuse, such as to readily absorb and release fluids.

A variety of materials may be suitable for the sample collector 400 or 120. Materials for the sample collector are described in U.S. Publication No: 20140128345 A1, and U.S. Pat. No. 8,241,086, which are incorporated herein in their entireties. The sample collector can comprise disposable, flushable, biodegradable, organic, natural, synthetic materials, or combinations thereof. The sample collector can comprise hydrophobic, hydrophilic, or both. The sample collector can comprise polymers, polymer matrix or polymatrix, polymer fibers, absorbent polymers, polyglycolic acid (PGA) beads, absorbent beads, glass fiber, carbon, aramid, brass, nylon, wool silk, viscose, cotton, or combinations thereof. The polymer matrix or polymatrix may have one or more disulfide bonds. The polymer fibers may comprise a polymer selected from the group consisting of poly(lactide-co-glycolide) (PLGA), polylactic acid (PLA), poly caprolactone (PCL), polyvinyl alcohol (PVA), polyethylene oxide (PLO), polyvinylpyrrolidone (PVP), poly methacrylic acid (PMAA), and ethyl cellulose (EC).

In some embodiments, the sample collector 400 or 120 comprises super absorbent polymers. In general, super absorbent polymers are polymerized with hydro monomers such as —OH, —NH2, —COOH, —SO3H, with crosslinkers to form networks of three-dimensional composition. For hydro monomers, partially neutralized acrylic acid may be used.

In some cases, the material for the sample collector is absorbent, and is dissolvable or biodegradable in the presence of a reagent. The reagent may have a pH that resembles the pH of a vaginal canal. The reagent may have a pH different from the pH of a vaginal canal. The reagent may resemble the pH of mucosal tissue. The reagent may be acidic, alkaline, or have neutral pH. The reagent may have a pH in a range between about pH 0.1 to pH 14.0, pH 0.5 to pH 13.5, pH 0.1 to pH 6.9, pH 1.0 to pH 7.0, pH 3.0 to pH 6.0, pH 2.0 to pH 8.0, pH 4.0 to pH 12.0, pH 5.0 to pH 9.0, pH 6.0 to pH 7.5, pH 6.5 to pH 8.5, or pH 7.1 to pH 8.5. The reagent may have a pH of at least about pH 0.1, pH 0.5, pH 1.0, pH 1.5, pH 2.0, pH 2.5, pH 3.0, pH 3.5, pH 4.0, pH 4.5, pH 5.0, pH 5.5, pH 6.0, pH 6.5, pH 7.0, pH 7.5, pH 8.0, pH 8.5, pH 9.0, pH 9.5, pH 10.0, pH 10.5, pH 011.0, pH 11.5, pH 12.0, pH 12.5, pH 13.0, pH 13.5, pH 13.9, or pH 14.0. The reagent may have a pH of at most about pH 0.1, pH 0.5, pH 1, pH 1.5, pH 2.0, pH 2.5, pH 3.0, pH 3.5, pH 4.0, pH 4.5, pH 5.0, pH 5.5, pH 6.0, pH 6.5, pH 7.0, pH 7.5, pH 8.0, pH 8.5, pH 9.0, pH 9.5, pH 10.0, pH 10.5, pH 11.0, pH 11.5, pH 12.0, pH 12.5, pH 13.0, pH 13.5, pH 13.9, or pH 14.0.

The reagent for releasing the collected biological sample from the sample collector can be non-toxic to cells or tissues in the form used. The reagent may not provoke an inflammatory or immune response in the individual to whom they are administered. In some cases, the reagent does not damage cell structures, lyse cells, cause nucleic acid degradation, or biological sample degradation. In some cases, the reagent damage cell structures and lyse cells to release the cell content including nucleic acids. The reagent may preserve the collected fluid released from the sample collector.

The sample collector material may absorb and retain a biological sample rapidly. The sample collector material may degrade and release the absorbed biological sample in the presence of the reagent. Degradation of the sample collector material or sample collector does not affect the quality or quantity of the biological sample. Degradation can occur over a range of seconds, minutes, hours, days, weeks, months, years, or decades. Degradation may occur within a range of time between about 0.1 to 1000, 10 to 900, 100 to 800, 200 to 600, 50 to 500, 20 to 250, 5 to 15, 1 to 2, or 0.5 to 1 hours. Degradation may occur within at most about 0.1, 0.5, 1, 2, 3, 4, 5, 6, 7, 8, 9, 10, 15, 20, 30, 40, 50, 60, 70, 80, 90, 100, 200, 500, 800, or 1000 hours. Degradation may occur within 30 seconds. Degradation may occur within 30 minutes. Degradation may occur within at least about 0.1, 0.5, 1, 2, 3, 4, 5, 6, 7, 8, 9, 10, 15, 20, 30, 40, 50, 60, 70, 80, 90, 100, 200, 500, 800, 1000, or more hours. Degradation may occur within about 0.1 to 1000, 10 to 900, 100 to 800, 200 to 600, 50 to 500, 20 to 250, 5 to 15, 1 to 2, or 0.5 to 1 years, Degradation may occur within a range of time between about 0.1 to 1000, 10 to 900, 100 to 800, 200 to 600, 50 to 500, 20 to 250, 5 to 15, 1 to 2, or 0.5 to 1 years. Degradation may occur within at most about 0.1, 0.5, 1, 2, 3, 4, 5, 6, 7, 8, 9, 10, 15, 20, 30, 40, 50, 60, 70, 80, 90, 100, 200, 500, 800, or 1000 years. Degradation may occur within at least about 0.1, 0.5, 1, 2, 3, 4, 5, 6, 7, 8, 9, 10, 15, 20, 30, 40, 50, 60, 70, 80, 90, 100, 200, 500, 800, or 1000 years.

The sample collector material may absorb and retain a biological sample rapidly. The sample collector material may dissolve and release the absorbed biological sample in the presence of the reagent. Dissolving of the sample collector material or sample collector does not affect the quality or quantity of the biological sample. Dissolving can occur over a range of seconds, minutes, hours, days, weeks, months, years, or decades. Dissolving may occur within a range of time between about 0.1 to 60, 1 to 50, 2 to 40, 3 to 30, 4 to 20, 5 to 10, 6 to 55, 7 to 45, 8 to 35, 9 to 25, 1 to 10, 2 to 9, 3 to 7, 4 to 6, 5 to 7, 6 to 8, 7 to 9, or 1 to 2 minutes. Dissolving may occur within a range of time between about 0.1 to 60, 1 to 50, 2 to 40, 3 to 30, 4 to 20, 5 to 10, 6 to 55, 7 to 45, 8 to 35, 9 to 25, 1 to 10, 2 to 9, 3 to 7, 4 to 6, 5 to 7, 6 to 8, 7 to 9, or 1 to 2 hours. Dissolving may occur within at most about 0.1, 0.5, 1, 2, 3, 4, 5, 6, 7, 8, 9, 10, 15, 20, 30, 40, 50, 60, 70, 80, 90, 100, 200, 500, 800, or 1000 minutes. Dissolving may occur within 30 seconds, Dissolving may occur within 30 minutes. Dissolving may occur within at least about 0.1, 0.5, 1, 2, 3, 4, 5, 6, 7, 8, 9, 10, 15, 20, 30, 40, 50, 60, 70, 80, 90, 100, 200, 500, 800, 1000, or more minutes. Dissolving may occur within about 0.1 to 1000, 10 to 900, 100 to 800, 200 to 600, 50 to 500, 20 to 250, 5 to 15, 1 to 2, or 0.5 to 1 days. Dissolving may occur within a range of time between about 0.1 to 1000, 10 to 900, 100 to 800, 200 to 600, 50 to 500, 20 to 250, 5 to 15, 1 to 2, or 0.5 to 1 day, Dissolving may occur within at most about 01, 0.5, 1, 2, 3, 4, 5, 6, 7, 8, 9, 10, 15, 20, 30, 40, 50, 60, 70, 80, 90, 100, 200, 500, 800, or 1000 days. Dissolving may occur within at least about 0, 1, 0.5, 1, 2, 3, 4, 5, 6, 7, 8, 9, 10, 15, 20, 30, 40, 50, 60, 70, 80, 90, 100, 200, 500, 800, or 1000 days.

The sample collector material may be temperature sensitive such that the reagent may absorb and retain the biological sample at a first temperature (or first temperature range) and dissolve or biodegrade at a different temperature (or different temperature range). As an example, the sample collector material may absorb and retain the biological sample at a temperature close to the human body temperature. The sample collector material may absorb and retain the biological sample at a temperature between about 25 to 45, 30 to 40, 34 to 39, 35 to 38, or 36 to 37° C. The sample collector material may absorb and retain the biological sample at a temperature between about 35 to 38° C. The sample collector material may dissolve or biodegrade to release the biological sample at a temperature between about 0.1 to 100, 1 to 35, 5 to 10, 15 to 25, or 20 to 30° C. The sample collector material may dissolve or biodegrade to release the biological sample at a temperature between about 15 to 30° C. The sample collector material may dissolve or biodegrade to release the biological sample at room temperature.

In some cases, the sample collector is a collection cup inserted into a body cavity. The cup can be worn internally, such as around the cervix to collect menstrual flow or cervicovaginal fluids. Non-limiting examples of collection cups are Softcup and DivaCup. The collected menstrual flow or cervicovaginal fluids can be extracted, stored, or transported using devices, methods, systems and kits disclosed herein.

In some cases, instead of being configured to be inserted into a body cavity, the sample collector is configured to collect or absorb biological samples such as cervicovaginal fluids external to the body. Non-limiting examples include a cup or receptacle (e.g., a diva cup or a funnel with a reservoir) and/or an external absorber (e.g., an absorbent pad or a reusable cloth). In some embodiments, the external sample collector is composed from the materials described herein for internal sample collectors, and soaks up fluid readily, but also compresses easily to release fluid.

Extractor

In an embodiment shown in FIGS. 3 and 4A-4C, an extraction device is included in the kit and includes a cylindrical housing or receptacle 140 in which a woman places her used sample collector 120 into the receptacle 140 via an open end 142 immediately upon removal of the sample collector from the vaginal canal. The extraction device is then sealed with a cap 144, which contains a spring-loaded compressor 146. After the extraction device is sealed, a button 148 located on the cap 144 is pressed, which releases the spring 146 and compresses the sample collector 120.

In some embodiments, a twist mechanism is employed to compress the sample collector 120. As the sample collector 120 is compressed, cervicovaginal fluid, blood, vaginal mucosa, female genital tract microbes, yeast, fungi, bacteria, or semen are squeezed out and passed through a filter 150 to remove cellular debris or mucosa that may clog the pressure valve leading to the assay cartridge. In some embodiments, the pore size of the filter 150 is about 10 microns, 25 microns, or 40 microns. In other embodiments, the diameter of the filter 150 is between about 28 mm and 30 mm. The sample collector and filter retain most of the endometrial tissue and cervicovaginal fluids. However, some of the vaginal mucosa and possibly un-clotted red blood cells are sheared through the extraction process. This shearing of vaginal mucosa allows for intracellular organisms to be passed through the filter into a sample collection reservoir 152 along with the extracted cervicovaginal fluid.

In some embodiments, a series of filters with sequentially decreasing pore size are present in the extractor. The filters collect analytes of various sizes, starting with larger analytes such as whole cells, and decreasing in size to cell fragments, organelles and macromolecules (e.g., proteins, nucleic acids, carbohydrates, lipids, etc.). The filters may be individually removable so the analytes of various sizes may be separately assayed, such as either by using the assay cartridge or by being packaged and sent to an outside lab. In some embodiments, a filter is sized to separate out sperm cells so that the sperm cells may be sent to an outside lab for DNA analysis. In some embodiments, the filters have pore sizes from about 0.01 millimeter ("mm") to 100 mm, 0.1 mm to 1 mm, 1 mm to 2 mm, 2 mm to 3 mm, 5 mm to 10 mm, or 3 mm to 30 mm, in diameter. In some embodiments, the filters have pore sizes of at least about 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, or more in diameter. In some embodiments, the filters have pore sizes of at most 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm in diameter. In some embodiments, the filters have pore sizes from about 0.01 micrometers ("microns") and 100 microns, 0.1 microns to 1 microns, 1 micron to 2 microns, 2 microns to 3 microns, 5 microns to 10 microns, or 3 microns to 30 microns, in diameter. In some embodiments, the filters have pore sizes of at least about 1 micron, 2 microns, 3 microns, 4 microns, 5 microns, 6 microns, 7 microns, 8 microns, 9 microns, 10 microns, 20 microns, 30 microns, 40 microns, 50 microns, 60 microns, 70 microns, 80 microns, 90 microns, 100 microns, or more in diameter. In some embodiments, the filters have pore sizes of at most about 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm in diameter.

In some embodiments, the serum or sample collection reservoir may be divided into two or more detachable compartments, such that each compartment can store an aliquot of a sample for storage and/or for different downstream analyses without contamination. For example, one compartment may be detached and sent to an outside lab for more detailed analysis, if needed.

Within the walls of the sample collection reservoir is a pressure valve 154 that inserts into the assay cartridge, thereby allowing for one-way passage of the extracted fluids into the assay cartridge. In some embodiments, the valve opens under a pressure of between about 1.5 pounds per square inch ("PSI") and 5 PSI. For example, the valve opens under a pressure of about 1.5 PSI, 3 PSI or 5 PSI. In some embodiments, the valve has a diameter from about 0.01 mm to 100 mm. In some embodiments, the valve has a diameter of from about 1 mm to 10 mm. In some embodiments, the valve has a diameter from about 3 mm to 5 mm. In some embodiments, the valve has a diameter of at least about 0.01 mm, 0.1 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, or more. In some embodiments, the valve has a diameter of at most about 0.01 mm, 0.1 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm.

In some embodiments, a press-lever mechanism is employed to compress the sample collector 120. In some embodiments, a manual-push mechanism is employed to compress the sample collector 120. In some embodiments, an air-tight plunger mechanism is employed to compress the sample collector 120. In some embodiments, a pressure-based mechanism is employed to compress the sample collector 120. In some embodiments, a roller-based mechanism is employed to compress the sample collector 120. In some embodiments, a compressible chamber is employed to compress the sample collector 120.

Figure 11:
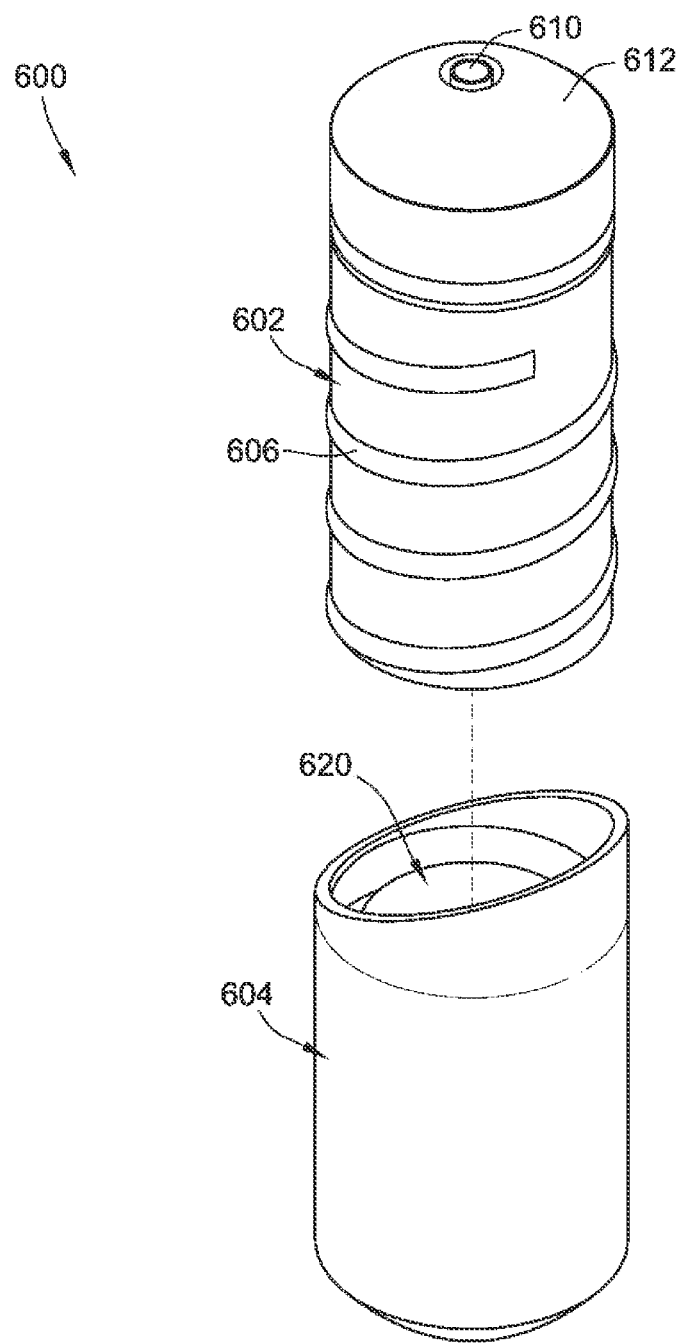
FIG. 11 is an exploded perspective view of an extractor system with an extractor top and an extractor bottom, in accordance with one exemplary embodiment.

In an embodiment shown in FIGS. 11-13, an extractor system 600 includes an extractor top 602 and an extractor bottom 604. The extractor top 602 can include an external thread 606 that is configured to threadedly engage an internal thread 608 of the extractor bottom 604 as the extractor top 602 is rotated and inserted within the extractor bottom 604. The extractor top 602 further includes a fluid port 610 centrally located along a top surface 612 via which biological fluids or other samples from within the extractor system 600 are fluidly communicated to the assay cartridge 500 (shown in FIGS. 14A-14E). In some embodiments, the fluid port comprises a luer lock valve, a one-way pressure valve, or a rubber resealable puncture slit. In some embodiments, the fluid port comprises a different valve.

The extractor system 600 has a sample receptacle 620 configured to receive a sample collector, such as the sample collector 400 illustrated in FIGS. 7A-7C. The sample receptacle 620 can include a top receptacle 622 and a bottom receptacle 624. The top receptacle 622 is within the extractor top 602 and is generally defined by top wall 624 of the extractor top 602. The bottom receptacle 624 is within the extractor bottom 604 and is generally defined by a bottom wall 626.

When a sample collector is placed within the sample receptacle 620 and the extractor top 602 is threaded within the extractor bottom 604, the resulting compressive force squeezes the sample collector causing it to release biological fluids F collected thereon. In turn, at least some of the biological fluids F are directed to flow towards the fluid port 610, passing through a filter 630 located in the extractor top 602. The filter 630 includes a plurality of pass-through holes 632 through which the fluid F exits towards the fluid port 610.

Although the above-described extractor system 600 is generally a screw-based compressor, in alternative embodiments, the extractor system can be a pressure-based compressor, a spring-loaded compressor, a roller-based compressor, a press-lever compressor, a manual push compressor, a wringing action, or an air-tight plunger compressor.

The extractor, e.g., extractor system 600, may have a roller-based mechanism to extract the collected bodily fluid. For example, the collected bodily fluid (e.g., blood, cervicovaginal fluid) may be extracted from the sample collector by squeezing it through a set of two rollers. The rollers may be free to rotate but are spaced apart in a way that applies local compression to the sample collector as it is passing through the rollers. This mechanism may be actuated by a twisting or a knob or spinning of a thumb wheel that mechanically drives the rollers. The rollers may have texture on them to engage the sample collector and move it through the rollers. As another example, the collected bodily fluid may be extracted from the sample collector through a wringing action. One side of the sample collector can be clamped and the other side can be rotated along the axis, causing the sample collector to twist on itself and release the collected bodily fluid. As yet another example, the collected bodily fluid may be extracted from the sample collector by placing the sample collector in a cylinder with an eccentric roller inside. Without being bound to any theory, rotating the eccentric roller may trap the sample collector between the inner wall of the cylinder and the eccentric roller. This mechanism may be actuated through a mechanical or electrical rotation of the roller.

The various, different mechanical configurations described herein are capable of extracting fluid from a sample collector. One or more configurations can include a compressible chamber. The filtration of the sample can include a filter of a specific pore size, a combination of filters, filter components that specifically bind hemoglobin, paper-based filters, silica filters, and/or microfluidic filters. The extractor, e.g., the extractor system 600, can include one or more buffers or reagents to dilute the sample to minimize background noise in the downstream assay, buffers or reagents with exogenous control compounds, buffers or reagents with spike-ins to normalize downstream data outputs, buffers to aid in elution of biological fluid, buffers or reagents to extract particular biological components (e.g., DNA, RNA, proteins, etc.), buffers or reagents to precipitate or otherwise remove hemoglobin or other biological components that can interfere with assay or results (e.g., $ZnSO_4$, etc.), buffers or reagents to bind and remove particular biological components, buffers to hydrolyze or dissolve the sample collector, buffers or reagents that are lyophilized, buffers that are housed in dissolvable membranes, and/or buffers or reagents that are housed in a puncturable or breakable (or pierceable) membrane. The extractor, e.g., extractor system 600, can include components that are biodegradable and/or recyclable. The extractor, e.g., extractor system 600 can have a sample outflow in which the outlet valve (e.g., the fluid port 610) has a rubber resealable puncture slit and/or a one-way pressure valve luer lock valve.

Referring to FIGS. 15A-15D, in an example, an assembled sample extraction collector 1500 comprises a top of an extractor 1505, an extractor chamber 1506 and reservoir 1510, a luer lock adaptor device 1503, and a sample collection chamber 1509. The top of the extractor 1505 is configured to have two winged features or protrusions 1501 to reduce the force needed to screw and otherwise compress the extractor. The top of the extractor chamber 1506 can have threads 1507 that are complementary to the threads (not shown) on the bottom interior of the top of the extractor 1505. The extraction collector 1500 comprises a small hole 1502 at the junction of 1506 and 1510. The small hole 1502 can be about 0.001 mm to 100 mm in diameter with a cannula fitted to the inside of the reservoir. The small hole 1502 can be about 1 mm to 10 mm in diameter. The small hole 1502 can be about 3 mm to 6 mm in diameter. The small hole 1502 can be about 1 mm to 3 mm in diameter. In some embodiments, the small hole 1502 is about 2 mm to 3 mm in diameter with a cannula fitted to the inside of the reservoir. The cannula can be plastic. The cannula can be metal. The cannula can be polypropylene. The cannula can be silicon. The small hole 1502 can relieve internal pressure of the extractor chamber 1506 and reservoir 1510 to enhance sample flow during sample extraction. The bottom of 1506 comprises a threaded fluid port 1504 for the connection to the luer lock adaptor device 1503. The sample collection chamber 1509 is inserted into the cavity of a luer lock adaptor device 1503 to collect flow through from the sample extractor. For example, a woman places her used sample collector 120 via an open end 1508 immediately upon removal from the vaginal canal. The extraction device is closed by placing the top of the extractor 1505 over the extractor chamber and reservoir 1506, and using the winged features or protrusions 1501 to twist the top of the extractor 1505 over the threads 1507 on the extraction chamber and reservoir 1506 to seal the extraction device 1500 and prevent leakage. The twisting mechanism employed on the extractor 1505 compresses the used sample 120 to release absorbed fluids to the extraction chamber and reservoir 1506. The compressing releases the absorbed fluid and cells, debris or molecules collected on the sample collector. In some embodiments, releasing the absorbed fluids involves pushing, smashing, or pulling the top of the extractor 1505 against 1506. Exemplary absorbed fluids include but are not limited to cervicovaginal fluid, blood, vaginal mucosa, female genital tract microbes, yeast, fungi, bacteria, and semen. Exemplary cells, debris and molecules include but are not limited to uterus lining cells, shed uterus cells, and shed vaginal cells. The small hole 1502 relieves internal pressure of 1506 to allow more efficient sample flow between the extractor chamber 1506 and reservoir 1510. The flow through is collected in a sample collection chamber 1509 via the threaded fluid port 1504. The sample collection chamber can be a clinical specimen collection tube, e.g., BD Vacutainer® CPT™ Mononuclear Cell Preparation Tube, BD Vacutainer® PPT™ Plasma Preparation Tube. The fluid port 1504 may be threaded for connection to a luer lock adapter device on the sample collection chamber 1509. In some embodiments, the fluid port 1504 is not threaded and has a Snap-on adaptor for connection to a device on the sample collection chamber 1509. In some cases, connecting the fluid port 1504 to the sample collection chamber 1509 involves a twist mechanism. In some cases, connecting the fluid port 1504 to the sample collection chamber 1509 involves a push mechanism. The connection of the fluid port 1504 and the sample collection chamber 1509 can prevent leakage and allow the absorbed fluid to flow from the extractor chamber 1506 to the sample collection chamber 1509. In some cases, connecting the fluid port 1504 to the sample collection chamber 1509 seals the junction between the fluid port 1504 and the sample collection chamber 1509. The sample collection chamber 1509 can be connected to the fluid port 1504 directly. The top of the extractor 1505 can be wider than the extractor chamber 1506. The top of the extractor 1505 and the extractor chamber 1506 can form a cylinder tube, a box, or a vase. In some embodiments, the top of the extractor 1505 and the extractor chamber 1506 are connected through a Snap-On device. The top of the extractor 1505 and the extractor chamber 1506 can be connected through a screw, push, or twist mechanism. The top of the extractor can have winged features or protrusions on the side for easy gripping and handling. The top of the extractor can have loops or ears on the side for easy gripping or handling. The top of the extractor can have groves or threads on the external side for easy gripping or handling.

The sample collection chamber 1509 can be in any form or material. For example, the sample collection chamber 1509 can be plastic, glass, polypropylene, silicon, or metal. The sample collection chamber 1509 can be cylindrical, rectangular, square, oval, or spherical. The sample collection chamber 1509 can be a tube, a vail, a vase, or a cup. The inner side of the sample collection chamber 1509 can be silicone coated. The sample collection chamber 1509 can be a BD™ P100 Blood Collection System, BD™ P800 Blood Collection System, PAXgene® Blood RNA Tube, or PAXgene® Blood DNA Tube.

The sample collection chamber 1509 may contain a preservation housing buffer or reagent for storage and transportation of the sample. The housing buffer or reagent may dissolve the sample collector to release the collected fluid, cells or tissues. In some cases, the housing buffer or reagent dissolves the sample collector in response to pH change, e.g., an increase or a decrease of pH in the housing buffer or reagent. In some cases, the housing buffer or reagent dissolves the sample collector in response to temperature change, e.g., an increase or a decrease of temperature in the housing buffer or reagent. The housing buffer or reagent can comprise blood anti-coagulants, buffer and sample preservatives for downstream analysis. Non-limiting examples of housing buffer or reagent and sample preservatives include silica gels, silica beads, buffered citrate, sodium fluoride, potassium oxalate, sodium heparin, inert polymer gel, lithium heparin silica clot activator, EDTA (K2), acid citrate dextrose solution (ACD A), and acid citrate dextrose solution (ACD B). The housing buffer or reagent may comprise silica gels or beads. The housing buffer or reagent may comprise dyes, fluorescent beads, cooling agents, DNA extraction reagents, RNA extraction reagents, protein extraction reagents, and antibodies. The sample collection chamber 1509 may contain silica gels or beads, or a combination thereof that may come into direct contact with the sample collector 120 or menstrual sample fluid to allow rapid adsorption of biomolecules. The silica gels, or beads, or a combination thereof can allow the filtered components to be extracted for downstream analysis. The silica gels and beads can enhance absorption of biomolecules from the sample collector. The silica gels and beads can enhance extraction of biomolecules from the sample collector. The silica gels, or beads, or a combination thereof may be stored in the sample collection chamber 1509. The silica gels, or beads, or a combination thereof may be stored in the extractor chamber 1506. The silica gels, or beads, or a combination thereof may be stored in the extractor chamber 1506 and the sample collection chamber 1509.

The sample collection chamber 1502 may have a diameter from about 0.01 mm to 100 mm. The sample collection chamber 1502 may have a diameter from about 1 mm to 10 mm. The sample collection chamber 1502 may have a diameter from about 3 mm to 5 mm. The sample collection chamber 1502 may have a diameter of at least about 0.01 mm, 0.1 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, or more. The sample collection chamber 1502 may have a diameter of at most about 0.01 mm, 0.1 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm.

In an example, FIGS. 16A-16D show a sample storage device comprising a cylindrical top 1601 and receptacle 1602. The receptacle 1602 has threads 1603 on the exterior, which are complementary to threads (not shown) on the interior of the top 1601. The top of the storage device 1601 comprises a top interior reservoir 1604 for a preservation housing buffer or wash buffer. The bottom of the top interior reservoir 1604 is covered with a breakable membrane 1605 that breaks to release the preservation housing buffer or wash buffer upon closure of the storage device. The receptacle 1602 comprises an internal retention wall 1606 that punctures the breakable membrane 1605 upon closure of the storage device. The receptacle 1602 further comprises a receptacle internal reservoir 1607 to house a sample collector, e.g., sample collector 120, for transportation and storage. The top of the storage device 1601 further comprises an internal O-ring 1608 to ensure proper sealing and prevent sample leakage during storage or transportation. For example, a woman places her used sample collector 120 via an open end 1609 into the receptacle internal reservoir 1607 immediately upon removal from the vaginal canal. The storage device is closed by placing the top 1601 over the receptacle 1602, and by twisting the top 1601 over the threads 1603 to seal the storage device. The twist mechanism on the top 1601 closes the storage device and brings the internal retention wall 1606 in contact with the top interior reservoir 1604 to puncture and break the breakable membrane 1605. Upon breakage of the breakable membrane 1605, preservation housing buffer or reagent or washing buffer stored in the top interior reservoir 1604 is released to the receptacle internal reservoir 1607, where the sample is stored. The sample storage device can be transported off-site for downstream analysis. For example, the sample storage device can be shipped to a clinical laboratory for downstream processing, molecular analysis, genetics analysis, or pathological analysis.

The sample storage device may contain a preservation housing buffer or reagent or washing buffer for storage and transportation of the sample. The housing buffer or reagent can comprise blood anti-coagulants, buffers and sample preservatives for downstream analysis. Non-limiting examples of housing buffers or reagents and sample preservatives include silica gels, silica beads, buffered citrate, sodium fluoride, potassium oxalate, sodium heparin, inert polymer gel, lithium heparin silica clot activator, EDTA (K2), acid citrate dextrose solution (ACD A), and acid citrate dextrose solution (ACD B). The housing buffer or reagent may comprise dyes, fluorescent beads, cooling agents, and antibodies. The housing buffers or reagents may comprise silica gels or beads. The sample storage device may contain silica gels or beads, or a combination thereof within the compartments that may come into direct contact with the sample collector 120 or menstrual sample fluid to allow rapid adsorption of biomolecules. The silica gels, or beads, or a combination thereof can allow the filtered components to be extracted for downstream analysis. The silica gels and beads can enhance absorption of biomolecules from the sample collector. The silica gels and beads can enhance extraction of biomolecules from the sample collector. The silica gels, or beads, or a combination thereof may be stored in the top interior reservoir 1604. The silica gels, or beads, or a combination thereof may be stored in the receptacle internal reservoir 1607. The silica gels, or beads, or a combination thereof may be stored in both the top interior 1604 and the receptacle internal reservoir 1607. The inner sides of the top internal reservoir 1604 and the receptacle internal reservoir 1607 can be silicone coated.

The storage device can store biological samples and absorbed fluids without degradation over a long period of time. The storage device can store and preserve the sample and absorbed fluids for at least about 1 day, 2 days, 3 days, 4 days, 5 days, 6 days, 7 days, 8 days, 9 days, 10 days, 15 days, 30 days, 2 months, 3 months, 6 months, 12 months, 2 years, 5 years, 10 years, or longer. In some cases, the storage device can store and preserve a sample and absorbed fluids for more than 1 day. In some cases, the storage device can store and preserve the sample and absorbed fluids for more than 1 month. In some cases, the storage device can store and preserve the sample and absorbed fluids for more than 1 year. The storage device can be kept or transported at room temperature. The storage device can be kept in a temperature regulator to keep the temperature desirable for the sample and absorbed fluids. Exemplary temperature regulators include but are not limited to refrigerator, dry ice, and liquid nitrogen. The storage device can comprise a thermal insulating layer to keep a desirable internal temperature to prevent degradation of the sample and absorbed fluids. Exemplary thermal insulators include but are not limited to glass wool, cellulose, rock wool, polystyrene foam (e.g., Styrofoam), urethane foam, vermiculite, perlite, and cork.

Figure 18:
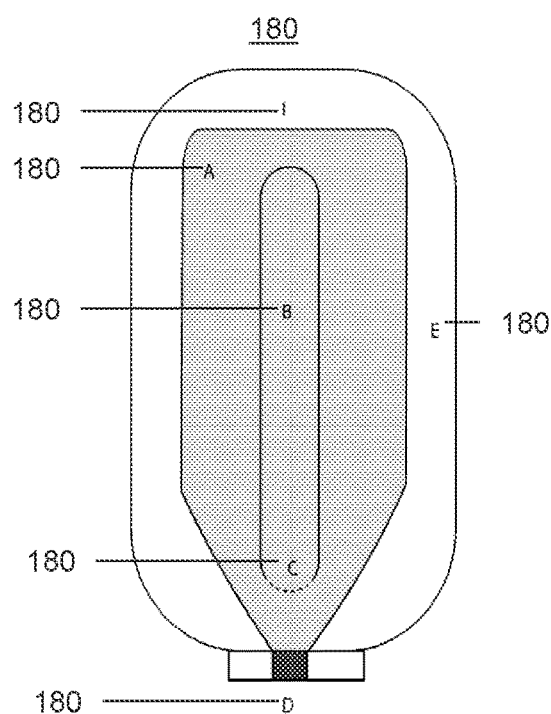
FIG. 18 shows a side view of an extractor comprising one chamber.

Referring to FIG. 18, in an example, an assembled sample extraction collector 1800 comprises an opening of the extractor 1801, an extractor chamber 1802, a reagent compartment or fluid reservoir 1803, a clam shell pressure unit 1804, a pressure breakable seal 1805, and a docking unit 1806. The clam shell mechanism 1804 may surround and enclose the extraction chamber 1802. The clam shell pressure unit 1804 may have an opening that allows, for example, a sample collector 120 for entering the extractor chamber 1802. The clam shell pressure unit 1804 may have a hinge that allows opening and/or closing of the clam shell pressure unit 1804. The clam shell pressure unit 1804 can be elastic. The extraction chamber 1802 can be elastic. The reagent compartment or fluid reservoir 1803 can be elastic. The clam shell pressure unit 1804 can be squeezable. The clam shell pressure unit 1804 can be solid. The clam shell pressure unit 1804 can be a compression element. Closing of the clam shell pressure unit 1804 may generate a compression force or pressure that moves towards the extractor chamber 1802 and the reagent compartment or fluid reservoir 1803. Closing of the clam shell pressure unit 1804 may generate a compression force or pressure that breaks the pressure breakable seal 1805 to release any reagent or fluid stored in the reagent compartment or fluid reservoir 1803. Closing of the clam shell pressure unit 1804 may generate a compression force or pressure that squeezes a sample collector 120 to release a biological sample retained in the sample collector 120. The reagent compartment or fluid reservoir 1803 can contain a reagent, fluid, solution, or buffer for hydrating the sample collector. The reagent compartment or fluid reservoir 1803 can be attached to the inner wall of the first extraction chamber 1802. The reagent compartment or fluid reservoir 1803 can be suspended inside the first extraction chamber 1802. The reagent compartment or fluid reservoir 1803 can contain a reagent, fluid, solution, or buffer that accelerates, facilitates, or enhances the release of biological sample from the sample collector 120. The reagent compartment or fluid reservoir 1803 can contain a reagent, fluid, solution, or buffer for dissolving the sample collector 120 and releasing any biological samples from the sample collector 120. The released biological sample and reagent, fluid, solution, or buffer released from the reagent compartment or fluid reservoir 1803 can form a mixture of solution comprising the biological sample and the reagent, fluid, solution, or buffer, which can be collected in a sample collection tube via a docking unit 1806. The docking unit can comprise a luer lock adaptor, a one-way pressure valve, a resealable slit, or a cannula. The cannula can be plastic. The cannula can be metal. The cannula can be polypropylene. The cannula can be silicon. The docking unit comprises a docking mechanism for a sample collection chamber that can be inserted into the cavity of a luer lock adaptor to collect flow through from the sample extractor. For example, a woman places her used sample collector 120 via an opening 1802 upon removal from the vaginal canal. The extraction device is closed by the clam shell pressure unit, such as by applying a clam shell pressure mechanism to generate an inward movement of the extraction chamber 1802 and the reagent compartment or fluid reservoir 1803. The clam shell pressure mechanism employed on the clam shell pressure unit 1804 compresses both the used sample collector 120 to release any biological sample to the extraction chamber 1802, and the reagent compartment or fluid reservoir 1803 to release any reagent, fluid, solution or buffer from the reagent compartment or fluid reservoir into the extraction chamber 1802, thereby bringing the sample collector 120 and the released biological sample into contact with the reagent, fluid, solution or buffer to form a mixture of biological sample and reagent, fluid, solution or buffer. The compressing can release the absorbed fluid and cells, debris or molecules on the sample collector. In some embodiments, releasing the absorbed fluids involves squeezing or pressing the clam shell pressure unit toward the extraction chamber 1802 and the reagent compartment or fluid reservoir 1803. Exemplary absorbed fluids include but are not limited to cervicovaginal fluid, blood, vaginal mucosa, cervicovaginal cells, female genital tract microbes, yeast, fungi, bacteria, and semen. Exemplary cells, debris and molecules include but are not limited to uterus lining cells, shed uterus cells, and shed vaginal cells. The flow through is collected in a sample collection chamber via the docking unit. The sample collection chamber can be a clinical specimen collection tube, a vacutainer, e.g., BD Vacutainer® CPT™ Mononuclear Cell Preparation Tube, BD Vacutainer® PPT™ Plasma Preparation Tube.

The sample collection chamber can be in any shape, form or material. For example, the sample collection chamber can be plastic, glass, polypropylene, silicon, or metal. The sample collection chamber can be cylindrical, rectangular, square, oval, or spherical. The sample collection chamber can be a tube, a vail, a vase, or a cup. The inner side of the sample collection chamber can be silicone coated. The sample collection chamber can be a BD™ P100 Blood Collection System, BD™ P800 Blood Collection System, PAXgene® Blood RNA Tube, or PAXgene® Blood DNA Tube.

The sample collection chamber may contain a preservation housing buffer or reagent for storage and transportation of the sample. The housing buffer or reagent may dissolve the sample collector to release the collected fluid, cells or tissues. In some cases, the housing buffer or reagent dissolves the sample collector in response to pH change, e.g., an increase or a decrease of pH in the housing buffer or reagent. In some cases, the housing buffer or reagent dissolves the sample collector in response to temperature change, e.g., an increase or a decrease of temperature in the housing buffer or reagent. The housing buffer or reagent can comprise blood anti-coagulants, buffers and sample preservatives for downstream analysis. Non-limiting examples of housing buffers or reagents and sample preservatives include silica gels, silica beads, buffered citrate, sodium fluoride, potassium oxalate, sodium heparin, inert polymer gel, lithium heparin silica clot activator, EDTA (K2), acid citrate dextrose solution (ACD A), and acid citrate dextrose solution (ACD B). The housing buffer or reagent may comprise silica gels or beads. The housing buffer or reagent may comprise dyes, fluorescent beads, cooling agents, DNA extraction reagents, RNA extraction reagents, protein extraction reagents, and antibodies. The sample collection chamber may contain silica gels or beads, or a combination thereof that may come into direct contact with the sample collector 120 or menstrual sample fluid to allow rapid adsorption of biomolecules. The silica gels, or beads, or a combination thereof can allow the filtered components to be extracted for downstream analysis. The silica gels and beads can enhance absorption of biomolecules from the sample collector. The silica gels and beads can enhance extraction of biomolecules from the sample collector. The silica gels, or beads, or a combination thereof may be stored in the sample collection chamber.

Figure 19:
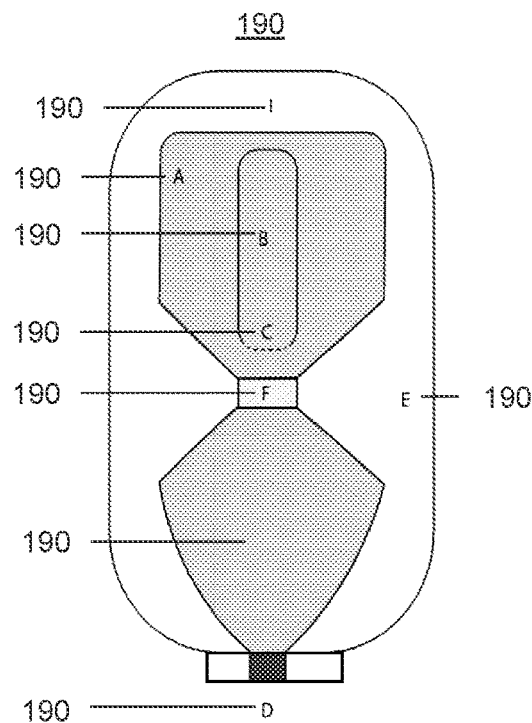
FIG. 19 shows a side view of an extractor comprising two chambers.

Referring to FIG. 19, in an example, an assembled sample extraction collector 1900 comprises an opening of the extractor 1901, a first extractor chamber 1902, a reagent compartment or fluid reservoir 1903, a clam shell pressure unit 1904, a pressure breakable seal 1905, a one-way pressure valve 1906, a second extraction chamber 1907, and a docking unit 1908. The clam shell pressure unit 1904 may surround and enclose the extraction chamber 1902. The clam shell pressure unit 1904 may have an opening that allows, for example, a sample collector 120 for entering the first extractor chamber 1902. The clam shell pressure unit 1904 may have a hinge that allows opening and/or closing of the clam shell pressure unit 1904. The clam shell pressure unit 1904 can be elastic. The extraction chamber 1902 can be elastic. The reagent compartment or fluid reservoir 1903 can be elastic. The clam shell pressure unit 1904 can be squeezable. The clam shell pressure unit 1904 can be solid. The clam shell pressure unit 1904 can be a compression element. Closing of the clam shell pressure unit 1904 may generate a compression force or pressure that moves towards the first extractor chamber 1902 and the reagent compartment or fluid reservoir 1903. Closing of the clam shell pressure unit 1904 may generate a compression force or pressure that breaks the pressure breakable seal 1905 to release any reagent or fluid stored in the reagent compartment or fluid reservoir 1903. Closing of the clam shell pressure unit 1904 may generate a compression force or pressure that squeezes a sample collector 120 to release a biological sample retained in the sample collector 120. The reagent compartment or fluid reservoir 1903 can be attached to the inner wall of the first extraction chamber 1902. The reagent compartment or fluid reservoir 1903 can be suspended inside the first extraction chamber 1902. The reagent compartment or fluid reservoir 1903 can contain a reagent, fluid, solution, or buffer for hydrating the sample collector. The reagent compartment or fluid reservoir 1903 can contain a reagent, fluid, solution, or buffer that accelerates, facilitates, or enhances the release of biological sample from the sample collector 120. The reagent compartment or fluid reservoir 1903 can contain a reagent, fluid, solution, or buffer for dissolving the sample collector 120 and releasing any biological samples from the sample collector 120. The released biological sample and reagent, fluid, solution, or buffer released from the reagent compartment or fluid reservoir 1903 can form a mixture of solution comprising the biological sample and the reagent, fluid, solution, or buffer, which can be collected in a sample collection tube via a docking unit 1908. The device can further comprise a second extraction chamber 1907, wherein the first extraction chamber 1902 and the second extraction chamber 1907 are connected via a one-way pressure valve 1906. The one-way pressure valve 1906 may have a diameter from about 0.01 mm to 100 mm. The one-way pressure valve 1906 may have a diameter from about 1 mm to 10 mm. The one-way pressure valve 1906 may have a diameter from about 3 mm to 5 mm. The one-way pressure valve 1906 may have a diameter of at least about 0.01 mm, 0.1 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, or more. The sample collection chamber 1502 may have a diameter of at most about 0.01 mm, 0.1 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. The docking unit 1908 can comprise a luer lock adaptor, a one-way pressure valve, a resealable slit, or cannula. The cannula can be plastic. The cannula can be metal. The cannula can be polypropylene. The cannula can be silicon. The docking unit comprises a docking mechanism for a sample collection chamber inserted into the cavity of a luer lock adaptor to collect flow through from the sample extractor. For example, a woman places her used sample collector 120 into a sample receptacle via an opening 1902 upon removal from the vaginal canal. The extraction device is closed by the clam shell pressure unit, such as by applying a clam shell pressure mechanism to generate an inward movement of the extraction chamber 1902 and the reagent compartment or fluid reservoir 1903. The clam shell pressure mechanism employed on the clam shell pressure unit 1904 compresses both the used sample collector 120 to release any biological sample to the extraction chamber 1902, and the reagent compartment or fluid reservoir 1903 to release any reagent, fluid, solution or buffer from the reagent compartment or fluid reservoir into the extraction chamber 1902, thereby bringing the sample collector 120 and the released biological sample into contact with the reagent, fluid, solution or buffer to form a mixture of biological sample and reagent, fluid, solution or buffer. The compressing releases the absorbed fluid and cells, debris or molecules on the sample collector. In some embodiments, releasing the absorbed fluids involves squeezing or pressing the clam shell pressure unit toward the extraction chamber 1902 and the reagent compartment or fluid reservoir 1903. In some embodiments, the one-way pressure valve allows the mixture of biological sample and reagent, fluid, solution or buffer, but not debris or particles from the sample collector 120, to flow through into the second extraction chamber 1907. Exemplary absorbed fluids include but are not limited to at least one of cervicovaginal fluid, blood, vaginal mucosa, cervicovaginal cells, female genital tract microbes, yeast, fungi, bacteria, and semen. Exemplary cells, debris and molecules include but are not limited to uterus lining cells, shed uterus cells, and shed vaginal cells. The flow through is collected in a sample collection chamber via the docking unit. The sample collection chamber can be a clinical specimen collection tube, a vacutainer, e.g., BD Vacutainer® CPT™ Mononuclear Cell Preparation Tube, BD Vacutainer® PPT™ Plasma Preparation Tube.

The sample collection chamber can be in any form or material. For example, the sample collection chamber can be plastic, glass, polypropylene, silicon, or metal. The sample collection chamber can be cylindrical, rectangular, square, oval, or spherical. The sample collection chamber can be a tube, a vail, a vase, or a cup. The inner side of the sample collection chamber can be silicone coated. The sample collection chamber can be a BD™ P100 Blood Collection System, BD™ P800 Blood Collection System, PAXgene® Blood RNA Tube, or PAXgene® Blood DNA Tube.

The sample collection chamber may contain a preservation housing buffer or reagent for storage and transportation of the sample. The housing buffer or reagent may dissolve the sample collector to release the collected fluid, cells or tissues. In some cases, the housing buffer or reagent can dissolve the sample collector in response to pH change, e.g., an increase or a decrease of pH in the housing buffer or reagent. In some cases, the housing buffer or reagent can dissolve the sample collector in response to temperature change, e.g., an increase or a decrease of temperature in the housing buffer or reagent. The housing buffer or reagent can comprise blood anti-coagulants, buffer and sample preservatives for downstream analysis. Non-limiting examples of housing buffers or reagents and sample preservatives include silica gels, silica beads, buffered citrate, sodium fluoride, potassium oxalate, sodium heparin, inert polymer gel, lithium heparin silica clot activator, EDTA (K2), acid citrate dextrose solution (ACD A), and acid citrate dextrose solution (ACD B). The housing buffer or reagent may comprise silica gels or beads. The housing buffer or reagent may comprise dyes, fluorescent beads, cooling agents, DNA extraction reagents, RNA extraction reagents, protein extraction reagents, and antibodies. The sample collection chamber may contain silica gels or beads, or a combination thereof that may come into direct contact with the sample collector 120 or menstrual sample fluid to allow rapid adsorption of biomolecules. The silica gels, or beads, or a combination thereof can allow the filtered components to be extracted for downstream analysis. The silica gels and beads can enhance absorption of biomolecules from the sample collector. The silica gels and beads can enhance extraction of biomolecules from the sample collector. The silica gels, or beads, or a combination thereof may be stored in the sample collection chamber.

Figure 20:
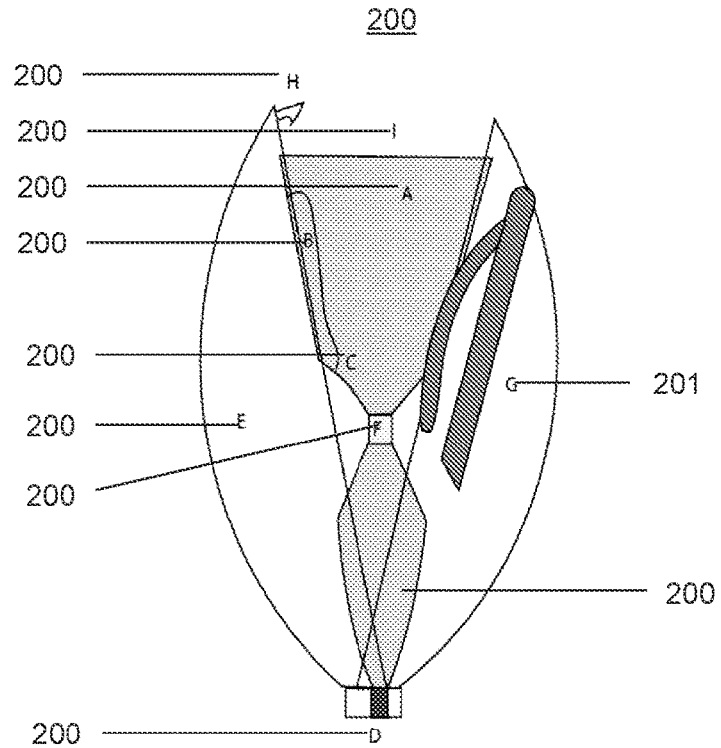
FIG. 20 shows a side view of an extractor comprising two chambers with a living spring.

Referring to FIG. 20, in an example, an assembled sample extraction collector 2000 comprises an opening of the extractor 2001, a first extractor chamber 2002, a reagent compartment or fluid reservoir 2003, a clam shell pressure unit 2004, a pressure breakable seal 2005, a one-way pressure valve 2006, a second extraction chamber 2007, a docking unit 2008, a locking clasp 2009, and a living spring 2010. The clam shell pressure unit 2004 may surround and enclose the extraction chamber 2002. The clam shell pressure unit 2004 may have an opening that allows a sample collector 120 for entering the first extractor chamber 2002. The clam shell pressure unit 2004 may have a hinge that allows opening and/or closing of the clam shell pressure unit 2004. The claim shell pressure unit can comprise a locking clasp for locking and sealing the first extraction chamber 2002 and the second extraction chamber 2007. The clam shell pressure unit can comprise a living spring that upon activation exerts a compression force onto the first extraction chamber 2002 and the reagent compartment or fluid reservoir 2003. The clam shell pressure unit 2004 can be elastic. The extraction chamber 2002 can be elastic. The reagent compartment or fluid reservoir 2003 can be elastic. The clam shell pressure unit 2004 can be squeezable. The clam shell pressure unit 2004 can be solid. The clam shell pressure unit 2004 can be a compression element. Closing of the clam shell pressure unit 2004 may generate a compression force or pressure that moves towards the first extractor chamber 2002 and the reagent compartment or fluid reservoir 2003. Closing of the clam shell pressure unit 2004 may generate a compression force or pressure that breaks the pressure breakable seal 2005 to release any reagent or fluid stored in the reagent compartment or fluid reservoir 2003. Closing of the clam shell pressure unit 2004 may generate a compression force or pressure that squeezes, for example, a sample collector 120, to release a biological sample retained in the sample collector 120. The reagent compartment or fluid reservoir 2003 can be attached to the inner wall of the first extraction chamber 2002. The reagent compartment or fluid reservoir 2003 can be suspended inside the first extraction chamber 2002. The reagent compartment or fluid reservoir 2003 can contain a reagent, fluid, solution, or buffer for hydrating the sample collector. The reagent compartment or fluid reservoir 2003 can contain a reagent, fluid, solution, or buffer that accelerates, facilitates, or enhances the release of the biological sample from the sample collector 120. The reagent compartment or fluid reservoir 2003 can contain a reagent, fluid, solution, or buffer for dissolving the sample collector 120 and releasing any biological samples from the sample collector 120. The released biological sample and reagent, fluid, solution, or buffer released from the reagent compartment or fluid reservoir 2003 can form a mixture of solution comprising the biological sample and the reagent, fluid, solution, or buffer, which can be collected in a sample collection tube via a docking unit 2008. The device further comprises a second extraction chamber 2007, wherein the first extraction chamber 2002 and the second extraction chamber 2007 is connected via a one-way pressure valve 2006. The one-way pressure valve 2006 may have a diameter from about 0.01 mm to 100 mm. The one-way pressure valve 2006 may have a diameter from 1 mm to 10 mm. The one-way pressure valve 2006 may have a diameter from about 3 mm to 5 mm. The one-way pressure valve 2006 may have a diameter of at least about 0.01 mm, 0.1 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, or more. The sample collection chamber 1502 may have a diameter of at most about 0.01 mm, 0.1 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. The docking unit 2008 can comprise a luer lock adaptor, a one-way pressure valve, a resealable slit, or cannula. The cannula can be plastic. The cannula can be metal. The cannula can be polypropylene. The cannula can be silicon. The docking unit comprises a docking mechanism for a sample collection chamber inserted into the cavity of a luer lock adaptor to collect flow through from the sample extractor. For example, a woman places her used sample collector 120 via an opening 2002 upon removal from the vaginal canal. She then closes and seals the clam shell pressure unit 2004 by locking the locking clasp 2009. Next, she applies a compression pressure by squeezing on living spring 2010 residing on the upper half of the clam shell pressure unit 2004. Closing of the clam shell pressure unit generates a clam shell pressure mechanism and an inward movement of the extraction chamber 2002 and the reagent compartment or fluid reservoir 2003. The clam shell pressure mechanism employed on 2004 compresses both the used sample collector 120 to release any biological sample to the extraction chamber 2002, and the reagent compartment or fluid reservoir 2003 to release any reagent, fluid, solution or buffer from the reagent compartment or fluid reservoir into the extraction chamber 2002, thereby bringing the sample collector 120 and the released biological sample into contact with the reagent, fluid, solution or buffer to form a mixture of biological sample and reagent, fluid, solution or buffer. The compressing releases the absorbed fluid and cells, debris or molecules on the sample collector. In some embodiments, releasing the absorbed fluids involves squeezing or pressing the clam shell pressure unit toward the extraction chamber 2002 and the reagent compartment or fluid reservoir 2003. In some embodiments, the one-way pressure valve allows the mixture of biological sample and reagent, fluid, solution or buffer, but not debris or particles from the sample collector 120, to flow through into the second extraction chamber 2007. Exemplary absorbed fluids include but are not limited to cervicovaginal fluid, blood, vaginal mucosa, cervicovaginal cells, female genital tract microbes, yeast, fungi, bacteria, and semen. Exemplary cells, debris and molecules include but are not limited to uterus lining cells, shed uterus cells, and shed vaginal cells. The flow through is collected in a sample collection chamber via the docking unit. The sample collection chamber can be a clinical specimen collection tube, a vacutainer, e.g., BD Vacutainer® CPT™ Mononuclear Cell Preparation Tube, BD Vacutainer® PPT™ Plasma Preparation Tube.

The sample collection chamber can be in any form or material. For example, the sample collection chamber can be plastic, glass, polypropylene, silicon, or metal. The sample collection chamber can be cylindrical, rectangular, square, oval, or spherical. The sample collection chamber can be a tube, a vail, a vase, or a cup. The inner side of the sample collection chamber can be silicone coated. The sample collection chamber can be a BD™ P100 Blood Collection System, BD™ P800 Blood Collection System, PAXgene® Blood RNA Tube, or PAXgene® Blood DNA Tube.

The sample collection chamber may contain a preservation housing buffer or reagent for storage and transportation of the sample. The housing buffer or reagent may dissolve the sample collector to release the collected fluid, cells or tissues. In some cases, the housing buffer or reagent dissolves the sample collector in response to pH change, e.g., an increase or a decrease of pH in the housing buffer or reagent. In some cases, the housing buffer or reagent dissolves the sample collector in response to temperature change, e.g., an increase or a decrease of temperature in the housing buffer or reagent. The housing buffer or reagent can comprise blood anti-coagulants, buffers and sample preservatives for downstream analysis. Non-limiting examples of housing buffers or reagents and sample preservatives include silica gels, silica beads, buffered citrate, sodium fluoride, potassium oxalate, sodium heparin, inert polymer gel, lithium heparin silica clot activator, EDTA (K2), acid citrate dextrose solution (ACD A), and acid citrate dextrose solution (ACD B). The housing buffer or reagent may comprise silica gels or beads. The housing buffer or reagent may comprise dyes, fluorescent beads, cooling agents, DNA extraction reagents, RNA extraction reagents, protein extraction reagents, and antibodies. The sample collection chamber may contain silica gels or beads, or a combination thereof that may come into direct contact with the sample collector 120 or menstrual sample fluid to allow rapid adsorption of biomolecules. The silica gels, or beads, or a combination thereof can allow the filtered components to be extracted for downstream analysis. The silica gels and beads can enhance absorption of biomolecules from the sample collector. The silica gels and beads can enhance extraction of biomolecules from the sample collector. The silica gels, or beads, or a combination thereof may be stored in the sample collection chamber.

Figure 21:
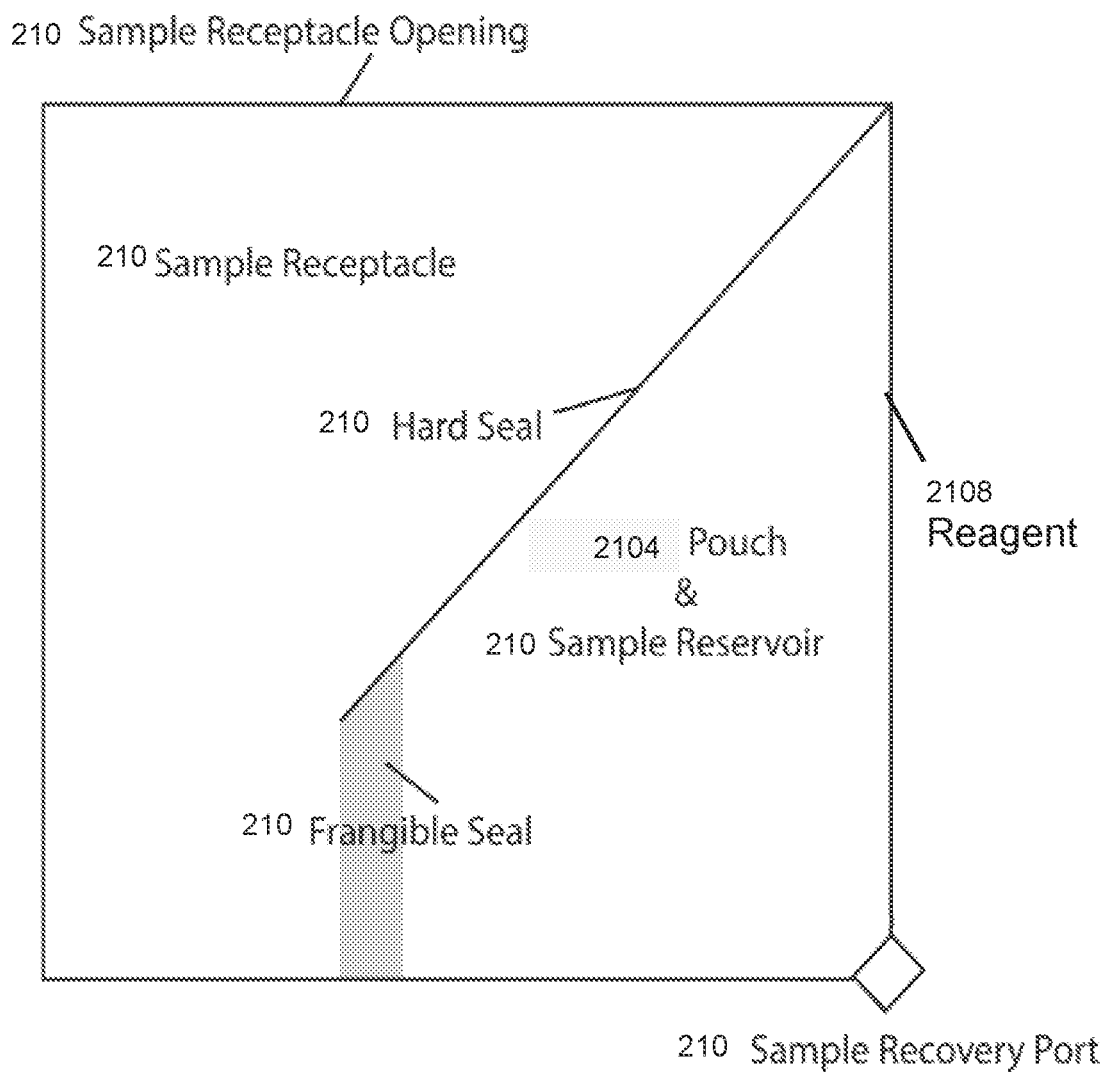
FIG. 21 depicts a pouch with a frangible seal and a hard seal.

Referring to FIG. 21, in an example, an assembled sample extraction collector 2100 comprises a sample receptacle opening 2101, a sample extraction receptacle 2102, a hard seal 2103, a pouch 2104, a sample reservoir 2105, a frangible seal 2106, and a sample recovery port 2107. The sample receptacle opening 2101 may have an open position and a closed position. The sample receptacle opening 2101 may comprise a lid, a cover, a stopper, a seal, and/or other mechanism to open and/or close the opening. In some cases, the sample receptacle opening 2101 may initially be in an open position. For example, the sample collector (e.g., used tampon) can be placed in the sample receptacle 2102 within the sample extraction collector 2100 through the open sample receptacle opening 2101. After the sample collector has been placed in the sample receptacle 2102, the opening can be placed in a closed position. When closed, the sample receptacle opening 2101 can prevent any leaking of the biological sample from the opening and/or the extraction collector 2100. The sample receptacle opening 2101 may be sealable and/or resealable. The sample receptacle opening 2101 may comprise a magnetic seal, a snap seal, and/or a zipper. In some cases, the sample receptacle opening 2101 may be sealable only once (e.g., permanently, such as via adhesives). For example, after the first seal, the sample collector (e.g., used tampon) may be recovered from the sample extraction collector 2100 only by permanently tearing and/or otherwise damaging at least a part of the sample extraction collector 2100. In some instances, signs of damage to the extraction collector 2100 can be indicative of compromise to the sample collector and/or the biological sample collected thereon.

The pouch 2104 and the sample reservoir 2105 may be located in the same compartment, and may be collectively referred to as a reagent compartment 2108. The sample receptacle 2102 and the reagent compartment 2108 may be adjacent to one another. The sample receptacle 2102 and the reagent compartment 2108 may be connected. The sample receptacle 2102 and the reagent compartment 2108 may share at least a part of their boundaries. The sample receptacle 2102 and the reagent compartment 2108 may be configured to allow fluid communication between the sample receptacle 2102 and the reagent compartment 2108 under certain conditions (e.g., broken seal, pierced seal, etc.). The sample receptacle 2102 and the reagent compartment 2108 may initially be fluidically isolated from each other via the hard seal 2103 and/or the frangible seal 2106. The sample receptacle 2102 and the reagent compartment 2108 may be separated. The sample receptacle 2102 and the reagent compartment 2108 may be separated by a hard seal 2103. Alternatively or in addition, the sample receptacle 2102 and the reagent compartment 2108 may be separated by a frangible seal 2106. The hard seal 2103 can be a hermetic seal. The frangible seal 2106 can be a hermetic seal. For example, the sample receptacle 2102 and the reagent compartment 2108 may be separated by both a hard seal 2103 and a frangible seal 2106. The hard seal 2103 can be adjacent to the frangible seal 2106 such that any shared boundary of the sample receptacle 2102 and the reagent compartment 2108 is either the hard seal 2103 or the frangible seal 2106 but not both. Alternatively, the hard seal 2103 can be adjacent to the frangible seal 2106 such that at least a part of the shared boundaries of the sample receptacle 2102 and the reagent compartment 2108 can be both the hard seal 2103 and the frangible seal 2106 layered on top of each other.

The hard seal 2103 may be flexible and movable in any direction in response to an external compression force or pressure applied to the sample extraction collector 2100. Alternatively, the hard seal 2103 may be not flexible and not movable. In some embodiments, the hard seal 2103 can be a hermatic seal. No fluid may pass through the hard seal 2103. For example, fluid may not communicate between the sample receptacles 2102 and the reagent compartment 2108 via the hard seal 2103. The frangible seal 2106 may be brittle, breakable, or fragile. The frangible seal 2106 may be breakable in response to a pressure force, compression force, vibration, shaking, or motion that applies a pressure or force onto the frangible seal 2106. For example, the frangible seal 2106 can be breakable in response to squeezing, rotating, pressing, pulling, pushing, or centrifuging. In some instances, the frangible seal 2106 can be breakable by a relatively weak pressure, such as manually squeezing the reagent compartment 2108 and/or the sample receptacle 2102 compartment between two or more fingers. In other instances, the frangible seal can be breakable by a relatively strong pressure that requires aid of a tool and/or a machine. The frangible seal may not be resealable upon breaking. No fluid may pass through the frangible seal 2106 before the seal is broken. Fluid may pass through the frangible seal 2106 when the seal is broken, such as to allow fluid communication between the sample receptacle 2102 and the reagent compartment 2108.

The frangible seal 2106 may further comprise a membrane and/or a filter. Alternatively, the sample extraction collector 2100 may comprise a separate membrane and/or filter adjacent to the frangible seal 2106, such that any fluid passing through the frangible seal 2106 may also pass through the membrane and/or filter. The membrane and/or filter may have pore sizes from about 0.01 millimeter ("mm") to 100 mm, 0.1 mm to 1 mm, 1 mm to 2 mm, 2 mm to 3 mm, 5 mm to 10 mm, or 3 mm to 30 mm, in diameter. In some embodiments, the filters have pore sizes of at least 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, or more in diameter. In some embodiments, the filters have pore sizes of at most about 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm in diameter. In some embodiments, the membrane and/or filter has pore sizes from about 0.01 micrometers ("microns") and 100 microns, 0.1 microns to 1 microns, 1 micron to 2 microns, 2 microns to 3 microns, 5 microns to 10 microns, or 3 microns to 30 microns, in diameter. In some embodiments, the membrane and/or filter has pore sizes of at least about 1 micron, 2 microns, 3 microns, 4 microns, 5 microns, 6 microns, 7 microns, 8 microns, 9 microns, 10 microns, 20 microns, 30 microns, 40 microns, 50 microns, 60 microns, 70 microns, 80 microns, 90 microns, 100 microns, or more in diameter. In some embodiments, the membrane and/or filter have pore sizes of at most about 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm in diameter.

The sample receptacle 2102 may contain a buffer, a solution, or reagent for preserving, hydrolyzing, or analyzing the biological sample, and/or for facilitating release of the biological sample from the sample collector. Alternatively and in a preferred embodiment, the sample receptacle 2102 may not contain a buffer or reagent. The pouch 2104 and/or the sample reservoir 2105 (e.g., collectively, reagent compartment 2108) may contain a buffer, a solution, or reagent for preserving, hydrolyzing, or analyzing the biological sample, and/or for facilitating, accelerating, or enhancing the release of the biological sample from the sample collector. The pouch 2104 may comprise a breakable membrane, such as the frangible seal 2106. Alternatively, the pouch 2104 may not comprise a breakable membrane. The pouch 2104 may comprise a permeable membrane. Alternatively, the pouch 2104 may not comprise a permeable membrane. Before the frangible seal 2106 is broken, the buffer, solution, and/or reagent can be isolated in the reagent compartment 2108. Beneficially, this may reduce exposure of such buffer, solution, and/or reagent to lay users of the sample extractor collector 2100 (e.g., source individual of the biological sample), such as via the sample receptacle opening 2101. The isolation may also prevent compromise, leak, and/or loss of the buffer, solution, and/or reagent. For example, the frangible seal 2106 can be broken after placing the sample collector in the sample receptacle 2102 and securely closing the sample receptacle opening 2101.

Fluid in the sample reservoir 2105 can exit the sample extraction collector 2100 through the sample recovery port 2107. The sample recovery port 2107 may comprise a docking unit. The docking unit may be a flexible docking unit. The docking unit may comprise a luer lock adaptor, a one-way pressure valve, a resealable slit, and/or a cannula. The cannula can be plastic. The cannula can be metal. The cannula can be polypropylene. The cannula can be silicon. The docking unit can comprise a docking mechanism to allow a sample collection chamber inserted into the cavity of a luer lock adaptor to collect flow through from the sample extraction collector 2100 (e.g., sample reservoir 2105). For example, the sample recovery port 2107 may comprise a docking unit for inserting into the cavity of a luer lock adaptor of a cartridge for receiving the extracted biological sample. In some embodiments, the sample recovery port 2017 does not have a docking unit while a cartridge configured for receiving the extracted biological sample comprises a docking unit.

The sample extraction collector 2100 may be compressible, elastic, and/or durable. Non-limiting examples of materials suitable for the sample extraction collector 2100 include plastic, polyester, rubber, polyvinyl chloride resin (PVC), stretch vinyl, spandex, nylon, synthetic fibers, and natural plant fibers. The sample extraction collector 2100 may be rigid, or substantially rigid. Non-limiting examples of materials suitable for the sample extraction collector 2100 include metal, glass, and wood. The sample extraction collector 2100 may extract a biological sample from a sample collector.

For example, a woman places her used sample collector (e.g., used tampon), such as sample collector 120, into the sample receptacle 2102 via the sample receptacle opening 2101 upon removal of the used sample collector from the vaginal canal. She then closes and seals the sample receptacle opening 2102. Next, she applies a compression force by squeezing on the outer surface of the sample extraction collector 2100. For example, she may squeeze an outer surface of the sample receptacle 2102 and/or the reagent compartment 2108. In some embodiments, closing and sealing the sample receptacle generates a compression force or pressure on the sample receptacle 2102 and/or the reagent compartment 2108. The compression force or pressure breaks the frangible seal 2106. The hard seal 2103 may remain intact. Breaking the frangible seal 2106 releases the buffer, solution, or reagent contained in the reagent compartment 2108 into the sample receptacle 2102, wherein the biological sample collected on the sample collector 120 is brought into contact with the buffer, solution, or reagent to form a mixture of biological sample and reagent, fluid, solution or buffer. The compression can release the absorbed fluid and cells, debris or molecules on the sample collector. In some instances, a second compression force can be applied on the sample receptacle 2102 to compress the sample collector 120 to release the absorbed fluid and cells, debris or molecules on the sample collector. In some embodiments, releasing the absorbed fluids involves squeezing or pressing the sample receptacle 2102 and/or the sample collector 120. The released biological sample and/or mixture of the released biological sample and reagent, solution, or buffer, can flow back into the reagent compartment 2108 through the broken frangible seal 2106. In some embodiments, the frangible seal 2106 can be configured to allow the mixture of biological sample, reagent, fluid, solution and/or buffer, but not debris or particles from the sample collector 120, to flow through the frangible seal 2106 into the reagent compartment 2108 when the frangible seal 2106 is broken, such as via a membrane and/or filter of the frangible seal 2106 or via a separate membrane and/or filter of the sample extraction collector 2100. The membrane and/or filter of the frangible seal 2106 may remain intact upon breaking of the frangible seal 2106. Exemplary absorbed fluids include but are not limited to cervicovaginal fluid, blood, vaginal mucosa, cervicovaginal cells, female genital tract microbes, yeast, fungi, bacteria, and semen. Exemplary cells, debris and molecules include but are not limited to uterus lining cells, shed uterus cells, and shed vaginal cells. The flow through is collected in a sample collection chamber via the sample recovery port 2107. The sample collection chamber can be a clinical specimen collection tube, a vacutainer, e.g., BD Vacutainer® CPT™ Mononuclear Cell Preparation Tube, BD Vacutainer® PPT™ Plasma Preparation Tube. The sample extraction collector 2100 can be disposable after a single use. In some instances, at least a part of the sample extraction collector 2100 (e.g., sample recovery port 2107) may be recycled.

The sample collection chamber can be in any form or material. For example, the sample collection chamber can be plastic, glass, polypropylene, silicon, or metal. The sample collection chamber can be cylindrical, rectangular, square, oval, or spherical. The sample collection chamber can be a tube, a vail, a vase, or a cup. The inner side of the sample collection chamber can be silicone coated. The sample collection chamber can be a BD™ P100 Blood Collection System, BD™ P800 Blood Collection System, PAXgene® Blood RNA Tube, or PAXgene® Blood DNA Tube.

The sample collection chamber may contain preservation a housing buffer or reagent for storage and transportation of the sample. The housing buffer or reagent may dissolve the sample collector to release the collected fluid, cells or tissues. In some cases, the housing buffer or reagent dissolves the sample collector in response to pH change, e.g., an increase or a decrease of pH in the housing buffer or reagent. In some cases, the housing buffer or reagent dissolves the sample collector in response to temperature change, e.g., an increase or a decrease of temperature in the housing buffer or reagent. The housing buffer or reagent can comprise blood anti-coagulants, buffers and sample preservatives for downstream analysis. Non-limiting examples of housing buffers or reagents and sample preservatives include silica gels, silica beads, buffered citrate, sodium fluoride, potassium oxalate, sodium heparin, inert polymer gel, lithium heparin silica clot activator, EDTA (K2), acid citrate dextrose solution (ACD A), and acid citrate dextrose solution (ACD B). The housing buffer or reagent may comprise silica gels or beads. The housing buffer or reagent may comprise dyes, fluorescent beads, cooling agents, DNA extraction reagents, RNA extraction reagents, protein extraction reagents, and antibodies. The sample collection chamber may contain silica gels or beads, or a combination thereof that may come into direct contact with the sample collector 120 or menstrual sample fluid to allow rapid adsorption of biomolecules. The silica gels, or beads, or a combination thereof can allow the filtered components to be extracted for downstream analysis. The silica gels and beads can enhance absorption of biomolecules from the sample collector. The silica gels and beads can enhance extraction of biomolecules from the sample collector. The silica gels, or beads, or a combination thereof may be stored in the sample collection chamber.

Assay Cartridge

The assay cartridge or cartridge can be a small, cuvette-shaped device that contains diluents, reagents, test strips, and other necessary chemistries for testing of the presence of certain fungi, bacteria, viruses, viroids, parasites, protozoa, biological markers present on these pathogens, markers present on molecules produced or induced by these pathogens, or antibodies produced in response to infection. The assay can detect STIs. The STIs can be gonorrhea and/or chlamydia. The assay can detect markers (e.g., chemical markers or biomarkers) indicative of cancer, such as breast cancer, cervical cancer, ovarian cancer, uterine cancer, endometrial cancer, fallopian tube cancer, a tumor, a leukemia such as acute leukemia, acute t-cell leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, or chronic lymphocytic leukemia, polycythemia vera, lymphomas such as Hodgkin's lymphoma, follicular lymphoma or non-Hodgkin's lymphoma, multiple myeloma, Waldenström's macroglobulinemia, heavy chain disease, solid tumors, sarcomas, carcinomas such as, e.g., fibrosarcoma, myxosarcoma, liposarcoma, chondrosarcoma, osteogenic sarcoma, lymphangiosarcoma, mesothelioma, Ewing's tumor, leiomyosarcoma, rhabdomyosarcoma, colon carcinoma, colorectal cancer, pancreatic cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic, carcinoma, renal cell carcinoma, hepatoma, bile duct carcinoma, choriocarcinoma, seminoma, embryonal carcinoma, Wilms' tumor, lung carcinoma, small cell lung carcinoma, bladder carcinoma, epithelial carcinoma, glioma, craniopharyngioma, ependymoma, pinealoma, hemangioblastoma, acoustic neuroma, oligodendroglioma, meningioma, melanoma, neuroblastoma, retinoblastoma, endometrial cancer, or non-small cell lung cancer. In some cases, the assay detect markers (e.g., chemical markers or biomarkers) can be indicative of breast cancer, cervical cancer, ovarian cancer, uterine cancer, endometrial cancer, or fallopian tube cancer. The assay can detect markers (e.g., chemical markers or biomarkers) present in semen, such as prostate-specific antigen (PSA), prostatic acid phosphatase (PAP). The reagents can also be used to measure hormone levels, detect pregnancy, or indicate other disease or disorders. The assay can detect markers (e.g., chemical markers or biomarkers) indicative of fertility, such as luteinizing hormone (LH), follicle-stimulating hormone (FSH), anti-Mullerian hormone (AMH), thyroid-stimulating hormone (TSH), progesterone. The assay can detect markers (e.g., chemical markers or biomarkers) indicative of pre-pregnancy health and/or nutrition, such as TSH, bisphenol-A (BPA), iron, folate, vitamin D. The assay can detect markers (e.g., chemical markers or biomarkers) indicative of pre-term birth, such as pH, fetal fibronectin (fFN), cathepsin-E. The assay can detect markers (e.g., chemical markers or biomarkers) indicative of endometriosis. The assay can detect markers (e.g., chemical markers or biomarkers) indicative of polycystic ovarian syndrome. The assay can detect markers (e.g., chemical markers or biomarkers) indicative of yeast infections, bacterial vaginosis, drug abuse, and alcohol abuse. The assay can detect markers (e.g., chemical markers or biomarkers) indicative of uterine fibroids. The assay can detect markers (e.g., chemical markers or biomarkers) indicative of adenomyosis. The assay can detect markers (e.g., chemical markers or biomarkers) indicative of immune disorders. The assay can detect markers (e.g., chemical markers or biomarkers) indicative of feminine reproductive disorders.

The assay cartridge can be configured to run a plurality of assays from a single sample. The assay cartridge may be configured to run 2, 3, 4, 5, 6, 7, 8, 9, 10 or more assays either in parallel or in series.

The assay cartridge can allow for expansion of future biomarkers that are aimed at long-term fertility management and pre-pregnancy health. The assay cartridge can be completely self-contained. The pressure valve located at the bottom of the reservoir/extractor is pushed down once it is docked with the assay cartridge, allowing a small amount of cervicovaginal fluid to enter into the assay cartridge.

Once the cervicovaginal fluid has transferred to the assay cartridge, the cartridge is undocked from the reservoir/extractor. The extractor device may be reused. The extractor device may be discarded. The extractor can be self-contained and allow for a hygienic way of disposing of the used sample extractor. Upon undocking of the assay cartridge from the reservoir/extractor, the assay cartridge is inserted into the cartridge reader and set aside, or put into a purse where the assay develops (see, e.g., FIG. 1).

Figure 8B:
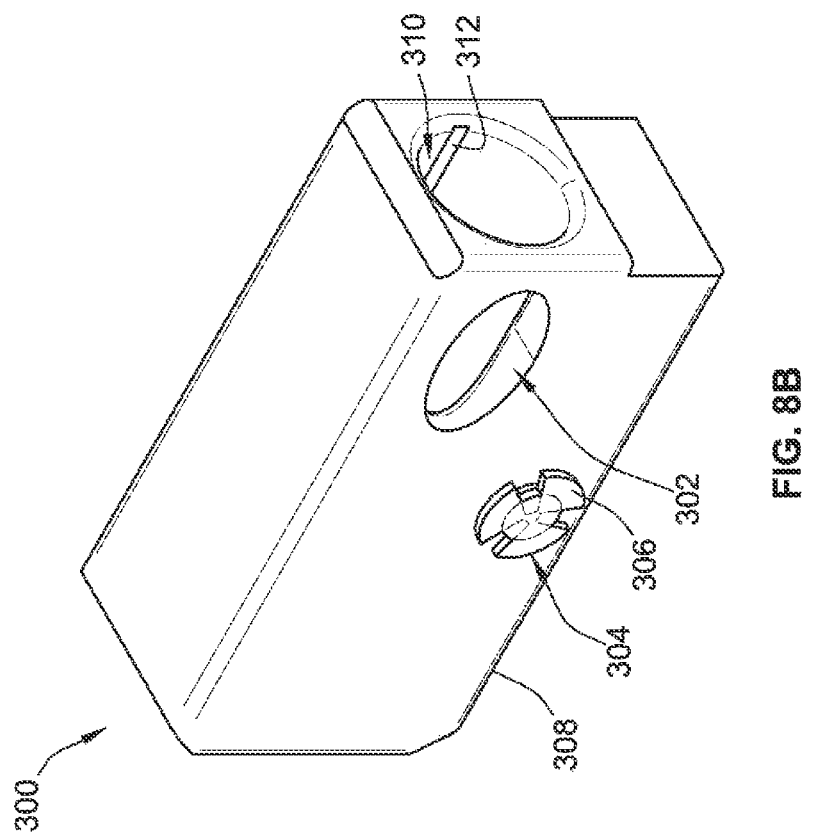
FIG. 8B is a back perspective view of the assay reader shown in FIG. 8A.
Figure 8A:
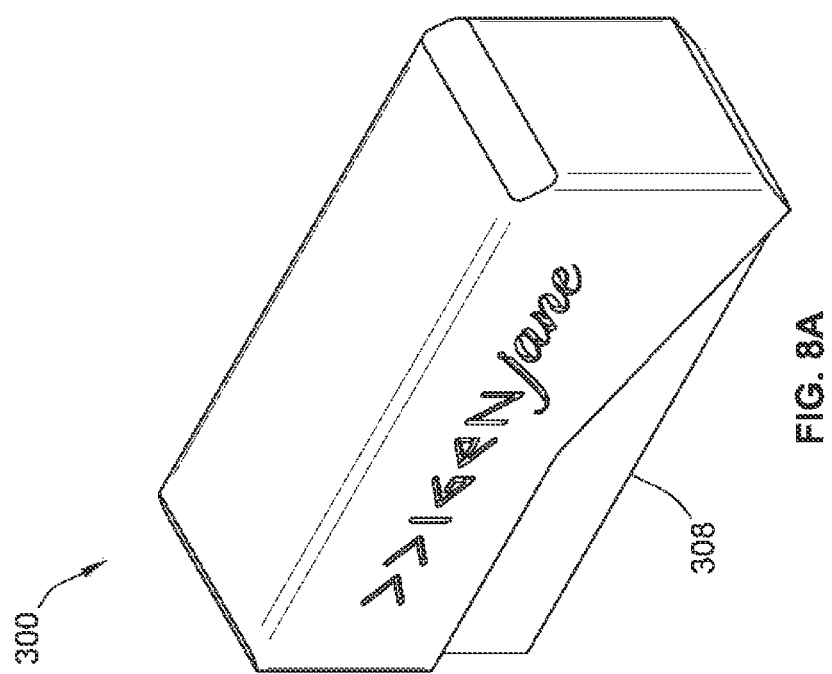
FIG. 8A is a front perspective view of an assay reader, in accordance with one exemplary embodiment.

Referring to FIGS. 14A-14E, the assay cartridge 500 includes an internal assay reservoir 502, a plurality of assay slots 504, a docking end 506, a docking port 508, and a cartridge window 510. The docking end 506 is configured to be placed adjacent to and/or in contact with the top surface 612 of the extractor top 602, and the docking port 508 inserted within and in fluid communication with the fluid port 610. Biological fluid (e.g., biological sample or mixture containing a biological asample) F from the extractor system 600 is transferred into the assay reservoir 502, from which the biological fluid F is further transmitted to one or more assays (located in the assay slots 504) to run desired tests and analysis. The results are displayed and/or viewed through the cartridge window 510. When the assay cartridge is inserted through the cartridge opening 300 of the assay reader 300 (shown in FIG. 8B), the cartridge window 510 is aligned with the reader window 302 for providing a clear viewing path to the camera 115 of the mobile phone 112 (which is attached to the assay reader 300 via the Snap-on adapter 200).

The assay cartridge 500 may include a puncture apparatus (e.g., a needle) to connect to an extractor system for fluid extraction. The assay cartridge 500 may include a docking or luer lock system to connect to an extractor system. The assay cartridge 500 may include a reservoir that stores a small amount of extracted fluid (e.g., 100 microliters).

The assay cartridge 500 may include one or more buffers or reagents for sample processing. For example, the buffers or reagents may include a buffer to dilute the sample for minimizing background noise in the assay; a buffer with exogenous controls or spike-ins to normalize downstream data outputs; a buffer to preserve cells, DNA, RNA, or other biological components for analysis at a later date or to send a sample for analysis by experts; a buffer to extract particular biological components (e.g., DNA, RNA, proteins, etc.); a buffer to chemically remove particular biological components (e.g., $ZnSO_4$ to precipitate hemoglobin); a buffer to bind and remove particular biological components; a buffer housed in dissolvable or puncturable membrane; and/or a buffer that is free-floating.

The assay cartridge 500 may have an assay chamber or chamber configured with multiple chamber slots to house one or more slots (e.g., similar to assay slots 504). The assay chamber and a sample collection reservoir (e.g., the assay reservoir 502) can be separated by a dissolvable membrane, a puncturable membrane, a chromatography plate for further filtration, and/or a porous filter to retain precipitated materials from a solution.

The assay chamber and the sample collection reservoir may include a single chamber/reservoir such that they are not separated. For example, if the sample is intended to be preserved and/or shipped to a referral laboratory, the assay cartridge 500 can lack an assay chamber, having only a sample collection reservoir. The sample can be sent to a Clinical Laboratory Improvement Amendments (CLIA) laboratory where downstream analyses are performed on the biological sample collected. These downstream analyses include Enzyme-Linked Immunosorbent Assays and Next Generation sequencing such as DNA, RNA, microRNA, Methylome, strand-specific, and bacterial biome sequencing. Other downstream test may include, but are not limited to Mass Spectrometry, High Performance Liquid Chromatography, quantitative PCR, PCR, complete blood counts, proteomic analysis and small molecule analysis, cell and bacterial/viral cultures, and other informative analysis tools as needed for proper diagnosis of specific health conditions.

The assay cartridge 500 may have electrodes for voltaic recording of electrochemical reactions and/or electrodes for passing a current through a test and migrating a charge molecule (such as DNA, RNA, or protein). The assay cartridge 500 may have electrodes to generate heat needed to catalyze a reaction.

Assays

The assay cartridge 500 may be further configured to include various multiplexed assays, chemistries, assay reporter systems, lateral flow materials, and/or controls. The multiplexed assays can include, by way of example, assays in series, which are likely to relay a more complete result than individual tests. Some exemplary multiplexed assays includes a rape test (e.g., PSA, ACP, and/or PEG), a sexual transmitted infection (STI) test (e.g., gonorrhea and/or chlamydia), a cancer screening test (e.g., endometrial, cervical, fallopian tube, ovarian, uteran), a preterm birth test (e.g., pH, fFN, catehpsin-E), a fertility test (e.g., LH, FSH, AMH, TSH, progesterone), a nutrition and/or pre-pregnancy test (e.g., TSH, BPA, iron, folate, vitamin D), and/or other tests (e.g., PCOS, endometriosis). Some exemplary chemistries include a lateral flow chemistry, an isothermal PCR chemistry, a chemistry with DNA or RNA switches and gel electrophoresis, an aptamer-based amplification chemistry, and/or a voltaic enzyme linked assays chemistry.

The assay reporter systems of the assay cartridge 500 can include, for example, a colorimetric-based or a chromogenic-based enzyme reporter. The configurations can include colloidal gold and paramagnetic mono-dispersed latex particles. In alternative embodiments the assay reporter system includes a fluorogenic enzyme-based reporter, a dye-based reporter, an Atto 430-LS-based reporter, an Atto 465-based reporter, a brilliant violet 605-based reporter, a chromeo 494-based reporter, an Alexa fluor 532-based reporter, an R-Phycoerythrin-based reporter, an SYBR-based reporter, a TAMRA-based reporter, a FAM-based reporter, and/or a voltaic reporter by enzyme catalysis of charged ions.

The lateral flow materials of the assay cartridge 500 include, for example, a hydrophilic surface with consistent flow rates; a highly regular surface, yielding cosmetically high-quality lines; a three-dimensional matrix with consistent pore size, thickness, and protein-binding capacity; and/or a true capillary flow with a variety of wicking rates. Some beneficial criteria of the lateral flow material include material thickness, with the desired criterion including having the material be as thin as reasonably possible; and material shelf-life, with the desired criterion including good fluid flow characteristics and/or low flow coefficients (Cvs) for capillary rise time over its entire shelf-life (independent of treatment). Other examples of beneficial lateral flow materials include materials with minimal metal contaminants and/or low background fluorescence; materials that are stable in storage and/or are non-flammable; materials that can be activated for covalent linkage; materials with multiple functionality that can act as a conjugate application area, a sample application area, a reaction surface, a separation medium, and a wick, all in one; and/or materials with a pore size in the range of about 8-15 microns. The beneficial lateral flow materials may have a pore size in the range of about 1 micron to 100 microns, 5 microns to 20 microns, 10 microns to 30 microns, or 2 microns to 25 microns. The beneficial lateral flow materials may have a pore size of at least about 1 micron, 2 microns, 3 microns, 4 microns, 5 microns, 7 microns, 8 microns, 9 microns, 10 microns, 12 microns, 15 microns, 20 microns, 30 microns, 40 microns, 50 microns, 60 microns, 70 microns, 80 microns, 90 microns, 100 microns, or more. In some embodiments, the beneficial lateral flow materials have a pore size of at most about 1 micron, 2 microns, 3 microns, 4 microns, 5 microns, 7 microns, 8 microns, 9 microns, 10 microns, 12 microns, 15 microns, 20 microns, 30 microns, 40 microns, 50 microns, 60 microns, 70 microns, 80 microns, 90 microns, or 100 microns.

The controls of the assay cartridge 500 include, for example, a series of controls to base algorithmic extrapolation of data to biologically relevant venous blood levels; internal controls to record a blood dilution factor; internal controls or standard dilutions to extrapolate concentrations of individual biomarker results; and/or external controls to normalize lot variations. In other embodiments, the controls include controls to measure extent of hemolysis within a biological sample and/or controls to measure cell shearing within the biological sample.

After the cervicovaginal fluid is in the assay cartridge, the fluid may come in contact with diluents and reagents that are housed in dissolvable membranes or on test strips. The delayed release of these reagents can be dependent upon the thickness of the dissolvable membranes that come in contact with a serum or the cervicovaginal fluid. The membranes can be housed in the upper portion of the assay cartridge. For example, the membranes can seal the upper portion of the cartridge from the lower portion, where the test strips are housed. After the membranes are dissolved, the cervicovaginal fluid and reagents can flow down to the test strips for assay development. In some embodiments, the dissolvable membranes are made of an aqueous polymer matrix. The polymer matrix may have one or more disulfide bonds.

The diluents and/or reagents may be housed in a puncturable membrane. The puncturable membrane can be punctured once the assay cartridge docks with and comes into fluid communication with the extractor. After the membrane is punctured, the cervicovaginal fluid and diluents and/or reagents can flow down the test strips for assay development. The puncturable membranes can be made of a flexible polymer matrix. The polymer matrix may have one or more disulfide bonds.

The test strips can be attached to plastic housings within the lower portion of the assay cartridge. The test strips may consist of nitrocellulose. The test strips may consist of Whatman® filter paper. The test strips may consist of other porous polymer materials suitable for biological processing with pre-designated wicking parameters. The first element of the test strips can act as a sponge and hold an excess of sample fluid. The fluid then migrates to the second element of the test strips which have conjugated reagents for detection of one or more specific analytes in a dried format. After binding of the analyte to the conjugated reagent, the sample/reagent complex then migrates to a portion of the strip where a capture molecule binds the complex. A time-released amplification solution is then released by the cartridge reader, and the resulting signal is amplified via a colorimetric amplification.

Several methods have been applied to the detection of pathogens and markers from clinical samples. These methods include, but are not limited to, conventional and real-time polymerase chain reaction (PCR), Isothermal PCR, restriction enzyme analysis, DNA, RNA, microRNA, methylome, and bacterial biome sequencing, DNA microarray analysis, flow cytometry, enzyme-linked immunosorbent assays ("ELISAs"), fluorescence in situ hybridization ("FISH"), and aptameric sensing platforms. PCR-based systems use consensus or degenerate primer sequences to allow for amplification and identification of DNA/RNA sequences associated with specific markers. ELISAs typically use antigens to detect the presence of specific antibodies that are made in response to infection, or antibodies that react with antigens, including markers of infection, disease or disorders.

The assay may use existing rapid diagnostic technologies. The disclosed diagnostic tests use readily available and inexpensive materials (e.g., paper) and reagents (e.g., stable organic compounds, antibodies) to develop an immunoassay for the detection of analytes. The disclosed diagnostic tests can use direct, indirect, and sandwich assays on paper supports, gel electrophoresis based tests, PCR based isothermal tests (in vitro or in silico), and other oligo- and probe-based technologies, as well as electrochemical sensing technologies.

The assay may be paper-based. Paper provides a number of advantages over supports used in other assays. For example, paper is commercially available, fabricated on a large scale all over the world, is widely abundant, inexpensive, biodegradable, renewable and allows for one-step functionalization (e.g., by periodate oxidation to form aldehyde-functionalized paper in wet solution or gas-phase silanization). The assays are also energy efficient, not requiring the use of pumps for liquids, as liquid wetting of the various components utilized is driven by capillary action. The assays do not require staining, instead allowing detection of analytes by more direct methods (e.g., direct visualization without the use of a stain). Because the support is paper, washing of the support is rapid and effective due to the large pore size of paper as compared to other supports, such as nylon membrane with smaller pores. The assays are flexible, allowing detection of both antigens (e.g., in direct, or sandwich methods) and antibodies (e.g., in indirect methods) as the analyte. Because of this flexibility, the disclosed diagnostics allow for detection of antigen or antibody analytes associated with any disease for which an antibody or antigen analyte is known (e.g., gonorrhea, chlamydia, HPV, etc.).

Paper supports useful in the assays include all types of cellulose materials that allow printing of wax-demarcated test zones. Wax printing can include two steps and can produce hydrophobic barriers (for the test zones) that extend through the thickness of the paper. After wax printing, the paper is heated, and the wax melts and spreads vertically into the paper, creating the hydrophobic barrier used to confine test reagents. Examples of useful paper supports include Whatman® filter papers, chromatography papers, polymeric-based membranes, and cotton or nylon fabric.

The paper support may be functionalized by oxidizing the surface with an oxidation agent to provide aldehyde-functionalized paper for antigen/antibody immobilization. The paper can be coated with agarose, which is then oxidized to provide the aldehyde functionalities useful for antigen/antibody immobilization. In some embodiments, the paper is coated with chitosan, which is then reacted with glutaraldehyde to provide the aldehyde functionalities useful for antigen/antibody immobilization. In some cases, multiple layers of antigen/antibody are prepared on the paper by alternatively adding antigen/antibody and glutaraldehyde on the paper. In some embodiments, the first layer of antigen/antibody is formed by using the original aldehyde functionalities present on the paper, followed by treatment with glutaraldehyde, which anchors the second layer to the first via cross-linking. In some embodiments, the exposed aldehyde functionalities are then reacted with an antigen or antibody to covalently bond these components to the paper support. In some embodiments, the unreacted aldehyde moieties are then blocked by treating the paper support with a non-reacting component (e.g., bovine serum albumin, casein, or ethanolamine) to provide a stable paper support ready to be shipped or used immediately in a diagnostic test.

The assay may use functionalized antibodies. A functionalized antibody is an antibody with affinity for an analyte or another antibody which is functionalized with and coupled to a polymerization catalyst.

In a direct assay the antigen analyte is immobilized on the paper support and the paper support is subsequently treated with a primary antibody functionalized with a polymerization catalyst. In some embodiments, the antigen analyte is present in the clinical sample suspected of containing the antigen analyte, and the sample is contacted with the paper support. The primary antibody has affinity for and binds the antigen analyte and thereby becomes immobilized on the paper support through the antigen analyte. The paper support is then contacted with a monomer composition and exposed to a polymerization initiator, which initiates polymerization of the monomer composition on the areas of the paper support in proximity to the primary antibody functionalized with the polymerization catalyst. Unreacted monomer composition may then be washed away, leaving polymer only on areas of the paper support in proximity to the primary antibody and the antigen analyte.

Presence of the polymer, indicating the presence of the analyte, is then detected. Exemplary detection methods include, but are not limited to, direct visual observation, colorimetric readout, staining, pH change, scanning, and spectroscopic methods such as fluorescence, UV absorption or transmission.

An indirect assay is similar to the direct method, except it is used to detect an antibody analyte. An antigen having affinity for the primary (analyte) antibody is immobilized on the paper support. A species-specific secondary antibody having affinity for the primary (analyte) antibody is coupled to a polymerization catalyst. Accordingly, the antigen has affinity for and binds the primary (analyte) antibody, and the secondary antibody has affinity for and binds the primary antibody, both of which become immobilized on the paper support, the primary antibody immobilized through the antigen, and the secondary antibody immobilized through the primary antibody, which is in turn immobilized through the antigen. Accordingly, in some embodiments, the analyte is present in the clinical sample suspected of containing the analyte, and the sample is contacted with the paper support. As in the direct method, the paper support is then contacted with a monomer composition and exposed to a polymerization initiator, which initiates polymerization of the monomer composition on the areas of the paper support in proximity to the secondary antibody functionalized with the polymerization catalyst. Unreacted monomer composition may then be washed away, leaving polymer only on areas of the paper support in proximity to the secondary antibody, primary antibody, and the antigen. Presence of the polymer, indicating the presence of the analyte, is then detected. Exemplary detection methods are as disclosed above with respect to the direct method.

The sandwich method is similar to the direct and indirect methods, except a capture antibody is bound to the paper support in place of the antigen. The antigen analyte is then immobilized on the paper support through the capture antibody, and the paper support is subsequently treated with a secondary antibody functionalized with a polymerization catalyst. In some embodiments, the antigen analyte is present in the clinical sample suspected of containing the antigen analyte, and the sample is contacted with the paper support (which comprises the capture antibody). The secondary antibody has affinity for and binds the antigen analyte, becoming immobilized on the paper support through the antigen analyte and the capture antibody. The paper support is then contacted with a monomer composition and exposed to a polymerization initiator, which initiates polymerization of the monomer composition on the areas of the paper support in proximity to the secondary antibody functionalized with the polymerization catalyst. Unreacted monomer composition may then be washed away, leaving polymer only on areas of the paper support in proximity to the secondary antibody, antigen analyte and capture antibody. Presence of the polymer, indicating the presence of the analyte, is then detected. Exemplary detection methods are as disclosed above with respect to the direct method.

The resultant polymer in turn becomes immobilized to the paper support, and can be clearly distinguished from polymers formed in bulk solution, which are easily washed away. Without wishing to be bound by theory, it is postulated that reaction of immobilized/activated radicals with radical species of the polymer in a termination step is responsible for the polymer immobilization phenomenon. Other mechanisms of polymer immobilization may involve some physical interactions between the polymer and the proteins on the surface, or interaction with paper support. In addition, in some embodiments the polymer is not soluble in water and so after attaching to the surface it cannot be washed away. In some embodiments, the polymer forms a hydrogel.

The assays may include (1) a paper support, (2) antibody functionalized with a polymerization catalyst, (3) a monomer composition capable of being polymerized in the presence of said polymerization catalyst, and (4) a polymerization initiator. In an exemplary assay, a clinical sample suspected of containing an analyte of interest is contacted either directly with the paper support (e.g., in a direct method) or to a paper support functionalized with an antigen having affinity for the primary (analyte) antibody (e.g., in an indirect method) or to a capture antibody having affinity for the antigen analyte (e.g., in a sandwich method) to immobilize at least a portion of the analyte, and unbound sample is removed by washing.

A functionalized antibody having affinity for the analyte of interest is then contacted with the resulting support, and excess functionalized antibody is removed by washing. The support is then treated with a monomer composition, and an initiator is introduced to induce polymerization via the polymerization catalyst. Polymerization results in hydrogel formation only in the areas of the support comprising bound analytes due to the fact that the polymerization catalyst is only present in these areas of the support due to the selective binding of the functionalized antibody to these areas. Unpolymerized monomer composition is removed by washing, and the analyte of interest can be detected by observing the areas of the support which comprise hydrogel, either directly (e.g., via a color change in the polymerized monomer composition in a colorimetric method) or indirectly (e.g., by various chemical, electrical, or spectroscopic methods, such as staining, scanning, fluorescence, UV absorption, magnetism, etc.).

The assay can be enzyme based, producing a time-dependent signal (i.e., producing a signal which changes over time). This type of assay can involve recording test results after a specific set time.

The assay can be non-enzyme based. This type of assay demonstrates improved stability over enzyme-based methods due to the lack of unstable enzymes. In some embodiments, the assay is based on gold-nanoparticle conjugated antibodies. Gold-nanoparticle-based assays in part eliminate the time-dependency problems of enzyme-linked antibody assays. This allows for signal amplification by polymerization to be conducted either immediately after capturing the antigen/antibody or at a later time, without affecting the diagnosis outcome. Notably, a typical assay according to the present disclosure is time-independent at a number of stages, providing for a flexible diagnostic method which can be readily prepared, shipped, and stored, and testing procedures which can be flexibly conducted without rigid adherence to time limits or storage conditions.

The assay may include eosin as the polymerization catalyst and a tertiary amine co-initiator. Although eosin is oxygen-sensitive, the conditions and time scales of the assay overcome oxygen inhibition, allowing detection in an ambient environment (Kaastrup et al., Lab Chip 12:4055-4058; 2012). This is particularly useful in non-laboratory settings. This type of assay is specific (avoiding false positive results), sensitive (avoiding false negative results), user-friendly (simple to perform, using specimens obtained by non-invasive methods), rapid, and deliverable (readily accessible to end users). This type of assay is low cost, fast, time-independent, sensitive and consistent.

An exemplary step-wise procedure for manufacturing an exemplary assay according to the present disclosure is depicted below:

1) react paper support with oxidizing agent to provide aldehyde-functionalized paper;
2) immobilize capture antibody on aldehyde-functionalized paper;
3) block unreacted aldehyde sites with non-reacting component;
4) treat paper support with sample suspected of containing analyte of interest;
5) wash paper support to remove unbound analyte;
6) treat paper support with functionalized antibody;
7) wash paper support to remove unbound functionalized antibody;
8) treat paper support with monomer composition;
9) expose paper support to stimulus to polymerize monomer composition in areas containing functionalized antibody bound to analyte;
10) wash to remove unpolymerized monomer composition; and
11) detect formation of the polymer formed in areas containing functionalized antibody bound to analyte.

As discussed herein, the items listed above can be categorized into three separate steps: (a) support preparation, steps 1-3; (b) analyte capture, steps 4-7; and (c) analyte detection, steps 8-11. After step 3 (block unreacted aldehyde sites with non-reacting component), a paper is produced which can be stored and shipped (for example, as part of a kit). The assay process can also be stopped indefinitely without risk of degradation of the components of the test after step 7 (wash paper support to remove unbound functionalized antibody). Further, the polymerization reaction can be largely time-independent (i.e., the polymerization can precisely be turned "on" and "off" with the stimulus), meaning the time after which step 11 is carried out (i.e., detect formation of the polymer formed in areas containing functionalized antibody bound to analyte) is not critical to the results of the test. The eosin molecules may be immobilized on a support and be capable of initiating polymerization after six months or more. The time of the detection process (i.e., the initiation step) can be short (about 60 seconds), in contrast with the time scale on the order of minutes for enzyme-based immunoassays. The initiation step itself can be performed in less than 35 seconds. The detection step can be effectively terminated (i.e., turned "on" or "off") by removing the light source, something which is not easily achieved in enzyme-linked immunoassays. The development of the color used as readouts may not be dependent on the time between the taking of sample and initiating the assay; that is, the color produced can be stable with time.

Step 11 referenced above can be achieved by adding phenolphthalein to the monomer composition. This assay mode is particularly useful under resource-limited settings, with no need for staining, scanning, or the use of spectroscopic methods. Phenolphthalein is colorless at a pH range of about 0 to less than 8.2, and does not affect polymerization. Upon polymerization (step 9), the indicator is trapped in the polymer which in turn is immobilized on the paper support. Its color changes to pink upon the addition of a basic solution (for example, about 2 to about 6 µL, of about 0.01 to about 0.51 M NaOH), thus providing a visual photometric detection of the polymer, which in turn can indicate the presence of analyte.

Disclosed herein is a method of detecting an analyte of interest in a clinical sample, the method comprising (a) providing a paper support; (b) contacting the paper support with a sample, the paper support capturing at least a portion of any analyte present in the sample; (c) contacting the paper support with a first antibody; wherein the first antibody has affinity for and binds to the analyte; and wherein the first antibody comprises a polymerization catalyst; (d) contacting the paper support with a monomer composition; wherein the monomer composition comprises a monomer component capable of being polymerized in the presence of the polymerization catalyst; wherein at least a portion of the monomer component forms a polymer in the presence of the polymerization catalyst, resulting in a polymer; and wherein detecting the presence of the polymer indicates presence of the analyte.

The method may further comprise the step of (e) applying a polymerization initiator to the paper support, initiating polymerization in the presence of the polymerization catalyst.

The method may comprise the step of (f) removing unpolymerized monomer composition from the paper support by washing with a first liquid. In some embodiments, the first liquid is deionized water.

The monomer composition may be adjusted or buffered to an appropriate pH. In some embodiments where the detection step requires a specific pH range, the monomer composition is adjusted or buffered appropriately to ensure this pH range is not reached until detection is desired. In some embodiments, the monomer composition comprises phenolphthalein, and the pH of the monomer composition is adjusted or buffered using an acid prior to the detection step. In some embodiments, the acid is hydrochloric acid.

The paper support may directly capture at least a portion of any analyte present in the sample. The paper support may be covalently bound to a capture antibody or antigen which has affinity for the analyte.

The paper may have affinity for the analyte and/or may not be nitrocellulose.

The capture antibody or antigen may be covalently bound to the paper support by reacting the capture antibody or antigen with an aldehyde-functionalized paper to produce the paper support.

The capture antibody or antigen may be covalently bound to the paper support by reacting the capture antibody or antigen with an aldehyde-functionalized paper, followed by blocking unreacted aldehydes to produce the paper support. The unreacted aldehydes may be blocked with an agent selected from at least one of bovine serum albumin, casein and ethanolamine.

The analyte may be selected from an antigen and an antibody.

The polymerization initiator may be selected from the group consisting of at least one of light, heat, cooling, application of a magnetic field, application of an electrical field, application of electrical current, a chemical reagent and electricity. The polymerization initiator can be light. The light may comprise light having a wavelength of about 522 nm. The polymerization initiator can be light. The light can be applied by way of a light box. The light box may comprise a timer. The light source can be an array of light-emitting diodes ("LEDs") which is capable of pulsing light at about 522 nm wavelength (about 30 miliwatts per centimeter squared (mW/cm$^2$)). The light box can apply light from above the paper support.

The monomer composition may further comprise an indicator. The indicator can be at least one of pH-sensitive, light-sensitive, temperature-sensitive, sensitive to electrical field or current, and sensitive to magnetic field. The indicator can comprise phenolphthalein and the method can further comprise the step of treating the paper support with a base prior to detecting formation of the polymer. The indicator can comprise phenolphthalein.

The detecting formation of the polymer may comprise observing a color change mediated by phenolphthalein under basic conditions.

The paper support can be covalently bound to the capture antibody or antigen.

The capture antibody or antigen can be covalently bound to the paper support by reacting the capture antibody or antigen with an aldehyde-functionalized paper to produce the paper support.

The capture antibody or antigen can be covalently bound to the paper support by reacting the capture antibody or antigen with an aldehyde-functionalized paper, followed by blocking unreacted aldehydes to produce the paper support. The unreacted aldehydes can be blocked with an agent selected from at least one of bovine serum albumin, casein and ethanolamine.

The assay can be carried out by Loop Mediated Isothermal Polymerase Chain Reaction LAMP), which is a single tube technique for the amplification of DNA. LAMP is specifically beneficial over regular PCR in that it amplifies DNA and RNA target sequences at a constant temperature (60-65° C.) without sophisticated instrumentation. In LAMP, either two or three sets of primers and a polymerase with high strand displacement activity and replication activity are used to amplify target sequences.

The detection of amplification product through LAMP can be determined via photometry for turbidity caused by an increasing quantity of magnesium pyrophosphate precipitate in solution as a byproduct of amplification. This allows easy visualization by the naked eye. The reaction can be visualized either by measuring the turbidity or by fluorescence using intercalating dyes such as SYTO 9, or colorimetric dyes such as SYBR green. In-tube detection of DNA amplification is possible using manganese loaded calcine which starts fluorescing upon complexation of manganese by pyrophosphate during in vitro DNA synthesis.

LAMP detection can be paired with a set of DNA-based standards of known size and quantity in order to calculate an exact quantity of measured analyte, giving a quantitative readout.

A paper filter can be utilized with dry or encapsulated reagents in order to perform nucleic acid extraction and purification for downstream isothermal amplification of target sequence or analyte.

The assay may utilize aptamer-sensing technologies for proteins and small molecule detection. Aptamers are single-stranded DNA/RNA oligonucleotides with characteristic 3D structures artificially selected from synthesized random-sequence nucleic acid libraries by in vitro evolution process called SELEX (Systematic Evolution of Ligands by Exponential Enrichment). Aptamers are able to bind their targets with high affinity and specificity, and they themselves by and large undergo the conformational transition that can be generally employed for designing analysis systems. Electrochemical aptameric assays are based on two signal transduction mechanisms: target binding-induced conformational change and strand displacement originating from competitive binding of target molecules with complementary oligonucleotides for recognition elements.

In some embodiments of aptamer-based assays the addition of gold nanoparticles, or other redox active moieties, mediators, enzymes, groove binders, or intercalators are used with modified electrode sensors. In the presence of target molecules are analytes, a detectable electrochemical signal can be generated and recorded for quantitative analysis of target analyte. Detection techniques can include cyclic voltammetry, differential pulse voltammetry, square wave voltammetry, anodic stripping voltammetry, chronopotentiametric detection, and electrochemical impedance spectroscopy.

In some embodiments of aptamer-based assays, a fluorescent marker is used instead of electrochemical sensors, giving a fluorescent emission that can be imaged through a mobile device or external image capture device. This can be done using two methods. Aptamer-sensing assays can be converted to fluorescent sensors by either modification with fluorescent oligonucleotide analogs, or double-end-labeling with fluorescent marker and quencher. These systems allow for fluorescent emission upon conformation change of aptamer upon binding of target molecule or ligand.

The assays can be coupled with carbon ink or silver/silver chloride ink printed electrode sensors (e.g., a working electrode, a counter electrode, and a reference electrode). In this indirect detection method, target metal ions conjugates are detected by printed electrodes upon migration to electrode front using lateral flow and capillary action.

The assays may allow for the monitoring and/or diagnosis of a wide variety of biological analytes and diseases, and enable mass screening by a limited number of health professionals, as well as self-testing by patients at home (which can also be developed and analyzed later, upon arrival at a health care facility). The assays may allow for detection of antigen, antibody, mineral, vitamin, hormone, or protein analytes present in semen, or associated with any disease, nutritive, or metabolic state for which an analyte, or with any disease, for which an antibody, antigen, mineral, vitamin, hormone, or protein analyte is known (e.g., gonorrhea, chlamydia, HPV, anemia, infertility, cancer, hypothyroidism, etc.).

Assay Reader

A small assay reader, for example the assay reader 110 shown in FIG. 1, is included in the first shipment of the testing kit. This assay reader is not disposable, and can be used repeatedly on a month-to-month basis. In some embodiments, the assay reader fits securely onto the headphone jack of a mobile device. In some embodiments, the assay reader can be coupled to other ports of a mobile device (e.g., charging port, USB port, microUSB port, lightning port, miniUSB port, etc.).

The reader can contain either rudimentary optics or the ability to hook up to available optics on the consumer's mobile device, and a small LED exposure light emitting a wide range of visual and hyperspectral wavelengths for colorimetric and fluorescent detection. In some embodiments, the assay cartridge slides into the assay reader and locks into place. Once the lock is engaged, an internal circuit begins a countdown to initiate the different steps in assay development. The circuit regulates the time of assay development and coordinates additional steps in the process of development and imaging of assay results. In some embodiments, after the analytes have bound to conjugated reagents, the assay reader rotates a lever that punctures a small pouch containing polymer solution. The polymer solution covers the assay test strip. The reader then briefly turns on an LED light that initiates catalyzed amplification of polymer formation. Once polymerization has occurred, the reader sends a notification to the mobile device that the assay is ready for development. The user can then initiate development and reading of test results. In some embodiments, the development and reading of results is done through a button initiator on the reader itself. After the assay has developed, the assay reader takes a burst of images from the assay cartridge. In some embodiments, the development and reading of results is done through an app on the mobile device.

The LED light can be reflected through a series of mirrors that directs the light to the assay result portion of the inserted assay cartridge. This allows the light to illuminate the assay results in a directed fashion and illuminates the test results for the optics to record the image. Some embodiments have one LED light or a series of LED lights housed within the reader to diffract light at specific angles to record more accurate absorptions and/or fluorescence. The assay results are stored in the reader and can be transmitted to a mobile device to the user. Results can be transmitted from the reader to a mobile device or a computer through a cable connecting the reader to the device through the audio port, or other port, of the mobile device. In some instances, the reader and the mobile device can communicate wirelessly (e.g., via Wi-Fi, Bluetooth, Near Field Communication (NFC) methods, etc.). These images can be used to standardize and read each individual assay and can be subject to both binary and quantitative analyses for future assay implementation. The data can then be used to track the patient's health through the comprehensive mobile interface, or it can be sent via short-message service ("SMS") to designated health professionals for further testing and treatment. The data can be communicated to designated health professionals and other personnel via other communications means, such as email, telephone call, voice messages, and fax.

The assay reader can couple to an adapter that fits securely onto a mobile device, using existing optics of the mobile device. The assay reader can be a stand-alone device with internal optics. The assay reader can have built-in Bluetooth or Wi-Fi connectivity to relay data to a mobile device or computer. The assay reader can relay data to a mobile device or computer through a USB or other data transfer port.

The results can be recorded as an image. The results can be recorded by the light spectrum emitted by the colored result front, and a small optical spectrophotometer can image the light spectrum emitted. The results can be recorded by a voltmeter which senses a voltage change or a charge differential.

As an example shown in FIGS. 8A-10B, the assay reader 300 is configured to connect with the Snap-on adapter 200 and the camera 115 of the mobile phone 112, as discussed above in reference to FIGS. 5A-6E. In addition to the reader window 302, the reader latch 304, the latch inserts 306, and the bottom surface 308, the assay reader 300 can also comprise a cartridge opening 310 configured to receive and connect an assay cartridge 500 (shown in FIGS. 14A-14E). The cartridge opening 310 can include a locating feature 312 configured for proper positioning and/or alignment of an assay cartridge within the assay reader 300. The assay reader 300 may lack the reader window 302 (i.e., is a window-less assay reader).

The assay reader 300 is configured to attach to a mobile device, such as the mobile phone 112 to interface with optics, an audio port, or a power source from the mobile device to run, image, record, and/or transfer data from an assay received internally via an assay cartridge. In another embodiment, the assay reader 300 includes integrated optics, audio port, and/or power source to independently perform an analysis of the assay. For example, the assay reader 300 includes one or more lenses, sensors, filters, and/or voltaic electrodes to run and image assay test results.

The assay reader 300 can include data recording. In some embodiments, assay test result data are recorded through a lens and sensor, with the lens being either internal or external and the sensor being configured to measure electromagnetic spectra in the visible or nonvisible spectra. The lens is configured to optically enhance a test image. By way of example, the sensor is a voltmeter that records charge differential. By way of a further example, the sensor records non-visual spectra or hyper spectral light wavelengths. The transmission of data occurs via one or more modes of communication including, for example wavelengths. In some embodiments, the sensor is a voltmeter. In some embodiments, the assay reader transmits data to a mobile device via a wired connection (e.g., an audio port adapter, a USB port, etc.) or a wireless connection (e.g., Wi-Fi, Bluetooth, etc.).

The reader 300 may include a filter, or a series of filters, configured to capture specific wavelengths. The filter can be configured to reduce noise generated by a respective assay.

The assay reader 300 may include one or more automation features. For example, the assay reader 300 includes a mechanical lever to automate the release of fluids, to puncture buffer membranes, and/or to initiate an initial catalyst for a reaction. In another example, the assay reader 300 includes a basic relay of assay status to report to a mobile device and/or to initiate next steps, e.g., imaging. In yet another example, the assay reader 300 includes electrodes to connect to an assay cartridge and/or to initiate electric components, such as a voltmeter. The electrodes, by way of further example, initiate a charge to separate ions and charged molecules.

The assay reader 300 may include a light source. For example, the light source is a single light-emitting diode (LED) or a series of LEDs that are housed within the assay reader 300 to diffract light at specific angles for recording absorptions and/or fluorescence with increased accuracy.

The assay reader can be an independent unit that does not associate with a mobile device. In these embodiments, the assay reader has its own power source or power adapter. Some embodiments contain lenses, sensors, filters, voltaic electrodes or any combination thereof to run and image assay results.

Snap-on Adapter

As an example shown in FIGS. 5A-6E, a Snap-on adapter 200 is configured for attaching an assay reader 300 (shown in FIGS. 8A-10C) to a mobile phone. The Snap-on adapter 200 includes a top-left end 202, a top-right end 203, a bottom-left end 204, and a bottom-right end 205. Each of the ends 202-205 flexibly conforms to capture within an internal area of a mobile phone (such as mobile phone 112 shown in FIG. 1), with an internal surface 206 of the Snap-on adapter 200 being in contact with a front surface of the mobile phone 112 when the Snap-on adapter 200 is attached to the mobile phone 112.

The Snap-on adapter 200 further includes a viewing window 210, a reader interface 212, and a locating element 214. The viewing window 210 is in proximity to the top-left end 202 and is configured to rest over the camera 115 of the mobile phone 112. The viewing window 210 is further configured to align the camera 115 with a reader window 302 (shown in FIG. 8B) such that external light leaks are prevented or greatly reduced. The reader interface 212 is configured to receive a reader latch 304 of the assay reader 300 (shown in FIG. 8B) and facilitate the direct coupling of the Snap-on adapter 200 and the assay cartridge 300. Specifically, the reader interface 212 has a three-pronged mating surface 218 with receiving holes 220 in-between each of the prongs for receiving respective latch inserts 306 of the reader latch 304.

The locating element 214 cooperates with the reader interface 212 to support a bottom surface 308 (shown in FIG. 9A) of the assay reader 300 and facilitate proper alignment and positioning of the assay reader 300 when the latch 304 is secured within the reader interface 212. To couple the Snap-on adapter 200 and the assay reader 300, the two components are aligned such that the latch inserts 306 are initially aligned, respectively, with the receiving holes 220. Then, the Snap-on adapter 200 and the assay reader 300 are rotated relative to each other to secure in place the latch inserts 306 relative and internal to the prongs of the three-pronged mating surface 218. The locating element 214 provides a stopping point for the rotation motion when the bottom surface 308 makes contact with a top surface of the locating element 214.

Mobile Interface

Systems, devices and kits disclosed herein can be connected with an interactive mobile application (app), such as the mobile app 112 illustrated in FIG. 1. The mobile app can tie data acquisition to comprehensive behavioral management. For example, the diagnostic assays can focus on STIs, where the mobile app may track monthly results. The individual user can detect the presence of semen in the cervicovaginal fluid sample. The individual user can track therapeutic interventions as prescribed by primary care physicians to that particular user. Therapeutic options, safe sex options, and education are all aspects of the mobile app. The app can recommend locations and clinics for women based on user verified and highly curated reviews and other data on the internet, such as recommendation sites.

The technology allows for assessment of pre-pregnancy health, including iron-deficiency, folate deficiency and vitamin optimization (ensuring a balance of all nutrients). A mobile app bundle can help women plan for pregnancy and recommend healthy habits before, during, and after pregnancy.

The individual user can detect and track hormone levels, nutrition markers, fertility markers such as AMH, LH and FSH, shed reproductive cancer cells, reproductive disorders such as endometriosis and polycystic ovarian syndrome, environmental toxins, and other blood based or mucosa based health biomarkers.

A website and emailing list can be used to form a community of users who rely on the extraction device to keep them informed of relevant health issues. In some embodiments, the website is a bi-directional mechanism to engage with a target audience and provide education on health risks and factors.

The website can serve as a portal to collect phenotypic and demographic data on consumers. Lifestyle choices, predispositions for certain diseases, age, pre-existing conditions and other health factors determine what tests a woman should be testing for on a regular basis. User engagement with the website, such as what conditions she researches, user input on proprietary mobile applications, such as a pain diary, and responses to explicit questions help customize her experience and allow for personalized recommendations on test selection and frequency.

Proprietary algorithms can determine a user's non-prescription based needs and offer to seamlessly facilitate the purchase and delivery of items such as food, consumables or OTC medications to her doorstep through integration with other vendors such as Amazon®, Target®, Walmart®, Whole Foods®, and other retailers.

Proprietary algorithms can determine appropriate support groups, on-line communities and other consumer introductions the user may want to access and be open to considering. The aggregate biological and phenotypic data provided by users can facilitate a unique opportunity to connect clients with appropriate resources, groups and other users.

The mobile app 112 can further include one or more automation protocols, secure data transmission features, data visualization features, and/or other functionalities. The automation protocols include, for example, a stored protocol or run parameters for lateral flow, isothermal PCR, aptamers, DNA/RNA switches, Voltage assays, and/or gel electrophoresis. In another example, for algorithm calculations, the automation protocols include imaging protocols for increased signal-to-noise ratios. In yet another example, the automation protocols include actionable next-step protocols after results are reported. The next-step protocols can include, for example, medical recommendations, health tips, nutrition suggestions, and/or purchasing on partner websites. In yet a further example, the automation protocols include curation protocols to external sites and/or partners for initiating next-step protocol recommendations.

The secure data transmission features include, for example, HIPPA compliance, anonymous log-in, identified log-in, de-identified data transmission, data encryption, and/or data transfer initiation to the cloud for storage and/or analysis. In another example, the secure data transmission features include transfer of data to medical personnel, a third-party insurer, and/or other individual, group, or entity. In yet another example, the secure data transmission features include syncing with other health applications and/or services.

The data visualization features include, by way of example, visualization of data trends from month to month, and/or throughout the medical history of the respective patient or user. In another example, the data visualization includes a comparison of data to national and/or company averages. In yet another example, the data visualization includes charting of personal reference ranges and/or correlation discovery between different analyte trends.

Other functionalities include, by way of example, importing data from previous doctor visits, adding to data trends, recording all tests throughout a user's history, and importing old data from a storage facility (such as from the Cloud). According to other examples, functionalities include collection of third-party insurance information, including copays and cost structure of medical codes, and/or collection of medical personnel information.

Some exemplary embodiments of various aspects of the disclosure disclosed herein can be described by one or more of the following:

1. A medical kit for analysis of vaginal biological samples, the kit comprising:
    a sample collector insertable in a vaginal canal for collecting biological samples, the sample collector being compressible and including a cup-shaped head configured to cradle a uterus cervix;
    an extractor comprising
        a sample receptacle configured to receive the sample collector via an open end,
        a compression mechanism with a compression element and a release element, the compression element being movable inwards into the open end of the sample receptacle to apply a compression force in response to activation of the release element, and
        a filter which separates particles and components of biological fluid specific to the size of filter pores and is engaged upon activation of compression force, and
        a reservoir in fluid communication with the sample receptacle via the filter, the reservoir receiving the biological samples from the sample collector in response to the compression force being applied within the sample receptacle; and
    an assay cartridge with a docking mechanism configured to fluidly communicate with the reservoir of the extractor.
2. The medical kit of paragraph 1, wherein the sample collector comprises:
    an inner shell with a diffusely permeated thread matrix that facilitates collapse of the sample collector in response to a compressive force;
    an outer shell with a dense and absorbent plant fiber material; and
    a base with at least one layer of absorbent cotton material for forming a reinforced seal.
3. The medical kit of paragraph 1 or 2, wherein the sample collector comprises a material selected from a group consisting of a disposable material, a flushable material, a biodegradable material, an organic material, and a natural material.
4. The medical kit of any one of paragraphs 1-3, wherein the sample collector comprises a body connected to a removal element.
5. The medical kit of any one of paragraphs 1-4, wherein the compression mechanism comprises a spring, threaded screw, lever, or manual push syringe, coupled between the release element and the compression element, the spring, threaded screw, lever, or manual push syringe forcing the compression element inwards into the open end of the sample receptacle in response to the activation of the release element.
6. The medical kit of any one of paragraphs 1-5, wherein the filter is a removable filter.
7. The medical kit of any one of paragraphs 1-6, wherein the reservoir of the extractor comprises a plurality of detachable compartments, each detachable compartment of the plurality of detachable compartments being configured to receive a portion of the biological samples.
8. The medical kit of any one of paragraphs 1-7, wherein the extractor further comprises a filter having a plurality of pores and being selected from a group consisting of a cellulose filter, a plastic filter, a metal filter, and any combination thereof, wherein the filter is positioned between the sample receptacle and the reservoir.
9. The medical kit of any one of paragraphs 1-8, wherein the extractor further comprises a one-way pressure valve or resealable rubber slit, positioned within the reservoir, the pressure valve or rubber slit releasing biological samples collected in the reservoir in response to the docking mechanism of the assay cartridge being connected with the reservoir.
10. The medical kit of any one of paragraphs 1-9, wherein the assay cartridge comprises a viewing window for visualization of assay results.
11. The medical kit of any one of paragraphs 1-10, further comprising a cartridge reader comprising cartridge optics, a cartridge interface, and a mobile interface, the cartridge interface configured to receive the assay cartridge, the mobile interface being configured to communicate with a mobile device.
12. A method for home-care monitoring of a health condition, the method comprising:
    inserting a sample collector in a vaginal canal and collecting biological samples;

removing the sample collector from the vaginal canal and placing the sample collector inside a sample receptacle of an extractor;

compressing the sample collector within the sample receptacle by applying a force via a compression mechanism;

eluting the biological material from the sample collector through a breakable pouch;

receiving the biological samples and buffer from the sample collector into a reservoir of the extractor;

docking an assay cartridge in fluid communication with the reservoir, thereby allowing at least some of the biological samples to make contact with diluents or reagents of the assay cartridge; and determining a health condition based on a reaction between the biological samples and the diluents or reagents.

13. The method of paragraph 12, further comprising inserting the assay cartridge in a cartridge reader, the cartridge reader having internal circuitry for determining the health condition.

14. The method of paragraph 12 or 13, further comprising inserting the assay cartridge in a cartridge reader, the cartridge reader communicating data associated with the biological samples to an external device.

15. The method of any one of paragraphs 12-14, further comprising receiving health next-step instructions based on the determined health condition.

16. The method of any one of paragraphs 12-15, wherein the health condition is related to sexually transmitted infections (STIs), semen, cancer, fertility, or nutrient levels.

17. A medical kit for analysis of biological samples, the kit comprising:
a sample collector insertable in a body cavity for collecting biological samples, the sample collector being compressible and including an absorbent-diffuse material for absorbing and releasing fluids;
an extractor for acquiring the biological samples from the sample collector, the extractor including a receptacle in which the sample collector is received, the extractor including a compression mechanism for applying a force within the receptacle to release the biological samples from an inserted sample collector; the extractor including a breakable pouch of buffer or reagent to aid in elution of biological sample from sample collector;
an assay cartridge with an extractor interface and a reader interface, the extractor interface configured to be coupled in fluid communication with the extractor, the biological samples being transferred from the extractor to the assay cartridge via the extractor interface; and
a cartridge reader with a cartridge interface configured for interfacing with the reader interface, the cartridge reader receiving assay data from the assay cartridge and communicating at least some of the assay data to a mobile device via a mobile interface.

18. The medical kit of paragraph 17, wherein the assay cartridge comprises internal circuitry configured to determine a health condition based on the biological samples.

19. The medical kit of paragraph 18, wherein the health condition is automatically determined without user intervention.

20. The medical kit of any one of paragraphs 17-19, wherein the assay cartridge comprises one or more readouts selected from a group consisting of a visual readout, a colorimetric readout, a fluorescent readout, a voltage readout, or a hyperspectral readout, the one or more readouts indicating the health condition.

21. The medical kit of any one of paragraphs 17-20, wherein the assay cartridge comprises a pouch with one or more reagents or buffers and the cartridge reader includes a puncture element, the pouch being punctured to release at least one of the one or more reagents or buffers in response to activation of the puncture element.

Methods of Use

Disclosed herein are systems, devices and methods for collecting and analyzing a biological sample from a subject. The subject can be a female. The subject can be pregnant. The subject can be non-pregnant. Some aspects relate to methods for collecting and analyzing a biological sample, e.g., menstrual flow, blood, cervicovaginal fluid, or secretion, from the subject's cervicovaginal canal. The methods may comprise detecting or testing the presence of nucleic acids of interest, disease, and/or infections in the collected biological sample. The methods may comprise analyzing and determining the status of a disease and/or infection. The methods may comprise communicating the analysis result to the subject. The methods may further comprise recommending a medicine, a therapeutic regimen, a physician, a medical specialist, and/or a diet to the subject. The methods may further comprise preserving, storing and/or transporting the collected biological sample to a different location (e.g., CLIA certified clinical laboratory) for downstream analysis.

Clinical research often involves collecting blood sample from a subject for screening for a disease, monitoring a disease status, monitoring effectiveness of a therapeutic regimen, verifying a diagnosed disease, or follow-up analysis of a test. The maximum allowable total blood drawn volume from a subject is often determined by the subject's body weight (Table 1) and growth. According to a guideline from the University of California Davis Medical Center, the maximum allowable volume in one blood draw from an adult subject having about 40-45 kilograms (kg) body weight is about 82-90 mL. The Stanford Hospital recommends that the minimum whole blood volume for laboratory testing on chemistry is between about 0.6 mL to 1.2 mL, on hematology and coagulation is between about 0.5 to 1.8 mL, and on microbiology, and transfusion is between about 0.5 mL to 20 mL. See www.staanfordlab.com/LabTestGuide/Documents/Minimum%20Volume%20%2010-2-12%20RevB.pdf. For example, the recommended minimum whole blood volume for laboratory tests for blood culture for an adult is about 20 mL for aerobic bacteria and about 10 mL for anaerobic bacteria.

TABLE 1

Maximum allowable total blood draw volumes for clinical and research purposes.
CMRC IRB MAXIMUM ALLOWABLE TOTAL BLOOD DRAW VOLUMES
(CLINICAL + RESEARCH)

| Body Wt (Kg) | Body Wt (lbs) | Total blood volume (mL) | Maximum allowable volume (mL) in one blood draw (=2.5% of total blood volume) | Total volume (clinical + research) maximum volume (mL) drawn in a 30-day period | Minimum Hgb required at time of blood draw | Minimum Hgb required at time of blood draw if subject has respiratory/CV compromise |
|---|---|---|---|---|---|---|
| 1 | 2.2 | 100 | 2.5 | 5 | 7.0 | 9.0-10.0 |
| 2 | 4.4 | 200 | 5 | 10 | 7.0 | 9.0-10.0 |
| 3 | 6.3 | 240 | 6 | 12 | 7.0 | 9.0-10.0 |
| 4 | 8.8 | 320 | 8 | 16 | 7.0 | 9.0-10.0 |
| 5 | 11 | 400 | 10 | 20 | 7.0 | 9.0-10.0 |
| 6 | 13.2 | 480 | 12 | 24 | 7.0 | 9.0-10.0 |
| 7 | 15.4 | 560 | 14 | 28 | 7.0 | 9.0-10.0 |
| 8 | 17.6 | 640 | 16 | 32 | 7.0 | 9.0-10.0 |
| 9 | 19.8 | 720 | 18 | 36 | 7.0 | 9.0-10.0 |
| 10 | 22 | 800 | 20 | 40 | 7.0 | 9.0-10.0 |
| 11-15 | 24-33 | 880-1200 | 22-30 | 44-60 | 7.0 | 9.0-10.0 |
| 16-20 | 35-44 | 1280-1600 | 32-40 | 64-80 | 7.0 | 9.0-10.0 |
| 21-25 | 46-55 | 1680-2000 | 42-50 | 64-100 | 7.0 | 9.0-10.0 |
| 26-30 | 57-66 | 2080-2400 | 52-60 | 104-120 | 7.0 | 9.0-10.0 |
| 31-35 | 68-77 | 2480-2800 | 62-70 | 124-140 | 7.0 | 9.0-10.0 |
| 36-40 | 79-88 | 2880-3200 | 72-80 | 144-160 | 7.0 | 9.0-10.0 |
| 41-45 | 90-99 | 3280-3600 | 82-90 | 164-180 | 7.0 | 9.0-10.0 |
| 46-50 | 101-110 | 3680-4000 | 92-100 | 184-200 | 7.0 | 9.0-10.0 |
| 51-55 | 112-121 | 4080-4400 | 102-110 | 204-220 | 7.0 | 9.0-10.0 |
| 56-60 | 123-132 | 4480-4800 | 112-120 | 224-240 | 7.0 | 9.0-10.0 |
| 61-65 | 134-143 | 4880-5200 | 122-130 | 244-260 | 7.0 | 9.0-10.0 |
| 68-70 | 145-154 | 5280-5600 | 132-140 | 264-280 | 7.0 | 9.0-10.0 |
| 71-75 | 156-185 | 5680-6000 | 142-150 | 284-300 | 7.0 | 9.0-10.0 |
| 76-80 | 167-176 | 6080-6400 | 152-160 | 304-360 | 7.0 | 9.0-10.0 |
| 81-85 | 178-187 | 6480-6800 | 162-170 | 324-340 | 7.0 | 9.0-10.0 |
| 86-90 | 189-198 | 6880-7200 | 172-180 | 344-360 | 7.0 | 9.0-10.0 |
| 91-95 | 200-209 | 7280-7600 | 182-190 | 364-380 | 7.0 | 9.0-10.0 |
| 96-100 | 211-220 | 7680-8000 | 192-200 | 384-400 | 7.0 | 9.0-10.0 |

In a randomly selected group of premenopausal women, the most common amount of menstrual flow (measured in a laboratory from all collected tampons and pads) is about two tablespoons (30 mL) in a whole period (www.cemcor.ubc.ca/resources/very-heavy-menstrual-flow). The amount of flow is highly variable and can range from a spot to over two cups (540 mL) in one period. The usual length of menstrual bleeding is about 3 to 7 days. The usual amount of blood loss per period is about 10 mL to about 35 mL. Because menstruation is a natural monthly bleeding of a pre-menopause woman and the procedure for collecting menstrual flow does not involve surgical procedure or performance of a trained profession, collecting menstrual flow provides opportunities for self-collecting large volume of blood, and bodily fluid, and shed cells for clinical test on a regular base. Exemplary clinical blood tests include, but are not limited to, tests for one or more of hormone, lipid, HIV, HPV, sexually transmitted diseases, blood sugar level, blood toxicity level, iron and nutrition concentration, and presence of antigen. Further, the menstrual flow comprises more than just blood. Often, shed cells from the lining of the uterus and endometriosis, secreted mucus, and cervicovaginal fluid (CVF) in the cervicovaginal canal are discharged along with the menstrual blood, which can be collected for diagnostic and/or screening test for diseases. The present application provides for systems, methods, devices and kits for self-collecting blood and/or bodily fluid from a female subject for use in health monitoring.

The first day of menstrual flow is defined as day number one of the next menstrual cycle. Menstruation lasts for approximately 3 to 7 days, although some women have shorter or longer periods. The average menstrual cycle lasts about 28 days, but can last anywhere from 24 to 42 days. There are three major phases of the menstrual cycle: the menstrual phase, the proliferate phase, and the secretory phase. The menstrual phase usually occurs during the first 1-7 days of a 28-day menstrual cycle. The menstrual phase is the phase during which the lining of the uterus, called the endometrium, is shed as menstrual flow out of the cervix and vagina. This process is what women experience during their menstrual periods or menstruation.

The proliferative phase, also referred to as the follicular phase, is the part of the menstrual cycle during which follicles inside the ovaries develop and mature in preparation for ovulation. The proliferative phase usually occurs from day 7-14 of a 28-day menstrual cycle. The levels of follicle-stimulating hormone (FSH) increase in the bloodstream during the proliferative phase, stimulating the maturation of follicles. Each follicle contains an ovum, or egg. A mature follicle may release the ovum at the time of ovulation.

Also during the proliferative phase, the ovaries produce estrogen. The rising levels of estrogen cause the lining of the uterus to begin thickening. Once the levels of estrogen are at their peak, the pituitary gland slows the secretion of FSH, and instead begins to secrete luteinizing hormone (LH). As a result of the increase in LH, the mature follicle ruptures and releases the ovum from inside, also termed ovulation. Ovulation occurs about 14 days before the beginning of the next menstrual period.

The secretary phase or luteal phase occurs after ovulation. LH causes the burst follicle to develop into a structure called the corpus luteum. The corpus luteum is a small yellow structure in the ovary that secretes the hormones estrogen and progesterone. The progesterone and the estrogen are at a high level during the secretory phase, and they help prepare the endometrium to secrete nutrients that may nourish a conceptus if a fertilized egg were to implant in it. If conception and implantation do not occur, the pituitary gland may reduce LH and FSH production. Without the presence of LH, the corpus luteum deteriorates and subsequently the estrogen and progesterone levels decrease. The drop in estrogen and progesterone levels triggers the shedding of the endometrium, causing menstruation to begin and the cycle starts over again.

The endometrium is the tissue that lines the inside of the uterus. Endometriosis is defined as the presence of endometrial-like tissue (glands and stroma) outside the uterus, which induces a chronic inflammatory reaction, scar tissue, and adhesions that may distort a woman's pelvic anatomy (Bulletti et. al., Endometriosis and infertility. J Assist Reprod Genet. 2010 August; 27(8): 441-447, which is incorporated herein in its entirety.). Endometriosis is primarily found in young women, but its occurrence is not related to ethnic or social group distinctions. Patients with endometriosis mainly complain of pelvic pain, dysmenorrhea, and/or dyspareunia. The associated symptoms can impact the patient's general physical, mental, and/or social well-being.

Endometriosis can be assessed by determining the presence or absence of a biomarker in a biological sample collected from the endometrium or uterus lining. Methods for assessing endometriosis are described in International Patent Application Publication No. WO2015050875, which is incorporated herein in its entirety. The biological sample can be an endometrium tissue collected by biopsy. The biological sample can be a cell from shedding of the endometrium during the menstrual cycle. The biological sample can be collected during menstrual phase (MP), proliferative phase (PE), early secretory phase (ESE), mid-secretory phase (MSE), and/or independent of cycle phase. The presence or absence, or change of expression level of a biomarker may be associated with the presence and/or severity of endometriosis. Thus, determining the expression level of a biomarker in a tissue sample provides a diagnosis of the presence, absence and/or severity of endometriosis based on the association. The biomarker can comprise nucleic acids encoding a gene set forth in Tables 2, 3, 4, 5, 6, 7, 8, 9 and/or 10. In some embodiments, the expression level of a set of biomarkers is determined. The set of biomarkers can comprise about 1-10,000, 1-1000, 1-100, 200-8000, 300-5000, 400-2000, 500-1000, 50-200, 20-100, 15-30, 10-20, 5-15, or 1-10 genes. The set of biomarkers can comprise about 1, 2, 3, 4, 5, 6, 7, 8, 9, 10, 15, 20, 25, 30, 40, 50, 60, 70, 80, 90, 100, or more genes. The set of biomarkers can comprise at most about 1, 2, 3, 4, 5, 6, 7, 8, 9, 10, 15, 20, 25, 30, 40, 50, 60, 70, 80, 90, 100, 1000, or 10,000 genes. The expression level of the biomarker in the endometriosis sample from a subject diagnosed of endometriosis can be increased or decreased when compared to the expression level of the biomarker in a sample from a second subject that is not diagnosed with endometriosis. The expression level of the biomarker in the endometriosis sample from a subject diagnosed of endometriosis can be increased or decreased when compared to the expression level of the biomarker in a sample from the subject that is not is expressed in a different region of the body other than the reproductive system, e.g., muscle from a limb, hair follicle. The expression level of the biomarker in the endometriosis sample can be increased or decreased by about 1-100%, 10-90%, 20-80%, 30-70%, 40-60%, 15-85%, 25-75%, 35-65%, or 45-55%. The expression level of the biomarker in the endometriosis sample can be increased or decreased by at least about 10%, 15%, 20%, 30% 40%, 50%, 60%, 70%, 80%, 90%, 95%, 99%, or 100%. The determination of the biomarker may comprise determining the nucleic acid sequence by using an Illumina sequencing platform or any sequencing techniques and platforms in the field. The biomarker may have a change of nucleic acid sequence in the endometriosis sample. The change of nucleic acid can be a mutation, e.g., point mutation or single nucleotide polymorphism, multiple nucleotide polymorphism, insertion (e.g., insertion of one or more nucleotides at a locus), multiple nucleotide change, deletion (e.g., deletion of one or more nucleotides at a locus), and inversion (e.g., reversal of a sequence of one or more nucleotides).

In general, biological sample comprising endometrial cells collected using systems, methods, and devices described herein are tested for the presence or absence of pathology. The testing may involve evaluating a change of expression level of biomarkers set forth in Tables 2, 3, 5, 6, 8, and 9. Evaluation of a biomarker expression level can be achieved by QPCR, microarray, deep-sequencing, or Western blot. Once a biological sample is determined to have pathology, the biological sample is evaluated for the type of pathology. The pathology can be endometriosis, uterine pathology, or pelvic pathology. For instance, the biological sample is evaluated for the presence of endometriosis pathology or non-endometriosis pathology. Subsequently, the biological sample is evaluated for severity of the endometriosis pathology, e.g., mild or moderate. The severity of endometriosis can be evaluated by associating the expression level of at least one biomarker or at least one set of biomarkers set forth in Tables 4, 7, and 15. The evaluation can be menstrual cycle phase specific (e.g., PE, ESE, MSE) or non-phase specific.

In some embodiments, biomarkers are used for determining the presence or absence of pathology in a biological sample comprising endometrial cells, wherein the biological sample is collected from proliferation phase (PE) using systems, methods and devices described herein. The biomarkers can comprise at least one set of genes set forth in Table 2.

TABLE 2

Biomarkers for determining the presence or absence of a pathology in a biological sample comprising endometrial cells from proliferation phase (PE).

| Gene Symbol* | Gene Title* |
|---|---|
| GenBank: B1547087 | 603190322F1 NIH_MGC_95 Homo sapiens cDNA clone IMAGE: 5261717 5-, mRNA sequence |

TABLE 2-continued

Biomarkers for determining the presence or absence of a pathology in a
biological sample comprising endometrial cells from proliferation phase (PE).

| Gene Symbol* | Gene Title* |
| --- | --- |
| GenBank: BG389789 | 602415167F1 NIH_MGC_92 Homo sapiens cDNA clone IMAGE: 4523513 5-, mRNA sequence |
| FOSB | FBJ murine osteosarcoma viral oncogene homolog B; GenBank: NM_006732 |
| DIO2 | deiodinase, iodothyronine, type II |
| DDX17 | DEAD (Asp-Glu-Ala-Asp) box polypeptide 17; Genbank Nos: Z97056, AA521056, U59321, AW188131, NM_030881. |
| FOS | FBJ murine osteosarcoma viral oncogene homolog; GenBank: BC004490 |
| MALAT1 | metastasis associated lung adenocarcinoma transcript 1 (non-protein coding) |
| SNTN | sentan, cilia apical structure protein |

*GenBank accession number and definition are provided for non-characterized transcripts.

As described herein, biomarkers can be used for determining the presence or absence of endometriosis or other pathology in a biological sample that has been determined to have pathology. The pathology can comprise endometriosis, uterine pathology, or pelvic pathology. The biomarkers can comprise at least one set of genes set forth in Table 3.

TABLE 3

Biomarkers for determining the presence or absence of endometriosis in a
biological sample comprising endometrial cells from proliferation phase (PE).

| Gene Symbol* | Gene Title* |
| --- | --- |
| SLC8A1 | Solute carrier family 8 (sodium/calcium exchanger), member 1; GenBank: AW452398 |
| LOC728613 | programmed cell death 6 pseudogene |
| LTF | Lactotransferrin; Gen Bank: NM_002343 |
| HLA-DQA1 | major histocompatibility complex, class II, DQ alpha 1 |
| SLC7A4 | solute carrier family 7 (cationic amino acid transporter, y+ system), member 4; GenBank: NM_004173 |
| PCDH8 | protocadherin 8 |
| CDKN2A | cyclin-dependent kinase inhibitor 2A (melanoma, p16, inhibits CDK4) |
| MUC5B | mucin 5B, oligomeric mucus/gel-forming |
| IQGAP1 | IQ motif containing GTPase activating protein 1 |
| RBM6 | RNA binding motif protein 6 |
| GenBank: AA5210576 | aa71e05.s1 NCI_CGAP_GCB1 Homo sapiens cDNA clone IMAGE: 826400 3-, mRNA sequence |
| DDX17 | DEAD (Asp-Glu-Ala-Asp) box helicase 17 |
| SCGB3A1 | secretoglobin, family 3A, member 1 |
| GenBank: AW629304 | hi56d01.x1 Soares_NFL_T_GBC_S1 Homo sapiens cDNA clone IMAGE: 2976289 3-, mRNA sequence |
| LOC401522 | hypothetical LOC401522 |
| NASP | Nuclear autoantigenic sperm protein (histone-binding) |
| ACTA2 | Actin, alpha 2, smooth muscle, aorta |

*GenBank accession number and definition are provided for non-characterized transcripts.

As described herein, biomarkers can be used for determining the severity of endometriosis in a biological sample that has been determined to have endometriosis. Severity of endometriosis can be classified as mild or moderate. The biomarkers can comprise at least one set of genes set forth in Table 4.

TABLE 4

Biomarkers for determining the severity of endometriosis in a biological
sample comprising endometrial cells from proliferation phase (PE).

| Gene Symbol* | Gene Title* |
| --- | --- |
| ANLN | anillin, actin binding protein; Genbank: AK023208, NM_018685. |
| LOC142937 | hypothetical protein BC008131 |
| GINS4 | GINS complex subunit 4 (Sld5 homolog) |
| VIM | vimentin |
| LOC100127980 | Hypothetical protein LOC 100127980 |
| GenBank: A1741292 | wg08h02.x1 Soares_NSF_F8_9W_OT_PA_P_S1 *Homo sapiens* cDNA clone IMAGE: 2364531 3-, mRNA sequence |
| GenBank: AL390180 | *Homo sapiens* genomic DNA; cDNA DKFZp761L149 (from clone DKFZp761L149) |

TABLE 4-continued

Biomarkers for determining the severity of endometriosis in a biological sample comprising endometrial cells from proliferation phase (PE).

| Gene Symbol* | Gene Title* |
|---|---|
| LOC100505967 | hypothetical LOC100505967 |
| GenBank: AL832142 | *Homo sapiens* mRNA; cDNA DKFZp686A22111 (from clone DKFZp686A22111) |
| GenBank: AK026037 | *Homo sapiens* cDNA: FLJ22384 fis, clone HRC07594 |
| CASP8AP2 | caspase 8 associated protein 2 |
| LTF | lactotransferrin |
| FBN1 | fibrillin 1; Genbank: NM_000138, AW955612. |
| CDH3 | cadherin 3, type 1, P-cadherin (placental) |
| EPHA2 | EPH receptor A2 |
| GSTT1 | glutathione S-transferase theta 1 |
| MAPRE3 | microtubule-associated protein, RP/EB family, member 3 |
| PRKX /// PRKY | protein kinase, X-linked /// protein kinase, Y-linked |
| PRKX | protein kinase, X-linked |
| GSTM4 | glutathione S-transferase mu 4 |
| SLC12A2 | solute carrier family 12 (sodium/potassium/chloride transporters), member 2 |
| GSTM2 | glutathione S-transferase mu 2 (muscle) |
| FOSL1 | FOS-like antigen 1 |
| GSTM1 | glutathione S-transferase mu 1 |
| HSD17B2 | hydroxysteroid (17-beta) dehydrogenase 2 |
| NMT2 | N-myristoyltransferase 2 |
| GABRP | gamma-aminobutyric acid (GABA) A receptor, pi |
| PDZK1 | PDZ domain containing 1 |
| VNN1 | vanin 1 |
| PLCL1 | phospholipase C-like 1 |
| REN | renin |
| CDKN2A | carcinoembryonic antigen-related cell adhesion molecule 1 (biliary glycoprotein) |
| CRYBB2 /// CRYBB2P1 | crystallin, beta B2 /// crystalin, beta B2 pseudogene 1 |
| SCGB1D2 | secretoglobin, family 1D, member 2 |
| LPHN2 | latrophilin 2 |
| CDKN2A | cyclin-dependent kinase inhibitor 2A (melanoma, p16, inhibits CDK4) |
| SFRP5 | secreted frizzled-related protein 5 |
| D4S234E | DNA segment on chromosome 4 (unique) 234 expressed sequence |
| BMP7 | bone morphogenetic protein 7 |
| MYCN | v-myc myelocytomatosis viral related oncogene, neuroblastoma derived (avian) |
| PTPN11 | protein tyrosine phosphatase, non-receptor type 11 |
| SF1 | splicing factor 1 |
| GZMH | granzyme H (cathepsin G-like 2, protein h-CCPX) |
| FGF18 | fibroblast growth factor 18 |
| PEG10 | paternally expressed 10 |
| SLC7A1 | solute carrier family 7 (cationic amino acid transporter, y+ system), member 1 |
| MUC5B | mucin 5B, oligomeric mucus/gel-forming |
| GenBank: AI345238 | tb81b07.x1 NCI_CGAP_Lu26 *Homo sapiens* cDNA clone IMAGE: 2060725 3- similar to gb: M10119 FERRITIN LIGHT CHAIN (HUMAN);, mRNA sequence |
| CEACAM21 | carcinoembryonic antigen-related cell adhesion molecule 21 |
| GenBank: H92070 | vs84f02.s1 Soares retina N2b4HR *Homo sapiens* cDNA clone IMAGE: 221499 3-similar to contains Alu repetitive element; contains PTR5 repetitive element;, mRNA sequence |
| CALD1 | caldesmon 1 |
| LOC100507804 /// TPSAB1 | tryptase alpha-1-like /// tryptase alpha/beta 1 |
| HYMAI | hydatidiform mole associated and imprinted (non-protein coding) |
| LOC642869 /// SET | SET translocation (myeloid leukemia-associated) pseudogene /// SET nuclear oncogene |
| KIAA1661 | KIAA1661 protein |
| FAM48A | Family with sequence similarity 48, member A |
| BEX1 | brain expressed, X-linked 1 |
| SYBU | syntabulin (syntaxin-interacting) |
| ECEL1 | endothelin converting enzyme-like 1 |
| HELLS | helicase, lymphoid-specific |
| ZBBX | zinc finger, B-box domain containing |
| IQCG | IQ motif containing G |
| KLHL24 | kelch-like 24 (*Drosophila*) |
| LOC389906 | hypothetical LOC389906 |
| LOC100510224 | hypothetical LOC100510224 |
| WHSC1L1 | Wolf-Hirschhorn syndrome candidate 1-like 1 |
| TMEM106B | transmembrane protein 106B |
| GNG12 | guanine nucleotide binding protein (G protein), gamma 12 |
| ENPP3 | ectonucleotide pyrophatase/phosphodiesterase 3 |
| FOXP1 | forkhead box P1 |
| PRO2852 | hypothetical protein PRO2852 |

TABLE 4-continued

Biomarkers for determining the severity of endometriosis in a biological
sample comprising endometrial cells from proliferation phase (PE).

| Gene Symbol* | Gene Title* |
| --- | --- |
| SECISBP2 | SECIS binding protein 2 |
| MS4A8B | membrane-spanning 4-domains, subfamily A, member 8B |
| MALAT1 | metasis associated lung adenocarcinoma transcript 1 (non-protein coding) |
| PDK4 | pyruvate dehydrogenase kinase, isozyme 4 |
| SNRPN | small nuclear ribonucleoprotein polypeptide N |
| FAM110C | family with sequence similarity 110, member C |
| LOC100131564 | hypothetical LOC100131564 |
| LOC727820 | hypothetical protein LOC727820 |
| ERAP2 | endoplasmic reticulum aminopeptidase 2 |
| SDCCAG8 | serologically defined colon cancer antigen 8 |
| NKAIN4 | Na+/K+ transporting ATPase interacting 4 |
| GenBank: AA601031 | nk67d10.s1 NCI_CGAP_Sch1 Homo sapiens cDNA clone IMAGE: 1018579 3-, mRNA sequence |
| CDC42SE2 | CDC42 small effector 2 |
| EMID2 | EMI domain containing 2 |
| GOLT1A | golgi transport 1A |
| SLC20A1 | solute carrier family 20 (phosphate transporter), member 1 |
| PKHD1L1 | polycystic kidney and hepatic disease 1 (autosomal recessive)-like 1 |
| GenBank: BE858984 | 7g45a06.x1 NCI_CGAP_Pr28 Homo sapiens cDNA clone IMAGE: 33093943 mRNA sequence |
| GenBank: AI683621 | tw52g09.x1 NCI_CGAP_Ut1 Homo sapiens cDNA clone IMAGE: 2263360 3-, mRNA sequence |
| LOC100506125 | hypothetical LOC100506125 |
| FBXO15 | F-box protein 15 |
| GenBank: AV660825 | AV660825 GLC Homo sapiens cDNA clone GLCGLGO3 3-, mRNA sequence |
| LOC253039 | hypothetical LOC253039 |
| GenBank: AL157491 | Homo sapiens genomic DNA; cDNA DKFZp434K1111 (from clone DKFZp434K1111) |
| GenBank: AF339813 | Homo sapiens clone IMAGE: 297403, mRNA sequence |
| SP3 | spa transcription factor |
| GenBank: AU144005 | AU144005 HEMBA1 Homo sapiens cDNA clone HEMBA1000622 3-, mRNA sequence |
| GenBank: AF119847 | Homo sapiens PRO1550 mRNA, partial cds |
| Gen Bank: AW297731 | UI-H-BWO-aiy-a-04-0-UI.s1 NCI_CGAP_Sub6 Homo sapiens cDNA clone IMAGE: 2730894 3-, mRNA sequence |
| GenBank: BF125564 | 60176331811 N H MGC 20 Homo sapiens cDNA clone IMAGE: 4026173 5-, mRNA sequence |
| ILDR1 | immunoglobulin-like domain containing receptor 1 |
| GenBank: AI431345 | ar55f07.x1 Barstead aorta HPLRB6 Homo sapiens cDNA clone IMAGE: 2126533 3-, mRNA sequence |
| GenBank: AI732617 | zo89e10.x5 Stratagene ovarian cancer (#937219) Homo sapiens cDNA clone IMAGE: 594090 3-, mRNA sequence |
| GenBank: AA228366 | nc39f01.r1 NCI_CGAP_Pr2 Homo sapiens cDNA clone IMAGE: 1010521, mRNA sequence |
| UNC5A | unc-5 homolog A (C. elegans) |
| GenBank: AW197431 | xm49b03.x1 NCI_CGAP_GC6 Homo sapiens cDNA clone IMAGE: 2686541 3-, similar to contains element KER repetitive element;, mRNA sequence |
| NAA25 | N(alpha)-acetyltransferase 25, NatB auxiliary subunit |
| GenBank: BE222109 | hu05h12.x1 NCI_CGAP_Lu24 Homo sapiens cDNA clone IMAGE: 3165767 3-, mRNA sequence |
| PRKRA | protein kinase, interferon-inducible double stranded RNA dependent activator |
| GenBank: AW205632 | UI-H-BI1-afr-e-09-0-UI.s1 NCI_CGAP_Sub3 Homo sapiens cDNA clone IMAGE: 2722673 3-, mRNA sequence |
| RXFP1 | relaxin/insulin-like family peptide receptor 1 |
| GenBank: BF438300 | 7q07e12.x1 NCI_CGAP_Pr28 Homo sapiens cDNA clone IMAGE: 3676918 3-, mRNA sequence |
| GenBank: BE295812 | 601176827F1 NIH_MGC_17 Homo sapiens cDNA clone IMAGE: 3532039 5-, mRNA sequence |
| FLJ39739 | Hypothetical FLI39739 |
| GenBank: AW203986 | UI-H-BI1-aeu-f-12-0-UI.s1 NCI_CGAP_Sub3 Homo sapiens cDNA clone IMAGE: 2720782 3-, mRNA sequence |
| GenBank: AA908970 | ol10a05s1 Soares_NFL_T_GBC_S1 Homo sapiens cDNA clone IMAGE: 1523024 3-, mRNA sequence |
| TULP4 | Tubby like protein 4 |
| FAM81B | family with sequence similarity 81, member B |
| GenBank: BE349858 | ht05b06.x1 NCI_CGAP_Kid13 Homo sapiens cDNA clone IMAGE: 3145811 3-, mRNA sequence |
| GenBank: BF508634 | UI-H-BI4-aop-a-02-0-UI.s1 NCI_CGAP_Sub8 Homo sapiens cDNA clone IMAGE: 3085347 3-, mRNA sequence |
| WDR1 | WD repeat domain 1 |
| GenBank: BE467916 | hz75g08.x1 NCI_CGAP_Lu24 Homo sapiens cDNA clone IMAGE: 32135854 3-, mRNA sequence |

TABLE 4-continued

Biomarkers for determining the severity of endometriosis in a biological sample comprising endometrial cells from proliferation phase (PE).

| Gene Symbol* | Gene Title* |
|---|---|
| C21orf121 | chromosome 21 open reading frame 121 |
| GenBank: R68807 | yi43b01.s1 Soares placenta Nb2HP *Homo sapiens* cDNA clone IMAGE: 141961 3-, mRNA sequence |
| GenBank: AW117264 | xd86f06.x1 Soares__NFL__T__GBC__S1 *Homo sapiens* cDNA clone IMAGE: 2604515 3-, mRNA sequence |
| NUPL1 | nucleoporin like 1 |
| LOC400931 | hypothetical LOC400931 |
| GenBank: AW962458 | EST374531 MAGE resequences, MAGG *Homo sapiens* cDNA, mRNA sequence |
| QKI | Quaking homolog, KH domain RNA binding (mouse) |
| GenBank: AW976631 | EST388740 MAGE resequences, MAGN *Homo sapiens* cDNA, mRNA sequence |
| GenBank: AA608834 | af103h05.s1 Soares__testis__NHT *Homo sapiens* cDNA clone IMAGE: 1030617 3-, mRNA sequence |
| SNRPA1 | Small nuclear ribionucleoprotein polypeptiele A' |
| TMF1 | TATA element modulatory factor 1 |
| IREB2 | iron-responsive element binding protein 2 |
| ASXL1 | additional sex combs like 1 (*Drosophila*) |
| GenBank: BF055144 | 7j75e01.x1 Soares__NSF__F8__9W__OT__PA__P__Si *Homo sapiens* cDNA clone IMAGE: 3392282 3-, mRNA sequence |
| LRPAP1 | low density lipoprotein receptor-related protein associated protein 1 |
| GenBank: N39188 | yv2d08.s1 Soares fetal liver spleen 1NFLS *Homo sapiens* cDNA clone IMAGE: 243855 3- similar to contains Alu repetitive element; contains element MER35 repetitive element;, mRNA sequence |
| GenBank: A1650364 | wa90a01.x1 NCI_CGAP_GC6 *Homo sapiens* cDNA clone IMAGE: 2303400 3- similar to contains Alu repetitive element;, mRNA sequence |
| GenBank: A1467945 | tj84d07.x1 Soares__NSF__F8__9W__OT__PA__P__S1 *Homo sapiens* cDNA clone IMAGE: 2148205 3-, mRNA sequence |
| GenBank: AA682674 | zj20h10.s1 Soares__fetal_liver__spleen__1NFLS__S1 *Homo sapiens* cDNA clone IMAGE: 450883 3-, mRNA sequence |
| RAB18 | RAB18, member RAS oncogene family |
| GJC1 | gap junction protein, gamma 1, 45 kDa |
| CMIP | C-Maf-inducing protein |
| GenBank: AV691872 | AV691872 GKC *Homo sapiens* cDNA clone GKCDSB09 5-, mRNA sequence |
| GenBank: AW972881 | EST384976 MAGE resequences, MAGL *Homo sapiens* cDNA, mRNA sequence |

*GenBank accession number and definition are provided for non-characterized transcripts.

In some embodiments, biomarkers are used for determining the presence or absence of pathology in a biological sample comprising endometrial cells, wherein the biological sample is collected from early secretory phase (ESE) using systems, methods and devices described herein. The biomarkers can comprise at least one set of genes set forth in Table 5.

TABLE 5

Biomarkers for determining the presence or absence of a pathology in a biological sample comprising endometrial cells from early secretory phase (ESE).

| Gene Symbol* | Gene Title* |
|---|---|
| LYZ | Lysozyme; Genbank: AV711904, U25677. |
| POSTN | periostin, osteoblast specific factor |
| LOC201651 | similar to arylacetamide deacetylase (AADAC) |
| APOD | apolipoprotein D |
| FOSB | FBJ murine osteosarcoma viral oneogene homolog B |
| S100A8 | S100 calcium binding protein A8 |
| HBG1 /// HBG2 | hemoglobin, gamma A /// hemoglobin, gamma G |
| BAI3 | brain-specific angiogenesis inhibitor 3 |
| CST1 | cystatin SN |
| CST4 | cystatin S |
| SF1 | splicing factor 1 |
| CXCL14 | chemokine (C-X-C motif) ligand 14 |
| TAF7L | TAF7-like RNA polymerase II, TATA box binding protein (TBP)-associated factor, 50 kDa |
| CORIN | corin, serine peptidase |
| IL17RB | interleukin 17 receptor B |
| GDAP1 | ganglioside-induced differentiation-associated protein 1 |

TABLE 5-continued

Biomarkers for determining the presence or absence of a pathology in a biological sample comprising endometrial cells from early secretary phase (ESE).

| Gene Symbol* | Gene Title* |
|---|---|
| MUC15 | mucin 15, cell surface associated |
| EGR1 | Early growth response 1 |
| LRRC3B | leucine rich repeat containing 3B |
| EPHB1 | EPH receptor B1 |
| GenBank: AA151917 | zo02d03.s1 Stratagene colon (#937204) Homo sapiens cDNA clone IMAGE: 566501 3-, mRNA sequence |
| GenBank: AL137429 | Homo sapiens mRNA; cDNA DKFZp761C0524 (from clone DKFZp761C0524) |
| GenBank: AA569225 | nm30h11.s1 NCI_CGAP_Lip2 Homo sapiens cDNA clone IMAGE: 1061733, mRNA sequence |
| PTEN | phosphatase and tensin homolog |
| GenBank: AA523939 | ng24h09.s1 NCI_CGAP_Co3 Homo sapiens cDNA clone IMAGE: 935777 3-, mRNA sequence |
| GenBank: AA826176 | od60e07.s1 NCI_CGAP_GCB1 Homo sapiens cDNA clone IMAGE: 1372356 3-, mRNA sequence |
| TMEM132B | transmembrane protein 132B |
| NCKAP5 | NCK-associated protein 5 |
| GenBank: BF001514 | 7g89c05.x1 NCI_CGAP_Col6 Homo sapiens cDNA clone IMAGE: 136941 3-, mRNA sequence |
| GenBank: R36546.1 | yh89f11.s1 Soares placentia Nb2HP Homo sapiens cDNA clone IMAGE: 136941 3-, mRNA sequence |
| GenBank: T70087.1 | yc17g11.s1 Stratagene lung (#937210) Homo sapiens cDNA clone IMAGE: 80996 3-, mRNA sequence |
| NAMPT | Nicotinamide phosphoribosyltransferase |
| GenBank: AW975013 | EST387118 MAGE resequences, MAGN Homo sapiens cDNA, mRNA sequence |
| NUS193 | Nuclear undecaprenyl pyrophosphate synthase 1 homolog (S. cerevisiae) pseudogene 3 |

*GenBank accession number and definition are provided for non-characterized transcripts.

As described herein, biomarkers can be used for determining the presence or absence of endometriosis or other pathology in a biological sample that has been determined to have pathology. The pathology can comprise endometriosis, uterine pathology, or pelvic pathology. The biomarkers can comprise at least one set of genes set forth in Table 6.

TABLE 6

Biomarkers for determining the presence or absence of endometriosis in a biological sample comprising endometrial cells from early secretary phase (ESE).

| Gene Symbol* | Gene Title* |
|---|---|
| CEE /// LOC100508206 | carboxyl ester lipase (bile salt-stimulated lipase) /// bile salt-activated lipase-like |
| GenBank: BC1024490 | U1-1-BB1p-aut-f-08-0-Ul.s1 NCI_CGAP_PI6 Homo sapiens cDNA clone U1-1-BB1p-aut-f-08-0-UI 3-, mRNA sequence |
| GenBank: BU955063 | AGENCOURT_10609489 NIH_MGC_126 Homo sapiens cDNA clone IMAGE: 6726950 5-, mRNA sequence |
| THBS1 | thrombospondin 1; Genbank Nos: BF109732, AW956580, BF084105, A1812030, NM_003246, BF055462, AV726673. |
| HBA1 /// HBA2 | hemoglobin, alpha 1 /// hemoglobin, alpha 2 |
| CD52 | CD52 molecule |
| CFTR | cystic fibrosis transmembrane conductance regulator (ATP-binding cassette sub-family C, member 7) |
| GSTT2 | glutathione S-transferase theta 2 |
| GPR64 | G protein-coupled receptor 64; Genbank: NM_005756. |
| CRISP3 | cysteine-rich secretory protein 3 |
| HBB | hemoglobin, beta |
| SLC9A3R2 | solute carrier family 9 (sodium/hydrogen exchanger), member 3 regulator 2 |
| ART3 | ADP-ribosytransferase 3 |
| HIST1H2BG | histone cluster 1, H2bg |
| OLFM4 | olfactomedin 4 |
| SOS1 | son of sevenless homolog 1 (Drosophila) |
| MUC5B | mucin 5B, oligomeric mucus/gel-forming |
| GAL | galanin prepropeptide |
| IF144 | interferon-induced protein 44 |
| ODAM | odontogenic, ameloblast associated |
| CATSPERB | cation channel, sperm-associated beta |
| AGTR2 | angiotensin II receptor, type 2 |
| C15orf48 | chromosome 15 open reading frame 48 |
| PPP1R1B | protein phosphatase 1, regulatory (inhibitor) subunit 1B |
| ZG16B | zymogen granule protein 16 homolog B (rat) |
| C20orf54 | chromosome 20 open reading frame 54 |

TABLE 6-continued

Biomarkers for determining the presence or absence of endometriosis in a biological sample comprising endometrial cells from early secretary phase (ESE).

| Gene Symbol* | Gene Title* |
| --- | --- |
| GenBank: AA601031 | nk67d10.s1 NCI_CGAP_Sch1 Homo sapiens cDNA clone IMAGE: 1018579 3-, mRNA sequence |
| GenBank: AI147867 | qb34a07.x1 Soares_pregnant_uterus_NbHPU Homo sapiens cDNA clone IMAGE: 1698132 3-, mRNA sequence |
| GenBank: AW297731 | UI-H-BWO-aiy-a-04-0-UI.s1 NCI_CGAP_Sub6 Homo sapiens cDNA clone IMAGE: 2730894 3-, mRNA sequence |
| CCDC58 | coiled-coil domain containing 58 |
| GenBank: BF003148 | 7g55h08.x1 NCI_CGAP_Pr28 Homo sapiens cDNA clone IMAGE: 33104313 3-, mRNA sequence |
| GenBank: BF508634 | UI-H-B14-aop-a-02-0-UI.s1 NCI_CGAP_Sub8 Homo sapiens cDNA clone IMAGE: 3085347 3-, mRNA sequence |
| GenBank: AI672553 | wb32f06.x1 NCI_CGAP_GC6 sequence cDNA clone IMAGE: 2307395 3-, mRNA sequence |
| GenBank: AA121544 | zk89g09.s1 Soares_pregnant_uterus_NbHPU Homo sapiens cDNA clone IMAGE: 490048 3- similar to contains element PTR5 repetitive element mRNA sequence |

*GenBank accession number and definition are provided for non-characterized transcripts.

As described herein, biomarkers can be used for determining the severity of endometriosis in a biological sample that has been determined to have endometriosis. The severity of endometriosis can be classified as mild or moderate. The biomarkers can comprise at least one set of genes set forth in Table 7.

TABLE 7

Biomarkers for determining the severity of endometriosis in a biological sample comprising endometrial cells from early secretary phase (ESE).

| Gene Symbol | Gene Title |
| --- | --- |
| IGF2 /// INS-IGF2 | insulin-like growth factor 2 (somatomedin A) /// INS-IGF2 readthrough transcript |
| FOSB | FBJ murine osteosarcoma viral oncogene homolog B |
| ALPP | alkaline phosphatase, placental |
| MSLN | mesothelin |
| CPA3 | carboxypeptidase A3 (mast cell) |
| PROK1 | prokineticin 1; Genbank: AW183087 |
| PHACTR2 | phosphatase and actin regulator 2 |

*GenBank accession number and definition are provided for non-characterized transcripts.

In some embodiments, biomarkers are used for determining the presence or absence of pathology in a biological sample comprising endometrial cells, wherein the biological sample is collected from mid-secretary phase (MSE) using systems, methods and devices described herein. The biomarkers can comprise at least one set of genes set forth in Table 8.

TABLE 8

Biomarkers for determining the presence or absence of a pathology in a biological sample comprising endometrial cells from mid-secretary phase (MSE).

| Gene Symbol | Gene Title |
| --- | --- |
| JAK1 | Janus kinase 1 |
| PHF21A | PHD finger protein 21A |
| CTNNB1 | catenin (cadherin-associated protein), beta 1, 88 kDa |
| CBX3 | chromobox homolog 3; Genbank: NM_016587 |
| SLC39A6 | solute carrier family 39 (zinc transporter), member 6 |
| CP | ceruloplasmin (ferroxidase) |
| LUZP1 | leucine zipper protein 1 |
| ADAMTS5 | ADAM metallopeptidase with thrombospondin type 1 motif, 5 |
| CLIP1 | CAP-GLY domain containing linker protein 1 |
| SOCS2-AS1 | SOCS2 antisense RNA 1 (non-protein coding) |
| CACNB2 | calcium channel, voltage-dependent, beta 2 subunit |
| NMRK1 | nicotinamide riboside kinase 1 |
| RARA | retinoic acid receptor, alpha |
| MACC1 | metastasis associated in colon cancer 1 |
| ACTR2 | ARP2 actin-related protein 2 homolog (yeast) |
| RERE | arginine-glutamic acid dipeptide (RE) repeats |

TABLE 8-continued

Biomarkers for determining the presence or absence of a pathology in a biological sample comprising endometrial cells from mid-secretary phase (MSE).

| Gene Symbol | Gene Title |
|---|---|
| JUNB | jun B proto-oncogene |
| EGR1 | early growth response 1 |
| TBL1X | transducin (beta)-like 1X-linked |
| PKP4 | plakophillin 4 |
| MX1 | myxovirus (influenza virus) resistance 1, interferon-inducible protein p78 (mouse) |
| TACSTD2 | tumor-associated calcium signal transducer 2 |
| SERPINE1 | serpin peptidase inhibitor, clade E (nexin, plasminogen activator inhibitor type 1), member 1 |
| EFNB2 | ephrin-B2 |
| FOSB | FBJ murine osteosarcoma viral oncogene homolog B |
| MMP14 | matrix metallopeptidase 14 (membrane-inserted) |
| PRDM2 | PR domain containing 2, with ZNF domain |
| PSD3 | pleckstrin and Sec7 domain containing 3 |
| DIO2 | deiodinase, iodothyronine, type II |
| AQP3 | aquaporin 3 (Gill blood group) |
| SLC4A4 | solute carrier family 4, sodium bicarbonate cotransporter, member 4 |
| HBA1 /// HBA2 | hemoglobin, alpha 1 /// hemoglobin, alpha 2 |
| POMZP3 /// ZP3 | POM121 and ZP3 fusion /// zona pellucida glycoprotein 3 (sperm receptor); Genbank: NM_012230 |
| EEA1 | early endosome antigen 1 |
| MSLN | mesothelin |
| LYPD3 | LY6/PLAUR domain containing 3 |
| FGB | fibrinogen beta chain |
| ENPP1 | ectonucleotide pyrophosphatase/phosphodiesterase 1 |
| CLE3B /// EXOSC7 | C-type lectin domain family 3, member B /// exosome component 7 |
| IGFBP1 | insulin-like growth factor binding protein 1 |
| KLK11 | kallikrein-related peptidase 11 |
| PIP5K1B | phosphatidylinositol-4-phosphate-5-kinase, type I, beta |
| MMP10 | matrix metallopeptidase 10 (stromelysin 2) |
| GPR64 | G protein-coupled receptor 64 |
| LEFTY2 | left-right determination factor 2 |
| CST1 | cystatin SN |
| SPINK1 | serine peptidase inhibitor, Kazal type 1 |
| PRLR | prolactin receptor |
| EPYC | epiphycan |
| CYP24A1 | cytochrome P450, family 24, subfamily A, polypeptide 1 |
| TRPC6 | transient receptor potential cation channel, subfamily C, member 6 |
| SOGA1 | suppressor of glucose, autophagy associated 1 |
| CRISP3 | cysteine-rich secretory protein 3 |
| CDC42 | cell division cycle 42 (GTP binding protein, 25 kDa) |
| CADM1 | cell adhesion molecule 1 |
| HBB | hemoglobin, beta |
| FOS | FBJ murine osteosarcoma viral oncogene homolog |
| CHI3L1 | chitinase 3-like 1 (cartilage glycoprotein-39) |
| ABAT | 4-aminobutyrate aminotransferase |
| CTSZ | cathespin Z |
| UPK1B | uroplakin 1B |
| POMZP3 | POM1211 and ZP3 fusion; Genbank: BC000487 |
| IL6ST | interleukin 6 signal transducer (gp130, oncostatin M receptor) |
| NF1 | neurofibromin 1 |
| DHX9 | DEAH (Asp-Glu-Ala-His) box polypeptide 9 |
| EIF1 | eukaryotic translation initiation factor 1 |
| SECISBP2L | SECIS binding protein 2-like |
| MFAP4 | microfibrillar-associated protein 4 |
| SOS1 | son of sevenless homolog 1 (*Drosophila*) |
| MFAP5 | microfibrillar associated protein 5 |
| LRRC15 | leucine rich repeat containing 15 |
| SST | somatostatin |
| ID2 /// ID2B | inhibitor of DNA binding 2, dominant negative helix-loop-helix protein /// inhibitor of DNA binding 2B, dominant negative helix-loop-helix protein (pseudogene) |
| CTBP1 | C-terminal binding protein 1 |
| CYP2C9 | cytochrome P450, family 2, subfamily C, polypeptide 9 |
| HSPA12A | heat shock 70 kDa protein 12A |
| TWISTNB | TWIST neighbor |
| GUSBP3 /// GUSBP9 /// SMA4 /// SMA5 | glucuronidase, beta pseudogene 3 /// glucuronidase, beta pseudogene 9 /// glucuronidase, beta pseudogene /// glucuronidase, beta pseudogene |
| DYRK1B | dual-specificity tyrosine-(Y)-phosphorylation regulated kinase IB |
| ATP13A3 | ATPase type 13A3 |
| CHODL | chondrolectin |
| ALDH8A1 | aldehyde dehydrogenase 8 family, member A1 |
| TGFB2 | transforming growth factor, beta 2 |
| SETD2 | SET domain containing 2 |
| UGCG | UDP-glucose ceramide glucosyltransferase |

TABLE 8-continued

Biomarkers for determining the presence or absence of a pathology in a biological sample comprising endometrial cells from mid-secretary phase (MSE).

| Gene Symbol | Gene Title |
| --- | --- |
| ABHD2 | abhydrolase domain containing 2 |
| VPS35 | vacuolar protein sorting 35 homolog (S. cerevisiae) |
| ZCCHC2 | zinc finger, CCHC domain containing 2 |
| TEX101 | testis expressed 101 |
| NUPL1 | nucleoporin like 1 |
| ANGPTL1 | angiopoietin-like 1 |
| LOC100507645 /// MALAT1 | uncharacterized LOC100507645 /// metastasis associated lung adenocarcinoma transcript 1 (non-protein coding) |
| WASF2 | WAS protein family, member 2 |
| CPEB4 | cytoplasmic polyadenylation element binding protein 4 |
| SLAIN2 | SLAIN motif family, member 2 |
| BTBD7 | BTB (POZ) domain containing 7 |
| EDIL3 | EGF-like repeats and discoidin I-like domains 3 |
| FBX032 | F-box protein 32 |
| CUX1 | cut-like homeobox 1 |
| ITGB6 | integrin, beta 6 |
| ZNF800 | zinc finger protein 800 |
| C12orf35 | chromosome 12 open reading frame 35 |
| HS3ST3B1 | heparan sulfate (glucosamine) 3-O-sulfotransferase 3B1 |
| LOC100653132 | uncharacterized LOC100653132 |
| MALAT1 | metastasis associated lung adenocarcinoma transcript 1 (non-protein coding) |
| SORCS1 | sortillin-related VPS10 domain containing receptor 1 |
| CAPN8 | calpain 8 |
| IHH | Indian hedgehog |
| DDX17 | DEAD (Asp-Glu-Ala-Asp) box helicase 17 |
| FER | fer (fps/fes related) tyrosine kinase |
| U2AF1 | U2 small nuclear RNA auxilliary factor 1 |
| LOC100287497/// LOC100287934 | uncharacterized LOC100287497 /// uncharacterized LOC100287934 |
| BOD1L1 | biorientation of chromosomes in cell division 1-like 1 |
| RAB12 | RAB12, member RAS oncogene family |
| GALNTL2 | UDP-N-acetyl-alpha-D-galactosamine: polypeptide N-acetylgalactosaminyltransferase-like 2 |
| LOC100505989 | uncharacterized LOC100505989 |
| LOC100506582 | uncharacterized LOC100506582 |
| CLK4 | CDC-like kinase 4 |
| HECTD1 | HECT domain containing E3 ubiquitin protein ligase 1 |
| ZNF24 | Zinc finger protein 24 |
| PHKB | phosphorylase kinase, beta |
| NIPBL | Nipped-B homolog (Drosophila) |
| TMED8 | transmembrane emp24 protein transport domain containing 8 |
| PHACTR2 | phosphatase and actin regulator 2 |

As described herein, biomarkers can be used for determining the presence or absence of endometriosis or other pathology in a biological sample that has been determined to have pathology. The pathology can comprise endometriosis, uterine pathology, or pelvic pathology. The biomarkers can comprise at least one set of genes set forth in Table 9.

TABLE 9

Biomarkers for determining the presence or absence of endometriosis in a biological sample comprising endometrial cells from mid-secretary phase (MSE).

| Gene Symbol | Gene Title |
| --- | --- |
| CDC42SE2 | CDC42 small effector 2; Genbank: NM_020240 |
| CDYL2 | chromodomain protein, Y-like 2 |
| WBSCR27 | Williams Beuren syndrome chromosome region 27 |
| CEL | carboxyl ester lipase (bile salt-stimulated lipase) |
| NT5E | 5'-nucleotidase, ecto (CD73) |
| C1orf210 | chromosome 1 open reading frame 210 |
| ZBED1 | zinc finger, BED-type containing 1 |
| CYP4B1 | cytochrome P450, family 4, subfamily B, polypeptide 1 |
| LINC00476 | long intergenic non-protein coding RNA 476 |
| CP | ceruloplasmin (ferroxidase) |
| LOC201477 | uncharacterized LOC201477 |
| SLC8A1 | solute carrier family 8 (sodium/calcium exchanger), member 1 |
| SYTL3 | synaptotagmin-like 3 |
| DEFB124 | defensin, beta 124 |
| SERPINE1 | serpin peptidase inhibitor, clade E (nexin, plasminogen activator inhibitor type 1), member 1 |

TABLE 9-continued

Biomarkers for determining the presence or absence of endometriosis in a biological sample comprising endometrial cells from mid-secretary phase (MSE).

| Gene Symbol | Gene Title |
| --- | --- |
| DACT2 | dapper, antagonist of beta-catenin, homolog 2 (*Xenopus laevis*) |
| BCLAF1 | BCL2-associated transcription factor 1 |
| ATP1B1 | ATPase, Na+/K+ transporting, beta 1 polypeptide |
| LTF | lactotransferrin |
| CPNE3 | copine III |
| ITPR2 | inositol 1,4,5-trisphosphate receptor, type 2 |
| S100A8 | S100 calcium binding protein A8 |
| STMN2 | stathmin-like 2 |
| MY06 | myosin VI |
| ATXN1 | ataxin 1 |
| HLA-DQA1 | major histocompatibility complex, class II, DQ alpha 1 |
| F13A1 | coagulation factor XIII, A1 polypeptide |
| ABP1 | amiloride binding protein 1 (amine oxidase (copper-containing)) |
| FGFR2 | fibroblast growth factor receptor 2 |
| PLA2G2A | phospholipase A2, group IIA (platelets, synovial fluid) |
| HMOX1 | heme oxygenase (decycling) 1 |
| PRKAR2B | protein kinase, cAMP-dependent, regulatory, type II, beta |
| PCYOX1 | prenylcysteine oxidase 1 |
| PCCA | propionyl CoA carboxylase, alpha polypeptide |
| VCAM1 | vascular cell adhesion molecule 1 |
| HNMT | histamine N-methyltransferase |
| POMZP3 /// ZP3 | POM121 and ZP3 fusion /// zona pellucida glycoprotein 3 (sperm receptor) |
| S100A2 | S100 calcium binding protein A2 |
| FGFR3 | fibroblast growth factor receptor 3 |
| KYNU | kynureninase |
| ACPP | acid phosphatase, prostate |
| MMP1 | matrix metallopeptidase 1 (interstitial collagenase) |
| MAL | mal, T-cell differentiation protein |
| ORM1 | orosomucoid 1; Genbank: NM_000607 |
| ORM1 /// ORM2 | orosomucoid 1 /// orosomucoid 2; Genbank: NM_000607 /// NM_000608. |
| CFTR | cystic fibrosis transmembrane conductance regulator (ATP-binding cassette sub-family C, member 7) |
| PSPH | phosphoserine phosphatase |
| SLC26A2 | solute carrier family 26 (sulfate transporter), member 2 |
| CXCL13 | chemokine (C-X-C motif) ligand 13 |
| TMSB15A ///TMSB15B | thymosin beta 15a /// thymosin beta 15B |
| MST1R | macrophage stimulating 1 receptor (c-met related tyrosine kinase) |
| PPP1R1A | protein phosphatase 1, regulatory (inhibitor) subunit 1A |
| PCSK5 | proprotein convertase subtilisin/kexin type 5 |
| RASGRP1 | RAS guanyl releasing protein 1 calcium and DAG-regulated) |
| MMP10 | matrix metallopeptidase 10 (stromelysin 2) |
| BCL2A1 | BCL2-related protein A1 |
| ABLIM3 | actin binding LIM protein family, member 3 |
| CYP3A5 | cytochrome P450, family 3, subfamily A, polypeptide 5 |
| LEFTY2 | left-right determination factor 2 |
| CST1 | cystatin SN |
| SPINK1 | serine peptidase inhibitor, Kazal type1 |
| GRP | gastrin-releasing peptide |
| SLC1A1 | solute carrier family 1 (neuronal/epithelial high affinity glutamate transporter, system Xag), member 1 |
| CDH16 | cadherin 16, KSP-cadherin |
| GAGE12B /// GAGE12C /// GAGE12D /// GAGE12E /// IGAGE12F /// GAGE12G /// GAGE12H /// GAGE12I /// GAGE2A /// GAGE2B /// GAGE2C /// GAGE4 /// GAGE5 /// GAGE6 /// GAGE7 | G antigen 12B /// G antigen 12C /// G antigen 12D /// G antigen 12E /// G antigen 12F /// G antigen 12G /// G antigen 12H /// G antigen 12I/// G antigen 2A /// G antigen 2B ///G antigen 2C /// G antigen 4 /// G antigen 5 /// G antigen 6 /// G antigen 7 |
| HOXC6 | homeobox C6 |
| NFIC | nuclear factor 1/C (CCAAT-binding transcription factor) |
| GABRA2 | gamma-aminobutyric acid (GABA) A receptor, alpha 2 |

TABLE 9-continued

Biomarkers for determining the presence or absence of endometriosis in a biological sample comprising endometrial cells from mid-secretary phase (MSE).

| Gene Symbol | Gene Title |
| --- | --- |
| CSF2RA | colony stimulating factor 2 receptor, alpha, low-affinity (granulocyte-macrophage) |
| GAGE1 /// GAGE12B /// GAGE12C ///GAGE12D /// GAGE12E /// GAGE12F ///GAGE12G /// GAGE12H /// GAGE12I ///GAGE12J /// GAGE2A /// GAGE2B /// GAGE2C/// GAGE2D /// GAGE2E /// GAGE4 /// GAGE5/// GAGE6 /// GAGE7 /// GAGE8 | G antigen 1 /// G antigen 12B /// G antigen12C /// G antigen 12D /// G antigen 12E ///G antigen 12F /// G antigen 12G /// G antigen 12H /// G antigen 12I /// G antigen 12J /// G antigen 2A /// G antigen 2B /// G antigen 2C /// G antigen 2D /// G antigen 2E/// G antigen 4 /// G antigen 5 /// G antigen 6 /// G antigen 7 /// G antigen 8 |
| FAM107A /// LOC100506924 | family with sequence similarity 107, member A /// uncharacterized LOC100506924 |
| GAGE3 | G antigcn3 |
| GAGE1 /// GAGE12C /// GAGE12D /// GAGE12E /// GAGE12F /// GAGE12G /// GAGE12H /// GAGE12I /// GAGE12J /// GAGE2A /// GAGE2B /// GAGE2C /// GAGE2D /// GAGE2E /// GAGE3 /// GAGE4 /// GAGE5 /// GAGE6 /// GAGE7 /// GAGE8 | G antigen 1 /// G antigen 12C /// G antigen 12D /// G antigen 12E /// G antigen 12F /// G antigen 12G /// G antigen 12H /// G antigen 12I /// G antigen 12J /// G antigen 2A /// G antigen 2B /// G antigen 2C /// G antigen 2D /// G antigen 2E /// G antigen 3 /// G antigen 4 /// G antigen 5 /// G antigen 6 /// G antigen 7 /// G antigen 8 |
| GAST | gastrin |
| GAGE1 /// GAGE12C /// GAGE12D /// GAGE12E /// GAGE12F /// GAGE12G /// GAGE12H /// GAGE12I /// GAGE12J /// GAGE2D /// GAGE4 /// GAGE5 /// GAGE6 /// GAGE7 | G antigen 1 /// G antigen 12C /// G antigen 12D /// G antigen 12E /// G antigen 12F /// G antigen 12G /// G antigen 12H /// G antigen 12I/// G antigen 12J /// G antigen2D /// G antigen 4 /// G antigen 5 /// G antigen 6 /// G antigen 7 |
| GAGE12F /// GAGE12G /// GAGE12I /// GAGE4 /// GAGE5 /// GAGE6 /// GAGE7 | G antigen 12F /// G antigen 12G /// G antigen 12I /// G antigen 4 /// G antigen 5 /// G antigen 6 /// G antigen 7 |
| DMBT1 | deleted in malignant brain tumors 1 |
| WNT4 | wingless-type MMTV integration site family, member 4 |
| TOP1 | topoisomerase (DNA) I |
| HBB | hemoglobin, beta |
| NR2F2 | nuclear receptor subfamily 2, group F , member 2 |
| KLHDC10 | ketch domain containing 10 |
| LAMB3 | laminin, beta 3 |
| HLA-DQB1 | major histocompatibility complex, class II, DQ beta 1 |
| PNMA2 | paraneoplastic Ma antigen 2 |
| ADH1B | alcohol dehydrogenase 1B (class I), beta polypeptide |
| HLA-DRB4 /// LOC100509582 | major histocompatibility complex, class II DR beta 4 /// HLA class II histocompatibility antigen, DR beta 4 chain-like |
| CRISP2 | cysteine-rich secretory protein 2 |
| MT1G | Metallothionein 1G |
| RORA | RAR-related orphan receptor A |
| CYR61 | cysteine-rich, angiogenic inducer, 61 |
| POMZP3 | POM121 and ZP3 fusion |
| LEPR | leptin receptor |
| KIR3DL1 | killer cell immunoglobulin-like receptor, three domains, long cytoplasmic tail, 1 |
| CXCR4 | chemokine (C-X-C motif) receptor 4 |
| PRRC2C | proline-rich coiled-coil 2C |
| IGFBP3 | insulin like growth factor binding protein 3 |
| SULF1 | sulfatase 1 |
| MFAP4 | microfibrillar-associated protein 4 |
| OLFM4 | olfactomedin 4 |
| IGHM | immunoglobulin heavy constant mu |
| APOE | Apolipoprotein E |
| HLA-DQB1 /// LOC100293977 | major histocompatibility complex, class II, DQ beta 1 /// HLA class II histocompatibility antigen, DQ beta 1 chain-like |
| LTBP4 | latent transforming growth factor beta binding protein 4 |
| MUC5B | mucin 5B, oligomeric mucus gel-forming |
| CFH | complement factor H |
| HLA-DQA1 /// LOC100507718 /// LOC100509457 | major histocompatibility complex, class II, DQ alpha 1 /// HLA class II histocompatibility antigen, DQ alpha 1 chain-like /// HLA class II histocompatibility antigen, DQ alpha 1 chain-like |
| EEF1E1 | Eukaryotic translation elongation factor 1 epsilon 1 |
| CTCF | CCCTC-binding factor (zinc finger protein) |
| CYP2C9 | cytochrome P450, family 2, subfamily C, polypeptide 9 |

TABLE 9-continued

Biomarkers for determining the presence or absence of endometriosis in a biological sample comprising endometrial cells from mid-secretary phase (MSE).

| Gene Symbol | Gene Title |
| --- | --- |
| ADAMTS2 | ADAM metallopeptidase with thrombospondin type 1 motif, 2 |
| CDC42BPA | CDC42 binding protein kinase alpha (DMPK-like) |
| CFH /// CFHR1 | complement factor H /// complement factor H-related 1 |
| DACT1 | dapper, antagonist of beta-catenin, homolog 1 (Xenopus laevis) |
| FAM118A | family with sequence similarity 118, member A |
| HPCAL4 | hippocalcin like 4 |
| DCF16 | DDB1 and CUL4 associated factor 16 |
| BCMO1 | beta-carotene 15,15'-monooxygenase 1 |
| SPDEF | SAM pointed domain containing ets transcription factor |
| CATSPERB | catsper channel auxiliary subunit beta |
| LRRC31 | leucine rich repeat containing 31 |
| ST6GALNAC5 | ST6 (alpha-N-acetyl-neuraminyl-2,3-beta-galactosyl-1,3)-N-acetylgalactosaminide alpha-2,6-sialyltransferase 5 |
| COLEC12 | collectin sub-family member |
| HLA-DRB1 /// HLA-DRB3 /// HLA-DRB4 /// HLA-DRB5 /// LOC100507709 /// LOC100507714 /// LOC100509582 | major histocompatibility complex, class II, DR beta 1 /// major histocompatibility complex, class II, DR beta 3 /// major histocompatibility complex, class II, DR beta4 /// major histocompatibility complex, class II, DR beta 5 /// HLA class II histocompatibility antigen, DRB1-7 beta chain-like /// HLA class II histocompatibility antigen, DRB1-7 beta chain-like /// HLA class II histocompatibility antigen, DR beta 4 chain-like |
| LOC1006530 | uncharacterized LOC100653010 |
| GDF15 | growth differentiation factor 15 |
| SIKE1 | suppressor of IKBKE 1 |
| TFG | TRK-fused gene |
| PTER | phosphotriesterase relate |
| COL4A3BP | collagen, type IV, alpha 3 (Goodpasture antigen) binding protein |
| CFC /// CFC1B | cripto, FRL-1, cryptic family 1 /// crypto, FRL-1, cryptic family 1B |
| SLC46A2 | solute carrier family 46, member 2 |
| MS4A8B | membrane-spanning 4-domains, subfamily A, member 8B |
| H19 /// MIR675 | H19, imprinted maternally expressed transcript (non-protein coding) /// microRNA 675 |
| LIFR | leukemia inhibitory factor receptor alpha |
| COL12A1 | collagen, type XII, alpha 1 |
| BPIFB1 | BPI fold containing family B, member 1 |
| DNER | delta/notch-like EGF repeat containing |
| MEGF6 | multiple EGF-like-domains 6 |
| CCDC146 | coiled-coil domain containing 146 |
| TAOK1 | TAO kinase 1 |
| ERAP2 | endoplasmic reticulum aminopeptidase 2 |
| LOC100505806 | uncharacterized LOC100505806 |
| NAPSB | napsin B aspartic peptidase pseudogene |
| ZG16B | zymogen granule protein 16 homolog B (rat) |
| IGSF11 | immunoglobulin superfamily, member 11 |
| NFYA | nuclear transcription factor y, alpha |
| LOC100506029 /// LOC100506051 | uncharacterized LOC100506029 /// uncharacterized LOC100506051 |
| THRB | thyroid hormone receptor, beta |
| CYS1 | cystin 1 |
| MCTP2 | multiple C2 domains, transmembrane 2 |
| NPAS3 | neuronal PAS domain protein 3 |
| C20orf85 | chromosome 20 open reading frame 85 |
| FAM69C | family with sequence similarity 69, member C |
| SCARA5 | scavenger receptor class A, member 5 (putative) |
| FNDC3B | fibronectin type III domain containing 3B |
| PI15 | peptidase inhibitor 15 |
| SCGB3A1 | secretoglobin, family 3A, member 1 |
| KLF9 | Kruppel71.i.ke factor 9 |
| GBP1 | guanylate binding protein 1, interferon- inducible |
| MAVS | mitochondrial antiviral signaling protein |
| ANKRD33B | ankyrin repeat domain 33B |
| SNORD3B-1 /// SNORD3B-2 /// SNORD3D | small nucleolar RNA, C/D box 3B-1 /// small nucleolar RNA, C/D box 3B-2 /// small nucleolar RNA, C/D box 3D |

TABLE 9-continued

Biomarkers for determining the presence or absence of endometriosis in a biological sample comprising endometrial cells from mid-secretary phase (MSE).

| Gene Symbol | Gene Title |
|---|---|
| FAM178A | family with sequence similarity 178, member A |
| THAP6 | THAP domain containing 6 |
| LOC100422737 | uncharacterized LOC100422737 |
| SCARA5 | scavenger receptor class A, member 5 (putative) |
| SUZ12P | Suppressor of zeste 12 homolog pseudogene |
| BCL2L10 | BCL2-like 10 (apoptosis facilitator) |
| RIMKLB | ribosomal modification protein rimK-like family member B |
| PLEKHA2 | pleckstrin homology domain containing, family A (phosphoinositide binding specific) member 2 |
| EIF4E3 | eukaryotic translation initiation factor 4E family member 3 |
| SGPP2 | sphingosine-1-phosphate phosphatase 2 |
| RAB3IP | RAB3A interacting protein (rabin3) |
| DOK7 | docking protein 7 |
| MIB2 | mindbomb E3 ubiquitin protein ligase 2 |
| LOC100653229 | uncharacterized LOC100653229 |
| ITGB8 | integrin, beta 8 |
| WDR38 | WD repeat domain 38 |
| SHISA8 | shisa homolog 8 (*Xenopus laevis*) |

As described herein, biomarkers can be used for determining the severity of endometriosis in a biological sample that has been determined to have endometriosis. The severity of endometriosis can be classified as mild or moderate. The biomarkers can comprise at least one set of genes set forth in Table 10.

TABLE 10

Biomarkers for determining the severity of endometriosis in a biological sample comprising endometrial cells from mid-secretary phase (MSE).

| Gene Symbol | Gene Title |
|---|---|
| HSPA6 | heat shock 70 kDa protein 6 (HSP70B'); Genbank: NM_002155, X51757. |
| THRA | thyroid hormone receptor, alpha |
| GIMAP1 | GTPase, IMAP family member 1 |
| TIRAP | toll-interleukin 1 receptor (TIR) domain containing adaptor protein |
| ACVR1C | activin A receptor, type IC |
| IL12RB1 | interleukin 12 receptor, beta 1 |
| JAK1 | Janus kinase 1 |
| RAD51L3-RFFL /// RFFL | RAD51L3-RFFL readthrough /// ring finger and FYVE-like domain containing E3 ubiquitin protein ligase |
| ZNF417 | zinc finger protein 417 |
| SEC62 | SEC62 homolog (*S. cerevisiae*) |
| SIGLEC10 | sialic acid binding Ig-like lectin 10 |
| KCNG3 | potassium voltage-gated channel, subfamily G, member 3 |
| CD300LF | CD300 molecule-like family member f |
| MOGAT1 | monoacylglycerol O-acyltransferase 1 |
| SLC5A3 | solute carrier family 5 (sodium/myo-inositol cotransporter), member 3 |
| FOXC1 | forkhead box C1 |
| PRF1 | perforin 1 (pore forming protein) |
| WBSCR27 | Williams Beuren syndrome chromosome region 27 |
| ARSB | arylsulfatase B |
| CCDC60 | coiled-coil domain containing 60 |
| COCH | coagulation factor C homolog, cochlin (*Limulus polyphemus*) |
| SLC25A48 | solute carrier family 25, member 48 |
| CELF2 | CUGBP, Elav-like family member 2 |
| DUOXA1 | dual oxidase maturation factor 1 |
| METTL8 | methyltransferase like 8 |
| TACC1 | transforming, acidic coiled-coil containing protein 1 |
| TBC1D16 | TBC1 domain family, member 16 |
| ZBED1 | zinc finger, BED-type containing 1 |
| DOK5 | docking protein 5 |
| FCER1G | Fc fragment of IgE, high affinity I, receptor for; gamma polypeptide |
| ATF3 | activating transcription factor 3 |
| FCHO2 | FCH domain only 2 |
| CCNL1 | cyan L1 |
| CYP4B1 | cytochrome P450, family 4, subfamily B, polypeptide 1 |
| CLEC7A | C-type lectin domain family 7, member A |

TABLE 10-continued

Biomarkers for determining the severity of endometriosis in a biological sample comprising endometrial cells from mid-secretary phase (MSE).

| Gene Symbol | Gene Title |
| --- | --- |
| TRIB3 | tribbles homolog 3 (*Drosophila*) |
| LOC284454 | uncharacterized LOC284454 |
| CACNA1D | calcium channel, voltage-dependent, L type, alpha 1D subunit |
| DIAPH3-AS1 | DIAPH3 antisense RNA 1 (non-protein coding) |
| LOC100506523 /// ZNF814 | uncharacterized LOC100506523 /// zinc finger protein 814 |
| RPPH1 | ribonuclease P RNA component H1 |
| SERPINB6 | serpin peptidase inhibitor, clade B (ovalbumin), member 6 |
| LEPR | leptin receptor |
| LOC100507250 | uncharacterized LOC100507250 |
| LOC100506258 | uncharacterized LOC100506258 |
| ACSL4 | Acyl-CoA synthetase long-chain family member 4 |
| BIN3 | bridging integrator 3 |
| PTRF | polymerase I and transcript release factor |
| ZKSCAN1 | zinc finger with KRAB and SCAN domains 1 |
| ZNF587 /// ZNF587B | zinc finger protein 587 /// zinc finger protein 587B |
| MIR1204 /// PVT1 | microRNA 1204 /// Pvt1 oncogene (non-protein coding) |
| ZDHHC18 | zinc finger, DHHC-type containing 18 |
| SIRT2 | sirtuin 2 |
| AHNAK2 | AHNAK nucleoprotein 2 |
| C1orf53 | chromosome 1 open reading frame 53 |
| LOC100507645 /// MALAT1 | uncharacterized LOC100507645 /// metastasis associated lung adenocarcinoma transcript 1 (non-protein coding) |
| ZNF321P /// ZNF816 /// ZNF816-ZNF321P | zinc finger protein 321, pseudogene /// zinc finger protein 816 /// ZNF816-ZNF321P readthrough |
| CACNB2 | calcium channel, voltage-dependent, beta 2 subunit |
| LOC642852 | uncharacterized LOC642852 |
| FLJ38717 | FLJ8717 protein |
| SFXN3 | Sideroflexin 3 |
| LOC100506387 | uncharacterized LOC100506387 |
| LOC201477 | uncharacterized LOC201477 |
| SLC8A1 | solute carrier family 8 (sodium/calcium exchanger), member 1 |
| KIAA1908 | uncharacterized LOC114796 |
| SF3B14 | Splicing factor 3B, 14 kDa subunit |
| OR7D2 | olfactory receptor, family 7, subfamily D, member |
| TNRC18 | trinucleotide repeat containing 18 |
| LOC100630923 | LOC100289561-PRKRIP1 readthrough |
| ATF1 | activating transcription factor 1 |
| IKZF1 | IKAROS family zinc finger 1 (Ikaros) |
| PNN | pinin desmosome associated protein |
| CD74 | CD74 molecule, major histocompatibility complex, class II invariant chain |
| PAAF1 | proteasomal ATPase-associated factor 1 |
| BRE-AS1 | BRE antisense RNA 1 (non-protein coding) |
| LINC00240 | long intergenic non-protein coding RNA 240 |
| ANKRD20A1 /// ANKRD20A11P /// ANKRD20A2 /// ANKRD20A3 /// ANKRD20A4 /// ANKRD20A5P /// ANKRD20A9P /// LOC644339 | ankyrin repeat domain 20 family, member A1 /// ankyrin repeat domain 20 family, member A11, pseudogene /// ankyrin repeat domain 20 family, member A2 /// ankyrin repeat domain 20 family, member A3 /// ankyrin repeat domain 20 family, member A4 /// ankyrin repeat domain 20 family, member A5, pseudogene /// ankyrin repeat domain 20 family, member A9, pseudogene /// ankyrin repeat domain-containing protein 20B-like |
| CATSPERB | catsper channel auxiliary subunit beta |
| SCD | stearoyl-CoA desaturase (delta-9-desaturase |
| DHCR24 | 24-dehy drocholesterol reductase |
| DUSP1 | dual specificity phosphatase 1 |
| CYR61 | cysteine-rich, angiogenic inducer, 61 |
| NREP | neuronal regeneration related protein homolog (rat) |
| GPX3 | glutathione peroxidase 3 (plasma) |
| MYH11 | myosin, heavy chain 11, smooth muscle |
| ZFP36 | zinc finger protein 36, C3H type, homolog (mouse) |
| INSIG1 | insulin induced gene 1 |
| TNC | tenascin C |
| ACSL3 | acyl-CoA synthetase long-chain family member 3 |
| NIPSNAP1 | nipsnap homolog 1 (*C. elegans*) |
| ENG | endoglin |
| CPD | carboxypeptidase D |
| PPP1R12B | protein phosphatase 1, regulatory subunit 12B |
| LTF | lactotransferrin |
| DKK3 | dickkopf 3 homolog (Xenopus lavaeis) |
| AMFR | autocrine motility factor receptor, E3 ubiquitin protein ligase |
| NR4A1 | nuclear receptor subfamily 4, group A, member 1 |
| COL1A2 | collagen, type I, alpha 2 |
| IGF2 /// INS-IGF | insulin-like growth factor 2 (somatomedin A) /// INS-IGF2 readthrough |
| KIAA0101 | KIAA0101 |

TABLE 10-continued

Biomarkers for determining the severity of endometriosis in a biological sample comprising endometrial cells from mid-secretary phase (MSE).

| Gene Symbol | Gene Title |
| --- | --- |
| DHFR | dihydrofolate reductase |
| NRIP1 | nuclear receptor interacting protein 1 |
| ICAM1 | intercellular adhesion molecule 1 |
| SERTAD2 | SERTA domain containing 2 |
| GPX2 | glutathione peroxidase 2 (gastrointestinal) |
| ANPEP | alanyl (membrane) aminopeptidase |
| ADM | adrenomedullin |
| SOX9 | SRY (sex determining region Y)-box 9 |
| CAPN6 | calpain 6 |
| STMN2 | stathmin-like 2 |
| FH | fumarate hydratase |
| C2 | complement component 2 |
| FBN2 | fibrillin 2 |
| ST3GAL5 | ST3 beta-galactoside alpha-2,3-sialyltransferase 5 |
| TLE1 | transducin-like enhancer of split 1 (E(sp1) homolog, *Drosophila*) |
| ATXN1 | ataxin 1 |
| FCGBP | Fc fragment of IgG binding protein |
| CDH3 | cadherin 3, type 1, P-cadherin (placental) |
| HLA-DQA1 | major histocompatibility complex, class II, DQ alpha1 |
| PSD3 | pleckstrin and Sec7 domain containing 3 |
| EPN2 | epsin 2 |
| S100A9 | S100 calcium binding protein A9 |
| KLF9 | Kruppel-like factor 9 |
| LOXL1 | lysyl oxidase-like 1 |
| CSF3R | colony stimulating factor 3 receptor (granulocyte) |
| GPRC5B | G protein-coupled receptor, family C, group 5, member B |
| PLA2G2A | phospholipase A2, group IIA (platelets, synovial fluid) |
| BCL2 | B-cell CLL/lymphoma 2 |
| PI3 | peptidase inhibitor 3, skin-derived |
| PDE4B | phosphodiesterase 4B, cAMP-specific |
| MPZL2 | myelin protein zero-like 2 |
| SEMA3C | sema domain, immunoglobulin domain (Ig), short basic domain, secreted, (semaphorin) 3C |
| PCGF2 | polycomb group ring finger 2 |
| GSTT1 | glutathione S-transferase theta 1 |
| TSPAN8 | tetraspanin 8 |
| SCG5 | secretogranin V (7B2 protein) |
| MMP9 | matrix metallopeptidase 9 (gelatinase B, 92 kDa gelatinase, 92 kDa type IV collagenase) |
| HBA1 /// HBA2 | hemoglobin, alpha 1 /// hemoglobin, alpha 2 |
| RFC4 | replication factor C (activator 1) 4, 37 kDa |
| CTAGE5 | CTAGE family, member 5 |
| AGAP1 | ArfGAP with GTPase domain, ankyrin repeat and PH domain 1 |
| PRAME | preferentially expressed antigen in melanoma |
| IL2RG | interleukin 2 receptor, gamma |
| GADD45G | growth arrest and DNA-damage-inducible, gamma |
| GSTM4 | glutathione S-transferase mu 4 |
| ENPP4 | Ectonucleotide pyrophosphatase/phosphodiesterase 4 (putative) |
| CD37 | CD37 molecule |
| S100A2 | S100 calcium binding protein A2 |
| SKI | v-ski sarcoma viral oncogene homolog (avian) |
| FARS2 | phenylalanyl-tRNA synthetase 2, mitochondrial |
| PROM1 | prominin 1 |
| AK4 /// LOC100507855 | adenylate kinase 4 /// adenylate kinase isoenzyme 4, mitochondrial-like |
| SLC43A1 | solute carrier family 43, member 1 |
| GSTM2 | glutathione S-transferase mu 2 (muscle) |
| FOLR1 | folate receptor 1 (adult) |
| IFI44L | interferon-induced protein 44-like |
| MMP1 | matrix metallopeptidase 1 (interstitial collagenase) |
| CDC7 | cell division cycle 7 homolog (*S. cerevisiae*) |
| TOX | thymocyte selection-associated high mobility group box |
| CXCL10 | chemokine (C-X-C motif) ligand 10 |
| GABRE /// MIR224 /// MIR452 | gamma-aminobutyric acid (GABA) A receptor, epsilon /// microRNA 224 /// microRNA 452 |
| GSTM1 | glutathione S-transferase mu 1 |
| APOC2 /// APOC4 /// APOC4-APOC2 | apolipoprotein C-II /// apolipoprotein C-IV /// APOC4-APOC2 readthrough |
| ABCG1 | ATP-binding cassette, sub-family G (WHITE), member 1 |
| MMP12 | matrix metallopeptidase 12 (macrophage elastase) |
| DKK1 | dickkopf 1 homolog (*Xenopus laevis*) |
| SERPINB2 | serpin peptidase inhibitor, Glade B (ovalbumin) member 2 |
| TFF3 | trefoil factor 3 (intestinal) |

TABLE 10-continued

Biomarkers for determining the severity of endometriosis in a biological sample comprising endometrial cells from mid-secretary phase (MSE).

| Gene Symbol | Gene Title |
| --- | --- |
| SRD5A1 | steroid-5-alpha-reductase, alpha polypeptide 1 (3-oxo-5 alpha-steroid delta 4-dehydrogenase alpha 1) |
| ABCA8 | ATP-binding cassette, sub-family A (ABC1), member 8 |
| RIMS3 | regulating synaptic membrane exocytosis 3 |
| DUSP2 | dual specificity phosphatase 2 |
| CKM | creatine kinase, muscle |
| FOLR2 | folate receptor 2 (fetal) |
| MLH3 | mutL homolog 3 (E. coli) |
| ENPEP | glutamyl aminopeptidase (aminopeptidase A) |
| MSLN | mesothelin |
| LYPD3 | LY6/PLAUR domain containing 3 |
| ASNS | asparagine synthetase (glutamine-hydrolyzing) |
| PSPH | phosphoserine phosphatase |
| AOX1 | aldehyde oxidase 1 |
| SLC26A2 | solute carrier family 26 (sulfate transporter), member 2 |
| CCR1 | chemokine (C-C motif) receptor 1 |
| NEFM | neurofilament, medium polypeptide |
| CCL3 /// CCL3L1 /// CCL3L3 | chemokine (C-C motif) ligand 3 /// chemokine (C-C motif) ligand 3-like 1 /// chemokine (C-C motif) ligand 3-like 3 |
| PTGS1 | prostaglandin-endoperoxide synthase 1 (prostaglandin G/H synthase and cyclooxygenase) |
| ACTC1 | actin, alpha, cardiac muscle 1 |
| ITGB3BP | integrin beta 3 binding protein (beta3-endonexin) |
| AP1S1 | adaptor-related protein complex 1, sigma 1 subunit |
| HCAR3 | hydroxycarboxylic acid receptor 3 |
| SOD3 | superoxide dismutase 3, extracellular |
| LIF | leukemia inhibitory factor |
| IGFBP1 | insulin-like growth factor binding protein 1 |
| TMSB15A /// TMSB15B | thymosin beta 15a /// thymosin beta 15B |
| GGCX | gamma-glutamyl carboxylase |
| CBR3 | carbonyl reductase 3 |
| PRSS2 | protease, serine, 2 (trypsin 2) |
| SLC22A3 | solute carrier family 22 (extraneuronal monoamine transporter), member 3 |
| GSTT2 | glutathione s-transferase theta 2 |
| PRL | prolactin |
| MST1R | macrophage stimulating 1 receptor (c-met-related tyrosine kinase) |
| CD3E | CD3e molecule, epsilon (CD3-TCR complex) |
| KLK11 | kallikrein-related peptidase 11 |
| GZMA | granzyme A (granzyme 1, cytotoxic T-lymphocyte-associated serine esterase 3) |
| GNLY | granulysin |
| AVIL | advillin |
| BPI | bactericidal/permeability-increasing protein |
| HRH1 | histamine receptor H1 |
| NOS3 | nitric oxide synthase 3 (endothelial cell) |
| OLFM1 | olfactomedin 1 |
| C4BPA | complement component 4 binding protein alpha |
| OASL | 2'-5'-oligoadenylate synthetase-like |
| TPSAB1 | tryptase alpha/beta 1 |
| SYNGR3 | synaptogyrin 3 |
| CBLN1 | cerebellin 1 precursor |
| CD8A | CD8a molecule |
| CYP3A5 | cytochrome P450, family 3, subfamily A, polypeptide 5 |
| WISP2 | WNT1 inducible signaling pathway protein 2 |
| CD2 | CD2 molecule |
| PART1 | prostate androgen-regulated transcript 1 (non-protein coding) |
| SLC7A4 | solute carrier family 7 (orphan transporter), member 4 |
| GABBR1 /// UBD | gamma-aminobutyric acid (GABA) B receptor, 1 /// ubiquitin D |
| SLC22A4 | solute carrier family 22 (organic cation/ergothioneine transporter) member 4 |
| PLCL1 | phospholipase C-like 1 |
| EPHA1 | EPH receptor A1 |
| HABP2 | hyaluronan binding protein 2 |
| LEFTY2 | left-right determination factor 2 |
| TNFAIP6 | tumor necrosis factor, alpha-induced protein 6 |
| ACADL | acyl-CoA dehydrogenase, long chain |
| PTPRR | protein tyrosine phosphatase, receptor type, R |
| LRRC37A3 | leucine rich repeat containing 37, member A3 |
| MATN3 | matrilin 3 |
| UGT1A1 /// UGT1A10 /// UGT1A3 /// UGT1A4 /// UGT1A5 /// UGT1A6 /// UGT1A7 /// UGT1A8 /// UGT1A9 | UDP glucuronosyltransferase 1 family, polypeptide A1 /// UDP glucuronosyltransferase 1 family, polypeptide A10 /// UDP glucuronosyltransferase 1 family, polypeptide A3 /// UDP glucuronosyltransferase 1 family, polypeptide A4 /// UDP |

TABLE 10-continued

Biomarkers for determining the severity of endometriosis in a biological sample comprising endometrial cells from mid-secretary phase (MSE).

| Gene Symbol | Gene Title |
|---|---|
| | glucuronosyltransferase 1 family, polypeptide A5 /// UDP glucuronosyltransferase 1 family, polypeptide A6 /// UDP glucuronosyltransferase 1 family, polypeptide A7 /// UDP glucuronosyltransferase 1 family, polypeptide A8 /// UDP glucuronosyltransferase 1 family, polypeptide A9 |
| KLK8 | kallikrein-related peptidase 8 |
| CYP4F11 | cytochrome P450, family 4, subfamily F, polypeptide 11 |
| ARHGAP6 | Rho GTPase activating protein 6 |
| IL13RA2 | interleukin 13 receptor, alpha 2 |
| CST1 | cystatin SN |
| MMP17 | matrix metallopeptidase 17 (membrane-inserted) |
| ARHGAP22 | Rho GTPase activating protein 22 |
| FAM155B | family with sequence similarity 155, member B |
| PTHLH | parathyroid hormone-like hormone |
| SPINK2 | serine peptidase inhibitor, Kazal type 2 (acrosin-trypsin inhibitor) |
| GRP | gastrin-releasing peptide |
| CXCL6 | chemokine (C-X-C motif) ligand 6 (granulocyte chemotactic protein 2) |
| COX6A2 | cytochrome c oxidase subunit VIa polypeptide 2 |
| XCL1 | chemokine(C motif) ligand 1 |
| SCGB2A2 | secretoglobin, family 2A, member 2 |
| PF4 | platelet factor 4 |
| B4GALNT1 | beta-1,4-N-acetyl-galactosaminyl transferase 1 |
| S1PR4 | sphingosine-1-phosphate receptor 4 |
| LTC4S | leukotriene C4 synthase |
| ABAT | 4-aminobutyrate aminotransferase |
| AKR1B10 | aldo-keto reductase family 1, member B10 (aldose reductase) |
| LY96 | lymphocyte antigen 96 |
| SLC16A5 | solute carrier family 16, member 5 (monocarboxylic acid transporter 6) |
| ZMYM5 | zinc finger, MYM-type 5 |
| GP2 | glycoprotein 2 (zymogen granule membrane) |
| FAM65B | family with sequence similarity 65, member B |
| CRYBB2 /// CRYBB2P1 | crystallin, beta B2 /// crystallin, beta B2 pseudogene 1 |
| WISP1 | WNT1 inducible signaling pathway protein 1 |
| PAEP | progestagen-associated endometrial protein |
| IL11 | interleukin 11 |
| BGLAP /// PMF1-BGLAP | bone gamma-carboxy glutamate (gla) protein /// PMF1-BGLAP readthrough |
| TNF | tumor necrosis factor |
| TPSB2 | tryptase beta 2 (gene/pseudogene) |
| DIO3 | deiodinase, iodothyronine, type III |
| ALOX12 | arachidonate 12-lipoxygenase |
| CD300C | CD300c molecule |
| CD209 | CD209 molecule |
| KIR3DL1 /// KIR3DL2 /// LOC727787 | killer cell immunoglobulin-like receptor, three domains, long cytoplasmic tail, 1 /// killer cell immunoglobulin-like receptor, three domains, long cytoplasmic tail, 2 /// killer cell immunoglobulin-like receptor, three domains, long cytoplasmic tail, 2-like |
| KIR3DL2 /// LOC727787 | killer cell immunoglobulin-like receptor, three domains, long cytoplasmic tail, 2 /// killer cell immunoglobulin-like receptor, three domains, long cytoplasmic tail, 2-like |
| DEFB4A /// DEFB4B | defensin, beta 4A /// defensin, beta |
| RAC2 | ras-related C3 botulinum toxin substrate 2 (rho family, small GTP binding protein Rac2) |
| GZMM | granzyme M (lymphocyte met-ase 1) |
| PIR | pirin (iron-binding nuclear protein) |
| BDKRB1 | bradykinin receptor B1 |
| GADD45B | growth arrest and DNA-damage-inducible, beta |
| PSG9 | pregnancy specific beta-1-glycoprotein 9 |
| GAGE1 /// GAGE12C /// GAGE12D /// GAGE12E /// GAGE12F /// GAGE12G /// GAGE12H /// GAGE12I /// GAGE12J /// GAGE2A /// GAGE2B /// GAGE2C /// GAGE2D /// GAGE2E /// GAGE3 /// GAGE4 /// GAGE5 /// GAGE6 /// GAGE7 /// GAGE8 | G antigen 1 /// G antigen 12C /// G antigen 12D /// G antigen 12E /// G antigen 12F /// G antigen 12G /// G antigen 12H /// G antigen 12I /// G antigen 12J /// G antigen 2A /// G antigen 2B /// G antigen 2C /// G antigen 2D /// G antigen 2E /// G antigen 3 /// G antigen 4 /// G antigen 5 /// G antigen 6 /// G antigen 7 /// G antigen 8 |
| FGFR1 | fibroblast growth factor receptor 1 |
| MUC1 | mucin 1, cell surface associated |
| KRT13 | keratin 13 |

TABLE 10-continued

Biomarkers for determining the severity of endometriosis in a biological sample comprising endometrial cells from mid-secretary phase (MSE).

| Gene Symbol | Gene Title |
|---|---|
| NFAT5 | nuclear factor of activated T-cells 5, tonicity-responsive |
| LINC00597 | long intergenic non-protein coding RNA 597 |
| KIR2DS3 | killer cell immunoglobulin-like receptor, two domains, short cytoplasmic tail, 3 |
| PTGIS | prostaglandin I2 (prostacyclin) synthase |
| GAST | gastrin |
| KIR2DS1 | killer cell immunoglobulin-like receptor, two domains, short cytoplasmic tail, 1 |
| KIR2DS5 | killer cell immunoglobulin-like receptor, two domains, short cytoplasmic tail, 5 |
| DMBT1 | deleted in malignant brain tumors 1 |
| TH | tyrosine hydroxylase |
| ANK1 | ankyrin 1, erythrocytic |
| KIR2DL2 /// KIR2DL4 /// KIR2DL5A /// KIR2DL5B /// KIR3DL3 /// KIR3DS1 /// LOC100287534 | killer cell immunoglobulin-like receptor, two domains, long cytoplasmic tail, 2 /// killer cell immunoglobulin-like receptor, two domains, long cytoplasmic tail, 4 /// killer cell immunoglobulin-like receptor, two domains, long cytoplasmic tail, 5A /// killer cell immunoglobulin-like receptor, two domains, long cytoplasmic tail, 5B /// killer cell immunoglobulin-like receptor three domains long cytoplasmic tail 3 /// killer cell immunoglobulin-like receptor, three domains, short cytoplasmic tail, 1 /// killer cell immunoglobulin-like receptor 2DL4-like |
| RASA4 /// RASA4B /// RASA4CP/// UPK3BL | RAS p21 protein activator 4 /// RAS p21 protein activator 4B /// RAS p21 protein activator 4C, pseudogene /// uroplakin 3B-like |
| WNT4 | wingless-type MMTV integration site family, member 4 |
| AP3D1 | adaptor-related protein complex 3, delta 1 subunit |
| LGALS8 | lectin, galactoside-binding, soluble, 8 |
| UPF1 | UPF1 regulator of nonsense transcripts homolog (yeast) |
| KRT7 | keratin 7 |
| CORO1A | coronin, actin binding protein 1A |
| UBN1 | ubinuclein 1 |
| HBB | hemoglobin, beta |
| AKR1C3 | aldo-keto reductase family 1, member C3 (3-alpha hydroxysteroid dehydrogenase, type II) |
| FOS | FBJ murine osteosarcoma viral oncogene homolog |
| TFPI2 | tissue factor pathway inhibitor 2 |
| CA2 | carbonic anhydrase II |
| AZGP1 | alpha-2-glycoprotein 1, zinc-binding |
| RGS16 | regulator of G-protein signaling 16 |
| MALL | mal, T-cell differentiation protein-like |
| SCAF11 | SR-related CTD-associated factor 11 |
| DLK1 | delta-like 1 homolog (*Drosophila*) |
| CES1 /// LOC100653057 | carboxylesterase 1 /// liver carboxylesterase 1-like |
| HLA-DRB4 /// LOC100509582 | major histocompatibility complex, class II, DR beta 4 /// HLA class II histocompatibility antigen, DR beta 4 chain-like |
| NR1D2 | nuclear receptor subfamily 1, group D, member 2 |
| RRM2 | ribonucleotide reductase M2 |
| CXCL2 | chemokine (C-X-C motif) ligand 2 |
| CASP6 | caspase 6, apoptosis-related cysteine peptidase |
| KLK10 | kallikrein-related peptidase 10 |
| TARP | TCR gamma alternate reading frame protein |
| SPP1 | secreted phosphoprotein 1 |
| TNNC1 | troponin C type 1 (slow) |
| TGFB2 | transforming growth factor, beta 2 |
| SLC7A11 | solute carrier family 7 (anionic amino acid transporter light chain, xc- system), member 11 |
| CD247 | CD247 molecule |
| RND1 | Rho family GTPase 1 |
| MAPK13 | mitogen-activated protein kinase 13 |
| UPK1B | uroplakin 1B |
| ARC | activity-regulated cytoskeleton-associated protein |
| CYP4B1 | cytochrome P450, family 4, subfamily B, polypeptide 1 |
| PLA2G4A | phospholipase A2, group IVA (cytosolic, calcium-dependent) |
| GZMB | granzyme B (granzyme 2, cytotoxic T-lymphocyte-associated serine esterase 1) |
| IRX5 | iroquois homeobox 5 |
| DLG5 | discs, large homolog 5 (*Drosophila*) |
| CTAG1A /// CTAG1B | cancer/testis antigen 1A /// cancer testis antigen 1B |
| CCL23 | chemokine (C-C motif) ligand 23 |
| LAIR1 | leukocyte-associated immunoglobulin-like receptor 1 |
| NRTN | neurturin |
| CLDN14 | claudin 14 |
| SLC43A3 | solute carrier family 43, member 3 |
| NCR3 | natural cytotoxicity triggering receptor 3 |
| POSTN | periostin, osteoblast specific factor |

TABLE 10-continued

Biomarkers for determining the severity of endometriosis in a biological sample comprising endometrial cells from mid-secretary phase (MSE).

| Gene Symbol | Gene Title |
| --- | --- |
| KIR2DL1 /// KIR2DL2 /// KIR2DL3 /// KIR2DL4 /// KIR2DL5A /// KIR2DL5B /// KIR3DL3 /// KIR3DS1 /// LOC100287534 /// LOC100653050 | killer cell immunoglobulin-like receptor, two domains, long cytoplasmic tail, 1 /// killer cell immunoglobulin-like receptor, two domains, long cytoplasmic tail, 2 /// killer cell immunoglobulin-like receptor, two domains, long cytoplasmic tail, 3 /// killer cell immunoglobulin-like receptor, two domains, long cytoplasmic tail, 4 /// killer cell immunoglobulin-like receptor, two domains, long cytoplasmic tail, 5A /// killer cell immunoglobulin-like receptor, two domains, long cytoplasmic tail, 5B /// killer cell immunoglobulin-like receptor three domains long cytoplasmic tail 3 /// killer cell immunoglobulin-like receptor, three domains, short cytoplasmic tail, 1 /// killer cell immunoglobulin-like receptor 2DL4-like /// killer cell immunoglobulin-like receptor 2DL2-like |
| AP3D1 | adaptor-related protein complex 3, delta 1 subunit |
| HLA-DRA | major histocompatibility complex, class II, DR alpha |
| HGF | hepatocyte growth factor (hepapoietin A; scatter factor) |
| PSTPIP1 | proline-serine-threonine phosphatase interacting protein 1 |
| KIR2DL4 | killer cell immunoglobulin-like receptor, two domains, long cytoplasmic tail, 4 |
| KIR2DL2 | killer cell immunoglobulin-like receptor, two domains, long cytoplasmic tail, 2 |
| MAPK11 | mitogen-activated protein kinase 11 |
| KIR2DS1 /// KIR2DS2 /// KIR2DS3 /// KIR2DS4 /// KIR2DS5 /// KIR3DL3 | killer cell immunoglobulin-like receptor, two domains, short cytoplasmic tail, 1 /// killer cell immunoglobulin-like receptor, two domains, short cytoplasmic tail, 2 /// killer cell immunoglobulin-like receptor, two domains, short cytoplasmic tail, 3 /// killer cell immunoglobulin-like receptor, two domains, short cytoplasmic tail, 4 /// killer cell immunoglobulin-like receptor, two domains, short cytoplasmic tail, 5 /// killer cell immunoglobulin-like receptor three domains long cytoplasmic tail 3 |
| CEACAM6 | carcinoembryonic antigen-related cell adhesion molecule 6 (non-specific cross reacting antigen) |
| KIR3DL1 | killer cell immunoglobulin-like receptor, three domains, long cytoplasmic tail, 1 |
| PRG2 | proteoglycan 2, bone marrow (natural killer cell activator, eosinophil granule major basic protein) |
| COL4A2 | collagen, type IV, alpha 2 |
| HLA-DPA1 | major histocompatibility complex, class II, DP alpha 1 |
| WNK1 | WNK lysine deficient protein kinase 1 |
| DAG1 | dystroglycan 1 (dystrophin-associated glycoprotein 1) |
| FNBP4 | formin binding protein 4 |
| PIK3R1 | phosphoinositide-3-kinase, regulatory subunit 1 (alpha) |
| SLC7A1 | solute carrier family 7 (cationic amino acid transporter, y+ system), member 1 |
| CLASP2 | cytoplasmic linker associated protein 2 |
| MYO1D | myosin 1D |
| KHNYN | KH and NYN domain containing |
| SEP6 | septin 6 |
| CERS6 | ceramide synthase 6 |
| COL5A1 | collagen, type V, alpha 1 |
| IL1RN | interleukin 1 receptor antagonist |
| RASA4 /// RASA4B /// RASA4CP | RAS p21 protein activator 4 /// RAS p21 protein activator 4B /// RAS p21 protein activator 4C pseudogene |
| NFATC2IP | nuclear factor of activated T-cells. cytoplasmic, calcineurin-dependent 2 interacting protein |
| PLEKHG3 | pleckstrin homology domain containing, family G (with RhoGef domain) member 3 |
| SUPV3L1 | suppressor of var1, 3-like 1 (*S. cerevisiae*) |
| COL6A1 | collagen, type VI, alpha 1 |
| BBX | bobby sox homolog (*Drosophila*) |
| GATAD1 | GATA zinc finger domain containing 1 |
| CHI3L2 | chitinase 3-like 2 |
| NEK3 | NIMA (never in mitosis gene a)-related kinase 3 |
| TIAM1 | T-cell lymphoma invasion and metastasis 1 |
| PLCB1 | phospholipase C, beta 1 (phosphoinositide-specific) |
| KRT4 | keratin 4 |
| ZNF248 | zinc finger protein 248 |
| TCF25 | transcription factor 25 (basic helix-loop-helix) |
| PAQR3 | progestin and adipoQ receptor family member III |
| MUC5B | mucin 5B, oligomeric mucus/gel-forming |
| RUFY3 | RUN and FYVE domain containing 3 |
| NPTX2 | neuronal pentraxin II |
| TRA2A | transformer 2 alpha homolog (*Drosophila*) |
| ENOSF1 | enolase superfamily member 1 |

TABLE 10-continued

Biomarkers for determining the severity of endometriosis in a biological sample comprising endometrial cells from mid-secretary phase (MSE).

| Gene Symbol | Gene Title |
| --- | --- |
| SLC1A1 | solute carrier family 1 (neuronal/epithelial high affinity glutamate transporter, system Xag), member 1 |
| FAM69A | family with sequence similarity 69, member A |
| GLB1L2 | galactosidase, beta 1-like 2 |
| KSR1 | kinase suppressor of ras 1 |
| STARD5 | StAR-related lipid transfer (START) domain containing 5 |
| CLMN | calmin (calponin-like, transmembrane) |
| THSD7A | thrombospondin, type I, domain containing 7A |
| PAX8 | paired box 8 |
| RPGRIP1L | RPGRIP1-like |
| ZAP70 | zeta-chain (TCR) associated protein kinase 70 kDa |
| CCL8 | chemokine (C-C motif) ligand 8 |
| GSN | gelsolin |
| PTPRD | protein tyrosine phosphatase, receptor type, D |
| MBD4 | methyl-CpG binding domain protein 4 |
| CD7 | CD7 molecule |
| MYRIP | myosin VIIA and Rab interacting protein |
| GNAS | GNAS complex locus |
| ABCB9 | ATP-binding cassette, sub-family B (MDR/TAP), member 9 |
| GAL | galanin prepropeptide |
| DKK3 | dickkopf 3 homolog (*Xenopus laevis*) |
| RPL17 /// RPL17-C18ORF32 | ribosomal protein L17 /// RPL17-C18orf32 readthrough |
| MUC5AC | mucin 5AC, oligomeric mucus/gel-forming |
| NOV | nephroblastoma overexpressed |
| JUND | jun D proto-oncogene |
| RASGRP2 | RAS guanyl releasing protein 2 (calcium and DAG-regulated) |
| HSPA12A | heat shock 70 kDa protein 12A |
| CTSW | cathepsin W |
| CDC42BPA | CDC42 binding protein kinase alpha (DMPK-like) |
| KLRB1 | killer cell lectin-like receptor subfamily B, member |
| ADAMTS2 | ADAM metallopeptidase with thrombospondin type1 motif, 2 |
| CD7 | CD7 molecule |
| LILRP2 | leukocyte immunoglobulin-like receptor pseudogene 2 |
| XCL1 /// XCL2 | chemokine (C motif) ligand 1 /// chemokine(C motif) ligand 2 |
| MNX1 | motor neuron and pancreas homeobox 1 |
| SEP10 | septin 10 |
| ADD1 | adducin 1 (alpha) |
| HSPB6 | heat shock protein, alpha-crystallin-related, B6 |
| N4BP3 | NEDD4 binding protein 3 |
| MEGF8 | multiple EGF-like-domains 8 |
| CTTN | cortactin |
| SP140L | SP140 nuclear body protein-like |
| ATP2C2 | ATPase, Ca++ transporting, type 2C, member 2 |
| DOK5 | docking protein 5 |
| LOC100170939 | glucuronidase, beta pseudogene |
| CXCL5 | chemokine (C-X-C motif) ligand 5 |
| TM4SF1 | transmembrane 4 L six family member 1 |
| RC3H1 | ring finger and CCCH-type domains 1 |
| SLC35E2 | solute carrier family 35, member E2 |
| KRT86 /// LOC100509764 | keratin 86 /// uncharacterized LOC100509764 |
| PRSS3P2 | protease, serine, 3 pseudogene 2 |
| HLA-DQB2 | major histocompatibility complex, class II, DQ beta 2 |
| CTAG2 | cancer/testis antigen 2 |
| DUOX1 | dual oxidase 1 |
| TARP /// TRGC2 | TCR gamma alternate reading frame protein /// T cell receptor gamma constant 2 |
| PTGDR | prostaglandin D2 receptor (DP) |
| GABRA2 | gamma-aminobutyric acid (GABA) A receptor, alpha 2 |
| TRDV3 | T cel receptor delta variable 3 |
| SMPD1 | sphingomyelin phosphodiesterase 1, acid lysosomal |
| FAS | Fas (TNF receptor superfamily, member 6) |
| LOC100288594 | uncharacterized LOC100288594 |
| TPSAB1 /// TPSB2 | tryptase alpha/beta 1 /// tryptase beta 2 (gene pseudogene) |
| CCL2 | chemokine (C-C motif) ligand 2 |
| KIR3DL3 | killer cell immunoglobulin-like receptor, three domains, long cytoplasmic tail, 3 |
| FAM48A | family with sequence similarity 48, member A |
| RGS1 | regulator of G-protein signaling 1 |
| YME1L1 | YME1-like 1 (*S. cerevisiae*) |
| C14orf1 | chromosome 14 open reading frame 1 |
| LOC100287387 | Uncharacterized LOC100287387 |
| COL7A1 | collagen, type VII, alpha 1 |
| KLK13 | kallikrein-related peptidase 13 |
| LOC283683 /// LOC646278 | uncharacterized LOC283683 /// programmed cell death 6 interacting protein pseudogene |

TABLE 10-continued

Biomarkers for determining the severity of endometriosis in a biological
sample comprising endometrial cells from mid-secretory phase (MSE).

| Gene Symbol | Gene Title |
| --- | --- |
| HAL | histidine ammonia-lyase |
| SGSM2 | small G protein signaling modulator 2 |
| TRIM44 | tripartite motif containing 44 |
| RNASET2 | ribonuclease T2 |
| CXCL14 | chemokine (C-X-C motif) ligand 14 |
| NUSAP1 | nucleolar and spindle associated protein 1 |
| CLDN1 | claudin 1 |
| MLPH | melanophilin |
| C1QA | complement component 1, q subcomponent, A chain |
| TYW1 /// TYW1B | tRNA-yW synthesizing protein 1 homolog S. cerevisiae) /// tRNA-yW synthesizing protein 1 homolog B (S. cerevisiae) |
| SNX10 | sorting nexin 10 |
| GCFC1 | GC-rich sequence DNA-binding factor 1 |
| LIMD2 | LIM domain containing 2 |
| UPF3B | UPF3 regulator of nonsense transcripts homolog B (yeast) |
| ACP6 | acid phosphatase 6, lysophosphatidic |
| COL5A3 | collagen, type V, alpha 3 |
| SPRR3 | small proline-rich protein 3 |
| ASPN | asporin |
| DACT1 | dapper, antagonist of beta-catenin, homolog 1 (Xenopus laevis) |
| HSPA14 | heat shock 70 kDa protein 14 |
| ZNF331 | zinc finger protein 331 |
| ECHDC3 | enoyl CoA hydratase domain containing 3 |
| IFT81 | intraflagellar transport 81 homolog (Chlamydomonas) |
| NKAIN1 | Na+ K+ transporting ATPase interacting 1 |
| RAB3IL1 | RAB3A interacting protein (rabin3)-like 1 |
| ZNF767 | zinc finger family member 767 |
| ZNF606 | zinc finger protein 606 |
| ATP8A2 | ATPase, aminophospholipid transporter, class I, type 8A, member 2 |
| RASAL1 | RAS protein activator like 1 (GAP 1 like) |
| ERAP2 | endoplasmic reticulum aminopeptidase 2 |
| DENND1A | DENN/MADD domain containing 1A |
| FZD10 | frizzled family receptor 10 |
| PVRIG | poliovirus receptor related immunoglobulin domain containing |
| FKRP | fukutin related protein |
| C1orf116 | chromosome 1 open reading frame 116 |
| CHODL | chondrolectin |
| FRAT1 | frequently rearranged in advanced T-cell lymphomas |
| MAGIX | MAGI family member, X-linked |
| APBB1IP | amyloid beta (A4) precursor protein-binding, family B, member 1 interacting protein |
| ZNF750 | zinc finger protein 750 |
| EPHX3 | epoxide hydrolase 3 |
| STAP1 | signal transducing adaptor family member 1 |
| CSPP1 | centrosome and spindle pole associated protein 1 |
| FXYD7 | FXYD domain containing ion transport regulator 7 |
| ALDH8A1 | aldehyde dehydrogenase 8 family, member A1 |
| FAM86C1 | family with sequence similarity 86, member C1 |
| GPR97 | G protein-coupled receptor 97 |
| UBASH3A | ubiquitin associated and SH3 domain containing A |
| CHD9 | chromodomain helicase DNA binding protein 9 |
| UIMC1 | ubiquitin interaction motif containing 1 |
| WDR19 | WD repeat domain 19 |
| ST6GALNAC5 | ST6 (alpha-N-acetyl-neuraminyl-2,3-beta-galactosyl-1,3)-N-acetylgalactosaminide alpha-2,6-sialyltransferase 5 |
| CHST8 | carbohydrate (N-acetylgalactosamine 4-0) sulfotransferase 8 |
| DENND1C | DENN/MADD domain containing 1C |
| OTOR | otoraplin |
| BACH2 | BTB and CNC homology 1, basic leucine zipper transcription factor 2 |
| YIPF5 | Yip1 domain family, member 5 |
| TBL1XR1 | Transducin (beta)-like 1 X-linked receptor 1 |
| B4GALT5 | UDP-Gal: betaGlcNAc beta 1,4-galactosyltransferase, polypeptide 5 |
| HLA-DRB1 /// HLA-DRB3 /// HLA-DRB4 /// HLA-DRB5 /// LOC100507709 /// LOC100507714 /// LOC100509582 | major histocompatibility complex, class II, DR beta 1 /// major histocompatibility complex, class II, DR beta 3 /// major histocompatibility complex, class II, DR beta 4 /// major histocompatibility complex, class II, DR beta 5 /// HLA class II histocompatibility antigen, DRB1-7 beta chain-like /// HLA class II histocompatibility antigen, DRB1-7 beta chain-like /// HLA class II histocompatibility antigen, DR beta 4 chain-like |
| PARD3 | par-3 partitioning defective 3 homolog (C. elegans) |
| BHLHE41 | basic helix-loop-helix family, member e41 |
| GDF15 | growth differentiation factor 15 |

TABLE 10-continued

Biomarkers for determining the severity of endometriosis in a biological sample comprising endometrial cells from mid-secretary phase (MSE).

| Gene Symbol | Gene Title |
| --- | --- |
| ZNF83 | zinc finger protein 83 |
| AGMAT | agmatine ureohydrolase (agmatinase) |
| NLRP2 | NLR family, pyrin domain containing 2 |
| PIK3IP1 | phosphoinositide-3-kinase interacting protein 1 |
| UGCG | UDP-glucose ceramide glucosyltransferase |
| ANGEL2 | angel homolog 2 (*Drosophila*) |
| HNRNPA1 | heterogeneous nuclear ribonucleoprotein A1 |
| FLJ42627 | uncharacterized LOC645644 |
| SLCO4C1 | solute carrier organic anion transporter family, member 4C1 |
| FAM63B | family with sequence similarity 63, member B |
| DESI2 | desumoylating isopeptidase 2 |
| EGOT | eosinophil granule ontogeny transcript (non-protein coding) |
| C4orf34 | chromosome 4 open reading frame 34 |
| TUBBP5 | tubulin, beta pseudogene 5 |
| PDCD6 | Programmed cell death 6 |
| APPL1 | adaptor protein, phosphotyrosine interaction, PH domain and leucine zipper containing 1 |
| CPPED1 | calcineurin-like phosphoesterase domain containing 1 |
| ZAK | sterile alpha motif and leucine zipper containing kinase AZK |
| MANEA | mannosidase, endo-alpha |
| ANKH | ankylosis, progressive homolog (mouse) |
| TRIM8 | tripartite motif containing 8 |
| CGN | cingulin |
| GJB2 | gap junction protein, beta 2, 26 kDa |
| MS4A7 | membrane-spanning 4-domains, subfamily A, member 7 |
| C21orf56 | chromosome 21 open reading frame 56 |
| GBP3 | guanylate binding protein 3 |
| CRISPLD1 | cysteine-rich secretory protein LCCL domain containing 1 |
| C15orf48 | chromosome 15 open reading frame 48 |
| MGEA5 | meningioma expressed antigen 5 (hyaluronidase) |
| SEMA6B | sema domain, transmembrane domain (TM), and cytoplasmic domain, (semaphorin) 6B |
| MALAT1 | metastasis associated lung adenocarcinoma transcript 1 (non-protein coding) |
| ZMYND12 | zinc finger, MYND-type containing 12 |
| SLC4A11 | solute carrier family 4, sodium borate transporter, member 11 |
| DIO3OS | DIO3 opposite strand/antisense RNA (non-protein coding) |
| TEX101 | testis expressed 101 |
| CISH | cytokine inducible SH2-containing protein |
| CRLS1 | cardiolipin synthase 1 |
| PXMP4 | peroxisomal membrane protein 4, 24 kDa |
| PCDHA1 /// PCDHA10 /// PCDHA11 /// PCDHA12 /// PCDHA13 /// PCDHA2 /// PCDHA3 /// PCDHA4 /// PCDHA5 /// PCDHA6 /// PCDHA7 /// PCDHA8 /// PCDHA9 /// PCDHAC1 /// PCDHAC2 | protocadherin alpha 1 /// protocadherin alpha 10 /// protocadherin alpha 11 /// protocadherin alpha 12 /// protocadherin alpha 13 /// protocadherin alpha 2 /// protocadherin alpha 3 /// protocadherin alpha 4 /// protocadherin alpha 5 /// protocadherin alpha 6 /// protocadherin alpha 7 /// protocadherin alpha 8 /// protocadherin alpha 9 /// protocadherin alpha subfamily C, 1 /// protocadherin alpha subfamily C, 2 |
| MS4A8B | membrane-spanning 4-domains, subfamily A, member 8B |
| BEX2 | brain expressed X-linked 2 |
| TRPM6 | transient receptor potential cation channel, subfamily M, member 6 |
| ARHGAP9 | Rho GTPase activating protein 9 |
| SMEK2 | SMEK homolog 2, suppressor of mek1 (*Dictyostelium*) |
| KREMEN1 | kringle containing transmembrane protein 1 |
| TNFRSF18 | tumor necrosis factor receptor superfamily, member 18 |
| WASF2 | WAS protein family, member 2 |
| SNHG1 /// SNORD22 /// SNORD25 /// SNORD26 /// SNORD27 /// SNORD28 /// SNORD29 /// SNORD31 | small nucleolar RNA host gene 1 (non-protein coding) /// small nucleolar RNA, C/D box 22 /// small nucleolar RNA, C/D box 25 /// small nucleolar RNA, C/D box 26 /// small nucleolar RNA, C/D box 27 /// small nucleolar RNA, C/D box 28 /// small nucleolar RNA, C/D box 29 /// small nucleolar RNA, C/D box 31 |
| GPATCH4 | G patch domain containing 4 |
| H19 /// MIR675 | H19, imprinted maternally expressed transcript (non-protein coding) /// microRNA 675 |
| LOC100506548 /// RPL37 | uncharacterized LOC100506548 /// ribosomal protein L37 |
| GPCPD1 | glycerophosphocholine phosphodiesterase GDE1 homolog (*S. cerevisiae*) |
| SLAIN2 | SLAIN motif family, member 2 |
| PDPR | pyruvate dehydrogenase phosphatase regulatory subunit |
| ASPH | aspartate beta-hydroxylase |

TABLE 10-continued

Biomarkers for determining the severity of endometriosis in a biological sample comprising endometrial cells from mid-secretary phase (MSE).

| Gene Symbol | Gene Title |
| --- | --- |
| SPIRE1 | spire homolog 1 (*Drosophila*) |
| ST3GAL1 | ST3 beta-galactoside alpha-2,3-sialyltransferase 1 |
| RABEP1 | rabaptin, RAB GTPase binding effector protein 1 |
| OGFOD1 | 2-oxoglutarate and iron-dependent oxygenase domain containing 1 |
| TMEM18 | transmembrane protein 18 |
| SLC1A2 | solute carrier family 1 (glial high affinity glutamate transporter), member 2 |
| ZNF295 | zinc finger protein 295 |
| MRPL50 | mitochondrial ribosomal protein L50 |
| SLC45A4 | solute carrier family 45, member 4 |
| PAG1 | phosphoprotein associated with glycosphingolipid microdomains 1 |
| COL12A1 | collagen, type XII, alpha 1 |
| CEP95 | centrosomal protein 95 kDa |
| HNRNPU-AS1 | HNRNPU antisense RNA 1 (non-protein coding) |
| CGNL1 | cingulin-like 1 |
| EIF2C2 | eukaryotic translation initiation factor 2C, 2 |
| PHLDA1 | pleckstrin homology-like domain, family A, member 1 |
| DDHD1 | DDHD domain containing 1 |
| BPIFB1 | BPI fold containing family B, member 1 |
| SYT13 | synaptotagmin XIII |
| ELL2 | elongation factor, RNA polymerase II, 2 |
| ZFP90 | zinc finger protein 90 homolog (mouse) |
| LOC100288152 | uncharacterized LOC100288152 |
| COL8A1 | collagen, type VIII, alpha 1 |
| CLCN5 | chloride channel, voltage-sensitive 5 |
| DNER | delta/notch-like EGF repeat containing |
| SPTBN1 | spectrin, beta, non-erythrocytic 1 |
| ZMAT1 | zinc finger, matrin-type 1 |
| AMMECR1 | Alport syndrome, mental retardation, midface hypoplasia and elliptocytosis chromosomal region gene 1 |
| RMI2 | RMI2, RecQ mediated genome instability 2, homolog (*S. cerevisiae*) |
| TM7SF3 | transmembrane 7 superfamily member 3 |
| NHSL1 | NHS-like 1 |
| HINT3 | histidine triad nucleotide binding protein 3 |
| CD109 | CD109 molecule |
| GTPBP5 | GTP binding protein 5 (putative) |
| ZNF251 | zinc finger protein 251 |
| C8orf42 | chromosome 8 open reading frame 42 |
| ADAMTS9 | ADAM metallopeptidase with thrombospondin type 1 motif, 9 |
| FST | follistatin |
| UNC5B | unc-5 homolog B (*C. elegans*) |
| LRIG3 | leucine-rich repeats and immunoglobulin-like domains 3 |
| SOX8 | SRY (sex determining region Y)-box 8 |
| DEPDC1B | DEP domain containing IB |
| NOTCH2NL | notch 2 N-terminal like |
| GLT8D2 | glycosyltransferase 8 domain containing 2 |
| INHBA | inhibin, beta A |
| ELOVL7 | ELOVL fatty acid elongase 7 |
| SUSD3 | sushi domain containing 3 |
| KIAA1211 | KIAA1211 |
| POC5 | POC5 centriolar protein homolog (*Chlamydomonas*) |
| CCT6P1 /// CCT6P3 | chaperonin containing TCP1, subunit 6 (zeta) pseudogene 1 /// chaperonin containing TCP1, subunit 6 (zeta) pseudogene 3 |
| VGLL3 | vestigial like 3 (*Drosophila*) |
| FOXQ1 | forkhead box Q1 |
| MGC16121 /// MIR503 | uncharacterized protein MGC16121 ///microRNA 503 |
| GFRA1 | GDNF family receptor alpha 1 |
| TSPAN11 | tetraspanin 11 |
| FBXL16 | F-box and leucine-rich repeat protein 16 |
| TMEM63C | transmembrane protein 63C |
| RBMXL1 | RNA binding motif protein, X-linked-like 1 |
| PDCD5 | programmed cell death 5 |
| C16orf74 | chromosome 16 open reading frame 74 |
| FMNL3 | formin-like 3 |
| LOC154761 | family with sequence similarity 115, member C pseudogene |
| LOC100506234 /// TMEM185A | uncharacterized LOC100506234 /// transmembrane protein 185A |
| FGD4 | FYVE, RhoGEF and PH domain containing 4 |
| ZG16B | zymogen granule protein 16 homolog B (rat) |
| LRCH3 | leucine-rich repeats and calponin homology (CH) domain containing 3 |
| CTXN1 | cortexin 1 |
| CP | ceruloplasmin (ferroxidase) |

TABLE 10-continued

Biomarkers for determining the severity of endometriosis in a biological sample comprising endometrial cells from mid-secretary phase (MSE).

| Gene Symbol | Gene Title |
| --- | --- |
| SORCS1 | sortilin-related VPS10 domain containing receptor 1 |
| ZNF252P | zinc finger protein 252, pseudogene |
| GAS5 /// SNORD44 /// SNORD47 /// SNORD76 /// SNORD77 /// SNORD79 /// SNORD80 /// SNORD81 | growth arrest-specific 5 (non-protein coding) /// small nucleolar RNA, C/D box 44 /// small nucleolar RNA, C/D box 47 /// small nucleolar RNA, C/D box 76 /// small nucleolar RNA, C/D box 77 /// small nucleolar RNA, C/D box 79 /// small nucleolar RNA, C/D box 80 /// small nucleolar RNA, C/D box 81 |
| AGR3 | anterior gradient 3 homolog (*Xenopus laevis*) |
| LOC283788 | FSHD region gene 1 pseudogene |
| CLDN11 | claudin 11 |
| NANOS1 | nanos homolog 1 (*Drosophila*) |
| C1orf162 | chromosome 1 open reading frame 162 |
| DPP6 | dipeptidyl-peptidase 6 |
| ODF2L | outer dense fiber of sperm tails 2-like |
| SNHG9 /// SNORA78 | small nucleolar RNA host gene 9 (non-protein coding) /// small nucleolar RNA, H/ACA box 78 |
| SOX7 | SRY (sex determining region Y)-box 7 |
| FLJ43663 | uncharacterized LOC378805 |
| RAB27B | RAB27B, member RAS oncogene family |
| CD36 | CD36 molecule (thrombospondin receptor) |
| PTGR1 | prostaglandin reductase 1 |
| ATF7 | activating transcription factor 7 |
| DERL3 | derlin 3 |
| CES4A | carboxylesterase 4A |
| DACH1 | dachshund homolog 1 (*Drosophila*) |
| C9orf24 | chromosome 9 open reading frame 24 |
| SARNP | SAP domain containing ribonucleoprotein |
| C17orf100 | chromosome 17 open reading frame 100 |
| PRTG | protogenin |
| PROK1 | prokineticin 1 |
| PRTG | protogenin |
| ATG9B | autophagy related 9B |
| LOC728613 | programmed cell death 6 pseudogene |
| ANKRD28 | ankyrin repeat domain 28 |
| ATG16L2 | autophagy related 16-like 2 (*S. cerevisiae*) |
| RBM26 | RNA binding motif protein 26 |
| IFIT3 | interferon-induced protein with tetratricopeptide repeats 3 |
| FAM46B | family with sequence similarity 46, member B |
| C14orf118 | chromosome 14 open reading frame 118 |
| ZNF502 | zinc finger protein 502 |
| C20orf85 | chromosome 20 open reading frame 85 |
| DISP2 | dispatched homolog 2 (*Drosophila*) |
| FAM132B | family with sequence similarity 132, member B |
| LOC728431 | uncharacterized LOC728431 |
| SMTNL2 | smoothelin-like 2 |
| ZNF207 | zinc finger protein 207 |
| SNAP23 | synaptosomal-associated protein, 23 kDa |
| FAM166B | family with sequence similarity 166, member B |
| PI15 | peptidase inhibitor 15 |
| EWSR1 | Ewing sarcoma breakpoint region 1 |
| RNF213 | ring finger protein 213 |
| CDCA7 | cell division cycle associated 7 |
| PITPNM3 | PITPNM family member 3 |
| LOC220729 /// SDHA /// SDHAP1 /// SDHAP2 | succinate dehydrogenase complex, subunit A, flavoprotein (Fp) pseudogene /// succinate dehydrogenase complex, subunit A, flavoprotein (Fp) /// succinate dehydrogenase complex, subunit A, flavoprotein pseudogene 1 /// succinate dehydrogenase complex, subunit A, flavoprotein pseudogene 2 |
| USP53 | ubiquitin specific peptidase 53 |
| F2RL2 | coagulation factor II (thrombin) receptor-like 2 |
| DDX17 | DEAD (Asp-Glu-Ala-Asp) box helicase 17 |
| LOC100507100 | uncharacterized LOC100507100 |
| C2orf82 | chromosome 2 open reading frame 82 |
| LPAR5 | lysophosphatidic acid receptor 5 |
| BAG5 | BCL2-associated athanogene 5 |
| LOC100507008 | uncharacterized LOC100507008 |
| PKHD1L1 | polycystic kidney and hepatic disease 1 (autosomal recessive)-like 1 |
| MIR210HG | MIR210 host gene (non-protein coding) |
| FAM210A | family with sequence similarity 210, member A |
| LOC100505875 | uncharacterized LOC100505875 |
| ACRBP | acrosin binding protein |
| SPG7 | spastic paraplegia 7 (pure and complicated autosomal recessive) |
| PALM3 | paralemmin 3 |
| C1orf194 | chromosome 1 open reading frame 194 |

TABLE 10-continued

Biomarkers for determining the severity of endometriosis in a biological sample comprising endometrial cells from mid-secretary phase (MSE).

| Gene Symbol | Gene Title |
|---|---|
| C1orf192 | chromosome 1 open reading frame 192 |
| MIR30C2 | microRNA 30c-2 |
| IP6K3 | inositol hexakisphosphate kinase 3 |
| WIPF1 | WAS/WASL interacting protein family, member 1 |
| FDPSL2A | MGC44478 |
| GBP1 | guanylate binding protein 1, interferon-inducible |
| GJB6 | gap junction protein, beta 6, 30 kDa |
| EOMES | eomesodermin |
| NOG | noggin |
| FLJ14186 /// LOC441124 /// LOC729021 /// LOC729218 | uncharacterized LOC401149 /// uncharacterized LOC441124 /// uncharacterized LOC729021 /// uncharacterized LOC729218 |
| KRT80 | keratin 80 |
| NCKAP5L | NCK-associated protein 5-like |
| C16orf53 | chromosome 16 open reading frame 53 |
| DCAF17 | DDB1 and CUL4 associated factor 17 |
| IKZF2 | IKAROS family zinc finger 2 (Helios) |
| FILIP1 | filamin A interacting protein 1 |
| BICD1 | bicaudal D homolog 1 (*Drosophila*) |
| ZNF678 | zinc finger protein 678 |
| EPPK1 | epiplakin 1 |
| NKD2 | naked cuticle homolog 2 (*Drosophila*) |
| ULK4 | unc-51-like kinase 4 (*C. elegans*) |
| SLA2 | Src-like-adaptor 2 |
| ZNF880 | zinc finger protein 880 |
| ZNF274 | zinc finger protein 274 |
| COL3A1 | Collagen, type III, alpha 1 |
| TRMT13 | tRNA methyltransferase 13 homolog (*S. cerevisiae*) |
| RALGAPA2 | Ral GTPase activating protein, alpha subunit 2 (catalytic) |
| MEGF10 | multiple EGF-like-domains 10 |
| SP3 | Sp3 transcription factor |
| PROK2 | prokineticin 2 |
| LOXL1-AS1 | LOXL1 antisense RNA 1 (non-protein coding) |
| ANXA1 | Annexin Al |
| NTNG2 | netrin G2 |
| CCDC114 | coiled-coil domain containing 114 |
| KIAA1609 | KIAA1609 |
| RAB12 | RAB12, member RAS oncogene family |
| KCNK3 | potassium channel, subfamily K, member 3 |
| GNGT2 | guanine nucleotide binding protein (G protein), gamma transducing activity polypeptide 2 |
| GIMAP8 | GTPase, IMAP family member 8 |
| C14orf28 | chromosome 14 open reading frame 28 |
| LOC100507316 | uncharacterized LOC100507316 |
| LRPAP1 | low density lipoprotein receptor-related protein associated protein 1 |
| DLGAP1 | discs, large (*Drosophila*) homolog-associated protein 1 |
| GPAT2 | glycerol-3-phosphate acyltransferase 2, mitochondrial |
| MASP1 | mannan-binding lectin serine peptidase 1 (C4/C2 activating component of Ra-reactive factor) |
| LOC100422737 | uncharacterized LOC100422737 |
| MRTO4 | mRNA turnover 4 homolog (*S. cerevisiae*) |
| SCARA5 | scavenger receptor class A, member 5 (putative) |
| YPEL4 | yippee-like 4 (*Drosophila*) |
| CDK9 | cyclin-dependent kinase 9 |
| KIAA1609 | KIAA1609 |
| CAPSL | calcyphosine-like |
| VPS13B | vacuolar protein sorting 13 homolog B (yeast) |
| RDH5 | retinol dehydrogenase 5 (11-cis/9-cis) |
| FAM3C | family with sequence similarity 3, member C |
| PTPN5 | protein tyrosine phosphatase, non-receptor type 5 (striatum-enriched) |
| TMEM132B | transmembrane protein 132B |
| GPR110 | G protein-coupled receptor 110 |
| BCL2L10 | BCL2-like 10 (apoptosis facilitator) |
| ZNF667 | zinc finger protein 667 |
| GSG1L | GSG1-like |
| CCDC78 | coiled-coil domain containing 78 |
| LHFPL3 | lipoma HMGIC fusion partner-like 3 |
| HOXB-AS3 | HOXB cluster antisense RNA 3 (non-protein coding) |
| HGD | Homogentisate 1,2-dioxygenase |
| SLC6A13 | solute carrier family 6 (neurotransmitter transporter, GABA), member 13 |
| PRKRA | protein kinase, interferon-inducible double stranded RNA dependent activator |

TABLE 10-continued

Biomarkers for determining the severity of endometriosis in a biological sample comprising endometrial cells from mid-secretary phase (MSE).

| Gene Symbol | Gene Title |
| --- | --- |
| PCNP | PEST proteolytic signal containing nuclear protein |
| SOX5 | SRY (sex determining region Y)-box 5 |
| PLEKHA2 | pleckstrin homology domain containing, family A (phosphoinositide binding specific) member 2 |
| ARID1B | AT rich interactive domain 1B (SWI1-like) |
| HAP1 | huntingtin-associated protein 1 |
| TMEM136 | transmembrane protein 136 |
| C11orf80 | chromosome 11 open reading frame 80 |
| C1orf168 | chromosome 1 open reading frame 168 |
| MTHFD2L | methylenetetrahydrofolate dehydrogenase (NADP+ dependent) 2-like |
| LOC494150 | prohibitin pseudogene |
| AVPR1A | arginine vasopressin receptor 1A |
| NSUN7 | NOP2/Sun domain family, member 7 |
| DOCK8 | dedicator of cytokinesis 8 |
| MTHFR | methylenetetrahydrofolate reductase (NAD(P)H) |
| ZNF786 | zinc finger protein 786 |
| LOC100505912 | uncharacterized LOC100505912 |
| FBXL20 | F-box and leucine-rich repeat protein 20 |
| PLCXD3 | phosphatidylinositol-specific phospholipase C, X domain containing 3 |
| CEP152 | centrosomal protein 152 kDa |
| RBP1 | retinol binding protein 1, cellular |
| HOXA11-AS | HOXA11 antisense RNA (non-protein coding) |
| ACOXL | acyl-CoA oxidase-like |
| ZFYVE16 | zinc finger, FYVE domain containing 16 |
| HR | hairless homolog (mouse) |
| CCDC15 | coiled-coil domain containing 15 |
| NUPL1 | nucleoporin like 1 |
| SCNN1G | sodium channel, non-voltage-gated 1, gamma subunit |
| C6orf132 | chromosome 6 open reading frame 132 |
| CPM | carboxypeptidase M |
| NFKBID | nuclear factor of kappa light polypeptide gene enhancer in B-cells inhibitor, delta |
| XDH | xanthine dehydrogenase |
| ANKRD33 | ankyrin repeat domain 33 |
| C1QTNF6 | C1q and tumor necrosis factor related protein 6 |
| LOC100505648 | uncharacterized LOC100505648 |
| ZNF420 | zinc finger protein 420 |
| LOC642236 | FSHD region gene 1 pseudogene |
| MAP6D1 | MAP6 domain containing 1 |
| LOC100506303 /// LOC100653149 /// LOC400879 | uncharacterized LOC100506303 /// uncharacterized LOC100653149 /// uncharacterized LOC400879 |
| PIP5KL1 | phosphatidylinositol-4-phosphate 5-kinase-like 1 |
| DCAF8 | DDB1 and CUL4 associated factor 8 |
| CASZ1 | castor zinc finger 1 |
| KANSL1 | KAT8 regulatory NSL complex subunit 1 |
| WDR38 | WD repeat domain 38 |
| ZNF793 | zinc finger protein 793 |
| ZNF300P1 | zinc finger protein 300 pseudogene 1 |
| LOC100505679 | uncharacterized LOC100505679 |
| CYCS | cytochrome c, somatic |
| MTHFSD | methenyltetrahydrofolate synthetase domain containing |
| PHACTR2 | phosphatase and actin regulator 2 |
| SGPP2 | sphingosine-1-phosphate phosphatase 2 |
| CRP | C-reactive protein, pentraxin-related |
| AQP3 | aquaporin 3 Gill blood group) |
| EPOR | erythropoietin receptor |
| CELSR1 | cadherin, EGF LAG seven-pass G-type receptor 1 (flamingo homolog, *Drosophila*) |
| LZTS1 | leucine zipper, putative tumor suppressor 1 |
| RAB15 | RAB15, member RAS oncogene family |
| ZNF814 | zinc finger protein 814 |
| ZNF718 | Zinc finger protein 718 |
| DUSP5P | dual specificity phosphatase 5 pseudogene |
| MFSD2A | major facilitator superfamily domain containing 2A |
| HINT1 | histidine triad nucleotide binding protein 1 |
| VASH1 | Vasohibin 1 |
| LOC440993 | uncharacterized LOC440993 |
| SLC38A10 | solute carrier family 38, member 10 |
| RPS16P5 | ribosomal protein S16 pseudogene 5 |
| SNORD8 | small nucleolar RNA, C/D box 8 |
| DEFB124 | defensin, beta 124 |
| LOC100505812 | uncharacterized LOC100505812 |
| TRIM13 | tripartite motif containing 13 |

TABLE 10-continued

Biomarkers for determining the severity of endometriosis in a biological sample comprising endometrial cells from mid-secretary phase (MSE).

| Gene Symbol | Gene Title |
|---|---|
| GPBP1L1 | GC-rich promoter binding protein 1-like 1 |
| TECR | trans-2,3-enoyl-CoA reductase |
| MLX | MAX-like protein X |
| MPZL3 | myelin protein zero-like 3 |
| LSM4 | LSM4 homolog, U6 small nuclear RNA associated (S. cerevisiae) |
| PCBP2 | poly(rC) binding protein 2 |
| MYL6 | myosin, light chain 6, alkali, smooth muscle and non-muscle |
| NENF | Neudesin neurotrophic factor |
| SH3BP2 | SH3-domain binding protein 2 |
| LOC100653010 | uncharacterized LOC100653010 |
| ERV3-2 | endogenous retrovirus group 3, member 2 |
| PRO2852 | uncharacterized protein PRO2852 |
| LMCD1 | LIM and cysteine-rich domains 1 |
| NUDT4 | Nudix (nucleoside diphosphate linked moiety X)-type 4 motif |
| CRIM1 | Cysteine rich transmembrane BMP regulator 1 (chordin-like) |
| SRGAP2P1 | SLIT-ROBO Rho GTPase activating protein 2 pseudogene 1 |
| DCBLD2 | Discoidin, CUB and LCCL domain containing 2 |
| ORAI2 | ORAI calcium release-activated calcium modulator 2 |
| LOC100653336 /// PGM5-AS1 | rmcharacterized LOC100653336 /// PGM5 antisense RNA 1 (non-protein coding) |
| RAPH1 | Ras association (RalGDS/AF-6) and pleckstrin homology domains 1 |
| CDAN1 | Congenital dyserythropoietic anemia, type I |
| LOC100506941 | uncharacterized LOC100506941 |
| LOC100506165 | uncharacterized LOC100506165 |
| B2M | Beta-2-microglobulin |
| KRR1 | KRR1, small subunit (SSU) processome component, homolog (yeast) |
| BCAR1 | breast cancer anti-estrogen resistance 1 |
| EBF1 | Early B-cell factor 1 |
| UBE2I | ubiquitin-conjugating enzy me E2I |
| CDC14B | CDC14 cell division cycle 14 homolog B (S. cerevisiae) |
| SNORD3B-1 /// SNORD3B-2 /// SNORD3D | small nucleolar RNA, C/D box 3B-1 /// small nucleolar RNA, C/D box 3B-2 /// small nucleolar RNA, C/D box 3D |
| NSD1 | nuclear receptor binding SET domain protein 1 |
| DCAF7 | DDB1 and CUL4 associated factor 7 |
| SUZ12P | Suppressor of zeste 12 homolog pseudogene |
| IFNAR1 | Interferon (alpha, beta and omega) receptor 1 |
| NUP62 | Nucleoporin 62 kDa |
| LOC100134445 | uncharacterized LOC100134445 |
| WWC1 | WW and C2 domain containing 1 |
| IRS1 | insulin receptor substrate 1 |
| LOC100653149 | uncharacterized LOC100653149 |
| RNF144B | Ring finger protein 144B |
| DAPK1-IT1 | DAPK1 intronic transcript 1 (non-protein coding) |
| SLC2A8 | Solute carrier family 2 (facilitated glucose transporter), member 8 |
| LOC441179 | uncharacterized LOC441179 |
| ZFAND6 | Zinc finger, AN1-type domain 6 |
| LOC100507153 | uncharacterized LOC100507153 |
| PSMG4 | Proteasome (prosome, macropain) assembly chaperone 4 |
| NAMPT | Nicotinamide phosphoribosyltransferase |
| ZNF652 | Zinc finger protein 652 |
| RAB18 | RAB18, member RAS oncogene family |
| MUC20 | mucin 20, cell surface associated |

In some cases, detection of endometriosis is achieved by detecting differential expression of methylation biomarkers set forth in Table 11.

TABLE 11

Overview of methylation biomarkers for detecting endometriosis

| Gene Symbol | | | | |
|---|---|---|---|---|
| MGMT | SNRK | HOXA10 | PLA2G16 | DNAH2 |
| CDCA2 | CDCP1 | HOXA11 | RCOR2 | SMCR5 |
| DUSP22 | PTH1R | SCRN1 | FERMT3 | RAI1 |
| ID2 | UCN2 | SFRP4 | EHD1 | EPN2 |
| RBBP7 | COL7A1 | BLVRA | SIPA1 | ERAL1 |

TABLE 11-continued

Overview of methylation biomarkers for detecting endometriosis

Gene Symbol

| | | | | |
|---|---|---|---|---|
| TNFRSF1B | FHIT | CAMK2B | PACS1 | ATP6V0A1 |
| BMPR1B | ST3GAL6 | TNS3 | CD248 | PLCD3 |
| ZNF681 | C3orf52 | UPP1 | KDM2A | NME1 |
| IGSF21 | MIR567 | EGFR | TCIRG1 | NME2 |
| TP73 | HEG1 | CCL26 | ANO1 | TBX2 |
| ERβ | CHCHD6 | HBP1 | ARHGEF17 | CYB561 |
| PRβ | SEC61A1 | COG5 | AQP11 | DDX5 |
| SF-1 | GATA2 | ATP6V0A4 | PGR | FAM20A |
| HOXA10 | RYK | TMEM213 | MMP3 | ABCA9 |
| E-Cadherin | PPP2R3A | ZC3HAV1 | DDX10 | SLC16A5 |
| Aromatase | ZBTB38 | NOS3 | APOA1 | RHBDF2 |
| COX-2 | PLOD2 | ATG9B | ZBTB44 | SEPT9 |
| Syncytin-1 | LOC100287227 | SMARCD3 | WNT5B | TIMP2 |
| KIAA1751 | TIPARP | WDR86 | CACNA1C | TBC1D16 |
| PRKCZ | CLDN11 | PRKAG2 | VWF | SLC38A10 |
| CHD5 | PLD1 | KBTBD11 | SCNN1A | RALBP1 |
| CASZ1 | NLGN1 | GATA4 | CDKN1B | GATA6 |
| ALPL | PDE6B | LONRF1 | FAR2 | DOK6 |
| EPHB2 | SPON2 | DLC1 | PKP2 | MBP |
| NIPAL3 | LOC100130872 | SH2D4A | CNTN1 | ADAT3 |
| RBBP4 | FGFR3 | BMP1 | KRT7 | SCAMP4 |
| SYNC | BST1 | ZNF395 | HOXC9 | GNG7 |
| KIAA1522 | SEL1L3 | GSR | HOXC8 | LPHN1 |
| STK40 | RBM47 | GPR124 | HOXC4 | CD97 |
| RSPO1 | PRDM8 | RAB11FIP1 | HOXC5 | NOTCH3 |
| MGC12982 | ARHGAP24 | TACC1 | HOXC6 | MYO9B |
| FOXD2 | HERC6 | IDO1 | IRAK3 | BST2 |
| AK3L1 | DAPP1 | ASPH | TSPAN8 | PDE4C |
| SGIP1 | HADH | ASPH | SOCS2 | MAG |
| LRRC8C | LOC641518 | C8orf34 | ANO4 | PSG9 |
| ABCA4 | LEF1 | JPH1 | TXNRD1 | FOSB |
| KIAA1324 | PDE5A | MATN2 | TBX3 | MEIS3 |
| ATP1A1 | USP38 | ZFPM2 | P2RX7 | SIGLEC11 |
| CTSK | PDGFC | ANGPT1 | VPS37B | RPS9 |
| ARNT | STOX2 | KIAA0196 | FAM101A | LENG9 |
| SPRR2C | ENPP6 | NDRG1 | TMEM132B | CDC42EP5 |
| S100A4 | SORBS2 | NFIB | RIMBP2 | SIRPA |
| ADAM15 | LPCAT1 | SHB | WASF3 | SMOX |
| SYT11 | SEMA5A | TJP2 | NBEA | RRBP1 |
| NES | FAM105A | DAPK1 | MAB21L1 | KIF3B |
| ITLN1 | TTC33 | NR5A1 | MIR548F5 | CHD6 |
| TSTD1 | PPAP2A | COL5A1 | DCLK1 | TOMM34 |
| RGS5 | RNF138P1 | DNLZ | FAM124A | TFAP2C |
| FMO1 | RGNEF | CARD9 | ABCC4 | NPEPL1 |
| FAM20B | ENC1 | ITIH5 | COL4A1 | ZBTB46 |
| GLT25D2 | DMGDH | CUGBP2 | COL4A2 | PDE9A |
| IPO9 | BHMT2 | CUGBP2 | RASA3 | HIC2 |
| SOX13 | FEM1C | FAM107B | REC8 | RAC2 |
| NFASC | SNCAIP | ARHGAP12 | ADCY4 | |
| KLHDC8A | C5orf32 | ITGB1 | MAP4K5 | |
| SERTAD4 | C5orf62 | CCNY | FRMD6 | |
| C1orf133 | GPX3 | CXCL12 | NID2 | |
| HHAT | KCNIP1 | C10orf25 | NRXN3 | |
| LBR | DBN1 | ZNF22 | DIO2 | |
| CABC1 | GMDS | ARHGAP22 | PTPN21 | |
| NID1 | SERPINB6 | TMEM26 | MEG3 | |
| GPR137B | RIPK1 | JMJD1C | MEG3 | |
| COLEC11 | NEDD9 | LOC84989 | DIO3OS | |
| RNF144A | ATXN1 | REEP3 | WDR20 | |
| HPCAL1 | RBM24 | PLAU | MTMR15 | |
| KCNK3 | FLJ22536 | C10orf55 | MTMR10 | |
| BRE | RNF39 | C10orf11 | GATM | |
| BRE | DDR1 | ZMIZ1 | LOC145663 | |
| QPCT | C6orf47 | C10orf58 | SEMA6D | |
| CYP1B1 | ATF6B | PTEN | TNFAIP8L3 | |
| HNRPL | FKBPL | SLC16A12 | RAB8B | |
| EML4 | PRRT1 | MXI1 | IGDCC4 | |
| PLEKHH2 | NUDT3 | AFAP1L2 | ISLR | |
| LOC728819 | GLO1 | EMX2OS | STRA6 | |
| PRKCE | TRERF1 | EMX2 | CYP11A1 | |
| SOCS5 | MEA1 | CTBP2 | SEMA7A | |
| B3GNT2 | KLHDC3 | DOCK1 | RPP25 | |
| SERTAD2 | TRAM2 | FAM196A | MIR549 | |
| MEIS1 | ZNF451 | VENTX | KIAA1199 | |
| ARHGAP25 | PRDM1 | HCCA2 | MESDC1 | |
| CYP26B1 | FOXO3 | DUSP8 | ADAMTSL3 | |

TABLE 11-continued

Overview of methylation biomarkers for detecting endometriosis

| Gene Symbol | | | |
|---|---|---|---|
| CCT7 | SMPDL3A | KRTAP5-2 | AKAP13 |
| SEMA4F | TPD52L1 | KRTAP5-4 | RAB11FIP3 |
| LIMS1 | L3MBTL3 | LOC338651 | MSLN |
| ARHGEF4 | EPB41L2 | FAM99B | CLUAP1 |
| RND3 | TCF21 | CTSD | SNX29 |
| RBMS1 | HECA | MRPL23 | NDE1 |
| WIPF1 | LRP11 | MIR483 | EEF2K |
| HOXD10 | ESR1 | IGF2AS | XPO6 |
| GULP1 | ZDHHC14 | INS-IGF2 | ZNF423 |
| SDPR | DLL1 | IGF2; | ADCY7 |
| C2orf69 | PRKAR1B | ASCL2 | SALL1 |
| GPR1 | ADAP1 | CD81 | LPCAT2 |
| IRS1 | MAD1L1 | OSBPL5 | EXOC3L |
| HTR2B | C7orf27 | OR51E2 | ELMO3 |
| PSMD1 | TTYH3 | DCHS1 | CDH3 |
| EFHD1 | CARD11 | OLFML1 | CMIP |
| COL6A3 | FOXK1 | DENND5A | E2F4 |
| MLPH | DFNA5 | DKK3 | HSD17B2 |
| SNED1 | HOXA2 | TMEM216 | WFDC1 |
| CHL1 | HOXA3 | DKFZP434K028 | KIAA0513 |
| VGLL4 | HOXA5 | C11orf9 | ZFPM1 |
| FBLN2 | HOXA7 | EEF1G | NXN |
| TOP2B | HOXA9 | TUT1 | KIAA0664 |

In some cases, detection of endometriosis is achieved by detecting differential expression of long-noncoding RNAs such as biomarkers set forth in Table 12.

TABLE 12

Overview of non-noncoding RNA biomarkers for detecting endometriosis

| Gene Symbol | | | |
|---|---|---|---|
| AC068282.3 | BC025370 | RP11-77A13.1 | LOC728730 |
| XLOC_004134 | BX571672.1 | RP11-408H20.1 | RP11-557H15.3 |
| GBP1P1 | XLOC_004134 | CHRM3-AS2 | |
| RP11-369C8.1 | RP3-417L20.4 | AC007246.3 | |
| RP11-369C8.1 | RP11-403H13.1 | AC006159.3 | |
| AX746484 | RP11-679C8.2 | FTX | |

In some cases, detection of endometriosis is achieved by detecting differential expression of microRNAs such as biomarkers set forth in Table 13.

TABLE 13

Overview of microRNA biomarkers for detecting endometriosis

| miRNA | | |
|---|---|---|
| hsa-let-7a | hsa-mir-23a 0.26 0.16 | hsa-miR-29b |
| hsa-mir-199a-3p | hsa-miR-1 | hsa-miR-29c |
| hsa-mir-199b-3p | hsa-miR-100 | hsa-miR-30e-3p |
| hsa-let-7b | hsa-miR-101 | hsa-miR-30e-5p |
| hsa-mir-21 | hsa-miR-106a | hsa-miR-34a |
| hsa-let-7c | hsa-miR-106b | hsa-miR-365 |
| hsa-let-7g | hsa-miR-126 | hsa-miR-368 |
| hsa-mir-143 | hsa-miR-130a | hsa-miR-375 |
| hsa-mir-103 | hsa-miR-130b | hsa-miR-376a |
| hsa-mir-140-3p | hsa-miR-132 | hsa-miR-379 |
| hsa-mir-29a | hsa-miR-143 | hsa-miR-411 |
| hsa-mir-101 | hsa-miR-145 | hsa-miR-425-5p |
| hsa-let-7e | hsa-miR-148a | hsa-miR-486 |
| hsa-mir-320a | hsa-miR-150 | hsa-miR-493-5p |
| hsa-let-7i | hsa-miR-17-5p | hsa-miR-503 |
| hsa-mir-26a | hsa-miR-182 | hsa-miR-638 |
| hsa-mir-1 | hsa-miR-183 | hsa-miR-663 |
| hsa-mir-145 | hsa-miR-186 | hsa-miR-671 |
| hsa-let-7d | hsa-miR-196b | hsa-miR-768-3p |
| hsa-mir-424 | hsa-miR-199a | hsa-miR-768-5p |

TABLE 13-continued

Overview of microRNA biomarkers for detecting endometriosis

| miRNA | | |
|---|---|---|
| hsa-mir-451 | hsa-miR-200a | hsa-miR-93 |
| hsa-mir-107 | hsa-miR-200b | hsa-miR-99a |
| hsa-mir-191 | hsa-miR-200c | miR-34c-5p |
| hsa-mir-29c | hsa-miR-202 | miR-34b* |
| hsa-mir-25 | hsa-miR-20a | miR-34c-3p |
| hsa-mir-221 | hsa-miR-221 | miR-9 |
| hsa-mir-99a | hsa-miR-25 | miR-9* |
| hsa-mir-152 | hsa-miR-28 | miRPlus_42 780 |
| hsa-mir-23a | hsa-miR-299-5p | |

The systems, methods, devices and kits disclosed herein can provide for methods for detecting a presence or absence of endometrial cancer. Endometrial cancer, also termed uterine cancer, is the most frequent invasive tumors of the female genital tract and the fourth most common in women in western countries (Jamel et. al., Cancer statistics. 2008. CA Cancer J. Clin 58:71-96). Biomarkers and methods for the detection diagnosis, and prognosis of endometrial cancer are described in U.S. Patent Application Publication No. 20120122726, which is incorporated herein in its entirety. For example, biomarkers are differentially expressed in control samples as compared to samples from patients having endometrial cancer. The differential expression of these biomarkers can be used for detecting endometrial cancer in a biological sample collected using systems, methods, devices and kits described herein. In some cases, expression of a biomarker is used for detecting endometrial cancer. In some cases, expression of a set of biomarkers is used for detecting endometrial cancer using systems, methods, devices and kits described herein. The set of biomarkers can comprise nucleic acids encoding a gene set forth in Tables 2, 3, 4, 5, 6, 7, 8, 9 and/or 10. In some embodiments, the expression level of a set of biomarkers is determined. The set of biomarkers can comprise about 1 to 10,000, 1 to 1000, 1 to 100, 200 to 8000, 300 to 5000, 400 to 2000, 500 to 1000, 50 to 200, 20 to 100, 15 to 30, 10 to 20, 5 to 15, 1 to 10, 2 to 8, 3 to 7, 4 to 6, 5 to 7, 6 to 7, 7 to 9, or 2 to 12 genes. The set of biomarkers can comprise about 1, 2, 3, 4, 5, 6, 7, 8, 9, 10, 15, 20, 25, 30, 40, 50, 60, 70, 80, 90, 100, or more genes. The set of biomarkers can comprise at most about 1, 2, 3, 4, 5, 6, 7, 8, 9, 10, 15, 20, 25, 30, 40, 50, 60, 70, 80, 90, 100, 1000, or 10,000 genes. The expression level of the biomarker in the endometriosis sample can be increased or decreased when compared to the expression level of the biomarker in a sample that is not diagnosed with endometriosis. The expression level of the biomarker in the endometriosis sample can be increased or decreased by about 1-100%, 10-90%, 20-80%, 30-70%, 40-60%, 15-85%, 25-75%, 35-65%, or 45-55%. The expression level of the biomarker in the endometriosis sample can be increased or decreased by at least about 10%, 15%, 20%, 30% 40%, 50%, 60%, 70%, 80%, 90%, 95%, 99%, or 100%. The determination of the biomarker may comprise determining the nucleic acid sequence by using an Illumina sequencing platform or any sequencing techniques and platforms in the field. The biomarker may have a change of nucleic acid sequence in the endometriosis sample. The change of nucleic acid can be a mutation, e.g., point mutation or single nucleotide polymorphism, multiple nucleotide polymorphism, insertion (e.g., insertion of one or more nucleotides at a locus), multiple nucleotide change, deletion (e.g., deletion of one or more nucleotides at a locus), and inversion (e.g., reversal of a sequence of one or more nucleotides). In some embodiments, the biomarkers for use to detect endometrial cancer are set forth in Table 14.

system of the female genital tract is modulated correctly as it needs to tolerate the presence of sperm and fertilized oocytes without starting an immune reaction. Nevertheless, a strong immune system in the genital tract is very important to protect the interior organs and the fetus or embryo against the large pathogenic stress. This obligation of a dual immune system, one that tolerates and one that reacts efficiently, is a biological challenge. The lower female genital tract is covered by numerous commensal bacteria which form an important protective factor. The normal vaginal bacterial flora consists predominantly of *Lactobacillus* spp. including, *Lactobacillus jenensii*, *Lactobacillus crispatus*, *Lactobacillus iners*, *Lactobacillus rhamnosus*, and *Lactobacillus acidophilus*, and facultative anaerobic species such as *Gardnerella vaginalis*.

The lower genital tract forms an important entry gate for a wide variety of pathogens such as *Candida* spp., *Trichomonas vaginalis*, human immunodeficiency virus (HIV) and human papillomavirus (HPV). The upper female genital tract is believed to be sterile under normal circumstances. Pathogens such as *Neisseria gonorrhoeae* and *Chlamydia trachomatis* can occasionally ascend from the lower to the higher genital tract and can cause pathogenic conditions such as pelvic inflammatory disease (PID). The clinical impact of these infections may not be underestimated since they can lead to serious conditions such as preterm birth, increased susceptibility to sexually transmitted infections (STI), infertility and cancer. As such, early diagnosis is

TABLE 14

Overview of biomarkers for detecting endometrial cancer.

| Gene Symbol | Gene Title |
|---|---|
| ACAA1 | Acetyl-CoA Acyltransferase 1 |
| AP1M2 | Adaptor Related Protein Complex 1 Mu 2 Subunit |
| CGN | Cingulin |
| DDR1 | Discoidin Domain Receptor Tyrosine Kinase 1 |
| EPS8L2 | EPS8 Like 2 |
| FASTKD1 | FAST Kinase Domains 1 |
| GMIP | GEM Interacting Protein |
| IKBKE | Inhibitor Of Kappa Light Polypeptide Gene Enhancer In B-Cells, Kinase Epsilon |
| P2RX4 | Purinergic Receptor P2X 4 |
| P4HB | Prolyl 4-Hydroxylase Subunit Beta |
| PHKG2 | Phosphorylase Kinase Gamma Subunit 2 |
| PPFIBP2 | PPFIA Binding Protein 2 |
| PPP1R16A | Protein Phosphatase 1 Regulatory Subunit 16A |
| RASSF7 | Ras Association Domain Family Member 7 |
| RNF183 | Ring Finger Protein 183 |
| SIRT6 | Sirtuin 6 |
| TJP3 | Tight Junction Protein 3 |
| EFEMP2 | EGF Containing Fibulin-Like Extracellular Matrix Protein 2 |
| SOCS2 | Suppressor Of Cytokine Signaling 2 |
| DCN | Decorin |

The systems, methods, devices and kits disclosed herein can provide for methods for detecting a presence or absence of gynecological pathologies in a subject. Cervicovaginal fluid (CVF) has an important function in the homeostasis and immunity of the lower female genital tract. Analysis of the cervicovaginal fluid proteome may therefore yield important information about the pathogenesis of numerous gynecological pathologies. Additionally, cervicovaginal fluid has great potential as a source of biomarkers for these conditions. See Zegels et al., Use of cervicovaginal fluid for the identification of biomarkers for pathologies of the female genital tract. Proteome Science. 2010.8:63, which is incorporated herein in its entirety. The female genital tract is characterized by a unique immunologic micro-environment. It is essential for human reproduction that the immune essential for the successful treatment of the underlying pathology and prevention of irreversible complications. For this reason, there is a high demand for new diagnostic tools, such as biomarkers, which allow for better and earlier treatment of gynecological pathologies.

CVF is another vital element of the immune system of the female genital tract. CVF comprises (i) vulvar secretions from sebaceous, sweat, Bartholins and Skene glands, (ii) plasma transudate through the vaginal wall, (iii) exfoliated cells, (iv) bacterial products, (v) cervical mucus (vi) endometrial and oviductal fluids and (vii) secretions from vaginal immune cells. Cervical mucus, endometrial and oviductal fluids, and secretions from vaginal immune cells are influenced by sex steroid hormones e.g., during the menstrual cycle and pregnancy. CVF comprises water and contains many different factors such as cholesterol, lipids, mucin, carbohydrates, amino acids, proteins and inorganic ions. It covers the lower female genital tract and hydrates the mucosa, creating a physical barrier for microbial invasion. CVF may be used as samples for the analysis of proteins, thereby finding correlations between different expression profiles and specific pathologies.

CVF may be used for the identification of diagnostic or prognostic biomarkers. The low cost and ease of sample collection, circumvention of the risk associated with biopsies and the possibility of observing high numbers of patients using multiple samples are clear advantages of CVF over body fluid such as plasma, serum, cerebrospinal fluid, urine, saliva, bronchoalveolar lavage fluid, nipple aspirate fluid, tear fluid and amniotic fluid. Four different methods are frequently applied for the collection of CVF: cervicovaginal washings (e.g., the cervicovaginal is rinsed with washing buffer after which the fluid is collected), cervicovaginal swabs (e.g., swabs or brushes are applied to the mucosal wall and rotated to collect the CVF), cervicovaginal wicks (e.g., wicks such as tampons, strips or sponges are inserted in the female genital tract which absorb cervicovaginal secretions), and diaphragm-like devices (e.g., cups placed over the cervix which collect cervical fluid).

In addition, it can be expected that biomarkers found in CVF, being a "proximal" fluid, show more specificity and sensitivity for gynecopathological conditions as compared to circulating blood, plasma, or serum. Table 15 shows potential biomarkers that are infection-correlated. The biomarkers are discovered using human CVF samples.

TABLE 15

Overview of potential CVF protein/peptide biomarkers for different diseases, conditions or statuses of the female genital tract.

| Condition or patient status | Potential CVF protein/peptide biomarker |
|---|---|
| Human papillomavirus (HPV) infection and cervical cancer | Il-6<br>Il-8<br>IL-12p40n<br>IFN-γ<br>Il-10<br>TGF-β1<br>TNF-α<br>Il-1β<br>Il-5<br>Anti HPV IgG<br>Anti HPV IgA<br>antigalactosyl (α1→3) galactose antibodies |
| Human immunodeficiency virus (HIV) resistance | Anti-HIV IgA and IgG antibodies<br>RANTES |
| Bacterial Vaginosis | antimicrobial peptides (e.g., SLPI, defensins, lysozyme and lactoferrin)<br>IL-1β<br>IL-8<br>IL-10<br>IL-4 |
| Preterm Birth | fetal fibronectin<br>C-reactive protein<br>interleukin-6<br>interleukin-8<br>interleukin-1β<br>granulocytic elastase α1-antiprotease<br>prolactin<br>sialidase<br>monocyte chemotactic protein 1<br>insulin-like growth factor-binding protein-1<br>defensins<br>lactoferrin |

TABLE 15-continued

Overview of potential CVF protein/peptide biomarkers for different diseases, conditions or statuses of the female genital tract.

| Condition or patient status | Potential CVF protein/peptide biomarker |
|---|---|
| Preterm premature rupture of membranes (PPROM) | matrix metalloproteinases<br>β-human chorionic gonadotrophin<br>β-human chorionic gonadotropin<br>insulin-like growth factor binding protein-1<br>diamine oxidase<br>active ceruloplasmin<br>fetal fibronectin<br>C-reactive protein<br>α-fetoprotein<br>prolactin<br>placental α-microglobulin-1<br>interleukin-1 receptor antagonist |

Human papillomavirus (HPV) is one of the most common sexually transmitted infections. It is estimated that about 70%-80% of the sexually active female population may acquire HPV before the age of 50 and about 80% of the HPV-infected patients may spontaneously clear the virus within 2 years. HPV is associated with high morbidity and mortality worldwide, since it can cause precancerous lesions and cervical cancer. Worldwide, cervical cancer is both the fourth-most common cause of cancer and the fourth-most common cause of death from cancer in women (World Cancer Report 2014. World Health Organization. 2014, pp. Chapter 5.12. ISBN 9283204298, which is incorporated herein in its entirety). There are more than 150 HPV types and almost 40 of them infect the anogenital region. HPV can be divided in low and high risk HPV. The most common low-risk types are type 6 and 11. The most common high-risk types are 16, 18, 45, 31 and 33. Cervical cancer is mainly caused by an infection with a high risk type. Infection of squamous or glandular epithelial cells with HPV causes morphological alterations which lead to the formation of squamous or glandular intra-epithelial lesions. The severity of this precancerous condition depends on the extent, the site as well as on the depth of the infected epithelial layer.

Because of the high prevalence, the severe consequences and the lack of a good treatment of advanced cervical carcinoma, the emphasis of managing this condition may lie on prevention and diagnosis in a stadium as early as possible. The prophylactic HPV vaccination may prevent at least about 70%, 80%, 90%, 95%, or 98% of infections with HPV 16 and 18 but may also prevent HPV 31 (about 89%), HPV 33 (about 82%), HPV 45 (about 100%), and any high risk HPV type 16/18/31/33/35/39/45/51/52/56/58/59/66/68 (about 70%). As such, the HPV vaccination may prevent about 70%-80% of all cervical cancers. Therefore, women between the ages of 25 and 65 may need to be screened on a frequent basis using, for example, a Pap test (liquid based cytology) for general testing or for a type specific HPV testing. Screening using the classical Pap test has led to a considerable reduction of the mortality, yet there are still some notable shortcomings. The current screening is (1) labor intensive, (2) difficult to automatize, (3) vulnerable to inter- and intra-observer variability, and (4) is not very sensitive. Testing for the presence of nucleic acids by, e.g., sequencing, may increase the sensitivity. HPV DNA or RNA can be isolated and purified from a biological sample obtained from the cervicovaginal canal of a subject, and tested for the presence of HPV DNA or RNA. The biological sample can be from a Pap test. The biological sample can be from a cotton swab. The biological sample can be from a biopsy. One disadvantage of nucleic acids sequencing is that it cannot predict progression to intra-epithelial lesions and eventually cervical cancer as it involves collection of a biological sample from the subject by a trained profession and a visit to a clinic. The systems, methods, and devices described herein provide for tools for self-collection of a biological sample from the cervicovaginal canal of a female subject in her privacy, without the involvement of a trained professional. The biological sample can be collected regularly by the female subject and sent to a laboratory for analysis including, but not limited to, testing for chemistry, testing for hematology, testing for microbiology, and testing for CVF biomarkers. Potential CVF biomarkers associated with diseases, conditions or statuses of the female genital tract are listed in Table 12.

Screening for CVF biomarkers may provide for HIV resistance. Exemplary CVF biomarkers for HIV resistance screening are listed in Table 12. In addition, nucleic acids isolated from CVF may be used for detecting nucleic acid changes in genes that are associated with HIV resistance, or for detecting the absence or presence of a gene or protein. For example, mutation of C—C chemokine receptor type 5 (CCR5 or CD195) induces upregulation of RANTES, MIP-1α and MIP-1β in exposed seronegative individuals (ESNs). ESNs are individuals (<5% of the population) from high-risk cohorts that remain IgG-seronegative despite frequent HIV-exposure and therefor show a certain degree of in vitro HIV resistance. As another example, the presence of nucleic acids encoding for a protein, antigen, or antibody, in ESNs suggests that the presence or upregulation of these nucleic acids may be associated with HIV resistance. Exemplary protein, antigen, or antibody are gp41, p24, anti-HIV IgA, anti-HIV IgG, or elafin/trappin-2. Therefore, detecting mutations in a gene associated with ESN may provide insight for developing microbicides, e.g., chemical entities that can prevent or reduce transmission infections, which can be applied locally as a potential approach in HIV prevention.

Bacterial vaginosis (BV) is a frequently observed condition by which the normal vaginal flora is disrupted. The imbalance of vaginal flora may be revealed by screening CVF biomarkers (see Table 12) in a biological sample obtained from the cervicovaginal canal of a subject. BV is a non-inflammatory condition characterized by the loss of hydrogen peroxide forming *Lactobacillus* spp. (e.g., *L. crispatus, L. acidophilus, L. rhamnosus*) and by an increased growth of anaerobic species (e.g., *Atopobium vaginae, Mobiluncus* spp., *Prevotella* spp.). Population change of commensal bacteria or presence of nonresident bacteria may be used to assess the balance of vaginal flora. The presence of absence of *Lactobacillus* spp., *Atopobium vaginae, Mobiluncus* spp., and *Prevotella* spp. can be detected by, e.g., nucleic acid sequencing, Western blot.

CVF also comprises biomarkers for assessing the risk of the occurrence of preterm birth and preterm premature rupture of membranes (Table 12). Preterm birth is defined as occurring before 37 complete weeks of gestation by the World Health Organization (WHO). Preterm birth is a major cause of neonatal morbidity and mortality. Preterm birth is difficult to treat and therapy is often inefficient because the underlying cause is seldom determined and the diagnosis is frequently made too late. As such, treatment for preterm birth relies on preventive strategies. Quantifying CV fetal fibronectin (FFN) concentration in combination with cervical ultrasound measurements may reveal correlations of risk for preterm labor/birth. For example, CVF can be collected from a female subject using the systems, methods, devices, and kits disclosed herein. The female subject may perform analysis on the CVF using the systems, methods, devices and kits described herein. The CVF can be shipped to a laboratory for analysis.

Sequencing

Detecting the presence or absence, or expression level of a biomarker associated with a disease or pathology can involve identifying a nucleic acid or polynucleotide sequence of the biomarker. The biomarker can be a gene or a part of a gene that encodes a functional protein. The identity of a biomarker (e.g., a gene or a partial of a gene) can involve sequencing, de novo sequencing, massive parallel sequencing, RNA sequencing, DNA sequencing, deep sequencing, methylation sequencing, bisulfite sequencing, or next-generation sequencing. For example, a biomarker (e.g., a gene or a partial of a gene) can be verified by sequencing of nucleic acids from a biological sample collected from a subject's cervicovaginal canal.

The next-generation sequencing platform can be a commercially available platform. Commercially available platforms include, e.g., platforms for sequencing-by synthesis, ion semiconductor sequencing, pyrosequencing, reversible dye terminator sequencing, sequencing by ligation, single-molecule sequencing, sequencing by hybridization, and nanopore sequencing. Platforms for sequencing by synthesis are available from, e.g., Illumina, Methylation Sequencing, 454 Life Sciences, Helicos Biosciences, and Qiagen. Illumina platforms can include, e.g., Illumina's Solexa platform, Illumina's Genome analyzer, which are described in Gudmundsson et al., Genome-wide association and replication studies identity four variants associated with prostate cancer susceptibility. Nat. Genet. 2009 41:1122-1126, Out et al. Deep sequencing to reveal new variants in pooled DNA samples. Hum. Mutat. 2009 30:1703-12, Turner, Massively parallel exon capture and library-free resequencing across 16 genomes. Nat. Methods 2009 6:315-6, U.S. Patent Application Publication nos. 20080160580 and 20080286795, and U.S. Pat. Nos. 6,306,597, 7,115,400, and 7,232,656, which are hereby incorporated in their entireties. 454 Life Science platforms include, e.g., the GS Flex and GS Junior, and are described in U.S. Pat. No. 7,323,305, which patent is hereby incorporated in its entirety. Platforms from Helicos Biosciences include the True Single Molecule Sequencing platform. Platforms for ion semiconductor sequencing include, e.g., the Ion Torrent Personal Genome Machine (PGM) and are described in U.S. Pat. No. 7,948,015, which patent is hereby incorporated in its entirety. Platforms for pyrosequencing include the GS Flex 454 system and are described in U.S. Pat. Nos. 7,211,390; 7,244,559; 7,264,929, which patents are hereby incorporated in their entireties. Platforms and methods for sequencing by ligation include, e.g., the SOLiD sequencing platform and are described in U.S. Pat. No. 5,750,341. Platforms for single-molecule sequencing include the SMRT system from Pacific Bioscience and the Helicos True Single Molecule Sequencing platform. Other platforms for sequencing can include, but are not limited to, Large Whole-Genome Sequencing, Small Whole-Genome Sequencing, Exome Sequencing, Targeted Gene Sequencing, Whole-Transcriptome Sequencing, Gene Expression Profiling with mRNA-Seq, Targeted Gene Expression Profiling, miRNA & Small RNA Analysis, and 16S Metagenomic Sequencing.

Computer Control Systems

Figure 17:
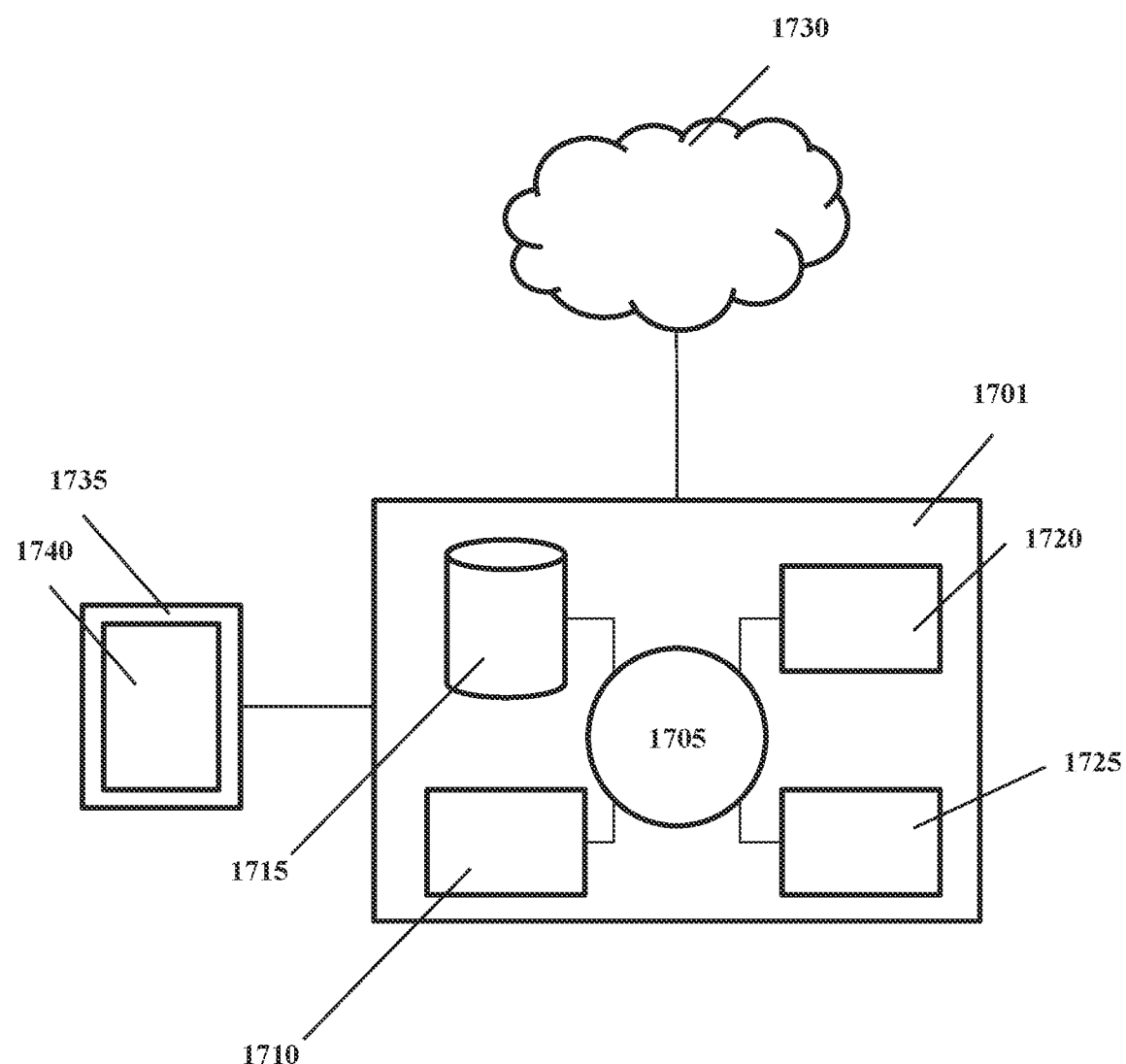
FIG. 17 illustrates various components of an exemplary computer system according to various embodiments of the present disclosure.

The present disclosure provides computer systems that are programmed to implement methods of the disclosure. Such computer systems may perform data analysis or presentation of the biological sample test results. FIG. 17 shows a computer system 1701 that is programmed or otherwise configured to perform methods of the present disclosure, including data analysis. The computer system 1701 can be an electronic device of a user or a computer system (e.g., computer server) that is remotely located with respect to the electronic device. The electronic device can be a mobile electronic device.

The computer system 1701 includes a central processing unit (CPU, also "processor" and "computer processor" herein) 1705, which can be a single core or multi core processor, or a plurality of processors for parallel processing. The computer system 1701 also includes memory or memory location 1710 (e.g., random-access memory, read-only memory, flash memory), electronic storage unit 1715 (e.g., hard disk), communication interface 1720 (e.g., network adapter) for communicating with one or more other systems, and peripheral devices 1725, such as cache, other memory, data storage and/or electronic display adapters. The memory 1710, storage unit 1715, interface 1720 and peripheral devices 1725 are in communication with the CPU 1705 through a communication bus (solid lines), such as a motherboard. The storage unit 1715 can be a data storage unit (or data repository) for storing data. The computer system 1701 can be operatively coupled to a computer network ("network") 1730 with the aid of the communication interface 1720. The network 1730 can be the Internet, an internet and/or extranet, or an intranet and/or extranet that is in communication with the Internet. The network 1730 in some cases is a telecommunication and/or data network. The network 1730 can include one or more computer servers, which can enable distributed computing, such as cloud computing. The network 1730, in some cases with the aid of the computer system 1701, can implement a peer-to-peer network, which may enable devices coupled to the computer system 1701 to behave as a client or a server.

The CPU 1705 can execute a sequence of machine-readable instructions, which can be embodied in a program or software. The instructions may be stored in a memory location, such as the memory 1710. The instructions can be directed to the CPU 1705, which can subsequently program or otherwise configure the CPU 1705 to implement methods of the present disclosure. Examples of operations performed by the CPU 1705 can include fetch, decode, execute, and write back.

The CPU 1705 can be part of a circuit, such as an integrated circuit. One or more other components of the system 1701 can be included in the circuit. In some cases, the circuit is an application specific integrated circuit (ASIC).

The storage unit 1715 can store files, such as drivers, libraries and saved programs. The storage unit 1715 can store user data, e.g., user preferences and user programs. The computer system 1701 in some cases can include one or more additional data storage units that are external to the computer system 1701, such as located on a remote server that is in communication with the computer system 1701 through an intranet or the Internet.

The computer system 1701 can communicate with one or more remote computer systems through the network 1730. For instance, the computer system 1701 can communicate with a remote computer system of a user (e.g., patient or healthcare provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1701 via the network 1730.

Methods as described herein can be implemented by way of machine (e.g., computer processor) executable code stored on an electronic storage location of the computer system 1701, such as, for example, on the memory 1710 or electronic storage unit 1715. The machine executable or machine readable code can be provided in the form of software. During use, the code can be executed by the processor 1705. In some cases, the code can be retrieved from the storage unit 1715 and stored on the memory 1710 for ready access by the processor 1705. In some situations, the electronic storage unit 1715 can be precluded, and machine-executable instructions are stored on memory 1710.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but are not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1701 can include or be in communication with an electronic display 1735 that comprises a user interface (UI) 1740. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1705.

The disclosure is further illustrated by the following examples which should not be construed as limiting. The examples are illustrative only, and are not intended to limit, in any manner, any of the aspects described herein.

EXAMPLES

The following examples illustrate some embodiments and aspects of the disclosure. It will be apparent to those skilled in the relevant art that various modifications, additions, substitutions, and the like can be performed without altering the spirit or scope of the disclosure, and such modifications and variations are encompassed within the scope of the disclosure as defined in the claims which follow. The following examples do not in any way limit the disclosure.

The device as disclosed herein can be applied to the detection of a wide variety of infections, as it allows for detection of antigen or antibody analytes associated with any disease or disorder for which an antibody or antigen analyte is known, such as for a variety of STIs and cancers. The device can also be used to detect the presence of semen, identify genetic signatures and genomic material, as well as detect small molecules like environmental toxins such as BPA. In some embodiments, the device is used to assay for one of the following conditions listed as examples below. In some embodiments, the device is used to simultaneously assay for more than one of the following conditions using a single sample of cervicovaginal fluid. In some embodiments, the device is used to assay for more than one of the following conditions at different times using a single sample of cervicovaginal fluid. In some embodiments, the device is used to assay for more than one of the following conditions at different times using different samples of cervicovaginal fluid.

Example 1: Gonorrhea

Gonorrhea is an infection caused by the bacterium *Neisseria gonorrhoeae*. Transmission of this pathogen occurs during vaginal, oral, or anal sex (Moran, Clin. Evid. 200: 1604; 2007). While men often experience painful urination upon infection, women are mostly asymptomatic. If left untreated, gonorrhea can cause local disease such as pelvic inflammatory disease (PID), or can also affect other parts of the body, such as the joints and heart valves.

Traditionally, gonorrhea was diagnosed with gram stain and culture; however, newer PCR-based testing methods are becoming more common. The USPTF recommends screening for gonorrhea in women at increased risk of infection, which includes all sexually active women younger than 25 years (Meyers et al., Am. Fam. Physician 77:819-824; 2008). Screening for gonorrhea in women who are or intend to become pregnant, and who are found to be at high risk for sexually transmitted diseases, is recommended as part of prenatal care in the United States.

Past treatments for gonorrhea included a range of antibiotics. However, as of 2010, injectable ceftriaxone appears to be one of the few effective antibiotics, due to increasing rates of antibiotic resistance (Deguchi et al., J. Urol., 184:851-858; 2010).

In some embodiments, the disclosed device can be used to detect gonorrheal infections from menstrual blood or cervicovaginal fluids.

Example 2: Chlamydia

Chlamydia is a common STI that is caused by the bacterium *Chlamydia trachomatis*. Transmission occurs during vaginal, anal, or oral sex, but the bacterium can also be passed from an infected mother to her baby during vaginal childbirth. It is estimated that about 1 million individuals in the United States are infected with this bacterium, making chlamydia one of the most common STIs worldwide. Like gonorrhea, chlamydial infection is asymptomatic for a majority of women. If symptoms are present, they include unusual vaginal bleeding or discharge, pain in the abdomen, painful sexual intercourse, fever, painful urination or the urge to urinate more frequently than usual. Of those who develop asymptomatic infection, approximately half may develop PID. Infants born to mothers with chlamydia may suffer from pneumonia and conjunctivitis, which may lead to blindness. They may also be subject to spontaneous abortion or premature birth.

Diagnosis of chlamydial infection is usually done by nucleic acid amplification techniques, such as PCR, using samples collected from cervical swabs or urine specimens (Gaydos et al., J. Clin. Microbio., 42:3041-3045; 2004). Treatment involves various antibiotic regimens.

In some embodiments, the disclosed device can be used to detect chlamydial infections from menstrual blood or cervicovaginal fluids.

Example 3: Trichomoniasis

Trichomoniasis is considered the most common curable sexually transmitted disease. In the United States, an estimated 3.7 million people have the infection, but only about 30% develop any symptoms of the disease (Center for Disease Control fact sheet, 2015). In women, the most commonly infected part of the body is the lower genital tract. Nearly 70% of infections are asymptomatic. Not only can infection with *Trichomonas* increase one's risk of contracting and spreading other STIs, and pregnant women with trichomoniasis are more likely to go into preterm labor, but also, babies born to infected mothers are more likely to have officially low birth weight—less than 5.5 pounds (CDC fact sheet, 2015). Trichomoniasis can also lead to pelvic inflammatory disease, which may lead to infertility if untreated.

Diagnosis of Trichomoniasis includes a visit to the doctor's office, a physical exam, and sampling of vaginal secretions by a wet preparation test to visualize bacterial flagella present on the *trichomonas* bacteria (L. Campbell et al, Journal of Clinical Microbio, 2008). More recent technologies for diagnosis include rapid dipstick immunoassay and antigen tests directed at flagellar proteins of the bacteria. Treatment for Trichomoniasis is a one dose administration of an antibiotic, either metronidazole or tinidazole (CDC fact sheet, 2015).

In some embodiments, the disclosed device can be used to detect trichomoniasis infections from menstrual blood or cervicovaginal fluids.

Example 4: Syphilis

Syphilis is an STI that can cause long-term complications if not treated correctly. Symptoms in adults are divided into stages. These stages are primary, secondary, latent, and late syphilis. In pregnant women, having syphilis can lead to giving birth to a low birth weight baby. It can also lead to delivering the baby too early or stillborn (CDC fact sheet, 2015).

Although *T. pallidum* cannot be grown in culture, there are many tests for the direct and indirect diagnosis of syphilis. Still, there is no single optimal test. Direct diagnostic methods include the detection of *T. pallidum* by microscopic examination of fluid or smears from lesions, histological examination of tissues or nucleic acid amplification methods such as polymerase chain reaction (PCR). Indirect diagnosis is based on serological tests for the detection of antibodies (Ratnam S, Can J Infect Dis Med Microbiol 2005). Treatment includes a single dose of intramuscular administration of penicillin (2.4 Million units).

In some embodiments, the disclosed device can be used to detect syphilis infections from menstrual blood or cervicovaginal fluids.

Example 5: Bacterial Vaginosis

Bacterial Vaginosis (BV) is an infection caused when too much of certain bacteria change the normal balance of bacteria in the vagina. Bacterial vaginosis (BV) is one of the most common lower genital tract conditions, occurring in 35% of women attending sexually transmitted infection (STI) clinics, 15% to 20% of pregnant women, and 5% to 15% of women attending gynecology clinics (Eschenbach D A, Am J Obstet Gynecol 1993). Pregnant women with BV are more likely to have babies who are born premature (early) or with low birth weight than women who do not have BV while pregnant. Low birth weight means having a baby that weighs less than 5.5 pounds at birth (CDC fact sheet, 2015).

Diagnosis of BV is typically done through a vaginal swab to assess the presence and balance of certain bacteria within the vaginal flora through PCR. A wet mount, whiff test, or pH test can also be performed in order to diagnose a possible bacterial infection.

In some embodiments, the disclosed device can be used to detect bacterial vaginosis from menstrual blood or cervicovaginal fluids.

Example 6: Pelvic Inflammatory Disease (PID)

Chronic and untreated infection with gonorrhea and chlamydia commonly leads to PID, a generic term for infection of the uterus, fallopian tubes, and/or ovaries. As the immune system tries to fight off the invading pathogens, it causes local inflammation and scarring. There are no tests for PID. A diagnosis is usually based on a combination of a patient's medical history, physical exam, and other test results. Since the most common causes of PID are gonorrhea and chlamydia, prevention of PID usually involves prompt diagnosis and treatment of these infections. However, since treatment of PID may not undo any damage that has already happened to one's reproductive system, successful treatment is heavily dependent on early diagnosis. Some patients may not realize they have PID because symptoms may be mild or nonexistent. However, if symptoms do exist, they include pain in the lower abdomen, fever, unusual discharge associated with odor, painful intercourse associated with bleeding, burning sensation during urination, or bleeding between periods. Women who have had a history of PID are more likely to have a diagnosis of endometriosis. Consequently, they are also more likely to be in need of a hysterectomy, have an ectopic pregnancy, or suffer from infertility.

In some embodiments, the disclosed device focuses on detecting gonorrheal and chlamydial infections from menstrual blood or cervicovaginal fluids, and includes the ability to send results to a physician, and educate on safe sex practice and available interventions/therapeutics. It also includes the ability to track monthly results and options for coping and dealing with STIs.

Example 7: Endometriosis

Endometriosis is a gynecological condition in which cells from the lining of the uterus (endometrium) appear and flourish outside the uterine cavity, most commonly on the membrane which lines the abdominal cavity, the peritoneum. Although the exact cause of endometriosis is not certain, there are several possible explanations, such as retrograde menstruation, surgical scar implantation, immune disorders, as well as heredity. Significantly, there is an established association between endometriosis and infertility (Buletti et al., J. Assist Reprod. Genet. 27:441-447; 2010). Current diagnostic methods for endometriosis involve a laparoscopy, an invasive surgical procedure. There is no cure for endometriosis, but it can be treated in a variety of ways, including with pain medication, hormonal drugs, and surgery.

In some embodiments the disclosed device focuses on detecting markers associated with endometriosis from menstrual blood or cervicovaginal fluids. This embodiment allows women to identify and track staging of the disease and helps them navigate therapeutic options such as hormonal therapy, nonsteroidal anti-inflammatory drugs ("NSAIDs") and surgery.

In some embodiments the disclosed device focuses on detecting markers associated with endometriosis from menstrual blood or cervicovaginal fluids. The markers, e.g., biomarkers disclosed herein or conventionally used for detecting the presence of endometriosis, can be detected through sequencing a biological sample collected from a female subject's vaginal canal. For example, the collected biological sample is subject to 16S rRNA sequencing, methylation sequencing, long-noncoding RNA sequencing, microRNA sequencing, RNA deep sequencing, genomic DNA sequencing, and/or cDNA sequencing.

Example 8: Polycystic Ovarian Syndrome and Ovarian Reserve

Antimüllerian hormone (AMH) is produced in the adult female exclusively by granulosa cells, declines with age, and is widely considered a highly sensitive marker of ovarian reserve. Serum AMH level is increased significantly more in women with polycystic ovary syndrome (PCOS).

Serum AMH level seems to be related to the severity of PCOS and correlates with its clinical diagnostic hallmarks, including hyperandrogenism, oligo/anovulation and polycystic ovarian morphology. AMH level may also be associated with qualitative assisted reproductive technology outcomes such as pregnancy and live birth rates independent of age (Tal R, et al, Amer J of OB & GYN, 2014).

The current method of evaluating a women's AMH level is through Enzyme Linked Immuno-Sorbedent Assay (ELISA), and is performed on blood serum. This test provides an absolute quantification of the amount of AMH circulating in the blood.

In some embodiments the disclosed device focuses on diagnosing or assessing risk of PCOS and ovarian reserve from menstrual blood or cervicovaginal fluids. In some embodiments the disclosed device focuses on detecting markers associated with polycystic ovarian syndrome and ovarian reserve from menstrual blood or cervicovaginal fluids. The markers, e.g., biomarkers disclosed herein or conventionally used for detecting the presence of polycystic ovarian syndrome and ovarian reserve, can be detected through sequencing a biological sample collected from a female subject's vaginal canal. For example, the collected biological sample is subject to 16S rRNA sequencing, methylation sequencing, long-noncoding RNA sequencing, microRNA sequencing, RNA deep sequencing, genomic DNA sequencing, and/or cDNA sequencing.

Example 9: Human Papillomavirus (HPV) Infection

Human genital papillomaviruses are amongst the most prevalent sexually transmitted human pathogens. Most genital HPV infections in women produce transient squamous cell abnormalities of the cervix that resolve completely, and so the probability of any one HPV infection progressing to cervical cancer is quite small. Nevertheless, HPV infection is a cause of nearly all cases of cervical cancer (Lynge et al., APMIS 122:667-673; 2014). Persistent infections increase the risk of precancerous lesions, which can progress to invasive cancer. Progression to invasive cancer can be prevented when subclinical HPV infection is detected early and regular examinations are performed.

The Pap smear is the current gold standard for the detection of HPV infection. Pap smears have reduced the incidence and fatalities of cervical cancer in the developed world; however, the USPTF now recommends Pap smears only every three years. Recently developed HPV vaccines (Cervarix and Gardasil), which prevent infection with HPV types 6, 11, 16, and 18, may lead to further decreases. However, these vaccines are currently only recommended for women of age 25 or younger.

In some embodiments, the disclosed device can be used to detect HPV infections from menstrual blood or cervicovaginal fluids. In some embodiments the disclosed device focuses on detecting markers associated with HPV infections from menstrual blood or cervicovaginal fluids. The markers, e.g., biomarkers disclosed herein or conventionally used for detecting the presence of HPV, can be detected through sequencing a biological sample collected from a female subject's vaginal canal. For example, the collected biological sample is subject to 16S rRNA sequencing, methylation sequencing, long-noncoding RNA sequencing, microRNA sequencing, RNA deep sequencing, genomic DNA sequencing, and/or cDNA sequencing.

Example 10: Yeast Infection

Vaginitis is one of the most common complaints for physician visits in the United States (Paavon J, et al, Infec Dis Clin North Am 1987) that results in 10 million office visits per year (Sparsk J M, J Reprod Med, 1991). 30% of all vaginitis cases are caused by infection with the *Candida* species, commonly referred to as yeast infections. Untreated vaginal candidiasis in pregnant women can result in passing the infection to the baby during delivery and the development of oral thrush in the newborn.

Current recommended guidelines regarding screening for *Candida*, as published by the Centers for Disease Control and Prevention (CDC) in 2004, consist of microscopy, saline wet mount, whiff test, pH determination, or gram stain. More current diagnostic tools include a rapid dipstick antigen test. Treatment for yeast infections is now available over the counter and includes oral administration as well as topical lotions. Probiotic treatment has also been shown to be effective in reestablishing vaginal flora to help treat and prevent yeast infections.

Although candidiasis can occur without any identifiable precipitating factor, certain conditions that disrupt the balance of normal vaginal flora can predispose women to the development of symptomatic infection. The use of antibiotics, oral contraceptive pills, contraceptive devices, high estrogen levels (as during pregnancy and hormone replacement therapy), or certain medical conditions such as uncontrolled diabetes mellitus and HIV can increase an individual's risk of the development of candidiasis (Sparsk J M, J Reprod Med, 1991).

In some embodiments, the disclosed device can be used to detect candidiasis based yeast infections from menstrual blood or cervicovaginal fluids.

Example 11: Fetal Trophoblasts

Trophoblast cells have been picked up in transcervical retrieval methods such as cervical lavage and brushing. These cells have a wealth of information that can be interrogated for data on the health of the fetus.

It is believed that small areas of erosions allow trophoblast cells to cross the decidua capillaries and reach the uterine cavity (Imudia, 2010).

Using a Y chromosome antibody, fetal trophoblast cells can be assayed for the presence or absence of Y chromosome DNA to uncover, at very early stages, the sex of the fetus.

Imudia et al. states that changes in the amount of fetal trophoblasts cells can be indicative of abnormal pregnancy. For example, a dramatic reduction of trophoblasts in cervical secretions is indicative of an ectopic pregnancy, as the fetal trophoblast does not enter into the uterine cavity (Imudia, 2010).

HLA-G is a fetal specific protein associated with fetal trophoblast and can be used to quantify the amount or relative number of trophoblasts present in a sample. Quantification of HLA-G as a proxy for trophoblast quantity can allow for the detection of abnormal pregnancies such as ectopic and molar pregnancies.

In some embodiments, the disclosed device can be used to detect the health of a fetus and pregnancy through monitoring trophoblasts, assess trophoblasts for development abnormalities and sex determination, and quantify number of trophoblasts from cervicovaginal fluids.

Example 12: HIV and CD4 Monitoring

According to the CDC, at the end of 2011, 23% of all people living with HIV in the United States were women. Not all US women who are living with HIV are getting the care they need. Of all women living with HIV in 2011, only 45% were engaged in care, and only 32% had achieved viral suppression (CDC Fact Sheet, 2015).

The risk of getting HIV during vaginal sex without a condom is much higher for women than it is for men. Women who have been sexually abused may be more likely than women with no abuse history to engage in sexual behaviors like exchanging sex for drugs, having multiple partners, or having sex with a partner who is physically abusive when asked to use a condom.

Diagnosis of the disease can occur at a doctor's office either through a blood test for either the virus or antibodies for the virus (either polymerase chain reaction or immunoassay). A rapid test is also available, both point-of-care and over-the-counter. Treatment can include a lifelong regiment of antiretroviral drugs. If HIV infection is suspected, a course of antiretroviral drugs can be given up to 72 hours after the potential exposure and greatly reduces one's risk of contracting the disease. This therapy is known as Post Exposure Prophylaxis (PEP).

Once an individual tests positive, regular doctor's visits are needed to test for the total number of T4 immune cells that are found in the blood. This particular cell type is the target for HIV infection and a low level of T4 cells is indicative of advanced disease. Therefore, constant monitoring is needed to assess therapeutic effectiveness and progression of the disease. Currently this is done in the laboratory through a process called flow cytometry. However more rapid tests are currently being developed, including the potential for a later flow, semi-quantitative dipstick test that may test for CD4 cells.

In some embodiments, the disclosed device can be used to detect HIV infection and monitor CD4 cell counts in menstrual blood or cervicovaginal fluids.

Example 13: Preterm Birth and Recurrent Pregnancy Loss

Preterm delivery and recurrent pregnancy loss are some of the most challenging problems in obstetrics to date, and the diagnosis of preterm labor is often inaccurate (Leitich, 1999). Normal and preterm birth is initiated through a cascade of physical and enzymatic changes that prepare the reproductive system to begin the birthing process (Quinzio, 2007). A key marker that can be used to determine a women's risk of preterm labor is the presence of fetal fibronectin (fFN) between 24-34 weeks in vaginal secretion. fFN plays an important role in securing the fetal sac to the uterine lining.

During early pregnancy, fFN is shed into the cervical matrix at high amounts as the fetus implants and secures into the uterine wall. In normal pregnancy, the levels of fFN dramatically drop until late in pregnancy as the fetus prepares for the birthing process and the adhesion of the fetal sac to the uterine wall begins to degrade. However, in preterm labor, fFN can be detected in weeks 24-34 as the adhesion between the fetal sac and uterine wall begin to prematurely degrade.

fFN is therefore used, and is available as a rapid lateral flow assay, to determine a women's risk of preterm labor. If caught early, administration of progesterone can help to prevent further degradation of the adhesion interface of the fetal sac and uterine wall, thus improving a women's chance of carrying the fetus to term (da Fonseca, 2003). Currently this test is performed in the clinic, where a cervical sponge is inserted into the vaginal canal, and placed against the uterine cervix to collect cervical fluid. This cervical fluid is then assayed for the presence of fFN. Other tests such as IL-6, PAMG-1, and IGFB are other similar immunotests that are utilized in some clinics to assess a women's imminent risk of preterm delivery.

Another marker that is used to determine the onset of the birthing process and risk of preterm labor is a change in pH of vaginal secretions due to the introduction of amniotic fluid as it begins to leak from the fetal sac before rupture. This pH change can increase the overall pH of the vagina from a normal range for 4.5-6 to a pH reading over 7. Currently a rapid pH test, known as a nitrazine stick, can be used to assess the pH of the vaginal canal to determine if amniotic leakage has occurred and can be used as a proxy for impending labor.

Both fFN and Nitrazine can be leveraged to assess a women's risk of preterm labor and provide actionable steps with a physician to treat the condition and improve preterm labor outcomes.

In some embodiments, the disclosed device can be used to detect and monitor preterm birth risk and recurrent pregnancy loss risk within cervicovaginal fluids.

Example 14: Breast Cancer

Signs of breast cancer may include a lump in the breast, a change in breast shape, dimpling of the skin, fluid coming from the nipple, or a red scaly patch of skin. In those patients exhibiting metastasis, there may be bone pain, swollen lymph nodes, shortness of breath, or yellow skin. Age and sex are the two primary risk factors for breast cancer. Other risk factors include obesity, lack of physical exercise, alcohol consumption, hormone replacement therapy during menopause, ionizing radiation, early age at first menstruation, and having children late or not at all. A small minority of breast cancer cases are due to genes inherited from a person's parents, including BRCA1 and BRCA2 among others.

Current methods of breast cancer screening include clinical and self-breast exams, mammography, genetic screening, ultrasound, and magnetic resonance imaging. The USPTF recommends mammography every two years in women between the ages of 50 and 74. The risks of more frequent mammograms include a small but significant increase in breast cancer induced by radiation.

Most breast cancer cases are discovered when the woman feels a lump in her breast. Lumps found in lymph nodes located in the armpits can also indicate the presence of breast cancer. However, currently, the earliest breast cancers are detected by a mammogram. Even so, most symptoms of breast disorders, including most lumps, do not turn out to represent underlying breast cancer, and in fact, fewer than 20% of lumps are cancerous.

Treatment of breast cancer usually involves a combination of surgery, radiation and chemotherapy. In some embodiments the disclosed device focuses on detecting markers associated with breast cancer from menstrual blood or cervicovaginal fluids. This embodiment allows women to identify and track staging of the disease and helps them navigate therapeutic options such as hormonal therapy, NSAIDs and surgery.

In some embodiments the disclosed device focuses on detecting markers associated with breast cancer from menstrual blood or cervicovaginal fluids. The markers, e.g., biomarkers disclosed herein or conventionally used for detecting the presence of breast cancer, can be detected through sequencing a biological sample collected from a female subject's vaginal canal. For example, the collected biological sample is subject to 16S rRNA sequencing, methylation sequencing, long-noncoding RNA sequencing, microRNA sequencing, RNA deep sequencing, genomic DNA sequencing, and/or cDNA sequencing.

Example 15: Ovarian Cancer

There are often no early signs of ovarian cancer. Later symptoms include bloating, pelvic pain, and abdominal swelling, among others. Ovarian cancer occurs more frequently in women who ovulate more, therefore, those who never have children are at increased risk. Other risk factors include hormone therapy after menopause, use of fertility medication, smoking, and obesity. Factors that decrease the risk include hormonal birth control, tubal ligation, and breast feeding. About 10% of cases are hereditary and those with the gene mutations BRCA1 and BRCA2 have an approximately 50% risk of developing the disease. Ovarian carcinomas are the most common type of ovarian cancer, making up more than 95% of breast cancer cases. They include five main subtypes, of which high-grade serous carcinoma is most common. These tumors are believed to usually start from the cells covering the ovaries, though some may form from the fallopian tubes (Piek et al., Adv. Exp. Med. Biol. 622:79-87; 2008). Less common types of ovarian cancer include germ cell tumors and sex cord stromal tumors.

Diagnosis of ovarian cancer starts with a physical examination (including a pelvic examination), a blood test (for CA-125 and sometimes other markers) and a transvaginal ultrasound. The diagnosis is confirmed by examination of a biopsy usually removed during surgery. If treated, early ovarian cancer may be curable. Treatments often include some combination of surgery, radiation therapy and chemotherapy.

Central to the application of the disclosed device is the identification of markers for ovarian cancer, including circulating and shed tumor cells. Ovarian cancer is curable if detected and treated early enough. However, signs of the disease can be absent in the early stages. Many of the symptoms are also non-specific (bloating, pelvic pain, etc.) and therefore difficult for a woman to disambiguate.

As a result, diagnosis often occurs in stages III/IV of the cancer. The literature points to multiple markers, such as CA-125, serum alpha-fetoprotein and lactate dehydrogenase ("LDH"), which can offer insight into diagnosis (Chudecka-Glaz et al., J. Ovarian Res. Epub; 2014; Jashnani et al., Indian J. Pathol. Microbiol. 56:54-56; 2013). Given the especially silent nature of ovarian cancer, a sentinel system optimized for constant surveillance is particularly germane to improve overall outcome of the disease.

In some embodiments the disclosed device focuses on detecting markers associated with ovarian cancer from menstrual blood or cervicovaginal fluids. The markers, e.g., biomarkers disclosed herein or conventionally used for detecting the presence of ovarian cancer, can be detected through sequencing a biological sample collected from a female subject's vaginal canal. For example, the collected biological sample is subject to 16S rRNA sequencing, methylation sequencing, long-noncoding RNA sequencing, microRNA sequencing, RNA deep sequencing, genomic DNA sequencing, and/or cDNA sequencing.

Example 16: Cervical Cancer

More than 90% of cervical cancer cases occur as a result of HPV infection. Most people who have had HPV infections, however, do not develop cervical cancer (Robbins Basic Pathology (8$^{th}$ ed.) pp. 718-721). Other risk factors for cervical cancer include smoking, immunosuppression, use of hormonal birth control pills, and early onset of sexual activity coupled with having multiple sexual partners. Early in infection, there are typically no symptoms. Later symptoms may include abnormal vaginal bleeding, pelvic pain or pain during sex. Diagnosis typically occurs by cervical screening with Pap smears followed by a biopsy. Medical imaging is then done to determine whether or not the cancer has spread.

Cervical cancer screening using the Pap smear or acetic acid can identify precancerous changes which when treated can prevent the development of cancer. Treatment of cervical cancer may consist of some combination of surgery, chemotherapy and radiotherapy.

In some embodiments the disclosed device focuses on detecting markers associated with cervical cancer from menstrual blood or cervicovaginal fluid. The markers, e.g., biomarkers disclosed herein or conventionally used for detecting the presence of cervical cancer, can be detected through sequencing a biological sample collected from a female subject's vaginal canal. For example, the collected biological sample is subject to 16S rRNA sequencing, methylation sequencing, long-noncoding RNA sequencing, microRNA sequencing, RNA deep sequencing, genomic DNA sequencing, and/or cDNA sequencing.

Example 17: Uterine or Endometrial Cancer

Uterine or Endometrial cancer is both the most common type of uterine cancer and the most common cancer of the female reproductive system, accounting for approximately 6 percent of all cancers in women in the United States (National Cancer Institute). Most uterine cancers start in the endometrium (the inner lining of the uterus). This is called endometrial cancer. Most endometrial cancers are adenocarcinomas (cancers that begin in cells that make mucus and other fluids). The most common sign of endometrial cancer is unusual vaginal bleeding. Since 2002, overall incidence rates have not changed significantly, whereas mortality rates have been slowly rising since 2001 (National Cancer Institute). Although the incidence rate of endometrial cancer is only slightly higher in African American women than in whites, the mortality rate of African American women is nearly twice as high as that of all other racial/ethnic groups.

Diagnosis for endometrial cancer is done either through an endometrial biopsy, through a procedure known as a dilatation and curettage—a procedure used to remove tissue from inner lining of the uterus, through physical exams and transvaginal ultrasound, or a CT scan. Because endometrial cancer begins inside the uterus, it does not usually show up in the results of a Pap test. For this reason, a sample of endometrial tissue may be removed and checked under a microscope to look for cancer cells. A recent genomic study characterized nearly 400-endometrial tumors identifying molecular signatures specific to endometrial cancer (CGASN, 2013). This work allows for future characterization of endometrial tumors for possible screening and more advanced diagnostics.

Diagnosis for endometrial cancer can be done through sequencing a biological sample collected from a female subject's vaginal canal. For example, the collected biological sample is subject to 16S rRNA sequencing, methylation sequencing, long-noncoding RNA sequencing, microRNA sequencing, RNA deep sequencing, and/or genomic DNA sequencing.

Uterine cancer is treated by one or a combination of treatments, including surgery, radiation therapy, chemotherapy, and hormone therapy. Combinations of treatments are often recommended. Surgery can include partial or full hysterectomy. Often the stage of cancer determines the specific combination of therapy.

In some embodiments the disclosed device focuses on detecting markers associated with uterine or endometrial cancers from menstrual blood or cervicovaginal fluid.

In one example, the biological materials collected using devices, methods, kits and compositions disclosed herein is used to extract blood, extracellular fluid, cervicovaginal fluid, and shed uterus cells, for nucleic acid molecules extraction. The nucleic acid molecules can be DNA, genomic DNA or RNA. The nucleic acid molecules are determined using next generation sequencing, e.g., Illumina sequencing technology. The sequencing result is used to determine the status of one biomarker or a set of biomarkers typically used to diagnose diseases, e.g., endometriosis, cancer, uterine cancer. The biomarkers can be FDA approved biomarkers. The sequencing result can be used to determine personalized medicine to treat a disease or for prophylactic advice on a disease. The sequencing result can be used to monitor the effectiveness of a drug that is used to treat the disease. The sequencing result can be used to test family genetic disorders and diseases.

Example 18: Pre-pregnancy Nutrition

It has been shown that many vitamins and minerals are essential for healthy pregnancy. For example, low maternal folate levels are associated with allergy sensitization and asthma (Lin J et al, J Allergy Clin Immunol, 2013). Low maternal iron levels have been associated with lower mental development (Chang S. et al, Pediatrics, 2013), and low iron may even increase a mother's risk of post-partum depression. Vitamin B12, which is essential for red blood cell formation, is essential for pregnant women and the health of their fetus. Folate, Iron, and Vitamin B12 can all cause anemia and increase a pregnant woman's risk of preterm labor, developmental delays of the child, as well as neural tube defects during development. Based on a WHO review of nationally representative samples from 1993 to 2005, 42 percent of pregnant women have anemia. Other essential vitamins and minerals that promote a healthy pregnancy are well validated and include Vitamins A, D, E, Other B Vitamins, Calcium, and Zinc.

In some embodiments the disclosed device focuses on detecting levels of vitamins and minerals from menstrual blood or cervicovaginal fluid that may help maintain healthy levels within the body for pregnancy.

Example 19: Hormones—Metabolism

The thyroid gland is primarily involved in the control of metabolism. Abnormal thyroid function directly and indirectly affects reproduction as well. Infertility and adverse pregnancy outcomes are more common when the thyroid gland is hypo- or hyperactive. Higher miscarriage rate, more frequent preterm deliveries, increased hypertension, diabetic complications, higher risk for placental abruption, and adverse fetal effects have all been reported with thyroid dysfunction in pregnancy. At least half of implanted embryos may not survive to delivery, and, on average, 20% of clinical pregnancies are lost (Schwartz N. et al, J Clin Enocrinol Metab. 2010).

During pregnancy, a 30%-40% increased need for thyroid hormones is the result of increased placental uptake, higher thyroid-binding globulin levels, and greater blood volume (Schwartz N. et al, J Clin Enocrinol Metab. 2010). Those with subclinical hypothyroidism and/or high-normal TSH levels at the beginning of pregnancy may not be able to meet these needs and may show signs of thyroid insufficiency during pregnancy.

Women with thyroid disease visit clinicians 2-4 times per year to check for thyroid hormone levels to adjust medications. And before pregnancy, regular monitoring of thyroid hormone and treatment can be an effective way of maintaining healthy TSH levels during pregnancy.

In some embodiments the disclosed device focuses on detecting levels of thyroid stimulating hormone from menstrual blood or cervicovaginal fluid.

Example 20: Hormones—Fertility and Menopause

Fertility—Progesterone is one of the most important hormones for pregnancy with myriad functions from ensuring implantation of the egg into a healthy uterine wall, to ensuring embryo survival and prevention of immune rejection of the developing baby. Many other hormones act in concert with progesterone, like Follicular Stimulating Hormone (FSH) and Luteinizing Hormone (LH) and can be used to assess optimal fertility windows on a monthly basis. And in fact an over dominant production of estrogen can lead to progesterone deficiency and thus difficulty getting or staying pregnant. It is important that women not only monitor FSH and LH to determine optimal fertility for getting pregnant, but ensure that sufficient levels or progesterone are being produced to ensure pregnancy and viability of the fetus. A study from the British Medical Journal, 2012, demonstrated that a single progesterone level test can help discriminate between viable and nonviable pregnancies. Among women who had an ultrasound, 73 percent had nonviable pregnancies. But among women with progesterone levels below 3 to 6 nanograms per milliliter, the probability of a nonviable pregnancy rose to more than 99 percent (Gallos L et al. British Medical J, 2012).

Perimenopause—Monitoring hormone levels during the menopausal transition may help women better understand important changes in their body and allow them to make more informed decisions about health, diet, and lifestyle. According to Hale G E (Best Pract Res Clin Obstet Gynaecol, 2009), data from endocrine studies on women throughout the menopausal transition show changes in levels of steroid hormones and gonadotropins (Progesterone, Estrodiol, LH, FSH and AMH) and follicle-stimulating hormone undergoes the first detectable change while menstrual cycles remain regular. Erratic and less predictable changes in steroid hormones follow, especially with the onset of irregular cycles. Later serum hormone studies on the inhibins and anti-Mullerian hormone established that diminishing ovarian follicle number contributes to the endocrine changes with advancing reproductive age.

Many fertility issues revolve around genetic, anatomical or other disorders that may either prevent a woman from becoming pregnant and/or staying pregnant. Some of these disorders include hormonal imbalances, diabetes, a short or insufficient cervix, and acute or chronic infections. A cascade of genes has been implicated in the occurrence of getting and staying pregnant. These genes have been studied using genotyping, gene expression, and proteomic analysis to assess a woman's ability to stay pregnant.

In some embodiments the disclosed device focuses on detecting levels of Progesterone, LH, FSH, Estradiol, AMH, genotyping, gene expression through RNA and methylome sequencing, qPCR and proteomic analysis for fertility and menopause management from menstrual blood or cervicovaginal fluid.

Example 21: Environmental Toxins

There is growing evidence that bisphenol A (BPA) may adversely affect humans. BPA is an endocrine disruptor that has been shown to be harmful in laboratory animal studies. As reported by Rochester J (Reproductive Toxicology, 2013) BPA has been shown to affect many endpoints of fertility, including poor ovarian response, viability of oocytes, and reduced yield of viable oocytes. BPA has also been correlated with PCOS, endometrial disorders, an increased rate of miscarriages, premature delivery, and lower birth weights.

Current methods of detecting BPA in blood are done through mass spectrometry. Monitoring of BPA levels in blood may help reduce or eliminate certain sources of BPA in a women's environment, aiding in overall health.

In some embodiments the disclosed device focuses on detecting levels of BPA toxin from menstrual blood or cervicovaginal fluid.

Example 22: Alcohol Abuse

Clinicians can use several biochemical measurements to objectively assess patients' current or past alcohol use. Several more experimental markers hold promise for measuring acute alcohol consumption and relapse. These include certain alcohol byproducts, such as acetaldehyde, ethyl glucuronide (EtG), and fatty acid ethyl esters (FAEE), as well as two measures of sialic acid, a carbohydrate that appears to be altered in alcoholics (Peterson K, Alcohol Research and Health, 2005). Clinicians have had access to a group of biomarkers that indicate a person's alcohol intake. Several of these reflect the activity of certain liver enzymes: serum gamma-glutamyltransferase (GGT), aspartate aminotransferase (AST), alanine aminotransferase (ALT), and carbohydrate-deficient transferrin (CDT), a protein that has received much attention in recent years. Another marker, N-acetyl-β-hexosaminidase (beta-Hex), indicates that liver cells, as well as other cells, have been breaking down carbohydrates, which are found in great numbers in alcohol (Javors and Johnson 2003).

In some embodiments the disclosed device focuses on detecting markers associated with alcohol abuse from menstrual blood or cervicovaginal fluid.

Example 23: Semen Exposure

In many cases of sexual assault, traces of semen are left behind in the vagina, allowing for later collection and analysis. Semen consists of a variety of proteins, vitamins, nutrients, blood group antigens, and DNA. The preservation and/or analysis of semen can facilitate later development of a DNA profile. In some embodiments, the disclosed kit allows for at-home detection of analytes from semen.

Devices, systems and methods of the present disclosure can be combined with or modified by other devices, systems and methods, such as, for example, those described in International Patent Publication No. WO/2016/025332, which is entirely incorporated herein by reference.

Example 24: Vaginal Microbiomes

The devices and systems disclosed herein can be used for collecting biological samples, such as vaginal fluid, cells, and/or menstrual fluid, for analysis of vaginal microbiomes. The collected biological sample is used for sequencing to detect a presence or absence of a vaginal microbiome, using any of the sequencing platforms described herein. The collected biological sample is subject to 16S rRNA sequencing, methylation sequencing, long-noncoding RNA sequencing, microRNA sequencing, RNA deep sequencing, genomic DNA sequencing, and/or cDNA sequencing. Common microbiomes found in the vagina canal include bacteria from the species of the genus *Lactobacillus*, such as *Lactobacillus crispatus, Lactobacillus iners, Lactobacillus jensenii*, and *Lactobacillus* gasseri, bacterial species, such as *Atopobium vaginae, Gardnerella vaginalis, Chlamydia trachomatis, Neisseria gonorrhoeae, Treponema pallidum*, parasites such *Trichomonas vaginalis*, bacterial vaginosis associated bacteria in the order Clostridiales, *Megasphaera* species, and *Sneathia* species. The detection of one or more vaginal microbiome can indicate a female subject's vaginal health, pregnancy complications, preterm labor, and/or bacterial infections.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A kit for analysis of a vaginal biological sample, the kit comprising:
   (a) a sample collector for collecting a vaginal biological sample; and
   (b) an extractor configured to receive and enclose the sample collector, the extractor comprising:
      (i) a first chamber configured to receive the sample collector via an opening such that the sample collector is primarily retained in the first chamber;
      (ii) a second chamber configured for selective fluid communication with the first chamber, the second chamber comprising a breakable reagent compartment,
wherein the breakable reagent compartment comprises a solution, said solution configured for preserving, storing, or analyzing the vaginal biological sample; and
(iii) a moveable compression element;
wherein the moveable compression element is configured to close onto the breakable reagent compartment creating a compression force with a projection or surface of the compression element to break the breakable reagent compartment and release said solution, thereby contacting said solution with said vaginal biological sample to form a mixture of said solution and said vaginal biological sample;
wherein said mixture is received in said second chamber;
wherein said mixture is free to flow between said first chamber, said second chamber, and said sample collector after said breakable reagent compartment is broken.

2. The kit of claim 1, wherein the solution comprises a reagent for (i) hydrolyzing, diffusing, or releasing the vaginal biological sample, (ii) analyzing, preserving or extracting deoxyribonucleic acid, ribonucleic acid or protein in the vaginal biological sample, (iii) reducing analysis background noise, (iv) precipitating or removing a contaminant in the vaginal biological sample, or (v) testing the vaginal biological sample for a presence or absence of an analyte in the vaginal biological sample.

3. The kit of claim 1, wherein the vaginal biological sample comprises one or more of cervicovaginal fluid, blood, vaginal mucosa, semen, interstitial fluid, cervical secretions, fetal tissues, reproductive cells, cervical cells, endometrial cells, fallopian cells, ovarian cells, natural flora in a female reproductive tract, invasive pathogens, and trophoblast cells.

4. The kit of claim 3, wherein the vaginal biological sample comprises blood.

5. The kit of claim 3, wherein the vaginal biological sample comprises an endometrial cell.

6. The kit of claim 1, wherein the vaginal biological sample comprises a volume of at least 0.1 mL.

7. The kit of claim 1, wherein the sample collector comprises an absorbent-diffuse material that absorbs, retains, or releases the vaginal biological sample.

8. The kit of claim 1, wherein the sample collector comprises a tampon.

9. The kit of claim 1, wherein the extractor comprises an extractor cap configured to seal the extractor.

10. The kit of claim 1, wherein the analysis of the vaginal biological sample comprises detecting a presence or absence of a biomarker in the vaginal biological sample.

11. The kit of claim 10, wherein the biomarker comprises a bacterial nucleotide sequence, a viral nucleotide sequence, a fungal nucleotide sequence, or a human nucleotide sequence.

12. The kit of claim 10, wherein a change of expression level of the biomarker is indicative of a pathological condition.

13. The kit of claim 12, wherein the pathological condition is endometriosis, endometrial cancer, an immune disorder in a female genital tract, cervical cancer, ovarian cancer, and a sexually transmitted infection.

14. The kit of claim 12, wherein the pathological condition is endometriosis, endometrial cancer, an immune disorder in a female genital tract, cervical cancer, ovarian cancer, and a sexually transmitted infection.

15. The kit of claim 10, wherein a change of nucleotide sequence of the biomarker is indicative of a pathological condition.

16. The kit of claim 1, wherein the analysis comprises sequencing nucleic acids in the vaginal biological sample.

\* \* \* \* \*